US012778811B2

(12) United States Patent
Ballamy et al.

(10) Patent No.: US 12,778,811 B2
(45) Date of Patent: Nov. 3, 2026

(54) WOUND DRESSING

(71) Applicant: ConvaTec Limited, Flintshire (GB)

(72) Inventors: Lucy Ballamy, Llangollen (GB); Amelia Lay, Flintshire (GB); Duncan Gilding, Flintshire (GB); Craig Jeffery, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 19/203,951

(22) Filed: May 9, 2025

(65) Prior Publication Data

US 2025/0325407 A1 Oct. 23, 2025

Related U.S. Application Data

(63) Continuation of application No. PCT/GB2023/052928, filed on Nov. 9, 2023.

(Continued)

(30) Foreign Application Priority Data

Dec. 22, 2022 (GB) ..................................... 2219611

(51) Int. Cl.

*A61F 13/05* (2024.01)
*A61F 13/0206* (2024.01)

(Continued)

(52) U.S. Cl.

CPC ........ *A61F 13/05* (2024.01); *A61F 13/51498* (2013.01); *A61L 15/28* (2013.01)

(58) Field of Classification Search

CPC ........ A61M 1/7487; A61M 1/90; A61M 1/91; A61M 1/912; A61M 1/915; A61M 1/916;

(Continued)

(56) References Cited

U.S. PATENT DOCUMENTS 6,268,544 B1 * 7/2001 Court ................ A61F 13/01008 602/44
2011/0195216 A1 * 8/2011 Keener ................. A61L 15/585 442/151

(Continued)

FOREIGN PATENT DOCUMENTS

CN 109223312 A 1/2019
EP 1962800 B1 10/2015
GB 800572 A 8/1958

OTHER PUBLICATIONS

ConvaTec, AQUACEL® Hydrofiber® Dressing, Oct. 31, 2008.*

(Continued)

*Primary Examiner* — Kari K Rodriquez
*Assistant Examiner* — Andrew Jun-Wai Mok
(74) *Attorney, Agent, or Firm* — TAFT STETTINIUS HOLLISTER LLP; Ryan O. White; Derek B. Lavender

(57) ABSTRACT

A negative pressure wound dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the skin adjacent the wound, and the wound contact layer may have a first surface and a second surface, wherein the first surface of the wound contact layer may contact the wound in use, wherein the first surface may comprise warp stitches, and the second surface may comprise warp and weft stitches.

16 Claims, 9 Drawing Sheets

Related U.S. Application Data

(60) Provisional application No. 63/424,162, filed on Nov. 10, 2022.

(51) Int. Cl.
*A61F 13/0246* (2024.01)
*A61F 13/514* (2006.01)
*A61L 15/28* (2006.01)

(58) Field of Classification Search
CPC .......... A61M 1/962; A61F 2013/00174; A61F 2013/00238; A61F 13/00; A61F 13/0246; A61F 13/05
See application file for complete search history.

(56) References Cited

U.S. PATENT DOCUMENTS

| | | | | |
|---|---|---|---|---|
| 2016/0270962 | A1* | 9/2016 | Wang | A61F 13/01012 |
| 2020/0107963 | A1* | 4/2020 | Mondal | A61F 13/00063 |
| 2021/0100691 | A1* | 4/2021 | Gilding | B01D 35/02 |
| 2021/0196525 | A1* | 7/2021 | Bishop | A61F 13/0203 |

OTHER PUBLICATIONS

BioSpace, ConvaTec Launches New AQUACEL(R) Ag Dressing with Strengthening Fiber, May 14, 2009.*
Amazon ConvaTec, ConvaTec AQUACEL Extra 2'x2', Sep. 12, 2013.*
International Preliminary Report on Patentability and prior Arguments/Amendments presented for PCT/GB2023/05292; dated Jan. 28, 2025; 13 Pages.

* cited by examiner

WOUND DRESSING

TECHNICAL FIELD OF THE INVENTION

The present invention relates to a wound dressing. In particular, the invention concerns a negative pressure wound dressing.

BACKGROUND TO THE INVENTION

Wound dressings are known and are generally suitable for treating a variety of wounds, including chronic and acute wound types, such as infected wounds, venous ulcers, diabetic ulcers, burns and surgical wounds.

Negative pressure has been used to treat a range of chronic and acute wounds. Negative pressure may facilitate wound healing through a number of mechanisms, including removal of excess exudate, reduction in periwound edema and increased perfusion. Combined with the physical forces exerted by the negative pressure which draw the wound edges together, this can result in improved wound outcomes.

Wound dressings typically comprise an adhesive skin contact layer for detachably adhering the dressing to a dermal surface. Conventionally, the adhesive skin contact layer comprises a plurality of perforations (i.e., through holes in the adhesive skin contact layer) which enable fluid, for example wound exudate, to flow through the layer but which prevent tissue ingrowth into other material comprised in the wound dressing. Typically, the perforations have a diameter of no more than 1.2 mm to facilitate adhesion of the skin contact layer to the dermal surface and to provide a skin contact layer with sufficient breathability, i.e., allowing water vapour and gas to pass through the layer. Typically, the skin contact layer comprises a silicone adhesive. Disadvantageously, some of the perforations are prone to closing, or at least reducing in diameter, after formation due to the silicone adhesive entering and, therefore, blocking the perforations. While this may increase adhesion of the layer to the dermal surface, this adversely affects the breathability of the skin contact layer, causing an accumulation of bodily fluid at and in proximity to the skin or wound site, therefore, preventing the formation of an environment optimised for wound healing. Conversely, it is known to increase the size of perforations in an adhesive skin contact layer to aid breathability. However, this is achieved at the expense of adhesion of the skin contact layer to a dermal surface and in such cases, the skin contact layer may only weakly adhere to a dermal surface such that movement of a patient while the wound dressing is adhered may cause the wound dressing to partially or completely detach from the patient, adversely affecting the dressing to transmit a negative pressure to the wound site.

Conventional techniques to form the perforations in the adhesive layer include using a hot pin process. However, disadvantageously, this results in the formation of 'slugs' around the perforation (i.e., the material intended to be removed to form the perforation is not wholly disconnected from the main body of material and, therefore, partially obstructs the perforation and results in a non-planar surface of the skin contact layer). To overcome this, ultrasound may be used to create the perforations. However, this process disadvantageously forms doughnut/volcano structure around the perforations.

Portable systems have been developed which include a means to manage the exudate produced by the wound by collecting exudate within the wound dressing, typically in an absorbent material, and by evaporation through the dressing. Such systems mean that a separate collection canister may not be an essential part of the system. An advantage of not needing a canister is that the device is less bulky and more portable. A disadvantage with such devices is that if the dressing exceeds its fluid handling capacity, exudate may be drawn from the absorbent material(s) and enter the pump. The presence of exudate in the pump will eventually cause it to fail and require its replacement. The therapy provided by the system may also be less than optimal due to the potential for excess exudate to collect, or pool, at the wound interface. In order to prevent fouling of the pump with exudate, it is known to provide a barrier layer between the absorbent material and the pump. However, the liquid barrier layer does not improve the ability of the absorbent material(s) to absorb exudate.

Wound contact layers are known to comprise a mixture of gelling and non-gelling fibres. Gelling fibres form a gel upon contact with exudate. However, upon forming a gel, many wound contact layers weaken and in some cases partially dissociate from other layers comprised in an absorbent structure. To overcome this, it is known to provide non-gelling fibres as part of the wound contact surface of the wound contact layer. Such arrangements aim to strike a balance between providing a sufficient amount of gelling fibres and preventing dissociation of the wound contact layer when it becomes wet with exudate.

However, known wound contact layers fail to adequately strike this balance and such layers either do not adequately prevent pooling of exudate at the wound contact surface or do not adequately adhere to other layers within the wound dressing when the wound contact layer becomes wet with exudate.

During negative pressure therapy, air as well as wound exudate material is removed from a wound site. The wound exudate must be collected remotely from the wound site. Some known negative pressure therapy systems comprise a waste cannister connected to a pump unit for the collection and storage of wound exudate material. However, the use of a canister can result in the therapy system itself being bulky and expensive to manufacture. Also, replacing a canister or a container in a canister in which wound exudate is collected can be a time consuming and a relatively unhygienic process.

Negative pressure wound dressings have been produced which comprise an absorbent layer to absorb wound exudate in an attempt to remove the need for a cannister and pump system. However, such wound dressings often fail to sufficiently meet two requirements of an absorbent layer in a wound dressing, i.e., that the absorbent layer has a high absorbance capacity and remains flexible (i.e., does not stiffen) when it absorbs wound exudate which subsequently dries.

Known absorbent layers with a relatively low absorbance capacity cause pooling of wound exudate at the wound site. This is both uncomfortable and unhygienic for the patient and for a healthcare professional who replaces the wound dressing. Moreover, there is a risk that the wound and/or surrounding skin will become macerated if in prolonged contact with excess wound exudate.

Moreover, known absorbent layers often become relatively stiff when wound exudate has been absorbed and subsequently dried. This results in the fabric of the absorbent layer 'doming' which, disadvantageously, provides a tunnel effect of air transfer and causes air to leak from the wound dressing, thereby adversely affecting the negative pressure transmitted to the wound site.

Conventional negative pressure wound dressings often comprise relatively rigid dressing and binding components which adversely affects system utility and which provides a relatively rigid wound dressing which is disadvantageous in respect of user comfort. Moreover, such components require individual manufacturing steps to incorporate them into the wound dressing, therefore, increasing the time of manufacture and cost.

The purpose of such components is to attempt to increase the integrity of the wound dressing to prevent, or at least reduce, dissociation of one or more of the layers comprised therein. However, the advantages of such components often do not outweigh the disadvantages associated with the additional manufacturing steps, complex processing and the rigidity of the final wound dressing. Further, the rigid dressing and binding components often have an adverse effect on the wicking, or movement, of wound exudate through the wound dressing away from the wound site. Additionally, existing negative pressure wound dressing systems do not utilise absorbent materials and additional wound dressing components arranged to maximise the management of wound exudate within the dressing.

It is known to provide a wound dressing comprising a wound contact layer, a transmission layer and an absorbent layer, arranged such that the transmission layer overlies the wound contact layer, and the absorbent layer overlies the transmission layer. This arrangement is disclosed in U.S. Pat. No. 10,507,141. However, such an arrangement does not provide a significant absorbency capacity. This means that the arrangement suffers from unnecessary pooling of wound exudate at the wound site. As such, the hygiene of the wound dressing and of the wound site could be improved which in turn would increase comfort for the user.

It is an object of embodiments of the present invention to at least partially overcome or alleviate the above problems and/or to provide an improved wound dressing.

SUMMARY OF THE INVENTION

According to a broad aspect of the invention, there is provided a wound dressing comprising an adhesive skin contact layer. The adhesive skin contact layer may have a weight of between 40 gsm and 250 gsm. The adhesive skin contact layer may be a perforated mesh. The adhesive skin contact layer may comprise perforations. Each of the perforations may have a diameter of between 1.25 mm and 5.00 mm.

The wound dressing may be a negative pressure wound dressing. The wound dressing may comprise a backing layer. The wound dressing may comprise an absorbent structure. The absorbent structure may be arranged between the backing layer and the adhesive skin contact layer. The adhesive skin contact layer may be configured to detachably adhere the dressing to a dermal surface. The backing layer may comprise a coupling member configured to connect the dressing to a negative pressure source.

According to a first aspect of the present invention there is provided a negative pressure wound dressing, the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the adhesive skin contact layer has a weight of between 40 gsm and 250 gsm, further wherein the adhesive skin contact layer is a perforated mesh comprising perforations each having a diameter of between 1.25 mm and 5.00 mm.

The adhesive skin contact layer comprises perforations each having a diameter of between 1.25 mm and 5.00 mm. Advantageously, this means that the perforations have a sufficient diameter to provide breathability to the wound dressing in the event that some of the perforations reduce in diameter after their formation. As such, the adhesive skin contact layer maintains an environment optimised for wound healing.

It has surprisingly been found that the relatively large perforations, compared to the perforations known in the prior art having a diameter of 1.20 mm, did not adversely affect adhesion to the dermal surface. Thus, advantageously, the invention functions without loss, or at least significant loss, of adhesion of the wound dressing to the dermal surface and, therefore, reliably transmits a negative pressure to the wound site.

Moreover, it has been found that following manufacture of the adhesive skin contact layer, perforations having a diameter of between 1.25 mm and 5.00 mm do not 'close-up', or at least do not substantially close-up. Comparatively, perforations having a smaller diameter, for example 1.20 mm, exhibit a tendency to close-up after formation due to the silicone adhesive entering and, therefore, blocking the perforations. Thus, the present invention provides for an adhesive skin contact layer which ensures sufficient breathability to the wound dressing, in use.

The perforations comprise through holes in the adhesive skin contact layer which enable fluid to flow through the layer. Thus, in use, if the adhesive skin contact layer is arranged covering and in contact with a wound, the adhesive skin contact layer prevents, or at least substantially prevents, tissue ingrowth into other materials of the wound dressing.

Beneficially, the adhesive skin contact layer helps to maintain the integrity of the wound dressing while also creating an airtight, or substantially airtight, seal around the absorbent structure in order to maintain negative pressure at the wound.

The absorbent structure may be arranged between the backing layer and the adhesive skin contact layer. Advantageously, this means that wound exudate is absorbed by the absorbent structure before the exudate contacts the backing layer.

The adhesive skin contact layer may have a weight of about 40 gsm, about 50 gsm, about 60 gsm, about 70 gsm, about 80 gsm, about 90 gsm, about 100 gsm, about 110 gsm, about 120 gsm, about 130 gsm, about 140 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or about 250 gsm.

The adhesive skin contact layer may have a weight of at least about 40 gsm, about 50 gsm, about 60 gsm, about 70 gsm, about 80 gsm, about 90 gsm, about 100 gsm, about 110 gsm, about 120 gsm, about 130 gsm, about 140 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or at least about 250 gsm.

The adhesive skin contact layer may have a weight of no more than about 40 gsm, about 50 gsm, about 60 gsm, about 70 gsm, about 80 gsm, about 90 gsm, about 100 gsm, about 110 gsm, about 120 gsm, about 130 gsm, about 140 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or no more than about 250 gsm.

The adhesive skin contact layer may have a weight of between about 40 gsm and about 250 gsm, about 50 gsm and about 250 gsm, about 60 gsm and about 250 gsm, about 70 gsm and about 250 gsm, about 80 gsm and about 250 gsm, about 90 gsm and about 250 gsm, about 100 gsm and about 250 gsm, 125 gsm and about 245 gsm, about 135 gsm and about 240 gsm, about 150 gsm and about 235 gsm, about 160 gsm and about 230 gsm, about 170 gsm and about 230 gsm, about 175 gsm and about 225 gsm, about 180 gsm and about 220 gsm, about 185 gsm and about 215 gsm, about 190 gsm and about 210 gsm, about 195 gsm and bout 205 gsm, or about 200 gsm.

The adhesive skin contact layer may have a weight of between about 40 gsm and about 250 gsm, between about 40 gsm and about 240 gsm, between about 40 gsm and about 230 gsm, between about 40 gsm and about 220 gsm, between about 40 gsm and about 210 gsm, between about 40 gsm and about 200 gsm, between about 40 gsm and about 190 gsm, between about 40 gsm and about 180 gsm, between about 40 gsm and about 170 gsm, between about 40 gsm and about 160 gsm, between about 40 gsm and about 150 gsm, between about 40 gsm and about 140 gsm, between about 40 gsm and about 130 gsm, between about 40 gsm and about 120 gsm, between about 40 gsm and about 110 gsm, between about 40 gsm and about 100 gsm, between about 40 gsm and about 90 gsm, between about 40 gsm and about 80 gsm, between about 40 gsm and about 70 gsm, between about 40 gsm and about 60 gsm, or between about 40 gsm and about 50 gsm.

The adhesive skin contact layer may have a weight of between about 50 gsm and about 250 gsm, between about 50 gsm and about 240 gsm, between about 50 gsm and about 230 gsm, between about 50 gsm and about 220 gsm, between about 50 gsm and about 210 gsm, between about 50 gsm and about 200 gsm, between about 50 gsm and about 190 gsm, between about 50 gsm and about 180 gsm, between about 50 gsm and about 170 gsm, between about 50 gsm and about 160 gsm, between about 50 gsm and about 150 gsm, between about 50 gsm and about 140 gsm, between about 50 gsm and about 130 gsm, between about 50 gsm and about 120 gsm, between about 50 gsm and about 110 gsm, between about 50 gsm and about 100 gsm, between about 50 gsm and about 90 gsm, between about 50 gsm and about 80 gsm, between about 50 gsm and about 70 gsm, or between about 50 gsm and about 60 gsm.

The adhesive skin contact layer may have a weight of between about 60 gsm and about 250 gsm, between about 60 gsm and about 240 gsm, between about 60 gsm and about 230 gsm, between about 60 gsm and about 220 gsm, between about 60 gsm and about 210 gsm, between about 60 gsm and about 200 gsm, between about 60 gsm and about 190 gsm, between about 60 gsm and about 180 gsm, between about 60 gsm and about 170 gsm, between about 60 gsm and about 160 gsm, between about 60 gsm and about 150 gsm, between about 60 gsm and about 140 gsm, between about 60 gsm and about 130 gsm, between about 60 gsm and about 120 gsm, between about 60 gsm and about 110 gsm, between about 60 gsm and about 100 gsm, between about 60 gsm and about 90 gsm, between about 60 gsm and about 80 gsm, or between about 60 gsm and about 70 gsm.

The adhesive skin contact layer may have a weight of between about 70 gsm and about 250 gsm, between about 70 gsm and about 240 gsm, between about 70 gsm and about 230 gsm, between about 70 gsm and about 220 gsm, between about 70 gsm and about 210 gsm, between about 70 gsm and about 200 gsm, between about 70 gsm and about 190 gsm, between about 70 gsm and about 180 gsm, between about 70 gsm and about 170 gsm, between about 70 gsm and about 160 gsm, between about 70 gsm and about 150 gsm, between about 70 gsm and about 140 gsm, between about 70 gsm and about 130 gsm, between about 70 gsm and about 120 gsm, between about 70 gsm and about 110 gsm, between about 70 gsm and about 100 gsm, between about 70 gsm and about 90 gsm, or between about 70 gsm and about 80 gsm.

The adhesive skin contact layer may have a weight of between about 80 gsm and about 250 gsm, between about 80 gsm and about 240 gsm, between about 80 gsm and about 230 gsm, between about 80 gsm and about 220 gsm, between about 80 gsm and about 210 gsm, between about 80 gsm and about 200 gsm, between about 80 gsm and about 190 gsm, between about 80 gsm and about 180 gsm, between about 80 gsm and about 170 gsm, between about 80 gsm and about 160 gsm, between about 80 gsm and about 150 gsm, between about 80 gsm and about 140 gsm, between about 80 gsm and about 130 gsm, between about 80 gsm and about 120 gsm, between about 80 gsm and about 110 gsm, between about 80 gsm and about 100 gsm, or between about 80 gsm and about 90 gsm.

The adhesive skin contact layer may have a weight of between about 90 gsm and about 250 gsm, between about 90 gsm and about 240 gsm, between about 90 gsm and about 230 gsm, between about 90 gsm and about 220 gsm, between about 90 gsm and about 210 gsm, between about 90 gsm and about 200 gsm, between about 90 gsm and about 190 gsm, between about 90 gsm and about 180 gsm, between about 90 gsm and about 170 gsm, between about 90 gsm and about 160 gsm, between about 90 gsm and about 150 gsm, between about 90 gsm and about 140 gsm, between about 90 gsm and about 130 gsm, between about 90 gsm and about 120 gsm, between about 90 gsm and about 110 gsm, or between about 90 gsm and about 100 gsm.

The adhesive skin contact layer may have a weight of between about 100 gsm and about 250 gsm, between about 100 gsm and about 240 gsm, between about 100 gsm and about 230 gsm, between about 100 gsm and about 220 gsm, between about 100 gsm and about 210 gsm, between about 100 gsm and about 200 gsm, between about 100 gsm and about 190 gsm, between about 100 gsm and about 180 gsm, between about 100 gsm and about 170 gsm, between about 100 gsm and about 160 gsm, between about 100 gsm and about 150 gsm, between about 100 gsm and about 140 gsm, between about 100 gsm and about 130 gsm, between about 100 gsm and about 120 gsm, or between about 100 gsm and about 110 gsm.

The adhesive skin contact layer may have a weight of between about 110 gsm and about 250 gsm, between about 110 gsm and about 240 gsm, between about 110 gsm and about 230 gsm, between about 110 gsm and about 220 gsm, between about 110 gsm and about 210 gsm, between about 110 gsm and about 200 gsm, between about 110 gsm and about 190 gsm, between about 110 gsm and about 180 gsm, between about 110 gsm and about 170 gsm, between about 110 gsm and about 160 gsm, between about 110 gsm and about 150 gsm, between about 110 gsm and about 140 gsm, between about 110 gsm and about 130 gsm, or between about 110 gsm and about 120 gsm.

The adhesive skin contact layer may have a weight of between about 120 gsm and about 250 gsm, between about 120 gsm and about 240 gsm, between about 120 gsm and about 230 gsm, between about 120 gsm and about 220 gsm, between about 120 gsm and about 210 gsm, between about 120 gsm and about 200 gsm, between about 120 gsm and about 190 gsm, between about 120 gsm and about 180 gsm, between about 120 gsm and about 170 gsm, between about 120 gsm and about 160 gsm, between about 120 gsm and about 150 gsm, between about 120 gsm and about 140 gsm, or between about 120 gsm and about 130 gsm.

The adhesive skin contact layer may have a weight of between about 130 gsm and about 250 gsm, between about 130 gsm and about 240 gsm, between about 130 gsm and about 230 gsm, between about 130 gsm and about 220 gsm, between about 130 gsm and about 210 gsm, between about 130 gsm and about 200 gsm, between about 130 gsm and about 190 gsm, between about 130 gsm and about 180 gsm, between about 130 gsm and about 170 gsm, between about 130 gsm and about 160 gsm, between about 130 gsm and about 150 gsm, or between about 130 gsm and about 140 gsm.

The adhesive skin contact layer may have a weight of between about 140 gsm and about 250 gsm, between about 140 gsm and about 240 gsm, between about 140 gsm and about 230 gsm, between about 140 gsm and about 220 gsm, between about 140 gsm and about 210 gsm, between about 140 gsm and about 200 gsm, between about 140 gsm and about 190 gsm, between about 140 gsm and about 180 gsm, between about 140 gsm and about 170 gsm, between about 140 gsm and about 160 gsm, or between about 140 gsm and about 150 gsm.

The adhesive skin contact layer may have a weight of between about 150 gsm and about 250 gsm, between about 150 gsm and about 240 gsm, between about 150 gsm and about 230 gsm, between about 150 gsm and about 220 gsm, between about 150 gsm and about 210 gsm, between about 150 gsm and about 200 gsm, between about 150 gsm and about 190 gsm, between about 150 gsm and about 180 gsm, between about 150 gsm and about 170 gsm, or between about 150 gsm and about 160 gsm.

The adhesive skin contact layer may have a weight of between about 160 gsm and about 250 gsm, between about 160 gsm and about 240 gsm, between about 160 gsm and about 230 gsm, between about 160 gsm and about 220 gsm, between about 160 gsm and about 210 gsm, between about 160 gsm and about 200 gsm, between about 160 gsm and about 190 gsm, between about 160 gsm and about 180 gsm, or between about 160 gsm and about 170 gsm.

The adhesive skin contact layer may have a weight of between about 170 gsm and about 250 gsm, between about 170 gsm and about 240 gsm, between about 170 gsm and about 230 gsm, between about 170 gsm and about 220 gsm, between about 170 gsm and about 210 gsm, between about 170 gsm and about 200 gsm, between about 170 gsm and about 190 gsm, or between about 170 gsm and about 180 gsm.

The adhesive skin contact layer may have a weight of between about 180 gsm and about 250 gsm, between about 180 gsm and about 240 gsm, between about 180 gsm and about 230 gsm, between about 180 gsm and about 220 gsm, between about 180 gsm and about 210 gsm, between about 180 gsm and about 200 gsm, or between about 180 gsm and about 190 gsm.

The adhesive skin contact layer may have a weight of between about 190 gsm and about 250 gsm, between about 190 gsm and about 240 gsm, between about 190 gsm and about 230 gsm, between about 190 gsm and about 220 gsm, between about 190 gsm and about 210 gsm, or between about 190 gsm and about 200 gsm.

The adhesive skin contact layer may have a weight of between about 200 gsm and about 250 gsm, between about 200 gsm and about 240 gsm, between about 200 gsm and about 230 gsm, between about 200 gsm and about 220 gsm, or between about 200 gsm and about 210 gsm.

The adhesive skin contact layer may have a weight of between about 210 gsm and about 250 gsm, between about 210 gsm and about 240 gsm, between about 210 gsm and about 230 gsm, or between about 210 gsm and about 220 gsm.

The adhesive skin contact layer may have a weight of between about 220 gsm and about 250 gsm, between about 220 gsm and about 240 gsm, or between about 220 gsm and about 230 gsm.

The adhesive skin contact layer may have a weight of between about 230 gsm and about 250 gsm, or between about 230 gsm and about 240 gsm.

The adhesive skin contact layer may have a weight of between about 240 gsm and about 250 gsm.

Advantageously, an adhesive skin contact layer having a weight of between about 100 gsm and about 250 gsm provides a more malleable, gelled structure so, in the event of an air leak, the layer can seal the leak more easily than if the layer had a weight below 100 gsm, in particular below 40 gsm. Further, adhesive skin contact layers having a weight greater than 250 gsm exhibit processing problems, for example the adhesive may 'flow out' from a cut shape, rendering the adhesive skin contact layer unusable.

The adhesive skin contact layer may comprise perforations each having a diameter of about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or about 5.00 mm.

The adhesive skin contact layer may comprise perforations each having a diameter of at least about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or at least about 5.00 mm.

The adhesive skin contact layer may comprise perforations each having a diameter of no more than about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or no more than about 5.00 mm.

The adhesive skin contact layer may comprise perforations each having a diameter of between about 1.25 mm and about 5.00 mm, about 1.50 mm and about 4.50 mm, about 1.75 mm and about 4.00 mm, about 1.90 mm and about 3.50 mm, about 2.00 mm and about 3.00 mm, about 2.05 mm and about 2.80 mm, about 2.10 mm and about 2.60 mm, about 2.15 mm and about 2.50 mm, about 2.18 mm and about 2.40 mm, about 2.19 mm and about 2.30 mm, or about 2.20 mm.

The adhesive skin contact layer may comprise perforations each having a diameter of between about 1.75 mm and about 4.00 mm, about 2.00 mm and about 3.50 mm, about 2.10 mm and about 3.00 mm, about 2.15 mm and about 2.50 mm, or about 2.20 mm.

The adhesive skin contact layer may comprise perforations each having a diameter of between about 1.25 mm and about 5.00 mm, about 1.25 mm and about 4.95 mm, about 1.25 mm and about 4.90 mm, about 1.25 mm and about 4.80 mm, about 1.25 mm and about 4.70 mm, about 1.25 mm and about 4.60 mm, about 1.25 mm and about 4.50 mm, about 1.25 mm and about 4.40 mm, about 1.25 mm and about 4.30 mm, about 1.25 mm and about 4.20 mm, about 1.25 mm and about 4.10 mm, about 1.25 mm and about 4.00 mm, about 1.25 mm and about 3.90 mm, about 1.25 mm and about 3.80 mm, about 1.25 mm and about 3.70 mm, about 1.25 mm and about 3.60 mm, about 1.25 mm and about 3.50 mm, about 1.25 mm and about 3.40 mm, about 1.25 mm and about 3.30 mm, about 1.25 mm and about 3.20 mm, about 1.25 mm and about 3.10 mm, about 1.25 mm and about 3.00 mm, about 1.25 mm and about 2.90 mm, about 1.25 mm and about 2.80 mm, about 1.25 mm and about 2.70 mm, about 1.25 mm and about 2.60 mm, about 1.25 mm and about 2.50 mm, about 1.25 mm and about 2.40 mm, about 1.25 mm and about 2.30 mm, about 1.25 mm and about 2.20 mm, about 1.25 mm and about 2.10 mm, about 1.25 mm and about 2.00 mm, about 1.25 mm and about 1.90 mm, about 1.25 mm and about 1.80 mm, about 1.25 mm and about 1.70 mm, about 1.25 mm and about 1.60 mm, about 1.25 mm and about 1.50 mm, about 1.25 mm and about 1.40 mm, or between about 1.25 mm and about 1.30 mm.

The adhesive skin contact layer may comprise perforations each having a diameter of between about 1.30 mm and about 5.00 mm, about 1.30 mm and about 4.95 mm, about 1.30 mm and about 4.90 mm, about 1.30 mm and about 4.80 mm, about 1.30 mm and about 4.70 mm, about 1.30 mm and about 4.60 mm, about 1.30 mm and about 4.50 mm, about 1.30 mm and about 4.40 mm, about 1.30 mm and about 4.30 mm, about 1.30 mm and about 4.20 mm, about 1.30 mm and about 4.10 mm, about 1.30 mm and about 4.00 mm, about 1.30 mm and about 3.90 mm, about 1.30 mm and about 3.80 mm, about 1.30 mm and about 3.70 mm, about 1.30 mm and about 3.60 mm, about 1.30 mm and about 3.50 mm, about 1.30 mm and about 3.40 mm, about 1.30 mm and about 3.30 mm, about 1.30 mm and about 3.20 mm, about 1.30 mm and about 3.10 mm, about 1.30 mm and about 3.00 mm, about 1.30 mm and about 2.90 mm, about 1.30 mm and about 2.80 mm, about 1.30 mm and about 2.70 mm, about 1.30 mm and about 2.60 mm, about 1.30 mm and about 2.50 mm, about 1.30 mm and about 2.40 mm, about 1.30 mm and about 2.30 mm, about 1.30 mm and about 2.20 mm, about 1.30 mm and about 2.10 mm, about 1.30 mm and about 2.00 mm, about 1.30 mm and about 1.90 mm, about 1.30 mm and about 1.80 mm, about 1.30 mm and about 1.70 mm, about 1.30 mm and about 1.60 mm, about 1.30 mm and about 1.50 mm, or between about 1.30 mm and about 1.40 mm.

The adhesive skin contact layer may comprise perforations each having a diameter of between about 1.40 mm and about 5.00 mm, about 1.40 mm and about 4.95 mm, about 1.40 mm and about 4.90 mm, about 1.40 mm and about 4.80 mm, about 1.40 mm and about 4.70 mm, about 1.40 mm and about 4.60 mm, about 1.40 mm and about 4.50 mm, about 1.40 mm and about 4.40 mm, about 1.40 mm and about 4.30 mm, about 1.40 mm and about 4.20 mm, about 1.40 mm and about 4.10 mm, about 1.40 mm and about 4.00 mm, about 1.40 mm and about 3.90 mm, about 1.40 mm and about 3.80 mm, about 1.40 mm and about 3.70 mm, about 1.40 mm and about 3.60 mm, about 1.40 mm and about 3.50 mm, about 1.40 mm and about 3.40 mm, about 1.40 mm and about 3.30 mm, about 1.40 mm and about 3.20 mm, about 1.40 mm and about 3.10 mm, about 1.40 mm and about 3.00 mm, about 1.40 mm and about 2.90 mm, about 1.40 mm and about 2.80 mm, about 1.40 mm and about 2.70 mm, about 1.40 mm and about 2.60 mm, about 1.40 mm and about 2.50 mm, about 1.40 mm and about 2.40 mm, about 1.40 mm and about 2.30 mm, about 1.40 mm and about 2.20 mm, about 1.40 mm and about 2.10 mm, about 1.40 mm and about 2.00 mm, about 1.40 mm and about 1.90 mm, about 1.40 mm and about 1.80 mm, about 1.40 mm and about 1.70 mm, about 1.40 mm and about 1.60 mm, or between about 1.40 mm and about 1.50 mm.

The adhesive skin contact layer may comprise perforations each having a diameter of between about 1.50 mm and about 5.00 mm, about 1.50 mm and about 4.95 mm, about 1.50 mm and about 4.90 mm, about 1.50 mm and about 4.80 mm, about 1.50 mm and about 4.70 mm, about 1.50 mm and about 4.60 mm, about 1.50 mm and about 4.50 mm, about 1.50 mm and about 4.40 mm, about 1.50 mm and about 4.30 mm, about 1.50 mm and about 4.20 mm, about 1.50 mm and about 4.10 mm, about 1.50 mm and about 4.00 mm, about 1.50 mm and about 3.90 mm, about 1.50 mm and about 3.80 mm, about 1.50 mm and about 3.70 mm, about 1.50 mm and about 3.60 mm, about 1.50 mm and about 3.50 mm, about 1.50 mm and about 3.40 mm, about 1.50 mm and about 3.30 mm, about 1.50 mm and about 3.20 mm, about 1.50 mm and about 3.10 mm, about 1.50 mm and about 3.00 mm, about 1.50 mm and about 2.90 mm, about 1.50 mm and about 2.80 mm, about 1.50 mm and about 2.70 mm, about 1.50 mm and about 2.60 mm, about 1.50 mm and about 2.50 mm, about 1.50 mm and about 2.40 mm, about 1.50 mm and about 2.30 mm, about 1.50 mm and about 2.20 mm, about 1.50 mm and about 2.10 mm, about 1.50 mm and about 2.00 mm, about 1.50 mm and about 1.90 mm, about 1.50 mm and about 1.80 mm, about 1.50 mm and about 1.70 mm, or between about 1.50 mm and about 1.60 mm.

The adhesive skin contact layer may comprise perforations each having a diameter of between about 1.60 mm and about 5.00 mm, about 1.60 mm and about 4.95 mm, about 1.60 mm and about 4.90 mm, about 1.60 mm and about 4.80 mm, about 1.60 mm and about 4.70 mm, about 1.60 mm and about 4.60 mm, about 1.60 mm and about 4.50 mm, about 1.60 mm and about 4.40 mm, about 1.60 mm and about 4.30 mm, about 1.60 mm and about 4.20 mm, about 1.60 mm and about 4.10 mm, about 1.60 mm and about 4.00 mm, about 1.60 mm and about 3.90 mm, about 1.60 mm and about 3.80 mm, about 1.60 mm and about 3.70 mm, about 1.60 mm and about 3.60 mm, about 1.60 mm and about 3.50 mm, about 1.60 mm and about 3.40 mm, about 1.60 mm and about 3.30 mm, about 1.60 mm and about 3.20 mm, about 1.60 mm and about 3.10 mm, about 1.60 mm and about 3.00 mm, about 1.60 mm and about 2.90 mm, about 1.60 mm and about 2.80 mm, about 1.60 mm and about 2.70 mm, about 1.60 mm and about 2.60 mm, about 1.60 mm and about 2.50 mm, about 1.60 mm and about 2.40 mm, about 1.60 mm and about 2.30 mm, about 1.60 mm and about 2.20 mm, about 1.60 mm and about 2.10 mm, about 1.60 mm and about 2.00 mm, about 1.60 mm and about 1.90 mm, about 1.60 mm and about 1.80 mm, or between about 1.60 mm and about 1.70 mm.

The adhesive skin contact layer may comprise perforations each having a diameter of between about 1.70 mm and about 5.00 mm, about 1.70 mm and about 4.95 mm, about 1.70 mm and about 4.90 mm, about 1.70 mm and about 4.80 mm, about 1.70 mm and about 4.70 mm, about 1.70 mm and about 4.60 mm, about 1.70 mm and about 4.50 mm, about 1.70 mm and about 4.40 mm, about 1.70 mm and about 4.30 mm, about 1.70 mm and about 4.20 mm, about 1.70 mm and about 4.10 mm, about 1.70 mm and about 4.00 mm, about 1.70 mm and about 3.90 mm, about 1.70 mm and about 3.80 mm, about 1.70 mm and about 3.70 mm, about 1.70 mm and about 3.60 mm, about 1.70 mm and about 3.50 mm, about 1.70 mm and about 3.40 mm, about 1.70 mm and about 3.30 mm, about 1.70 mm and about 3.20 mm, about 1.70 mm and about 3.10 mm, about 1.70 mm and about 3.00 mm, about 1.70 mm and about 2.90 mm, about 1.70 mm and about 2.80 mm, about 1.70 mm and about 2.70 mm, about 1.70 mm and about 2.60 mm, about 1.70 mm and about 2.50 mm, about 1.70 mm and about 2.40 mm, about 1.70 mm and about 2.30 mm, about 1.70 mm and about 2.20 mm, about 1.70 mm and about 2.10 mm, about 1.70 mm and about 2.00 mm, about 1.70 mm and about 1.90 mm, or between about 1.70 mm and about 1.80 mm.

The adhesive skin contact layer may comprise perforations each having a diameter of between about 1.80 mm and about 5.00 mm, about 1.80 mm and about 4.95 mm, about 1.80 mm and about 4.90 mm, about 1.80 mm and about 4.80 mm, about 1.80 mm and about 4.70 mm, about 1.80 mm and about 4.60 mm, about 1.80 mm and about 4.50 mm, about 1.80 mm and about 4.40 mm, about 1.80 mm and about 4.30 mm, about 1.80 mm and about 4.20 mm, about 1.80 mm and about 4.10 mm, about 1.80 mm and about 4.00 mm, about 1.80 mm and about 3.90 mm, about 1.80 mm and about 3.80 mm, about 1.80 mm and about 3.70 mm, about 1.80 mm and about 3.60 mm, about 1.80 mm and about 3.50 mm, about 1.80 mm and about 3.40 mm, about 1.80 mm and about 3.30 mm, about 1.80 mm and about 3.20 mm, about 1.80 mm and about 3.10 mm, about 1.80 mm and about 3.00 mm, about 1.80 mm and about 2.90 mm, about 1.80 mm and about 2.80 mm, about 1.80 mm and about 2.70 mm, about 1.80 mm and about 2.60 mm, about 1.80 mm and about 2.50 mm, about 1.80 mm and about 2.40 mm, about 1.80 mm and about 2.30 mm, about 1.80 mm and about 2.20 mm, about 1.80 mm and about 2.10 mm, about 1.80 mm and about 2.00 mm, or between about 1.80 mm and about 1.90 mm.

The adhesive skin contact layer may comprise perforations each having a diameter of between about 1.90 mm and about 5.00 mm, about 1.90 mm and about 4.95 mm, about 1.90 mm and about 4.90 mm, about 1.90 mm and about 4.80 mm, about 1.90 mm and about 4.70 mm, about 1.90 mm and about 4.60 mm, about 1.90 mm and about 4.50 mm, about 1.90 mm and about 4.40 mm, about 1.90 mm and about 4.30 mm, about 1.90 mm and about 4.20 mm, about 1.90 mm and about 4.10 mm, about 1.90 mm and about 4.00 mm, about 1.90 mm and about 3.90 mm, about 1.90 mm and about 3.80 mm, about 1.90 mm and about 3.70 mm, about 1.90 mm and about 3.60 mm, about 1.90 mm and about 3.50 mm, about 1.90 mm and about 3.40 mm, about 1.90 mm and about 3.30 mm, about 1.90 mm and about 3.20 mm, about 1.90 mm and about 3.10 mm, about 1.90 mm and about 3.00 mm, about 1.90 mm and about 2.90 mm, about 1.90 mm and about 2.80 mm, about 1.90 mm and about 2.70 mm, about 1.90 mm and about 2.60 mm, about 1.90 mm and about 2.50 mm, about 1.90 mm and about 2.40 mm, about 1.90 mm and about 2.30 mm, about 1.90 mm and about 2.20 mm, about 1.90 mm and about 2.10 mm, or between about 1.90 mm and about 2.00 mm.

The adhesive skin contact layer may comprise perforations each having a diameter of between about 2.00 mm and about 5.00 mm, about 2.00 mm and about 4.95 mm, about 2.00 mm and about 4.90 mm, about 2.00 mm and about 4.80 mm, about 2.00 mm and about 4.70 mm, about 2.00 mm and about 4.60 mm, about 2.00 mm and about 4.50 mm, about 2.00 mm and about 4.40 mm, about 2.00 mm and about 4.30 mm, about 2.00 mm and about 4.20 mm, about 2.00 mm and about 4.10 mm, about 2.00 mm and about 4.00 mm, about 2.00 mm and about 3.90 mm, about 2.00 mm and about 3.80 mm, about 2.00 mm and about 3.70 mm, about 2.00 mm and about 3.60 mm, about 2.00 mm and about 3.50 mm, about 2.00 mm and about 3.40 mm, about 2.00 mm and about 3.30 mm, about 2.00 mm and about 3.20 mm, about 2.00 mm and about 3.10 mm, about 2.00 mm and about 3.00 mm, about 2.00 mm and about 2.90 mm, about 2.00 mm and about 2.80 mm, about 2.00 mm and about 2.70 mm, about 2.00 mm and about 2.60 mm, about 2.00 mm and about 2.50 mm, about 2.00 mm and about 2.40 mm, about 2.00 mm and about 2.30 mm, about 2.00 mm and about 2.20 mm, or between about 2.00 mm and about 2.10 mm.

The adhesive skin contact layer may comprise perforations each having a diameter of between about 2.10 mm and about 5.00 mm, about 2.10 mm and about 4.95 mm, about 2.10 mm and about 4.90 mm, about 2.10 mm and about 4.80 mm, about 2.10 mm and about 4.70 mm, about 2.10 mm and about 4.60 mm, about 2.10 mm and about 4.50 mm, about 2.10 mm and about 4.40 mm, about 2.10 mm and about 4.30 mm, about 2.10 mm and about 4.20 mm, about 2.10 mm and about 4.10 mm, about 2.10 mm and about 4.00 mm, about 2.10 mm and about 3.90 mm, about 2.10 mm and about 3.80 mm, about 2.10 mm and about 3.70 mm, about 2.10 mm and about 3.60 mm, about 2.10 mm and about 3.50 mm, about 2.10 mm and about 3.40 mm, about 2.10 mm and about 3.30 mm, about 2.10 mm and about 3.20 mm, about 2.10 mm and about 3.10 mm, about 2.10 mm and about 3.00 mm, about 2.10 mm and about 2.90 mm, about 2.10 mm and about 2.80 mm, about 2.10 mm and about 2.70 mm, about 2.10 mm and about 2.60 mm, about 2.10 mm and about 2.50 mm, about 2.10 mm and about 2.40 mm, about 2.10 mm and about 2.30 mm, or between about 2.10 mm and about 2.20 mm.

The adhesive skin contact layer may comprise perforations each having a diameter of between about 2.20 mm and about 5.00 mm, about 2.20 mm and about 4.95 mm, about 2.20 mm and about 4.90 mm, about 2.20 mm and about 4.80 mm, about 2.20 mm and about 4.70 mm, about 2.20 mm and about 4.60 mm, about 2.20 mm and about 4.50 mm, about 2.20 mm and about 4.40 mm, about 2.20 mm and about 4.30 mm, about 2.20 mm and about 4.20 mm, about 2.20 mm and about 4.10 mm, about 2.20 mm and about 4.00 mm, about 2.20 mm and about 3.90 mm, about 2.20 mm and about 3.80 mm, about 2.20 mm and about 3.70 mm, about 2.20 mm and about 3.60 mm, about 2.20 mm and about 3.50 mm, about 2.20 mm and about 3.40 mm, about 2.20 mm and about 3.30 mm, about 2.20 mm and about 3.20 mm, about 2.20 mm and about 3.10 mm, about 2.20 mm and about 3.00 mm, about 2.20 mm and about 2.90 mm, about 2.20 mm and about 2.80 mm, about 2.20 mm and about 2.70 mm, about 2.20 mm and about 2.60 mm, about 2.20 mm and about 2.50 mm, about 2.20 mm and about 2.40 mm, or between about 2.20 mm and about 2.30 mm.

The adhesive skin contact layer may comprise perforations each having a diameter of between about 2.25 mm and about 5.00 mm, about 2.25 mm and about 4.95 mm, about 2.25 mm and about 4.90 mm, about 2.25 mm and about 4.80 mm, about 2.25 mm and about 4.70 mm, about 2.25 mm and about 4.60 mm, about 2.25 mm and about 4.50 mm, about 2.25 mm and about 4.40 mm, about 2.25 mm and about 4.30 mm, about 2.25 mm and about 4.20 mm, about 2.25 mm and about 4.10 mm, about 2.25 mm and about 4.00 mm, about 2.25 mm and about 3.90 mm, about 2.25 mm and about 3.80 mm, about 2.25 mm and about 3.70 mm, about 2.25 mm and about 3.60 mm, about 2.25 mm and about 3.50 mm, about 2.25 mm and about 3.40 mm, about 2.25 mm and about 3.30 mm, about 2.25 mm and about 3.20 mm, about 2.25 mm and about 3.10 mm, about 2.25 mm and about 3.00 mm, about 2.25 mm and about 2.90 mm, about 2.25 mm and about 2.80 mm, about 2.25 mm and about 2.70 mm, about 2.25 mm and about 2.60 mm, about 2.25 mm and about 2.50 mm, about 2.25 mm and about 2.40 mm, or between about 2.25 mm and about 2.30 mm.

The adhesive skin contact layer may comprise perforations each having a diameter of between about 2.30 mm and about 5.00 mm, about 2.30 mm and about 4.95 mm, about 2.30 mm and about 4.90 mm, about 2.30 mm and about 4.80 mm, about 2.30 mm and about 4.70 mm, about 2.30 mm and about 4.60 mm, about 2.30 mm and about 4.50 mm, about 2.30 mm and about 4.40 mm, about 2.30 mm and about 4.30 mm, about 2.30 mm and about 4.20 mm, about 2.30 mm and about 4.10 mm, about 2.30 mm and about 4.00 mm, about 2.30 mm and about 3.90 mm, about 2.30 mm and about 3.80 mm, about 2.30 mm and about 3.70 mm, about 2.30 mm and about 3.60 mm, about 2.30 mm and about 3.50 mm, about 2.30 mm and about 3.40 mm, about 2.30 mm and about 3.30 mm, about 2.30 mm and about 3.20 mm, about 2.30 mm and about 3.10 mm, about 2.30 mm and about 3.00 mm, about 2.30 mm and about 2.90 mm, about 2.30 mm and about 2.80 mm, about 2.30 mm and about 2.70 mm, about 2.30 mm and about 2.60 mm, about 2.30 mm and about 2.50 mm, or between about 2.30 mm and about 2.40 mm.

The adhesive skin contact layer may comprise perforations each having a diameter of between about 2.40 mm and about 5.00 mm, about 2.40 mm and about 4.95 mm, about 2.40 mm and about 4.90 mm, about 2.40 mm and about 4.80 mm, about 2.40 mm and about 4.70 mm, about 2.40 mm and about 4.60 mm, about 2.40 mm and about 4.50 mm, about 2.40 mm and about 4.40 mm, about 2.40 mm and about 4.30 mm, about 2.40 mm and about 4.20 mm, about 2.40 mm and about 4.10 mm, about 2.40 mm and about 4.00 mm, about 2.40 mm and about 3.90 mm, about 2.40 mm and about 3.80 mm, about 2.40 mm and about 3.70 mm, about 2.40 mm and about 3.60 mm, about 2.40 mm and about 3.50 mm, about 2.40 mm and about 3.40 mm, about 2.40 mm and about 3.30 mm, about 2.40 mm and about 3.20 mm, about 2.40 mm and about 3.10 mm, about 2.40 mm and about 3.00 mm, about 2.40 mm and about 2.90 mm, about 2.40 mm and about 2.80 mm, about 2.40 mm and about 2.70 mm, about 2.40 mm and about 2.60 mm, or between about 2.40 mm and about 2.50 mm.

The adhesive skin contact layer may comprise perforations each having a diameter of between about 2.50 mm and about 5.00 mm, about 2.50 mm and about 4.95 mm, about 2.50 mm and about 4.90 mm, about 2.50 mm and about 4.80 mm, about 2.50 mm and about 4.70 mm, about 2.50 mm and about 4.60 mm, about 2.50 mm and about 4.50 mm, about 2.50 mm and about 4.40 mm, about 2.50 mm and about 4.30 mm, about 2.50 mm and about 4.20 mm, about 2.50 mm and about 4.10 mm, about 2.50 mm and about 4.00 mm, about 2.50 mm and about 3.90 mm, about 2.50 mm and about 3.80 mm, about 2.50 mm and about 3.70 mm, about 2.50 mm and about 3.60 mm, about 2.50 mm and about 3.50 mm, about 2.50 mm and about 3.40 mm, about 2.50 mm and about 3.30 mm, about 2.50 mm and about 3.20 mm, about 2.50 mm and about 3.10 mm, about 2.50 mm and about 3.00 mm, about 2.50 mm and about 2.90 mm, about 2.50 mm and about 2.80 mm, about 2.50 mm and about 2.70 mm, or between about 2.50 mm and about 2.60 mm.

The adhesive skin contact layer may comprise perforations each having a diameter of between about 2.60 mm and about 5.00 mm, about 2.60 mm and about 4.95 mm, about 2.60 mm and about 4.90 mm, about 2.60 mm and about 4.80 mm, about 2.60 mm and about 4.70 mm, about 2.60 mm and about 4.60 mm, about 2.60 mm and about 4.50 mm, about 2.60 mm and about 4.40 mm, about 2.60 mm and about 4.30 mm, about 2.60 mm and about 4.20 mm, about 2.60 mm and about 4.10 mm, about 2.60 mm and about 4.00 mm, about 2.60 mm and about 3.90 mm, about 2.60 mm and about 3.80 mm, about 2.60 mm and about 3.70 mm, about 2.60 mm and about 3.60 mm, about 2.60 mm and about 3.50 mm, about 2.60 mm and about 3.40 mm, about 2.60 mm and about 3.30 mm, about 2.60 mm and about 3.20 mm, about 2.60 mm and about 3.10 mm, about 2.60 mm and about 3.00 mm, about 2.60 mm and about 2.90 mm, about 2.60 mm and about 2.80 mm, or between about 2.60 mm and about 2.70 mm.

The adhesive skin contact layer may comprise perforations each having a diameter of between about 2.70 mm and about 5.00 mm, about 2.70 mm and about 4.95 mm, about 2.70 mm and about 4.90 mm, about 2.70 mm and about 4.80 mm, about 2.70 mm and about 4.70 mm, about 2.70 mm and about 4.60 mm, about 2.70 mm and about 4.50 mm, about 2.70 mm and about 4.40 mm, about 2.70 mm and about 4.30 mm, about 2.70 mm and about 4.20 mm, about 2.70 mm and about 4.10 mm, about 2.70 mm and about 4.00 mm, about 2.70 mm and about 3.90 mm, about 2.70 mm and about 3.80 mm, about 2.70 mm and about 3.70 mm, about 2.70 mm and about 3.60 mm, about 2.70 mm and about 3.50 mm, about 2.70 mm and about 3.40 mm, about 2.70 mm and about 3.30 mm, about 2.70 mm and about 3.20 mm, about 2.70 mm and about 3.10 mm, about 2.70 mm and about 3.00 mm, about 2.70 mm and about 2.90 mm, or between about 2.70 mm and about 2.80 mm.

The adhesive skin contact layer may comprise perforations each having a diameter of between about 2.80 mm and about 5.00 mm, about 2.80 mm and about 4.95 mm, about 2.80 mm and about 4.90 mm, about 2.80 mm and about 4.80 mm, about 2.80 mm and about 4.70 mm, about 2.80 mm and about 4.60 mm, about 2.80 mm and about 4.50 mm, about 2.80 mm and about 4.40 mm, about 2.80 mm and about 4.30 mm, about 2.80 mm and about 4.20 mm, about 2.80 mm and about 4.10 mm, about 2.80 mm and about 4.00 mm, about 2.80 mm and about 3.90 mm, about 2.80 mm and about 3.80 mm, about 2.80 mm and about 3.70 mm, about 2.80 mm and about 3.60 mm, about 2.80 mm and about 3.50 mm, about 2.80 mm and about 3.40 mm, about 2.80 mm and about 3.30 mm, about 2.80 mm and about 3.20 mm, about 2.80 mm and about 3.10 mm, about 2.80 mm and about 3.00 mm, or between about 2.80 mm and about 2.90 mm.

The adhesive skin contact layer may comprise perforations each having a diameter of between about 2.90 mm and about 5.00 mm, about 2.90 mm and about 4.95 mm, about 2.90 mm and about 4.90 mm, about 2.90 mm and about 4.80 mm, about 2.90 mm and about 4.70 mm, about 2.90 mm and about 4.60 mm, about 2.90 mm and about 4.50 mm, about 2.90 mm and about 4.40 mm, about 2.90 mm and about 4.30 mm, about 2.90 mm and about 4.20 mm, about 2.90 mm and about 4.10 mm, about 2.90 mm and about 4.00 mm, about 2.90 mm and about 3.90 mm, about 2.90 mm and about 3.80 mm, about 2.90 mm and about 3.70 mm, about 2.90 mm and about 3.60 mm, about 2.90 mm and about 3.50 mm, about 2.90 mm and about 3.40 mm, about 2.90 mm and about 3.30 mm, about 2.90 mm and about 3.20 mm, about 2.90 mm and about 3.10 mm, or between about 2.90 mm and about 3.00 mm.

The adhesive skin contact layer may comprise perforations each having a diameter of between about 3.00 mm and about 5.00 mm, about 3.00 mm and about 4.95 mm, about 3.00 mm and about 4.90 mm, about 3.00 mm and about 4.80 mm, about 3.00 mm and about 4.70 mm, about 3.00 mm and about 4.60 mm, about 3.00 mm and about 4.50 mm, about 3.00 mm and about 4.40 mm, about 3.00 mm and about 4.30 mm, about 3.00 mm and about 4.20 mm, about 3.00 mm and about 4.10 mm, about 3.00 mm and about 4.00 mm, about 3.00 mm and about 3.90 mm, about 3.00 mm and about 3.80 mm, about 3.00 mm and about 3.70 mm, about 3.00 mm and about 3.60 mm, about 3.00 mm and about 3.50 mm, about 3.00 mm and about 3.40 mm, about 3.00 mm and about 3.30 mm, about 3.00 mm and about 3.20 mm, or between about 3.00 mm and about 3.10 mm.

The adhesive skin contact layer may comprise perforations each having a diameter of between about 3.10 mm and about 5.00 mm, about 3.10 mm and about 4.95 mm, about 3.10 mm and about 4.90 mm, about 3.10 mm and about 4.80 mm, about 3.10 mm and about 4.70 mm, about 3.10 mm and about 4.60 mm, about 3.10 mm and about 4.50 mm, about 3.10 mm and about 4.40 mm, about 3.10 mm and about 4.30 mm, about 3.10 mm and about 4.20 mm, about 3.10 mm and about 4.10 mm, about 3.10 mm and about 4.00 mm, about 3.10 mm and about 3.90 mm, about 3.10 mm and about 3.80 mm, about 3.10 mm and about 3.70 mm, about 3.10 mm and about 3.60 mm, about 3.10 mm and about 3.50 mm, about 3.10 mm and about 3.40 mm, about 3.10 mm and about 3.30 mm, or between about 3.10 mm and about 3.20 mm.

The adhesive skin contact layer may comprise perforations each having a diameter of between about 3.20 mm and about 5.00 mm, about 3.20 mm and about 4.95 mm, about 3.20 mm and about 4.90 mm, about 3.20 mm and about 4.80 mm, about 3.20 mm and about 4.70 mm, about 3.20 mm and about 4.60 mm, about 3.20 mm and about 4.50 mm, about 3.20 mm and about 4.40 mm, about 3.20 mm and about 4.30 mm, about 3.20 mm and about 4.20 mm, about 3.20 mm and about 4.10 mm, about 3.20 mm and about 4.00 mm, about 3.20 mm and about 3.90 mm, about 3.20 mm and about 3.80 mm, about 3.20 mm and about 3.70 mm, about 3.20 mm and about 3.60 mm, about 3.20 mm and about 3.50 mm, about 3.20 mm and about 3.40 mm, or between about 3.20 mm and about 3.30 mm.

The adhesive skin contact layer may comprise perforations each having a diameter of between about 3.30 mm and about 5.00 mm, about 3.30 mm and about 4.95 mm, about 3.30 mm and about 4.90 mm, about 3.30 mm and about 4.80 mm, about 3.30 mm and about 4.70 mm, about 3.30 mm and about 4.60 mm, about 3.30 mm and about 4.50 mm, about 3.30 mm and about 4.40 mm, about 3.30 mm and about 4.30 mm, about 3.30 mm and about 4.20 mm, about 3.30 mm and about 4.10 mm, about 3.30 mm and about 4.00 mm, about 3.30 mm and about 3.90 mm, about 3.30 mm and about 3.80 mm, about 3.30 mm and about 3.70 mm, about 3.30 mm and about 3.60 mm, about 3.30 mm and about 3.50 mm, or between about 3.30 mm and about 3.40 mm.

The adhesive skin contact layer may comprise perforations each having a diameter of between about 3.40 mm and about 5.00 mm, about 3.40 mm and about 4.95 mm, about 3.40 mm and about 4.90 mm, about 3.40 mm and about 4.80 mm, about 3.40 mm and about 4.70 mm, about 3.40 mm and about 4.60 mm, about 3.40 mm and about 4.50 mm, about 3.40 mm and about 4.40 mm, about 3.40 mm and about 4.30 mm, about 3.40 mm and about 4.20 mm, about 3.40 mm and about 4.10 mm, about 3.40 mm and about 4.00 mm, about 3.40 mm and about 3.90 mm, about 3.40 mm and about 3.80 mm, about 3.40 mm and about 3.70 mm, about 3.40 mm and about 3.60 mm, or between about 3.40 mm and about 3.50 mm.

The adhesive skin contact layer may comprise perforations each having a diameter of between about 3.50 mm and about 5.00 mm, about 3.50 mm and about 4.95 mm, about 3.50 mm and about 4.90 mm, about 3.50 mm and about 4.80 mm, about 3.50 mm and about 4.70 mm, about 3.50 mm and about 4.60 mm, about 3.50 mm and about 4.50 mm, about 3.50 mm and about 4.40 mm, about 3.50 mm and about 4.30 mm, about 3.50 mm and about 4.20 mm, about 3.50 mm and about 4.10 mm, about 3.50 mm and about 4.00 mm, about 3.50 mm and about 3.90 mm, about 3.50 mm and about 3.80 mm, about 3.50 mm and about 3.70 mm, or between about 3.50 mm and about 3.60 mm.

The adhesive skin contact layer may comprise perforations each having a diameter of between about 3.60 mm and about 5.00 mm, about 3.60 mm and about 4.95 mm, about 3.60 mm and about 4.90 mm, about 3.60 mm and about 4.80 mm, about 3.60 mm and about 4.70 mm, about 3.60 mm and about 4.60 mm, about 3.60 mm and about 4.50 mm, about 3.60 mm and about 4.40 mm, about 3.60 mm and about 4.30 mm, about 3.60 mm and about 4.20 mm, about 3.60 mm and about 4.10 mm, about 3.60 mm and about 4.00 mm, about 3.60 mm and about 3.90 mm, about 3.60 mm and about 3.80 mm, or between about 3.60 mm and about 3.70 mm.

The adhesive skin contact layer may comprise perforations each having a diameter of between about 3.70 mm and about 5.00 mm, about 3.70 mm and about 4.95 mm, about 3.70 mm and about 4.90 mm, about 3.70 mm and about 4.80 mm, about 3.70 mm and about 4.70 mm, about 3.70 mm and about 4.60 mm, about 3.70 mm and about 4.50 mm, about 3.70 mm and about 4.40 mm, about 3.70 mm and about 4.30 mm, about 3.70 mm and about 4.20 mm, about 3.70 mm and about 4.10 mm, about 3.70 mm and about 4.00 mm, about 3.70 mm and about 3.90 mm, or between about 3.70 mm and about 3.80 mm.

The adhesive skin contact layer may comprise perforations each having a diameter of between about 3.80 mm and about 5.00 mm, about 3.80 mm and about 4.95 mm, about 3.80 mm and about 4.90 mm, about 3.80 mm and about 4.80 mm, about 3.80 mm and about 4.70 mm, about 3.80 mm and about 4.60 mm, about 3.80 mm and about 4.50 mm, about 3.80 mm and about 4.40 mm, about 3.80 mm and about 4.30 mm, about 3.80 mm and about 4.20 mm, about 3.80 mm and about 4.10 mm, about 3.80 mm and about 4.00 mm, or between about 3.80 mm and about 3.90 mm.

The adhesive skin contact layer may comprise perforations each having a diameter of between about 3.90 mm and about 5.00 mm, about 3.90 mm and about 4.95 mm, about 3.90 mm and about 4.90 mm, about 3.90 mm and about 4.80 mm, about 3.90 mm and about 4.70 mm, about 3.90 mm and about 4.60 mm, about 3.90 mm and about 4.50 mm, about 3.90 mm and about 4.40 mm, about 3.90 mm and about 4.30 mm, about 3.90 mm and about 4.20 mm, about 3.90 mm and about 4.10 mm, or between about 3.90 mm and about 4.00 mm.

The adhesive skin contact layer may comprise perforations each having a diameter of between about 4.00 mm and about 5.00 mm, about 4.00 mm and about 4.95 mm, about 4.00 mm and about 4.90 mm, about 4.00 mm and about 4.80 mm, about 4.00 mm and about 4.70 mm, about 4.00 mm and about 4.60 mm, about 4.00 mm and about 4.50 mm, about 4.00 mm and about 4.40 mm, about 4.00 mm and about 4.30 mm, about 4.00 mm and about 4.20 mm, or between about 4.00 mm and about 4.10 mm.

The adhesive skin contact layer may comprise perforations each having a diameter of between about 4.10 mm and about 5.00 mm, about 4.10 mm and about 4.95 mm, about 4.10 mm and about 4.90 mm, about 4.10 mm and about 4.80 mm, about 4.10 mm and about 4.70 mm, about 4.10 mm and about 4.60 mm, about 4.10 mm and about 4.50 mm, about 4.10 mm and about 4.40 mm, about 4.10 mm and about 4.30 mm, or between about 4.10 mm and about 4.20 mm.

The adhesive skin contact layer may comprise perforations each having a diameter of between about 4.20 mm and about 5.00 mm, about 4.20 mm and about 4.95 mm, about 4.20 mm and about 4.90 mm, about 4.20 mm and about 4.80 mm, about 4.20 mm and about 4.70 mm, about 4.20 mm and about 4.60 mm, about 4.20 mm and about 4.50 mm, about 4.20 mm and about 4.40 mm, or between about 4.20 mm and about 4.30 mm.

The adhesive skin contact layer may comprise perforations each having a diameter of between about 4.30 mm and about 5.00 mm, about 4.30 mm and about 4.95 mm, about 4.30 mm and about 4.90 mm, about 4.30 mm and about 4.80 mm, about 4.30 mm and about 4.70 mm, about 4.30 mm and about 4.60 mm, about 4.30 mm and about 4.50 mm, or between about 4.30 mm and about 4.40 mm.

The adhesive skin contact layer may comprise perforations each having a diameter of between about 4.40 mm and about 5.00 mm, about 4.40 mm and about 4.95 mm, about 4.40 mm and about 4.90 mm, about 4.40 mm and about 4.80 mm, about 4.40 mm and about 4.70 mm, about 4.40 mm and about 4.60 mm, or between about 4.40 mm and about 4.50 mm.

The adhesive skin contact layer may comprise perforations each having a diameter of between about 4.50 mm and about 5.00 mm, about 4.50 mm and about 4.95 mm, about 4.50 mm and about 4.90 mm, about 4.50 mm and about 4.80 mm, about 4.50 mm and about 4.70 mm, or between about 4.50 mm and about 4.60 mm.

The adhesive skin contact layer may comprise perforations each having a diameter of between about 4.60 mm and about 5.00 mm, about 4.60 mm and about 4.95 mm, about 4.60 mm and about 4.90 mm, about 4.60 mm and about 4.80 mm, or between about 4.60 mm and about 4.70 mm.

The adhesive skin contact layer may comprise perforations each having a diameter of between about 4.70 mm and about 5.00 mm, about 4.70 mm and about 4.95 mm, about 4.70 mm and about 4.90 mm, or between about 4.70 mm and about 4.80 mm.

The adhesive skin contact layer may comprise perforations each having a diameter of between about 4.80 mm and about 5.00 mm, about 4.80 mm and about 4.95 mm, or between about 4.80 mm and about 4.90 mm.

The adhesive skin contact layer may comprise perforations each having a diameter of between about 4.90 mm and about 5.00 mm, or between about 4.90 mm and about 4.95 mm.

The adhesive skin contact layer may comprise perforations each having a diameter of between about 4.95 mm and about 5.00 mm.

The perforations may be arranged in a square-packed layout or a triangle packed layout.

A square-packed layout means that all, or a significant proportion, for example at least about 60%, about 65%, about 70%, about 75%, about 80%, about 85%, about 90%, or at least about 95%, of the perforations are arranged in parallel rows and columns.

A triangle-packed layout means that all, or a significant proportion, for example at least about 60%, about 65%, about 70%, about 75%, about 80%, about 85%, about 90%, or at least about 95%, of the perforations are arranged in adjacent rows of perforations which are offset from one another. By this we mean that the perforations in a first row are not arranged adjacent to the perforations in an adjacent second row but instead the perforations in the first row are arranged adjacent to the gap between perforations in the second row or adjacent to part of the gap and part of a perforation in the second row.

Each perforation may comprise an opening comprising a 2D shape selected from the group comprising: a circle, an oval, a triangle, a square, a rectangle, a hexagon or an octagon.

The person skilled in the art will understand that the size of the opening may be defined depending on the shape of the opening. In some embodiments, the size of a circle is the diameter. In other embodiments, the size of an oval is the longer diameter. In further embodiments, the size of a hexagon is the longest diagonal; and the size of a triangle, a square, a rectangle, an octagon or any other polygon perforation is the longest side.

The perforations may have a pitch (i.e., the distance between the centre point of a perforation and the centre point of an adjacent perforation) in a first direction of about 6.0 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, or about 12.0 mm.

The perforations may have a pitch in a first direction of at least about 6.0 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, or at least about 12.0 mm.

The perforations may have a pitch in a first direction of no more than about 6.0 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, or no more than about 12.0 mm.

The perforations may have a pitch in a first direction of between about 6.0 mm and about 10.0 mm, about 6.5 mm and about 9.5 mm, about 7.0 mm and about 9.0 mm, about 7.5 mm and about 8.5 mm, about 7.75 mm and about 8.25 mm, or about 8.0 mm.

The perforations may have a pitch in a first direction of between about 6.0 mm and about 10.0 mm, about 6.0 mm to about 9.5 mm, about 6.0 mm to about 9.0 mm, about 6.0 mm to about 8.50 mm, about 6.0 mm to about 8.0 mm, about 6.0 mm to about 7.5 mm, about 6.0 mm to about 7.0 mm, or between about 6.0 mm to about 6.5 mm.

The perforations may have a pitch in a first direction of between about 6.5 mm and about 10.0 mm, about 6.5 mm to about 9.5 mm, about 6.5 mm to about 9.0 mm, about 6.5 mm to about 8.50 mm, about 6.5 mm to about 8.0 mm, about 6.5 mm to about 7.5 mm, or between about 6.5 mm to about 7.0 mm.

The perforations may have a pitch in a first direction of between about 7.0 mm and about 10.0 mm, about 7.0 mm to about 9.5 mm, about 7.0 mm to about 9.0 mm, about 7.0 mm to about 8.50 mm, about 7.0 mm to about 8.0 mm, or between about 7.0 mm to about 7.5 mm.

The perforations may have a pitch in a first direction of between about 7.5 mm and about 10.0 mm, about 7.5 mm to about 9.5 mm, about 7.5 mm to about 9.0 mm, about 7.5 mm to about 8.50 mm, or between about 7.5 mm to about 8.0 mm.

The perforations may have a pitch in a first direction of between about 8.0 mm and about 10.0 mm, about 8.0 mm to about 9.5 mm, about 8.0 mm to about 9.0 mm, or between about 8.0 mm to about 8.50 mm.

The perforations may have a pitch in a first direction of between about 8.5 mm and about 10.0 mm, about 8.5 mm to about 9.5 mm, or between about 8.5 mm to about 9.0 mm.

The perforations may have a pitch in a first direction of between about 9.0 mm and about 10.0 mm, or between about 9.0 mm to about 9.5 mm.

The perforations may have a pitch in a first direction of between about 9.5 mm and about 10.0 mm.

The perforations may have a pitch in a second direction of about 3.0 mm, about 3.5 mm, about 4.0 mm, about 4.5 mm, about 5.0 mm, about 5.5 mm, about 5.6 mm, about 6.0 mm, about 6.5 mm, about 7.0 mm, about 7.5 mm, about 8.0 mm, about 8.5 mm, about 9.0 mm, about 9.5 mm, or about 10.0 mm.

The perforations may have a pitch in a second direction of at least about 3.0 mm, about 3.5 mm, about 4.0 mm, about 4.5 mm, about 5.0 mm, about 5.5 mm, about 5.6 mm, about 6.0 mm, about 6.5 mm, about 7.0 mm, about 7.5 mm, about 8.0 mm, about 8.5 mm, about 9.0 mm, about 9.5 mm, or at least about 10.0 mm.

The perforations may have a pitch in a second direction of no more than about 3.0 mm, about 3.5 mm, about 4.0 mm, about 4.5 mm, about 5.0 mm, about 5.5 mm, about 5.6 mm, about 6.0 mm, about 6.5 mm, about 7.0 mm, about 7.5 mm, about 8.0 mm, about 8.5 mm, about 9.0 mm, about 9.5 mm, or no more than about 10.0 mm.

The perforations may have a pitch in a second direction of between about 4.00 mm and about 7.00 mm, about 4.25 mm and about 6.75 mm, about 4.50 mm and about 6.50 mm, about 4.75 mm and about 6.25 mm, about 5.00 mm and about 6.00 mm, about 5.25 mm and about 5.75 mm, about 5.40 mm and about 5.70 mm, about 5.50 mm and about 5.65 mm, about 5.55 mm and about 5.62 mm, or about 5.60 mm.

The perforations may have a pitch in a second direction of between about 3.0 mm and about 10.0 mm, about 3.0 mm and about 9.5 mm, about 3.0 mm and about 9.0 mm, about 3.0 mm and about 8.5 mm, about 3.0 mm and about 8.0 mm, about 3.0 mm and about 7.5 mm, about 3.0 mm and about 7.0 mm, about 3.0 mm and about 6.5 mm, about 3.0 mm and about 6.0 mm, about 3.0 mm and about 5.5 mm, about 3.0 mm and about 5.0 mm, about 3.0 mm and about 4.5 mm, about 3.0 mm and about 4.0 mm, or between about 3.0 mm and about 3.5 mm.

The perforations may have a pitch in a second direction of between about 3.5 mm and about 10.0 mm, about 3.5 mm and about 9.5 mm, about 3.5 mm and about 9.0 mm, about 3.5 mm and about 8.5 mm, about 3.5 mm and about 8.0 mm, about 3.5 mm and about 7.5 mm, about 3.5 mm and about 7.0 mm, about 3.5 mm and about 6.5 mm, about 3.5 mm and about 6.0 mm, about 3.5 mm and about 5.5 mm, about 3.5 mm and about 5.0 mm, about 3.5 mm and about 4.5 mm, or between about 3.5 mm and about 4.0 mm.

The perforations may have a pitch in a second direction of between about 4.0 mm and about 10.0 mm, about 4.0 mm and about 9.5 mm, about 4.0 mm and about 9.0 mm, about 4.0 mm and about 8.5 mm, about 4.0 mm and about 8.0 mm, about 4.0 mm and about 7.5 mm, about 4.0 mm and about 7.0 mm, about 4.0 mm and about 6.5 mm, about 4.0 mm and about 6.0 mm, about 4.0 mm and about 5.5 mm, about 4.0 mm and about 5.0 mm, or between about 4.5 mm and about 4.5 mm.

The perforations may have a pitch in a second direction of between about 4.5 mm and about 10.0 mm, about 4.5 mm and about 9.5 mm, about 4.5 mm and about 9.0 mm, about 4.5 mm and about 8.5 mm, about 4.5 mm and about 8.0 mm, about 4.5 mm and about 7.5 mm, about 4.5 mm and about 7.0 mm, about 4.5 mm and about 6.5 mm, about 4.5 mm and about 6.0 mm, about 4.5 mm and about 5.5 mm, or between about 4.5 mm and about 5.0 mm.

The perforations may have a pitch in a second direction of between about 5.0 mm and about 10.0 mm, about 5.0 mm and about 9.5 mm, about 5.0 mm and about 9.0 mm, about 5.0 mm and about 8.5 mm, about 5.0 mm and about 8.0 mm, about 5.0 mm and about 7.5 mm, about 5.0 mm and about 7.0 mm, about 5.0 mm and about 6.5 mm, about 5.0 mm and about 6.0 mm, or between about 5.5 mm and about 5.5 mm.

The perforations may have a pitch in a second direction of between about 5.5 mm and about 10.0 mm, about 5.5 mm and about 9.5 mm, about 5.5 mm and about 9.0 mm, about 5.5 mm and about 8.5 mm, about 5.5 mm and about 8.0 mm, about 5.5 mm and about 7.5 mm, about 5.5 mm and about 7.0 mm, about 5.5 mm and about 6.5 mm, or between about 5.5 mm and about 6.0 mm.

The perforations may have a pitch in a second direction of between about 6.0 mm and about 10.0 mm, about 6.0 mm and about 9.5 mm, about 6.0 mm and about 9.0 mm, about 6.0 mm and about 8.5 mm, about 6.0 mm and about 8.0 mm, about 6.0 mm and about 7.5 mm, about 6.0 mm and about 7.0 mm, or between about 6.0 mm and about 6.5 mm.

The perforations may have a pitch in a second direction of between about 6.5 mm and about 10.0 mm, about 6.5 mm and about 9.5 mm, about 6.5 mm and about 9.0 mm, about 6.5 mm and about 8.5 mm, about 6.5 mm and about 8.0 mm, about 6.5 mm and about 7.5 mm, or between about 6.5 mm and about 7.0 mm.

The perforations may have a pitch in a second direction of between about 7.0 mm and about 10.0 mm, about 7.0 mm and about 9.5 mm, about 7.0 mm and about 9.0 mm, about 7.0 mm and about 8.5 mm, about 7.0 mm and about 8.0 mm, or between about 7.0 mm and about 7.5 mm.

The perforations may have a pitch in a second direction of between about 7.5 mm and about 10.0 mm, about 7.5 mm and about 9.5 mm, about 7.5 mm and about 9.0 mm, about 7.5 mm and about 8.5 mm, or between about 7.5 mm and about 8.0 mm.

The perforations may have a pitch in a second direction of between about 8.0 mm and about 10.0 mm, about 8.0 mm and about 9.5 mm, about 8.0 mm and about 9.0 mm, or between about 8.0 mm and about 8.5 mm.

The perforations may have a pitch in a second direction of between about 8.5 mm and about 10.0 mm, about 8.5 mm and about 9.5 mm, or between about 8.5 mm and about 9.0 mm.

The perforations may have a pitch in a second direction of between about 9.0 mm and about 10.0 mm, or between about 9.0 mm and about 9.5 mm.

The perforations may have a pitch in a second direction of between about 9.5 mm and about 10.0 mm.

Advantageously, the pitch of the perforations of the present invention, in particular in embodiments where the pitch is between about 7 mm and 9 mm, in particular about 8 mm, in a first direction, and between about 5.00 mm and about 6.00 mm, in particular about 5.6 mm, in a second direction, provides a good ratio of perforation:no-perforation of the adhesive skin contact layer. Beneficially, this provides for efficient moisture evaporation (for example to prevent pooling) and strong adhesion to the patient. Surprisingly, and advantageously, it has been found that the adhesive skin contact layer of the present invention, in particular in embodiments having the above-described pitch of the perforations, remains adhered to a user for at least seven days.

The adhesive skin contact layer may comprise at least two perforations having different diameters.

The difference in the diameter of the largest perforation and the smallest perforation may be no more than about 4.50 mm, about 4.40 mm, about mm, about 4.35 mm, about 4.30 mm, about 4.25 mm, about 4.20 mm, about 4.15 mm, about 4.10 mm, about 4.05 mm, about 4.00 mm, about 3.95 mm, about 3.90 mm, about 3.85 mm, about 3.80 mm, about 3.75 mm, about 3.70 mm, about 3.65 mm, about 3.60 mm, about 3.55 mm, about 3.50 mm, about 3.45 mm, about 3.40 mm, about 3.35 mm, about 3.30 mm, about 3.25 mm, about 3.20 mm, about 3.15 mm, about 3.10 mm, about 3.05 mm, about 3.00 mm, about 2.95 mm, about 2.90 mm, about 2.85 mm, about 2.80 mm, about 2.75 mm, about 2.70 mm, about 2.65 mm, about 2.60 mm, about 2.55 mm, about 2.50 mm, about 2.45 mm, about 2.40 mm, about 2.35 mm, about 2.30 mm, about 2.25 mm, about 2.20 mm, about 2.15 mm, about 2.10 mm, about 2.05 mm, about 2.00 mm, about 1.95 mm, about 1.90 mm, about 1.85 mm, about 1.80 mm, about 1.75 mm, about 1.70 mm, about 1.65 mm, about 1.60 mm, about 1.55 mm, about 1.50 mm, about 1.45 mm, about 1.40 mm, about 1.35 mm, about 1.30 mm, about 1.25 mm, about 1.20 mm, about 1.15 mm, about 1.10 mm, about 1.05 mm, about 1.00 mm, about 0.95 mm, about 0.90 mm, about 0.85 mm, about 0.80 mm, about 0.75 mm, about 0.70 mm, about 0.65 mm, about 0.60 mm, about 0.55 mm, about 0.50 mm, about 0.45 mm, about 0.40 mm, about 0.35 mm, about 0.30 mm, about 0.25 mm, about 0.20 mm, about 0.15 mm, about 0.10 mm, or no more than about 0.05 mm.

The perforations may have a total area of about 1300 $mm^2$, about 1350 $mm^2$, about 1400 $mm^2$, about 1450 $mm^2$, about 1500 $mm^2$, about 1550 $mm^2$, about 1600 $mm^2$, about 1650 $mm^2$, about 1700 $mm^2$, about 1750 $mm^2$, about 1800 $mm^2$, about 1850 $mm^2$, about 1900 $mm^2$, about 1950 $mm^2$, about 2000 $mm^2$, about 2050 $mm^2$, about 2100 $mm^2$, about 2150 $mm^2$, about 2200 $mm^2$, about 2250 $mm^2$, about 2300 $mm^2$, about 2350 $mm^2$, about 2400 $mm^2$, about 2450 $mm^2$, or about 2500 $mm^2$.

The perforations may have a total area of between about 1300 $mm^2$ and about 2500 $mm^2$, about 1400 $mm^2$ and about 2450 $mm^2$, about 1500 $mm^2$ and about 2400 $mm^2$, about 1600 $mm^2$ and about 2350 $mm^2$, about 1700 $mm^2$ and about 2300 $mm^2$, about 1800 $mm^2$ and about 2250 $mm^2$, about 1900 $mm^2$ and about 2200 $mm^2$, about 2000 $mm^2$ and about 2150 $mm^2$, or about 2100 $mm^2$.

The degree of perforation may be between about 5% and about 50%, about 6% and about 45%, about 7% and about 40%, about 8% and about 35%, about 9% and about 30%, about 10% and about 25%, about 10% and about 20%, about 10% and about 15%, or about 12%, of the area of the adhesive skin contact layer.

The degree of perforation may be about 5%, about 6%, about 7%, about 8%, about 9%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50%, of the area of the adhesive skin contact layer.

The degree of perforation may be at least about 5%, about 6%, about 7%, about 8%, about 9%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or at least about 50%, of the area of the adhesive skin contact layer.

The degree of perforation may be no more than about 5%, about 6%, about 7%, about 8%, about 9%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or no more than about 50%, of the area of the adhesive skin contact layer.

The adhesive skin contact layer may have a thickness of about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, or about 1.5 mm.

The adhesive skin contact layer may have a thickness of at least about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, or at least about 1.5 mm.

The adhesive skin contact layer may have a thickness of no more than about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, or no more than about 1.5 mm.

The adhesive skin contact layer may have a thickness of between about 0.5 mm and about 1.5 mm, about 0.6 mm and about 1.4 mm, about 0.7 mm and about 1.3 mm, about 0.8 mm and about 1.2 mm, about 0.9 mm and about 1.1 mm, or about 1.0 mm.

The perforations may be formed by punch perforating, a hot pin process, a laser ablation processor an ultrasound process. In particular, the perforations may be formed by mechanical punch perforating. Advantageously, mechanical punch perforating prevents, or at least significantly reduces, formation of a doughnut or volcano structure around the perforations after their formation. The perforations may be formed by mechanical punch perforating an adhesive layer comprising a release liner covering at least one surface of the adhesive layer. Following mechanical punch perforating the adhesive layer, the release liner may be removed from the at least one surface of the adhesive layer to remove any 'slugs' that remain after mechanical punch perforating.

The perforations may be formed by punch perforating, a hot pin process, or an ultrasound process.

Each of the perforations may be the same size, or at least substantially the same size.

The adhesive skin contact layer may be any shape, such as a circle, an oval, a triangle, a square, a rectangle, a hexagon, an octagon or any irregular shape, for example an irregular quadrilateral.

The adhesive skin contact layer may comprise a window. Thus, the adhesive skin contact layer may be an adhesive skin contact border layer having a perimetral shape. The window may be located central relative to the periphery of the adhesive skin contact layer. The border layer may comprise an outer periphery which defines the outer shape of the border, for example square, rectangle, circle. The border layer may comprise an inner periphery which defines the shape of the window. The window may be of the same, or similar shape, to that of the outer periphery of the border layer. In use, the wound dressing may be adhered to the dermal surface such that a wound site is located within the window. As such, the adhesive skin contact layer is not in direct contact with the wound site, but does partially, or wholly, surround it. Thus, the adhesive skin contact layer may be in contact with intact peri-wound skin only. Advantageously, this means that the wound dressing does not directly adhere to the wound site, therefore, removal of the wound dressing from a patient does not damage the wound and minimises discomfort to the patient. The window allows the adhesive skin contact layer to be adhered around a wound, such that the wound site is placed within the window, therefore, allowing the patient's wound to be in contact, or be in fluid communication with, for example and preferably, the wound contact layer when the wound dressing is applied to the skin of a patient.

In embodiments comprising a rectangle window, there may be provided a greater overlap of the absorbent structure (i.e., the structure which may comprise a wound contact later, transmission layer and/or superabsorbent layer) and the adhesive skin contact layer. The increased overlap may be found at or toward corresponding corner portions of the adhesive skin contact layer and the absorbent structure. Advantageously, the greater overlap allows for a greater surface area for adhesion between the adhesive skin contact layer and the absorbent structure, therefore, providing greater structural integrity to the wound dressing. The greater structural integrity means that the absorbent structure maintains its position within the wound dressing with reduced possibility of the absorbent structure becoming dislodged from its position within the wound dressing when in use, in particular when in use when the wound dressing is wet with exudate or other fluids.

The window may have an area of between about 900 $mm^2$ and about 50,000 $mm^2$, about 1600 $mm^2$ and about 45,000 $mm^2$, about 2500 $mm^2$ and about 40,000 $mm^2$, about 3600 $mm^2$ and about 35,000 $mm^2$, about 4900 $mm^2$ and about 30,000 $mm^2$, about 6400 $mm^2$ and about 25,000 $mm^2$, about 8100 $mm^2$ and about 20,000 $mm^2$, about 10,000 $mm^2$ and about 15,000 $mm^2$, or about 12,500 $mm^2$.

The window may have an area of about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 37,500 $mm^2$, about 40,000 $mm^2$, about 42,500 $mm^2$, about 45,000 $mm^2$, about 47,500 $mm^2$, or about 50,000 $mm^2$.

The window may have an area of at least about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 37,500 $mm^2$, about 40,000 $mm^2$, about 42,500 $mm^2$, about 45,000 $mm^2$, about 47,500 $mm^2$, or at least about 50,000 $mm^2$.

The window may have an area of no more than about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 37,500 $mm^2$, about 40,000 $mm^2$, about 42,500 $mm^2$, about 45,000 $mm^2$, about 47,500 $mm^2$, or no more than about 50,000 $mm^2$.

The perforations may be distributed along multiple concentric circles formed around a centre point of the skin contact layer. In some embodiments, the concentric circles may be evenly spaced from one another, and/or the perforations in the same concentric circle may be evenly distributed along the circle. The concentric circles may be spaced evenly from one another.

The perforations may be distributed along multiple concentric polygons around a centre point of the adhesive skin contact layer.

The perforations may be distributed along multiple concentric decagons formed around a centre point of the adhesive skin contact layer.

The perforations may be distributed along multiple concentric squares, pentagons, hexagons, heptagons, octagons or nonagons. The concentric polygons may be evenly spaced from one another, and/or the perforations in the same concentric polygon may be evenly distributed along the polygon.

The perforations may be cut-outs (i.e., elongated perforations) formed in the adhesive skin contact layer. The adhesive skin contact layer may have a circular shape and the cut-outs may have an at least partially circular or arc shape. The cut-outs may define at least portions of multiple concentric circles. The cut-outs may have a shape at least partially extending in a parallel fashion with an outer perimeter of the adhesive skin contact layer. The adhesive skin contact layer may comprise one or more connecting portions which extend between the cut-outs and/or connecting portions of the adhesive skin contact layer separated by the cut-outs.

The plurality of perforations may be distributed evenly, or substantially evenly throughout the adhesive skin contact layer. In some embodiments, the perforations may be distributed unevenly throughout the adhesive skin contact layer, such that perforations are more concentrated in a certain portion of the adhesive skin contact layer than other portions of the adhesive skin contact layer. The perforations may be concentrated in several areas of the adhesive skin contact layer, defining clusters of perforations. Each cluster may include the same number of perforations. Each cluster may include a different number of perforations. Each of the clusters may have the same or substantially the same size and/or shape. The clusters may each have a different size and/or shape. One or more of the clusters may have a substantially same shape with each of the perforations. The clusters may have one or more shapes selected from a circle, triangle, square, rectangle, diamond, pentagon, hexagon or octagon. The perforations may be evenly or substantially evenly distributed within each of the clusters.

The adhesive skin contact layer may comprise an upper surface and a lower surface. The upper surface and/or the lower surface may be flat, or at least substantially flat, for example owing to slight raised or lowered portions in the adhesive skin contact layer surrounding each perforation, such that the adhesive skin contact layer has an even, flat profile when viewed from a side.

At least a portion of the adhesive skin contact layer may be raised, or otherwise non-flatly shaped, such that the adhesive skin contact layer has an uneven or non-planar profile when viewed from a side.

The plurality of perforations may comprise a plurality of first perforations and a plurality of second perforations.

The adhesive skin contact layer may comprise perforations with the same shape but in different orientations. For example, the plurality of second perforations may be the same shape as the plurality of first perforations but have a different orientation, for example 20 degrees, 30 degrees, 45 degrees, 60 degrees, 90 degrees, or 180 degrees rotated from the orientation of the plurality of first perforations.

The plurality of first perforations and the plurality of second perforations may have a different shape. For example, the plurality of first perforations may have a circle shape, while the plurality of second perforations may have a square shape. In some embodiments, the plurality of first perforations and the plurality of second perforations may have the same or substantially the same shape. The plurality of first perforations and the plurality of second perforations may have a different shape.

The plurality of first perforations and the plurality of second perforations may have a different size. For example, the plurality of first perforations may each have a larger diameter than each of the plurality of second perforations. In some embodiments, the plurality of first perforations and the plurality of second perforations may each have the same or substantially the same size.

Each of the plurality of first perforations and each of the plurality of second perforations may have a diameter selected from about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or about 5.00 mm.

Each of the plurality of first perforations and each of the plurality of second perforations may have a diameter selected from at least about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or at least about 5.00 mm.

Each of the plurality of first perforations and each of the plurality of second perforations may have a diameter selected from no more than about 1.25 mm, about 1.30 mm, about 1.35 mm, about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.10 mm, about 3.20 mm, about 3.30 mm, about 3.40 mm, about 3.50 mm, about 3.60 mm, about 3.70 mm, about 3.80 mm, about 3.90 mm, about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or no more than about 5.00 mm.

The plurality of first perforations may be arranged in a border portion of the adhesive skin contact layer. The plurality of second perforations may be arranged in a central portion of the adhesive skin contact layer. The central portion may be surrounded by the border portion. The plurality of first perforations may each have a larger diameter than each of the plurality of second perforations.

In some embodiments, the plurality of first perforations and the plurality of second perforations may be distributed in a different configuration. For example, the plurality of first perforations may be distributed in multiple columns and the first perforations of the adjacent columns may be staggered to each other, such that the plurality of first perforations are distributed in a triangular packing layout, while the plurality of second perforations are distributed around each of the first perforations.

The invention according to the first aspect may of course individually include any one or more of the features, optional or otherwise, of the invention according to any other aspect.

According to a second aspect of the present invention, there is provided a method for forming a plurality of perforations in the adhesive skin contact layer of the negative pressure wound dressing, the method comprising:

a. Providing an adhesive skin contact layer; and
b. Forming a plurality of perforations in the adhesive skin contact layer by mechanical punch perforating.

The adhesive skin contact layer may have a weight of between 40 gsm and 250 gsm.

The adhesive skin contact layer may be a perforated mesh. The perforated mesh may comprise perforations each having a diameter of between 1.25 mm and 5.00 mm.

The invention according to the second aspect may of course individually include any one or more of the features, optional or otherwise, of the invention according to any other aspect. For example, the adhesive skin contact layer may be the adhesive skin contact layer as defined in the first aspect, optionally including any optional feature set out above, and the wound dressing may be the wound dressing of the first aspect, optionally including any optional feature set out above.

According to another broad aspect of the invention, there is provided a wound dressing comprising a wound contact layer. The wound contact layer may be arranged to contact a wound when the wound dressing is adhered to the skin adjacent the wound. The wound contact layer may have a first surface and a second surface. The first surface of the wound contact layer may contact a wound in use. The first surface of the wound contact layer may comprise warp stitches. The second surface of the wound contact layer may comprise warp stitches. The wound dressing may be a negative pressure wound dressing. The dressing may comprise a backing layer. The dressing may comprise an adhesive skin contact layer. The dressing may comprise an absorbent structure. The absorbent structure may be arranged between the backing layer and the adhesive skin contact layer. The backing layer may comprise a coupling member configured to connect the dressing to a negative pressure source. The second surface may comprise warp and weft stitches. The first surface may not comprise any weft stitches.

In a third aspect of the invention, there is provided a negative pressure wound dressing, the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the skin adjacent the wound, the wound contact layer having a first surface and a second surface, wherein the first surface of the wound contact layer contacts the wound in use, wherein the first surface comprises warp stitches and the second surface comprises warp stitches.

The warp stitches may comprise any non-gelling fibre.

Thus, the present invention provides a wound contact layer which has a reduced amount of non-gelling materials (for example, non-gelling fibres) at the wound contact surface. Advantageously, this facilitates absorption of wound exudate which, therefore, prevents pooling of exudate at the wound site. As such, an environment optimised for wound healing is maintained at the wound site.

Further advantageously, the present invention provides a wound dressing with greater adhesion between the wound contact layer and other layers of the absorbent structure which may be present, for example a transmission layer positioned between the wound contact layer and an absorbent layer or a backing layer. Thus, the present invention provides a wound dressing which exhibits sufficient strength, without compromising its absorption efficacy, to hold the layers of the wound dressing together even when the dressing is wetted, for example with exudate, and when the dressing is handled.

Thus, the wound contact layer of the present invention beneficially prevents, or at least substantially reduces, pooling of wound exudate at the wound site, maintains an environment optimised for wound healing at the wound site, and exhibits sufficient strength between the layers of the absorbent structure to prevent, or at least substantially reduce the possibility of, separation of the layers of the absorbent structure.

The second surface may comprise warp and weft stitches.

As such, in one embodiment, there is provided a negative pressure wound dressing the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the skin adjacent the wound, the wound contact layer having a first surface and a second surface, wherein the first surface of the wound contact layer contacts the wound in use, wherein the first surface comprises warp stitches, and characterised in that the second surface comprises warp and weft stitches.

The absorbent structure may be arranged between the backing layer and the adhesive skin contact layer.

The first surface may comprise fewer than 15.0 weft stitches/cm, fewer than 14.5 weft stitches/cm, fewer than 14.0 weft stitches/cm, fewer than 13.5 weft stitches/cm, fewer than 13.0 weft stitches/cm, fewer than 12.5 weft stitches/cm, fewer than 12.0 weft stitches/cm, fewer than 11.5 weft stitches/cm, fewer than 11.0 weft stitches/cm, fewer than 10.5 weft stitches/cm, fewer than 10.0 weft stitches/cm, fewer than 9.5 weft stitches/cm, fewer than 9.0 weft stitches/cm, fewer than 8.5 weft stitches/cm, fewer than 8.0 weft stitches/cm, fewer than 7.5 weft stitches/cm, fewer than 7.0 weft stitches/cm, fewer than 6.5 weft stitches/cm, fewer than 6.0 weft stitches/cm, fewer than 5.5 weft stitches/cm, fewer than 5.0 weft stitches/cm, fewer than 4.5 weft stitches/cm, fewer than 4.0 weft stitches/cm, fewer than 3.5 weft stitches/cm, fewer than 3.0 weft stitches/cm, fewer than 2.5 weft stitches/cm, fewer than 2.0 weft stitches/cm, fewer than 1.5 weft stitches/cm, fewer than 1.0 weft stitch/cm, fewer than 0.8 weft stitches/cm, fewer than 0.6 weft stitches/cm, fewer than 0.5 weft stitches/cm, fewer than 0.4 weft stitches/cm, fewer than 0.3 weft stitches/cm, fewer than 0.2 weft stitches/cm, or fewer than 0.1 weft stitch/cm.

The first surface may comprise about 15.0 weft stitches/cm, about 14.5 weft stitches/cm, about 14.0 weft stitches/cm, about 13.5 weft stitches/cm, about 13.0 weft stitches/cm, about 12.5 weft stitches/cm, about 12.0 weft stitches/cm, about 11.5 weft stitches/cm, about 11.0 weft stitches/cm, about 10.5 weft stitches/cm, about 10.0 weft stitches/cm, about 9.5 weft stitches/cm, about 9.0 weft stitches/cm, about 8.5 weft stitches/cm, about 8.0 weft stitches/cm, about 7.5 weft stitches/cm, about 7.0 weft stitches/cm, about 6.5 weft stitches/cm, about 6.0 weft stitches/cm, about 5.5 weft stitches/cm, about 5.0 weft stitches/cm, about 4.5 weft stitches/cm, about 4.0 weft stitches/cm, about 3.5 weft stitches/cm, about 3.0 weft stitches/cm, about 2.5 weft stitches/cm, about 2.0 weft stitches/cm, about 1.5 weft stitches/cm, about 1.0 weft stitch/cm, about 0.8 weft stitches/cm, about 0.6 weft stitches/cm, about 0.5 weft stitches/cm, about 0.4 weft stitches/cm, about 0.3 weft stitches/cm, about 0.2 weft stitches/cm, or about 0.1 weft stitch/cm.

The first surface may comprise no more than 15.0 weft stitches/cm, than 14.5 weft stitches/cm, than 14.0 weft stitches/cm, than 13.5 weft stitches/cm, than 13.0 weft stitches/cm, than 12.5 weft stitches/cm, than 12.0 weft stitches/cm, than 11.5 weft stitches/cm, than 11.0 weft stitches/cm, than 10.5 weft stitches/cm, than 10.0 weft stitches/cm, than 9.5 weft stitches/cm, than 9.0 weft stitches/cm, than 8.5 weft stitches/cm, than 8.0 weft stitches/cm, than 7.5 weft stitches/cm, than 7.0 weft stitches/cm, than 6.5 weft stitches/cm, than 6.0 weft stitches/cm, than 5.5 weft stitches/cm, than 5.0 weft stitches/cm, than 4.5 weft stitches/cm, than 4.0 weft stitches/cm, than 3.5 weft stitches/cm, than 3.0 weft stitches/cm, than 2.5 weft stitches/cm, than 2.0 weft stitches/cm, than 1.5 weft stitches/cm, than 1.0 weft stitch/cm, than 0.8 weft stitches/cm, than 0.6 weft stitches/cm, than 0.5 weft stitches/cm, than 0.4 weft stitches/cm, than 0.3 weft stitches/cm, than 0.2 weft stitches/cm, or no more than 0.1 weft stitches/cm.

The first surface may comprise at least 15.0 weft stitches/cm, 14.5 weft stitches/cm, 14.0 weft stitches/cm, 13.5 weft stitches/cm, 13.0 weft stitches/cm, 12.5 weft stitches/cm, 12.0 weft stitches/cm, 11.5 weft stitches/cm, 11.0 weft stitches/cm, 10.5 weft stitches/cm, 10.0 weft stitches/cm, 9.5 weft stitches/cm, 9.0 weft stitches/cm, 8.5 weft stitches/cm, 8.0 weft stitches/cm, 7.5 weft stitches/cm, 7.0 weft stitches/cm, 6.5 weft stitches/cm, 6.0 weft stitches/cm, 5.5 weft stitches/cm, 5.0 weft stitches/cm, 4.5 weft stitches/cm, 4.0 weft stitches/cm, 3.5 weft stitches/cm, 3.0 weft stitches/cm, 2.5 weft stitches/cm, 2.0 weft stitches/cm, 1.5 weft stitches/cm, 1.0 weft stitch/cm, 0.8 weft stitches/cm, 0.6 weft stitches/cm, 0.5 weft stitches/cm, 0.4 weft stitches/cm, 0.3 weft stitches/cm, 0.2 weft stitches/cm, or at least 0.1 weft stitches/cm.

The first surface may comprise between about 0.1 and about 15.0 weft stitches/cm, between about 0.1 and about 14.5 weft stitches/cm, between about 0.1 and about 14.0 weft stitches/cm, between about 0.1 and about 13.5 weft stitches/cm, between about 0.1 and about 13.0 weft stitches/cm, between about 0.1 and about 12.5 weft stitches/cm, between about 0.1 and about 12.0 weft stitches/cm, between about 0.1 and about 11.5 weft stitches/cm, between about 0.1 and about 11.0 weft stitches/cm, between about 0.1 and about 10.5 weft stitches/cm, between about 0.1 and about 10.0 weft stitches/cm, between about 0.1 and about 9.5 weft stitches/cm, between about 0.1 and about 9.0 weft stitches/cm, between about 0.1 and about 8.5 weft stitches/cm, between about 0.1 and about 8.0 weft stitches/cm, between about 0.1 and about 7.5 weft stitches/cm, between about 0.1 and about 7.0 weft stitches/cm, between about 0.1 and about 6.5 weft stitches/cm, between about 0.1 and about 6.0 weft stitches/cm, between about 0.1 and about 5.5 weft stitches/cm, between about 0.1 and about 5.0 weft stitches/cm, between about 0.1 and about 4.5 weft stitches/cm, between about 0.1 and about 4.0 weft stitches/cm, between about 0.1 and about 3.5 weft stitches/cm, between about 0.1 and about 3.0 weft stitches/cm, between about 0.1 and about 2.5 weft stitches/cm, between about 0.1 and about 2.0 weft stitches/cm, between about 0.1 and about 1.5 weft stitches/cm, between about 0.1 and about 1.0 weft stitches/cm, between about 0.1 and about 0.8 weft stitches/cm, between about 0.1 and about 0.6 weft stitches/cm, between about 0.1 and about 0.4 weft stitches/cm, or between about 0.1 and about 0.2 weft stitches/cm.

The first surface may comprise between about 0.2 and about 15.0 weft stitches/cm, between about 0.2 and about 14.5 weft stitches/cm, between about 0.2 and about 14.0 weft stitches/cm, between about 0.2 and about 13.5 weft stitches/cm, between about 0.2 and about 13.0 weft stitches/cm, between about 0.2 and about 12.5 weft stitches/cm, between about 0.2 and about 12.0 weft stitches/cm, between about 0.2 and about 11.5 weft stitches/cm, between about 0.2 and about 11.0 weft stitches/cm, between about 0.2 and about 10.5 weft stitches/cm, between about 0.2 and about 10.0 weft stitches/cm, between about 0.2 and about 9.5 weft stitches/cm, between about 0.2 and about 9.0 weft stitches/cm, between about 0.2 and about 8.5 weft stitches/cm, between about 0.2 and about 8.0 weft stitches/cm, between about 0.2 and about 7.5 weft stitches/cm, between about 0.2 and about 7.0 weft stitches/cm, between about 0.2 and about 6.5 weft stitches/cm, between about 0.2 and about 6.0 weft stitches/cm, between about 0.2 and about 5.5 weft stitches/cm, between about 0.2 and about 5.0 weft stitches/cm, between about 0.2 and about 4.5 weft stitches/cm, between about 0.2 and about 4.0 weft stitches/cm, between about 0.2 and about 3.5 weft stitches/cm, between about 0.2 and about 3.0 weft stitches/cm, between about 0.2 and about 2.5 weft stitches/cm, between about 0.2 and about 2.0 weft stitches/cm, between about 0.2 and about 1.5 weft stitches/cm, between about 0.2 and about 1.0 weft stitches/cm, between about 0.2 and about 0.8 weft stitches/cm, between about 0.2 and about 0.6 weft stitches/cm, or between about 0.2 and about 0.4 weft stitches/cm.

The first surface may comprise between about 0.4 and about 15.0 weft stitches/cm, between about 0.4 and about 14.5 weft stitches/cm, between about 0.4 and about 14.0 weft stitches/cm, between about 0.4 and about 13.5 weft stitches/cm, between about 0.4 and about 13.0 weft stitches/cm, between about 0.4 and about 12.5 weft stitches/cm, between about 0.4 and about 12.0 weft stitches/cm, between about 0.4 and about 11.5 weft stitches/cm, between about 0.4 and about 11.0 weft stitches/cm, between about 0.4 and about 10.5 weft stitches/cm, between about 0.4 and about 10.0 weft stitches/cm, between about 0.4 and about 9.5 weft stitches/cm, between about 0.4 and about 9.0 weft stitches/cm, between about 0.4 and about 8.5 weft stitches/cm, between about 0.4 and about 8.0 weft stitches/cm, between about 0.4 and about 7.5 weft stitches/cm, between about 0.4 and about 7.0 weft stitches/cm, between about 0.4 and about 6.5 weft stitches/cm, between about 0.4 and about 6.0 weft stitches/cm, between about 0.4 and about 5.5 weft stitches/cm, between about 0.4 and about 5.0 weft stitches/cm, between about 0.4 and about 4.5 weft stitches/cm, between about 0.4 and about 4.0 weft stitches/cm, between about 0.4 and about 3.5 weft stitches/cm, between about 0.4 and about 3.0 weft stitches/cm, between about 0.4 and about 2.5 weft stitches/cm, between about 0.4 and about 2.0 weft stitches/cm, between about 0.4 and about 1.5 weft stitches/cm, between about 0.4 and about 1.0 weft stitches/cm, between about 0.4 and about 0.8 weft stitches/cm, or between about 0.4 and about 0.6 weft stitches/cm.

The first surface may comprise between about 0.6 and about 15.0 weft stitches/cm, between about 0.6 and about 14.5 weft stitches/cm, between about 0.6 and about 14.0 weft stitches/cm, between about 0.6 and about 13.5 weft stitches/cm, between about 0.6 and about 13.0 weft stitches/cm, between about 0.6 and about 12.5 weft stitches/cm, between about 0.6 and about 12.0 weft stitches/cm, between about 0.6 and about 11.5 weft stitches/cm, between about 0.6 and about 11.0 weft stitches/cm, between about 0.6 and about 10.5 weft stitches/cm, between about 0.6 and about 10.0 weft stitches/cm, between about 0.6 and about 9.5 weft stitches/cm, between about 0.6 and about 9.0 weft stitches/cm, between about 0.6 and about 8.5 weft stitches/cm, between about 0.6 and about 8.0 weft stitches/cm, between about 0.6 and about 7.5 weft stitches/cm, between about 0.6 and about 7.0 weft stitches/cm, between about 0.6 and about 6.5 weft stitches/cm, between about 0.6 and about 6.0 weft stitches/cm, between about 0.6 and about 5.5 weft stitches/ cm, between about 0.6 and about 5.0 weft stitches/cm, between about 0.6 and about 4.5 weft stitches/cm, between about 0.6 and about 4.0 weft stitches/cm, between about 0.6 and about 3.5 weft stitches/cm, between about 0.6 and about 3.0 weft stitches/cm, between about 0.6 and about 2.5 weft stitches/cm, between about 0.6 and about 2.0 weft stitches/cm, between about 0.6 and about 1.5 weft stitches/cm, between about 0.6 and about 1.0 weft stitches/cm, or between about 0.6 and about 0.8 weft stitches/cm.

The first surface may comprise between about 0.8 and about 15.0 weft stitches/cm, between about 0.8 and about 14.5 weft stitches/cm, between about 0.8 and about 14.0 weft stitches/cm, between about 0.8 and about 13.5 weft stitches/cm, between about 0.8 and about 13.0 weft stitches/cm, between about 0.8 and about 12.5 weft stitches/cm, between about 0.8 and about 12.0 weft stitches/cm, between about 0.8 and about 11.5 weft stitches/cm, between about 0.8 and about 11.0 weft stitches/cm, between about 0.8 and about 10.5 weft stitches/cm, between about 0.8 and about 10.0 weft stitches/cm, between about 0.8 and about 9.5 weft stitches/cm, between about 0.8 and about 9.0 weft stitches/cm, between about 0.8 and about 8.5 weft stitches/cm, between about 0.8 and about 8.0 weft stitches/cm, between about 0.8 and about 7.5 weft stitches/cm, between about 0.8 and about 7.0 weft stitches/cm, between about 0.8 and about 6.5 weft stitches/cm, between about 0.8 and about 6.0 weft stitches/cm, between about 0.8 and about 5.5 weft stitches/cm, between about 0.8 and about 5.0 weft stitches/cm, between about 0.8 and about 4.5 weft stitches/cm, between about 0.8 and about 4.0 weft stitches/cm, between about 0.8 and about 3.5 weft stitches/cm, between about 0.8 and about 3.0 weft stitches/cm, between about 0.8 and about 2.5 weft stitches/cm, between about 0.8 and about 2.0 weft stitches/cm, between about 0.8 and about 1.5 weft stitches/cm, or between about 0.8 and about 1.0 weft stitches/cm.

The first surface may comprise between about 1.0 and about 15.0 weft stitches/cm, between about 1.0 and about 14.5 weft stitches/cm, between about 1.0 and about 14.0 weft stitches/cm, between about 1.0 and about 13.5 weft stitches/cm, between about 1.0 and about 13.0 weft stitches/cm, between about 1.0 and about 12.5 weft stitches/cm, between about 1.0 and about 12.0 weft stitches/cm, between about 1.0 and about 11.5 weft stitches/cm, between about 1.0 and about 11.0 weft stitches/cm, between about 1.0 and about 10.5 weft stitches/cm, between about 1.0 and about 10.0 weft stitches/cm, between about 1.0 and about 9.5 weft stitches/cm, between about 1.0 and about 9.0 weft stitches/cm, between about 1.0 and about 8.5 weft stitches/cm, between about 1.0 and about 8.0 weft stitches/cm, between about 1.0 and about 7.5 weft stitches/cm, between about 1.0 and about 7.0 weft stitches/cm, between about 1.0 and about 6.5 weft stitches/cm, between about 1.0 and about 6.0 weft stitches/cm, between about 1.0 and about 5.5 weft stitches/cm, between about 1.0 and about 5.0 weft stitches/cm, between about 1.0 and about 4.5 weft stitches/cm, between about 1.0 and about 4.0 weft stitches/cm, between about 1.0 and about 3.5 weft stitches/cm, between about 1.0 and about 3.0 weft stitches/cm, between about 1.0 and about 2.5 weft stitches/cm, between about 1.0 and about 2.0 weft stitches/cm, or between about 1.0 and about 1.5 weft stitches/cm.

The first surface may comprise between about 1.5 and about 15.0 weft stitches/cm, between about 1.5 and about 14.5 weft stitches/cm, between about 1.5 and about 14.0 weft stitches/cm, between about 1.5 and about 13.5 weft stitches/cm, between about 1.5 and about 13.0 weft stitches/cm, between about 1.5 and about 12.5 weft stitches/cm, between about 1.5 and about 12.0 weft stitches/cm, between about 1.5 and about 11.5 weft stitches/cm, between about 1.5 and about 11.0 weft stitches/cm, between about 1.5 and about 10.5 weft stitches/cm, between about 1.5 and about 10.0 weft stitches/cm, between about 1.5 and about 9.5 weft stitches/cm, between about 1.5 and about 9.0 weft stitches/cm, between about 1.5 and about 8.5 weft stitches/cm, between about 1.5 and about 8.0 weft stitches/cm, between about 1.5 and about 7.5 weft stitches/cm, between about 1.5 and about 7.0 weft stitches/cm, between about 1.5 and about 6.5 weft stitches/cm, between about 1.5 and about 6.0 weft stitches/cm, between about 1.5 and about 5.5 weft stitches/cm, between about 1.5 and about 5.0 weft stitches/cm, between about 1.5 and about 4.5 weft stitches/cm, between about 1.5 and about 4.0 weft stitches/cm, between about 1.5 and about 3.5 weft stitches/cm, between about 1.5 and about 3.0 weft stitches/cm, between about 1.5 and about 2.5 weft stitches/cm, or between about 1.5 and about 2.0 weft stitches/cm.

The first surface may comprise between about 2.0 and about 15.0 weft stitches/cm, between about 2.0 and about 14.5 weft stitches/cm, between about 2.0 and about 14.0 weft stitches/cm, between about 2.0 and about 13.5 weft stitches/cm, between about 2.0 and about 13.0 weft stitches/cm, between about 2.0 and about 12.5 weft stitches/cm, between about 2.0 and about 12.0 weft stitches/cm, between about 2.0 and about 11.5 weft stitches/cm, between about 2.0 and about 11.0 weft stitches/cm, between about 2.0 and about 10.5 weft stitches/cm, between about 2.0 and about 10.0 weft stitches/cm, between about 2.0 and about 9.5 weft stitches/cm, between about 2.0 and about 9.0 weft stitches/cm, between about 2.0 and about 8.5 weft stitches/cm, between about 2.0 and about 8.0 weft stitches/cm, between about 2.0 and about 7.5 weft stitches/cm, between about 2.0 and about 7.0 weft stitches/cm, between about 2.0 and about 6.5 weft stitches/cm, between about 2.0 and about 6.0 weft stitches/cm, between about 2.0 and about 5.5 weft stitches/cm, between about 2.0 and about 5.0 weft stitches/cm, between about 2.0 and about 4.5 weft stitches/cm, between about 2.0 and about 4.0 weft stitches/cm, between about 2.0 and about 3.5 weft stitches/cm, between about 2.0 and about 3.0 weft stitches/cm, or between about 2.0 and about 2.5 weft stitches/cm.

The first surface may comprise between about 2.5 and about 15.0 weft stitches/cm, between about 2.5 and about 14.5 weft stitches/cm, between about 2.5 and about 14.0 weft stitches/cm, between about 2.5 and about 13.5 weft stitches/cm, between about 2.5 and about 13.0 weft stitches/cm, between about 2.5 and about 12.5 weft stitches/cm, between about 2.5 and about 12.0 weft stitches/cm, between about 2.5 and about 11.5 weft stitches/cm, between about 2.5 and about 11.0 weft stitches/cm, between about 2.5 and about 10.5 weft stitches/cm, between about 2.5 and about 10.0 weft stitches/cm, between about 2.5 and about 9.5 weft stitches/cm, between about 2.5 and about 9.0 weft stitches/cm, between about 2.5 and about 8.5 weft stitches/cm, between about 2.5 and about 8.0 weft stitches/cm, between about 2.5 and about 7.5 weft stitches/cm, between about 2.5 and about 7.0 weft stitches/cm, between about 2.5 and about 6.5 weft stitches/cm, between about 2.5 and about 6.0 weft stitches/cm, between about 2.5 and about 5.5 weft stitches/cm, between about 2.5 and about 5.0 weft stitches/cm, between about 2.5 and about 4.5 weft stitches/cm, between about 2.5 and about 4.0 weft stitches/cm, between about 2.5 and about 3.5 weft stitches/cm, or between about 2.5 and about 3.0 weft stitches/cm.

The first surface may comprise between about 3.0 and about 15.0 weft stitches/cm, between about 3.0 and about 14.5 weft stitches/cm, between about 3.0 and about 14.0 weft stitches/cm, between about 3.0 and about 13.5 weft stitches/cm, between about 3.0 and about 13.0 weft stitches/cm, between about 3.0 and about 12.5 weft stitches/cm, between about 3.0 and about 12.0 weft stitches/cm, between about 3.0 and about 11.5 weft stitches/cm, between about 3.0 and about 11.0 weft stitches/cm, between about 3.0 and about 10.5 weft stitches/cm, between about 3.0 and about 10.0 weft stitches/cm, between about 3.0 and about 9.5 weft stitches/cm, between about 3.0 and about 9.0 weft stitches/cm, between about 3.0 and about 8.5 weft stitches/cm, between about 3.0 and about 8.0 weft stitches/cm, between about 3.0 and about 7.5 weft stitches/cm, between about 3.0 and about 7.0 weft stitches/cm, between about 3.0 and about 6.5 weft stitches/cm, between about 3.0 and about 6.0 weft stitches/cm, between about 3.0 and about 5.5 weft stitches/cm, between about 3.0 and about 5.0 weft stitches/cm, between about 3.0 and about 4.5 weft stitches/cm, between about 3.0 and about 4.0 weft stitches/cm, or between about 3.0 and about 3.5 weft stitches/cm.

The first surface may comprise between about 3.5 and about 15.0 weft stitches/cm, between about 3.5 and about 14.5 weft stitches/cm, between about 3.5 and about 14.0 weft stitches/cm, between about 3.5 and about 13.5 weft stitches/cm, between about 3.5 and about 13.0 weft stitches/cm, between about 3.5 and about 12.5 weft stitches/cm, between about 3.5 and about 11.0 weft stitches/cm, between about 3.5 and about 11.5 weft stitches/cm, between about 3.5 and about 11.0 weft stitches/cm, between about 3.5 and about 10.5 weft stitches/cm, between about 3.5 and about 10.0 weft stitches/cm, between about 3.5 and about 9.5 weft stitches/cm, between about 3.5 and about 9.0 weft stitches/cm, between about 3.5 and about 8.5 weft stitches/cm, between about 3.5 and about 8.0 weft stitches/cm, between about 3.5 and about 7.5 weft stitches/cm, between about 3.5 and about 7.0 weft stitches/cm, between about 3.5 and about 6.5 weft stitches/cm, between about 3.5 and about 6.0 weft stitches/cm, between about 3.5 and about 5.5 weft stitches/cm, between about 3.5 and about 5.0 weft stitches/cm, between about 3.5 and about 4.5 weft stitches/cm, or between about 3.5 and about 4.0 weft stitches/cm.

The first surface may comprise between about 4.0 and about 15.0 weft stitches/cm, between about 4.0 and about 14.5 weft stitches/cm, between about 4.0 and about 14.0 weft stitches/cm, between about 4.0 and about 13.5 weft stitches/cm, between about 4.0 and about 13.0 weft stitches/cm, between about 4.0 and about 12.5 weft stitches/cm, between about 4.0 and about 12.0 weft stitches/cm, between about 4.0 and about 11.5 weft stitches/cm, between about 4.0 and about 11.0 weft stitches/cm, between about 4.0 and about 10.5 weft stitches/cm, between about 4.0 and about 10.0 weft stitches/cm, between about 4.0 and about 9.5 weft stitches/cm, between about 4.0 and about 9.0 weft stitches/cm, between about 4.0 and about 8.5 weft stitches/cm, between about 4.0 and about 8.0 weft stitches/cm, between about 4.0 and about 7.5 weft stitches/cm, between about 4.0 and about 7.0 weft stitches/cm, between about 4.0 and about 6.5 weft stitches/cm, between about 4.0 and about 6.0 weft stitches/cm, between about 4.0 and about 5.5 weft stitches/cm, between about 4.0 and about 5.0 weft stitches/cm, or between about 4.0 and about 4.5 weft stitches/cm.

The first surface may comprise between about 4.5 and about 15.0 weft stitches/cm, between about 4.5 and about 14.5 weft stitches/cm, between about 4.5 and about 14.0 weft stitches/cm, between about 4.5 and about 13.5 weft stitches/cm, between about 4.5 and about 13.0 weft stitches/cm, between about 4.5 and about 12.5 weft stitches/cm, between about 4.5 and about 12.0 weft stitches/cm, between about 4.5 and about 11.5 weft stitches/cm, between about 4.5 and about 11.0 weft stitches/cm, between about 4.5 and about 10.5 weft stitches/cm, between about 4.5 and about 10.0 weft stitches/cm, between about 4.5 and about 9.5 weft stitches/cm, between about 4.5 and about 9.0 weft stitches/cm, between about 4.5 and about 8.5 weft stitches/cm, between about 4.5 and about 8.0 weft stitches/cm, between about 4.5 and about 7.5 weft stitches/cm, between about 4.5 and about 7.0 weft stitches/cm, between about 4.5 and about 6.5 weft stitches/cm, between about 4.5 and about 6.0 weft stitches/cm, between about 4.5 and about 5.5 weft stitches/cm, or between about 4.5 and about 5.0 weft stitches/cm.

The first surface may comprise between about 5.0 and about 15.0 weft stitches/cm, between about 5.0 and about 14.5 weft stitches/cm, between about 5.0 and about 14.0 weft stitches/cm, between about 5.0 and about 13.5 weft stitches/cm, between about 5.0 and about 13.0 weft stitches/cm, between about 5.0 and about 12.5 weft stitches/cm, between about 5.0 and about 12.0 weft stitches/cm, between about 5.0 and about 11.5 weft stitches/cm, between about 5.0 and about 11.0 weft stitches/cm, between about 5.0 and about 10.5 weft stitches/cm, between about 5.0 and about 10.0 weft stitches/cm, between about 5.0 and about 9.5 weft stitches/cm, between about 5.0 and about 9.0 weft stitches/cm, between about 5.0 and about 8.5 weft stitches/cm, between about 5.0 and about 8.0 weft stitches/cm, between about 5.0 and about 7.5 weft stitches/cm, between about 5.0 and about 7.0 weft stitches/cm, between about 5.0 and about 6.5 weft stitches/cm, between about 5.0 and about 6.0 weft stitches/cm, or between about 5.0 and about 5.5 weft stitches/cm.

The first surface may comprise between about 5.5 and about 15.0 weft stitches/cm, between about 5.5 and about 14.5 weft stitches/cm, between about 5.5 and about 14.0 weft stitches/cm, between about 5.5 and about 13.5 weft stitches/cm, between about 5.5 and about 13.0 weft stitches/cm, between about 5.5 and about 12.5 weft stitches/cm, between about 5.5 and about 12.0 weft stitches/cm, between about 5.5 and about 11.5 weft stitches/cm, between about 5.5 and about 11.0 weft stitches/cm, between about 5.5 and about 10.5 weft stitches/cm, between about 5.5 and about 10.0 weft stitches/cm, between about 5.5 and about 9.5 weft stitches/cm, between about 5.5 and about 9.0 weft stitches/cm, between about 5.5 and about 8.5 weft stitches/cm, between about 5.5 and about 8.0 weft stitches/cm, between about 5.5 and about 7.5 weft stitches/cm, between about 5.5 and about 7.0 weft stitches/cm, between about 5.5 and about 6.5 weft stitches/cm, or between about 5.5 and about 6.0 weft stitches/cm.

The first surface may comprise between about 6.0 and about 15.0 weft stitches/cm, between about 6.0 and about 14.5 weft stitches/cm, between about 6.0 and about 14.0 weft stitches/cm, between about 6.0 and about 13.5 weft stitches/cm, between about 6.0 and about 13.0 weft stitches/cm, between about 6.0 and about 12.5 weft stitches/cm, between about 6.0 and about 12.0 weft stitches/cm, between about 6.0 and about 11.5 weft stitches/cm, between about 6.0 and about 11.0 weft stitches/cm, between about 6.0 and about 10.5 weft stitches/cm, between about 6.0 and about 10.0 weft stitches/cm, between about 6.0 and about 9.5 weft stitches/cm, between about 6.0 and about 9.0 weft stitches/cm, between about 6.0 and about 8.5 weft stitches/cm, between about 6.0 and about 8.0 weft stitches/cm, between about 6.0 and about 7.5 weft stitches/cm, between about 6.0 and about 7.0 weft stitches/cm, or between about 6.0 and about 6.5 weft stitches/cm.

The first surface may comprise between about 6.5 and about 15.0 weft stitches/cm, between about 6.5 and about 14.5 weft stitches/cm, between about 6.5 and about 14.0 weft stitches/cm, between about 6.5 and about 13.5 weft stitches/cm, between about 6.5 and about 13.0 weft stitches/cm, between about 6.5 and about 12.5 weft stitches/cm, between about 6.5 and about 12.0 weft stitches/cm, between about 6.5 and about 11.5 weft stitches/cm, between about 6.5 and about 11.0 weft stitches/cm, between about 6.5 and about 10.5 weft stitches/cm, between about 6.5 and about 10.0 weft stitches/cm, between about 6.5 and about 9.5 weft stitches/cm, between about 6.5 and about 9.0 weft stitches/cm, between about 6.5 and about 8.5 weft stitches/cm, between about 6.5 and about 8.0 weft stitches/cm, between about 6.5 and about 7.5 weft stitches/cm, or between about 6.5 and about 7.0 weft stitches/cm.

The first surface may comprise between about 7.0 and about 15.0 weft stitches/cm, between about 7.0 and about 14.5 weft stitches/cm, between about 7.0 and about 14.0 weft stitches/cm, between about 7.0 and about 13.5 weft stitches/cm, between about 7.0 and about 13.0 weft stitches/cm, between about 7.0 and about 12.5 weft stitches/cm, between about 7.0 and about 12.0 weft stitches/cm, between about 7.0 and about 11.5 weft stitches/cm, between about 7.0 and about 11.0 weft stitches/cm, between about 7.0 and about 10.5 weft stitches/cm, between about 7.0 and about 10.0 weft stitches/cm, between about 7.0 and about 9.5 weft stitches/cm, between about 7.0 and about 9.0 weft stitches/cm, between about 7.0 and about 8.5 weft stitches/cm, between about 7.0 and about 8.0 weft stitches/cm, or between about 7.0 and about 7.5 weft stitches/cm.

The first surface may comprise between about 7.5 and about 15.0 weft stitches/cm, between about 7.5 and about 14.5 weft stitches/cm, between about 7.5 and about 14.0 weft stitches/cm, between about 7.5 and about 13.5 weft stitches/cm, between about 7.5 and about 13.0 weft stitches/cm, between about 7.5 and about 12.5 weft stitches/cm, between about 7.5 and about 12.0 weft stitches/cm, between about 7.5 and about 11.5 weft stitches/cm, between about 7.5 and about 11.0 weft stitches/cm, between about 7.5 and about 10.5 weft stitches/cm, between about 7.5 and about 10.0 weft stitches/cm, between about 7.5 and about 9.5 weft stitches/cm, between about 7.5 and about 9.0 weft stitches/cm, between about 7.5 and about 8.5 weft stitches/cm, or between about 7.5 and about 8.0 weft stitches/cm.

The first surface may comprise between about 8.0 and about 15.0 weft stitches/cm, between about 8.0 and about 14.5 weft stitches/cm, between about 8.0 and about 14.0 weft stitches/cm, between about 8.0 and about 13.5 weft stitches/cm, between about 8.0 and about 13.0 weft stitches/cm, between about 8.0 and about 12.5 weft stitches/cm, between about 8.0 and about 12.0 weft stitches/cm, between about 8.0 and about 11.5 weft stitches/cm, between about 8.0 and about 11.0 weft stitches/cm, between about 8.0 and about 10.5 weft stitches/cm, between about 8.0 and about 10.0 weft stitches/cm, between about 8.0 and about 9.5 weft stitches/cm, between about 8.0 and about 9.0 weft stitches/cm, or between about 8.0 and about 8.5 weft stitches/cm.

The first surface may comprise between about 8.5 and about 15.0 weft stitches/cm, between about 8.5 and about 14.5 weft stitches/cm, between about 8.5 and about 14.0 weft stitches/cm, between about 8.5 and about 13.5 weft stitches/cm, between about 8.5 and about 13.0 weft stitches/cm, between about 8.5 and about 12.5 weft stitches/cm, between about 8.5 and about 12.0 weft stitches/cm, between about 8.5 and about 11.5 weft stitches/cm, between about 8.5 and about 11.0 weft stitches/cm, between about 8.5 and about 10.5 weft stitches/cm, between about 8.5 and about 10.0 weft stitches/cm, between about 8.5 and about 9.5 weft stitches/cm, or between about 8.5 and about 9.0 weft stitches/cm.

The first surface may comprise between about 9.0 and about 15.0 weft stitches/cm, between about 9.0 and about 14.5 weft stitches/cm, between about 9.0 and about 14.0 weft stitches/cm, between about 9.0 and about 13.5 weft stitches/cm, between about 9.0 and about 13.0 weft stitches/cm, between about 9.0 and about 12.5 weft stitches/cm, between about 9.0 and about 12.0 weft stitches/cm, between about 9.0 and about 11.5 weft stitches/cm, between about 9.0 and about 11.0 weft stitches/cm, between about 9.0 and about 10.5 weft stitches/cm, between about 9.0 and about 10.0 weft stitches/cm, or between about 9.0 and about 9.5 weft stitches/cm.

The first surface may comprise between about 9.5 and about 15.0 weft stitches/cm, between about 9.5 and about 14.5 weft stitches/cm, between about 9.5 and about 14.0 weft stitches/cm, between about 9.5 and about 13.5 weft stitches/cm, between about 9.5 and about 13.0 weft stitches/cm, between about 9.5 and about 12.5 weft stitches/cm, between about 9.5 and about 12.0 weft stitches/cm, between about 9.5 and about 11.5 weft stitches/cm, between about 9.5 and about 11.0 weft stitches/cm, between about 9.5 and about 10.5 weft stitches/cm, or between about 9.5 and about 10.0 weft stitches/cm.

The first surface may comprise between about 10.0 and about 15.0 weft stitches/cm, between about 10.0 and about 14.5 weft stitches/cm, between about 10.0 and about 14.0 weft stitches/cm, between about 10.0 and about 13.5 weft stitches/cm, between about 10.0 and about 13.0 weft stitches/cm, between about 10.0 and about 12.5 weft stitches/cm, between about 10.0 and about 12.0 weft stitches/cm, between about 10.0 and about 11.5 weft stitches/cm, between about 10.0 and about 11.0 weft stitches/cm, or between about 10.0 and about 10.5 weft stitches/cm.

The first surface may comprise between about 10.5 and about 15.0 weft stitches/cm, between about 10.5 and about 14.5 weft stitches/cm, between about 10.5 and about 14.0 weft stitches/cm, between about 10.5 and about 13.5 weft stitches/cm, between about 10.5 and about 13.0 weft stitches/cm, between about 10.5 and about 12.5 weft stitches/cm, between about 10.5 and about 12.0 weft stitches/cm, between about 10.5 and about 11.5 weft stitches/cm, or between about 10.5 and about 11.0 weft stitches/cm.

The first surface may comprise between about 11.0 and about 15.0 weft stitches/cm, between about 11.0 and about 14.5 weft stitches/cm, between about 11.0 and about 14.0 weft stitches/cm, between about 11.0 and about 13.5 weft stitches/cm, between about 11.0 and about 13.0 weft stitches/cm, between about 11.0 and about 12.5 weft stitches/cm, between about 11.0 and about 12.0 weft stitches/cm, or between about 11.0 and about 11.5 weft stitches/cm.

The first surface may comprise between about 11.5 and about 15.0 weft stitches/cm, between about 11.5 and about 14.5 weft stitches/cm, between about 11.5 and about 14.0 weft stitches/cm, between about 11.5 and about 13.5 weft stitches/cm, between about 11.5 and about 13.0 weft stitches/cm, between about 11.5 and about 12.5 weft stitches/cm, or between about 11.5 and about 12.0 weft stitches/cm.

The first surface may comprise between about 12.0 and about 15.0 weft stitches/cm, between about 12.0 and about 14.5 weft stitches/cm, between about 12.0 and about 14.0 weft stitches/cm, between about 12.0 and about 13.5 weft stitches/cm, between about 12.0 and about 13.0 weft stitches/cm, or between about 12.0 and about 12.5 weft stitches/cm.

The first surface may comprise between about 12.5 and about 15.0 weft stitches/cm, between about 12.5 and about 14.5 weft stitches/cm, between about 12.5 and about 14.0 weft stitches/cm, between about 12.5 and about 13.5 weft stitches/cm, or between about 12.5 and about 13.0 weft stitches/cm.

The first surface may comprise between about 13.0 and about 15.0 weft stitches/cm, between about 13.0 and about 14.5 weft stitches/cm, between about 13.0 and about 14.0 weft stitches/cm, or between about 13.0 and about 13.5 weft stitches/cm.

The first surface may comprise between about 13.5 and about 15.0 weft stitches/cm, between about 13.5 and about 14.5 weft stitches/cm, or between about 13.5 and about 14.0 weft stitches/cm.

The first surface may comprise between about 14.0 and about 15.0 weft stitches/cm, or between about 14.0 and about 14.5 weft stitches/cm.

The first surface may comprise between about 14.5 and about 15.0 weft stitches/cm.

The first surface may comprise between about 0.1 and about 15.0 warp stitches/cm, between about 0.1 and about 14.5 warp stitches/cm, between about 0.1 and about 14.0 warp stitches/cm, between about 0.1 and about 13.5 warp stitches/cm, between about 0.1 and about 13.0 warp stitches/cm, between about 0.1 and about 12.5 warp stitches/cm, between about 0.1 and about 12.0 warp stitches/cm, between about 0.1 and about 11.5 warp stitches/cm, between about 0.1 and about 11.0 warp stitches/cm, between about 0.1 and about 10.5 warp stitches/cm, between about 0.1 and about 10.0 warp stitches/cm, between about 0.1 and about 9.5 warp stitches/cm, between about 0.1 and about 9.0 warp stitches/cm, between about 0.1 and about 8.5 warp stitches/cm, between about 0.1 and about 8.0 warp stitches/cm, between about 0.1 and about 7.5 warp stitches/cm, between about 0.1 and about 7.0 warp stitches/cm, between about 0.1 and about 6.5 warp stitches/cm, between about 0.1 and about 6.0 warp stitches/cm, between about 0.1 and about 5.5 warp stitches/cm, between about 0.1 and about 5.0 warp stitches/cm, between about 0.1 and about 4.5 warp stitches/cm, between about 0.1 and about 4.0 warp stitches/cm, between about 0.1 and about 3.5 warp stitches/cm, between about 0.1 and about 3.0 warp stitches/cm, between about 0.1 and about 2.5 warp stitches/cm, between about 0.1 and about 2.0 warp stitches/cm, between about 0.1 and about 1.5 warp stitches/cm, between about 0.1 and about 1.0 warp stitches/cm, between about 0.1 and about 0.8 warp stitches/cm, between about 0.1 and about 0.6 warp stitches/cm, between about 0.1 and about 0.4 warp stitches/cm, or between about 0.1 and about 0.2 warp stitches/cm.

The first surface may comprise between about 0.2 and about 15.0 warp stitches/cm, between about 0.2 and about 14.5 warp stitches/cm, between about 0.2 and about 14.0 warp stitches/cm, between about 0.2 and about 13.5 warp stitches/cm, between about 0.2 and about 13.0 warp stitches/cm, between about 0.2 and about 12.5 warp stitches/cm, between about 0.2 and about 12.0 warp stitches/cm, between about 0.2 and about 11.5 warp stitches/cm, between about 0.2 and about 11.0 warp stitches/cm, between about 0.2 and about 10.5 warp stitches/cm, between about 0.2 and about 10.0 warp stitches/cm, between about 0.2 and about 9.5 warp stitches/cm, between about 0.2 and about 9.0 warp stitches/cm, between about 0.2 and about 8.5 warp stitches/cm, between about 0.2 and about 8.0 warp stitches/cm, between about 0.2 and about 7.5 warp stitches/cm, between about 0.2 and about 7.0 warp stitches/cm, between about 0.2 and about 6.5 warp stitches/cm, between about 0.2 and about 6.0 warp stitches/cm, between about 0.2 and about 5.5 warp stitches/cm, between about 0.2 and about 5.0 warp stitches/cm, between about 0.2 and about 4.5 warp stitches/cm, between about 0.2 and about 4.0 warp stitches/cm, between about 0.2 and about 3.5 warp stitches/cm, between about 0.2 and about 3.0 warp stitches/cm, between about 0.2 and about 2.5 warp stitches/cm, between about 0.2 and about 2.0 warp stitches/cm, between about 0.2 and about 1.5 warp stitches/cm, between about 0.2 and about 1.0 warp stitches/cm, between about 0.2 and about 0.8 warp stitches/cm, between about 0.2 and about 0.6 warp stitches/cm, or between about 0.2 and about 0.4 warp stitches/cm.

The first surface may comprise between about 0.4 and about 15.0 warp stitches/cm, between about 0.4 and about 14.5 warp stitches/cm, between about 0.4 and about 14.0 warp stitches/cm, between about 0.4 and about 13.5 warp stitches/cm, between about 0.4 and about 13.0 warp stitches/cm, between about 0.4 and about 12.5 warp stitches/cm, between about 0.4 and about 12.0 warp stitches/cm, between about 0.4 and about 11.5 warp stitches/cm, between about 0.4 and about 11.0 warp stitches/cm, between about 0.4 and about 10.5 warp stitches/cm, between about 0.4 and about 10.0 warp stitches/cm, between about 0.4 and about 9.5 warp stitches/cm, between about 0.4 and about 9.0 warp stitches/cm, between about 0.4 and about 8.5 warp stitches/cm, between about 0.4 and about 8.0 warp stitches/cm, between about 0.4 and about 7.5 warp stitches/cm, between about 0.4 and about 7.0 warp stitches/cm, between about 0.4 and about 6.5 warp stitches/cm, between about 0.4 and about 6.0 warp stitches/cm, between about 0.4 and about 5.5 warp stitches/cm, between about 0.4 and about 5.0 warp stitches/cm, between about 0.4 and about 4.5 warp stitches/cm, between about 0.4 and about 4.0 warp stitches/cm, between about 0.4 and about 3.5 warp stitches/cm, between about 0.4 and about 3.0 warp stitches/cm, between about 0.4 and about 2.5 warp stitches/cm, between about 0.4 and about 2.0 warp stitches/cm, between about 0.4 and about 1.5 warp stitches/cm, between about 0.4 and about 1.0 warp stitches/cm, between about 0.4 and about 0.8 warp stitches/cm, or between about 0.4 and about 0.6 warp stitches/cm.

The first surface may comprise between about 0.6 and about 15.0 warp stitches/cm, between about 0.6 and about 14.5 warp stitches/cm, between about 0.6 and about 14.0 warp stitches/cm, between about 0.6 and about 13.5 warp stitches/cm, between about 0.6 and about 13.0 warp stitches/cm, between about 0.6 and about 12.5 warp stitches/cm, between about 0.6 and about 12.0 warp stitches/cm, between about 0.6 and about 11.5 warp stitches/cm, between about 0.6 and about 11.0 warp stitches/cm, between about 0.6 and about 10.5 warp stitches/cm, between about 0.6 and about 10.0 warp stitches/cm, between about 0.6 and about 9.5 warp stitches/cm, between about 0.6 and about 9.0 warp stitches/cm, between about 0.6 and about 8.5 warp stitches/cm, between about 0.6 and about 8.0 warp stitches/cm, between about 0.6 and about 7.5 warp stitches/cm, between about 0.6 and about 7.0 warp stitches/cm, between about 0.6 and about 6.5 warp stitches/cm, between about 0.6 and about 6.0 warp stitches/cm, between about 0.6 and about 5.5 warp stitches/cm, between about 0.6 and about 5.0 warp stitches/cm, between about 0.6 and about 4.5 warp stitches/cm, between about 0.6 and about 4.0 warp stitches/cm, between about 0.6 and about 3.5 warp stitches/cm, between about 0.6 and about 3.0 warp stitches/cm, between about 0.6 and about 2.5 warp stitches/cm, between about 0.6 and about 2.0 warp stitches/cm, between about 0.6 and about 1.5 warp stitches/cm, between about 0.6 and about 1.0 warp stitches/cm, or between about 0.6 and about 0.8 warp stitches/cm.

The first surface may comprise between about 0.8 and about 15.0 warp stitches/cm, between about 0.8 and about 14.5 warp stitches/cm, between about 0.8 and about 14.0 warp stitches/cm, between about 0.8 and about 13.5 warp stitches/cm, between about 0.8 and about 13.0 warp stitches/cm, between about 0.8 and about 12.5 warp stitches/cm, between about 0.8 and about 12.0 warp stitches/cm, between about 0.8 and about 11.5 warp stitches/cm, between about 0.8 and about 11.0 warp stitches/cm, between about 0.8 and about 10.5 warp stitches/cm, between about 0.8 and about 10.0 warp stitches/cm, between about 0.8 and about 9.5 warp stitches/cm, between about 0.8 and about 9.0 warp stitches/cm, between about 0.8 and about 8.5 warp stitches/cm, between about 0.8 and about 8.0 warp stitches/cm, between about 0.8 and about 7.5 warp stitches/cm, between about 0.8 and about 7.0 warp stitches/cm, between about 0.8 and about 6.5 warp stitches/cm, between about 0.8 and about 6.0 warp stitches/cm, between about 0.8 and about 5.5 warp stitches/cm, between about 0.8 and about 5.0 warp stitches/cm, between about 0.8 and about 4.5 warp stitches/cm, between about 0.8 and about 4.0 warp stitches/cm, between about 0.8 and about 3.5 warp stitches/cm, between about 0.8 and about 3.0 warp stitches/cm, between about 0.8 and about 2.5 warp stitches/cm, between about 0.8 and about 2.0 warp stitches/cm, between about 0.8 and about 1.5 warp stitches/cm, or between about 0.8 and about 1.0 warp stitches/cm.

The first surface may comprise between about 1.0 and about 15.0 warp stitches/cm, between about 1.0 and about 14.5 warp stitches/cm, between about 1.0 and about 14.0 warp stitches/cm, between about 1.0 and about 13.5 warp stitches/cm, between about 1.0 and about 13.0 warp stitches/cm, between about 1.0 and about 12.5 warp stitches/cm, between about 1.0 and about 12.0 warp stitches/cm, between about 1.0 and about 11.5 warp stitches/cm, between about 1.0 and about 11.0 warp stitches/cm, between about 1.0 and about 10.5 warp stitches/cm, between about 1.0 and about 10.0 warp stitches/cm, between about 1.0 and about 9.5 warp stitches/cm, between about 1.0 and about 9.0 warp stitches/cm, between about 1.0 and about 8.5 warp stitches/cm, between about 1.0 and about 8.0 warp stitches/cm, between about 1.0 and about 7.5 warp stitches/cm, between about 1.0 and about 7.0 warp stitches/cm, between about 1.0 and about 6.5 warp stitches/cm, between about 1.0 and about 6.0 warp stitches/cm, between about 1.0 and about 5.5 warp stitches/cm, between about 1.0 and about 5.0 warp stitches/cm, between about 1.0 and about 4.5 warp stitches/cm, between about 1.0 and about 4.0 warp stitches/cm, between about 1.0 and about 3.5 warp stitches/cm, between about 1.0 and about 3.0 warp stitches/cm, between about 1.0 and about 2.5 warp stitches/cm, between about 1.0 and about 2.0 warp stitches/cm, or between about 1.0 and about 1.5 warp stitches/cm.

The first surface may comprise between about 1.5 and about 15.0 warp stitches/cm, between about 1.5 and about 14.5 warp stitches/cm, between about 1.5 and about 14.0 warp stitches/cm, between about 1.5 and about 13.5 warp stitches/cm, between about 1.5 and about 13.0 warp stitches/cm, between about 1.5 and about 12.5 warp stitches/cm, between about 1.5 and about 12.0 warp stitches/cm, between about 1.5 and about 11.5 warp stitches/cm, between about 1.5 and about 11.0 warp stitches/cm, between about 1.5 and about 10.5 warp stitches/cm, between about 1.5 and about 10.0 warp stitches/cm, between about 1.5 and about 9.5 warp stitches/cm, between about 1.5 and about 9.0 warp stitches/cm, between about 1.5 and about 8.5 warp stitches/cm, between about 1.5 and about 8.0 warp stitches/cm, between about 1.5 and about 7.5 warp stitches/cm, between about 1.5 and about 7.0 warp stitches/cm, between about 1.5 and about 6.5 warp stitches/cm, between about 1.5 and about 6.0 warp stitches/cm, between about 1.5 and about 5.5 warp stitches/cm, between about 1.5 and about 5.0 warp stitches/cm, between about 1.5 and about 4.5 warp stitches/cm, between about 1.5 and about 4.0 warp stitches/cm, between about 1.5 and about 3.5 warp stitches/cm, between about 1.5 and about 3.0 warp stitches/cm, between about 1.5 and about 2.5 warp stitches/cm, or between about 1.5 and about 2.0 warp stitches/cm.

The first surface may comprise between about 2.0 and about 15.0 warp stitches/cm, between about 2.0 and about 14.5 warp stitches/cm, between about 2.0 and about 14.0 warp stitches/cm, between about 2.0 and about 13.5 warp stitches/cm, between about 2.0 and about 13.0 warp stitches/cm, between about 2.0 and about 12.5 warp stitches/cm, between about 2.0 and about 12.0 warp stitches/cm, between about 2.0 and about 11.5 warp stitches/cm, between about 2.0 and about 11.0 warp stitches/cm, between about 2.0 and about 10.5 warp stitches/cm, between about 2.0 and about 10.0 warp stitches/cm, between about 2.0 and about 9.5 warp stitches/cm, between about 2.0 and about 9.0 warp stitches/cm, between about 2.0 and about 8.5 warp stitches/cm, between about 2.0 and about 8.0 warp stitches/cm, between about 2.0 and about 7.5 warp stitches/cm, between about 2.0 and about 7.0 warp stitches/cm, between about 2.0 and about 6.5 warp stitches/cm, between about 2.0 and about 6.0 warp stitches/cm, between about 2.0 and about 5.5 warp stitches/cm, between about 2.0 and about 5.0 warp stitches/cm, between about 2.0 and about 4.5 warp stitches/cm, between about 2.0 and about 4.0 warp stitches/cm, between about 2.0 and about 3.5 warp stitches/cm, between about 2.0 and about 3.0 warp stitches/cm, or between about 2.0 and about 2.5 warp stitches/cm.

The first surface may comprise between about 2.5 and about 15.0 warp stitches/cm, between about 2.5 and about 14.5 warp stitches/cm, between about 2.5 and about 14.0 warp stitches/cm, between about 2.5 and about 13.5 warp stitches/cm, between about 2.5 and about 13.0 warp stitches/cm, between about 2.5 and about 12.5 warp stitches/cm, between about 2.5 and about 12.0 warp stitches/cm, between about 2.5 and about 11.5 warp stitches/cm, between about 2.5 and about 11.0 warp stitches/cm, between about 2.5 and about 10.5 warp stitches/cm, between about 2.5 and about 10.0 warp stitches/cm, between about 2.5 and about 9.5 warp stitches/cm, between about 2.5 and about 9.0 warp stitches/cm, between about 2.5 and about 8.5 warp stitches/cm, between about 2.5 and about 8.0 warp stitches/cm, between about 2.5 and about 7.5 warp stitches/cm, between about 2.5 and about 7.0 warp stitches/cm, between about 2.5 and about 6.5 warp stitches/cm, between about 2.5 and about 6.0 warp stitches/cm, between about 2.5 and about 5.5 warp stitches/cm, between about 2.5 and about 5.0 warp stitches/cm, between about 2.5 and about 4.5 warp stitches/cm, between about 2.5 and about 4.0 warp stitches/cm, between about 2.5 and about 3.5 warp stitches/cm, or between about 2.5 and about 3.0 warp stitches/cm.

The first surface may comprise between about 3.0 and about 15.0 warp stitches/cm, between about 3.0 and about 14.5 warp stitches/cm, between about 3.0 and about 14.0 warp stitches/cm, between about 3.0 and about 13.5 warp stitches/cm, between about 3.0 and about 13.0 warp stitches/ cm, between about 3.0 and about 12.5 warp stitches/cm, between about 3.0 and about 12.0 warp stitches/cm, between about 3.0 and about 11.5 warp stitches/cm, between about 3.0 and about 11.0 warp stitches/cm, between about 3.0 and about 10.5 warp stitches/cm, between about 3.0 and about 10.0 warp stitches/cm, between about 3.0 and about 9.5 warp stitches/cm, between about 3.0 and about 9.0 warp stitches/cm, between about 3.0 and about 8.5 warp stitches/cm, between about 3.0 and about 8.0 warp stitches/cm, between about 3.0 and about 7.5 warp stitches/cm, between about 3.0 and about 7.0 warp stitches/cm, between about 3.0 and about 6.5 warp stitches/cm, between about 3.0 and about 6.0 warp stitches/cm, between about 3.0 and about 5.5 warp stitches/cm, between about 3.0 and about 5.0 warp stitches/cm, between about 3.0 and about 4.5 warp stitches/cm, between about 3.0 and about 4.0 warp stitches/cm, or between about 3.0 and about 3.5 warp stitches/cm.

The first surface may comprise between about 3.5 and about 15.0 warp stitches/cm, between about 3.5 and about 14.5 warp stitches/cm, between about 3.5 and about 14.0 warp stitches/cm, between about 3.5 and about 13.5 warp stitches/cm, between about 3.5 and about 13.0 warp stitches/cm, between about 3.5 and about 12.5 warp stitches/cm, between about 3.5 and about 11.0 warp stitches/cm, between about 3.5 and about 11.5 warp stitches/cm, between about 3.5 and about 11.0 warp stitches/cm, between about 3.5 and about 10.5 warp stitches/cm, between about 3.5 and about 10.0 warp stitches/cm, between about 3.5 and about 9.5 warp stitches/cm, between about 3.5 and about 9.0 warp stitches/cm, between about 3.5 and about 8.5 warp stitches/cm, between about 3.5 and about 8.0 warp stitches/cm, between about 3.5 and about 7.5 warp stitches/cm, between about 3.5 and about 7.0 warp stitches/cm, between about 3.5 and about 6.5 warp stitches/cm, between about 3.5 and about 6.0 warp stitches/cm, between about 3.5 and about 5.5 warp stitches/cm, between about 3.5 and about 5.0 warp stitches/cm, between about 3.5 and about 4.5 warp stitches/cm, or between about 3.5 and about 4.0 warp stitches/cm.

The first surface may comprise between about 4.0 and about 15.0 warp stitches/cm, between about 4.0 and about 14.5 warp stitches/cm, between about 4.0 and about 14.0 warp stitches/cm, between about 4.0 and about 13.5 warp stitches/cm, between about 4.0 and about 13.0 warp stitches/cm, between about 4.0 and about 12.5 warp stitches/cm, between about 4.0 and about 12.0 warp stitches/cm, between about 4.0 and about 11.5 warp stitches/cm, between about 4.0 and about 11.0 warp stitches/cm, between about 4.0 and about 10.5 warp stitches/cm, between about 4.0 and about 10.0 warp stitches/cm, between about 4.0 and about 9.5 warp stitches/cm, between about 4.0 and about 9.0 warp stitches/cm, between about 4.0 and about 8.5 warp stitches/cm, between about 4.0 and about 8.0 warp stitches/cm, between about 4.0 and about 7.5 warp stitches/cm, between about 4.0 and about 7.0 warp stitches/cm, between about 4.0 and about 6.5 warp stitches/cm, between about 4.0 and about 6.0 warp stitches/cm, between about 4.0 and about 5.5 warp stitches/cm, between about 4.0 and about 5.0 warp stitches/cm, or between about 4.0 and about 4.5 warp stitches/cm.

The first surface may comprise between about 4.5 and about 15.0 warp stitches/cm, between about 4.5 and about 14.5 warp stitches/cm, between about 4.5 and about 14.0 warp stitches/cm, between about 4.5 and about 13.5 warp stitches/cm, between about 4.5 and about 13.0 warp stitches/cm, between about 4.5 and about 12.5 warp stitches/cm, between about 4.5 and about 12.0 warp stitches/cm, between about 4.5 and about 11.5 warp stitches/cm, between about 4.5 and about 11.0 warp stitches/cm, between about 4.5 and about 10.5 warp stitches/cm, between about 4.5 and about 10.0 warp stitches/cm, between about 4.5 and about 9.5 warp stitches/cm, between about 4.5 and about 9.0 warp stitches/cm, between about 4.5 and about 8.5 warp stitches/cm, between about 4.5 and about 8.0 warp stitches/cm, between about 4.5 and about 7.5 warp stitches/cm, between about 4.5 and about 7.0 warp stitches/cm, between about 4.5 and about 6.5 warp stitches/cm, between about 4.5 and about 6.0 warp stitches/cm, between about 4.5 and about 5.5 warp stitches/cm, or between about 4.5 and about 5.0 warp stitches/cm.

The first surface may comprise between about 5.0 and about 15.0 warp stitches/cm, between about 5.0 and about 14.5 warp stitches/cm, between about 5.0 and about 14.0 warp stitches/cm, between about 5.0 and about 13.5 warp stitches/cm, between about 5.0 and about 13.0 warp stitches/cm, between about 5.0 and about 12.5 warp stitches/cm, between about 5.0 and about 12.0 warp stitches/cm, between about 5.0 and about 11.5 warp stitches/cm, between about 5.0 and about 11.0 warp stitches/cm, between about 5.0 and about 10.5 warp stitches/cm, between about 5.0 and about 10.0 warp stitches/cm, between about 5.0 and about 9.5 warp stitches/cm, between about 5.0 and about 9.0 warp stitches/cm, between about 5.0 and about 8.5 warp stitches/cm, between about 5.0 and about 8.0 warp stitches/cm, between about 5.0 and about 7.5 warp stitches/cm, between about 5.0 and about 7.0 warp stitches/cm, between about 5.0 and about 6.5 warp stitches/cm, between about 5.0 and about 6.0 warp stitches/cm, or between about 5.0 and about 5.5 warp stitches/cm.

The first surface may comprise between about 5.5 and about 15.0 warp stitches/cm, between about 5.5 and about 14.5 warp stitches/cm, between about 5.5 and about 14.0 warp stitches/cm, between about 5.5 and about 13.5 warp stitches/cm, between about 5.5 and about 13.0 warp stitches/cm, between about 5.5 and about 12.5 warp stitches/cm, between about 5.5 and about 12.0 warp stitches/cm, between about 5.5 and about 11.5 warp stitches/cm, between about 5.5 and about 11.0 warp stitches/cm, between about 5.5 and about 10.5 warp stitches/cm, between about 5.5 and about 10.0 warp stitches/cm, between about 5.5 and about 9.5 warp stitches/cm, between about 5.5 and about 9.0 warp stitches/cm, between about 5.5 and about 8.5 warp stitches/cm, between about 5.5 and about 8.0 warp stitches/cm, between about 5.5 and about 7.5 warp stitches/cm, between about 5.5 and about 7.0 warp stitches/cm, between about 5.5 and about 6.5 warp stitches/cm, or between about 5.5 and about 6.0 warp stitches/cm.

The first surface may comprise between about 6.0 and about 15.0 warp stitches/cm, between about 6.0 and about 14.5 warp stitches/cm, between about 6.0 and about 14.0 warp stitches/cm, between about 6.0 and about 13.5 warp stitches/cm, between about 6.0 and about 13.0 warp stitches/cm, between about 6.0 and about 12.5 warp stitches/cm, between about 6.0 and about 12.0 warp stitches/cm, between about 6.0 and about 11.5 warp stitches/cm, between about 6.0 and about 11.0 warp stitches/cm, between about 6.0 and about 10.5 warp stitches/cm, between about 6.0 and about 10.0 warp stitches/cm, between about 6.0 and about 9.5 warp stitches/cm, between about 6.0 and about 9.0 warp stitches/cm, between about 6.0 and about 8.5 warp stitches/cm, between about 6.0 and about 8.0 warp stitches/cm, between about 6.0 and about 7.5 warp stitches/cm, between about 6.0 and about 7.0 warp stitches/cm, or between about 6.0 and about 6.5 warp stitches/cm.

The first surface may comprise between about 6.5 and about 15.0 warp stitches/cm, between about 6.5 and about 14.5 warp stitches/cm, between about 6.5 and about 14.0 warp stitches/cm, between about 6.5 and about 13.5 warp stitches/cm, between about 6.5 and about 13.0 warp stitches/cm, between about 6.5 and about 12.5 warp stitches/cm, between about 6.5 and about 12.0 warp stitches/cm, between about 6.5 and about 11.5 warp stitches/cm, between about 6.5 and about 11.0 warp stitches/cm, between about 6.5 and about 10.5 warp stitches/cm, between about 6.5 and about 10.0 warp stitches/cm, between about 6.5 and about 9.5 warp stitches/cm, between about 6.5 and about 9.0 warp stitches/cm, between about 6.5 and about 8.5 warp stitches/cm, between about 6.5 and about 8.0 warp stitches/cm, between about 6.5 and about 7.5 warp stitches/cm, or between about 6.5 and about 7.0 warp stitches/cm.

The first surface may comprise between about 7.0 and about 15.0 warp stitches/cm, between about 7.0 and about 14.5 warp stitches/cm, between about 7.0 and about 14.0 warp stitches/cm, between about 7.0 and about 13.5 warp stitches/cm, between about 7.0 and about 13.0 warp stitches/cm, between about 7.0 and about 12.5 warp stitches/cm, between about 7.0 and about 12.0 warp stitches/cm, between about 7.0 and about 11.5 warp stitches/cm, between about 7.0 and about 11.0 warp stitches/cm, between about 7.0 and about 10.5 warp stitches/cm, between about 7.0 and about 10.0 warp stitches/cm, between about 7.0 and about 9.5 warp stitches/cm, between about 7.0 and about 9.0 warp stitches/cm, between about 7.0 and about 8.5 warp stitches/cm, between about 7.0 and about 8.0 warp stitches/cm, or between about 7.0 and about 7.5 warp stitches/cm.

The first surface may comprise between about 7.5 and about 15.0 warp stitches/cm, between about 7.5 and about 14.5 warp stitches/cm, between about 7.5 and about 14.0 warp stitches/cm, between about 7.5 and about 13.5 warp stitches/cm, between about 7.5 and about 13.0 warp stitches/cm, between about 7.5 and about 12.5 warp stitches/cm, between about 7.5 and about 12.0 warp stitches/cm, between about 7.5 and about 11.5 warp stitches/cm, between about 7.5 and about 11.0 warp stitches/cm, between about 7.5 and about 10.5 warp stitches/cm, between about 7.5 and about 10.0 warp stitches/cm, between about 7.5 and about 9.5 warp stitches/cm, between about 7.5 and about 9.0 warp stitches/cm, between about 7.5 and about 8.5 warp stitches/cm, or between about 7.5 and about 8.0 warp stitches/cm.

The first surface may comprise between about 8.0 and about 15.0 warp stitches/cm, between about 8.0 and about 14.5 warp stitches/cm, between about 8.0 and about 14.0 warp stitches/cm, between about 8.0 and about 13.5 warp stitches/cm, between about 8.0 and about 13.0 warp stitches/cm, between about 8.0 and about 12.5 warp stitches/cm, between about 8.0 and about 12.0 warp stitches/cm, between about 8.0 and about 11.5 warp stitches/cm, between about 8.0 and about 11.0 warp stitches/cm, between about 8.0 and about 10.5 warp stitches/cm, between about 8.0 and about 10.0 warp stitches/cm, between about 8.0 and about 9.5 warp stitches/cm, between about 8.0 and about 9.0 warp stitches/cm, or between about 8.0 and about 8.5 warp stitches/cm.

The first surface may comprise between about 8.5 and about 15.0 warp stitches/cm, between about 8.5 and about 14.5 warp stitches/cm, between about 8.5 and about 14.0 warp stitches/cm, between about 8.5 and about 13.5 warp stitches/cm, between about 8.5 and about 13.0 warp stitches/cm, between about 8.5 and about 12.5 warp stitches/cm, between about 8.5 and about 12.0 warp stitches/cm, between about 8.5 and about 11.5 warp stitches/cm, between about 8.5 and about 11.0 warp stitches/cm, between about 8.5 and about 10.5 warp stitches/cm, between about 8.5 and about 10.0 warp stitches/cm, between about 8.5 and about 9.5 warp stitches/cm, or between about 8.5 and about 9.0 warp stitches/cm.

The first surface may comprise between about 9.0 and about 15.0 warp stitches/cm, between about 9.0 and about 14.5 warp stitches/cm, between about 9.0 and about 14.0 warp stitches/cm, between about 9.0 and about 13.5 warp stitches/cm, between about 9.0 and about 13.0 warp stitches/cm, between about 9.0 and about 12.5 warp stitches/cm, between about 9.0 and about 12.0 warp stitches/cm, between about 9.0 and about 11.5 warp stitches/cm, between about 9.0 and about 11.0 warp stitches/cm, between about 9.0 and about 10.5 warp stitches/cm, between about 9.0 and about 10.0 warp stitches/cm, or between about 9.0 and about 9.5 warp stitches/cm.

The first surface may comprise between about 9.5 and about 15.0 warp stitches/cm, between about 9.5 and about 14.5 warp stitches/cm, between about 9.5 and about 14.0 warp stitches/cm, between about 9.5 and about 13.5 warp stitches/cm, between about 9.5 and about 13.0 warp stitches/cm, between about 9.5 and about 12.5 warp stitches/cm, between about 9.5 and about 12.0 warp stitches/cm, between about 9.5 and about 11.5 warp stitches/cm, between about 9.5 and about 11.0 warp stitches/cm, between about 9.5 and about 10.5 warp stitches/cm, or between about 9.5 and about 10.0 warp stitches/cm.

The first surface may comprise between about 10.0 and about 15.0 warp stitches/cm, between about 10.0 and about 14.5 warp stitches/cm, between about 10.0 and about 14.0 warp stitches/cm, between about 10.0 and about 13.5 warp stitches/cm, between about 10.0 and about 13.0 warp stitches/cm, between about 10.0 and about 12.5 warp stitches/cm, between about 10.0 and about 12.0 warp stitches/cm, between about 10.0 and about 11.5 warp stitches/cm, between about 10.0 and about 11.0 warp stitches/cm, or between about 10.0 and about 10.5 warp stitches/cm.

The first surface may comprise between about 10.5 and about 15.0 warp stitches/cm, between about 10.5 and about 14.5 warp stitches/cm, between about 10.5 and about 14.0 warp stitches/cm, between about 10.5 and about 13.5 warp stitches/cm, between about 10.5 and about 13.0 warp stitches/cm, between about 10.5 and about 12.5 warp stitches/cm, between about 10.5 and about 12.0 warp stitches/cm, between about 10.5 and about 11.5 warp stitches/cm, or between about 10.5 and about 11.0 warp stitches/cm.

The first surface may comprise between about 11.0 and about 15.0 warp stitches/cm, between about 11.0 and about 14.5 warp stitches/cm, between about 11.0 and about 14.0 warp stitches/cm, between about 11.0 and about 13.5 warp stitches/cm, between about 11.0 and about 13.0 warp stitches/cm, between about 11.0 and about 12.5 warp stitches/cm, between about 11.0 and about 12.0 warp stitches/cm, or between about 11.0 and about 11.5 warp stitches/cm.

The first surface may comprise between about 11.5 and about 15.0 warp stitches/cm, between about 11.5 and about 14.5 warp stitches/cm, between about 11.5 and about 14.0 warp stitches/cm, between about 11.5 and about 13.5 warp stitches/cm, between about 11.5 and about 13.0 warp stitches/cm, between about 11.5 and about 12.5 warp stitches/cm, or between about 11.5 and about 12.0 warp stitches/cm.

The first surface may comprise between about 12.0 and about 15.0 warp stitches/cm, between about 12.0 and about 14.5 warp stitches/cm, between about 12.0 and about 14.0 warp stitches/cm, between about 12.0 and about 13.5 warp stitches/cm, between about 12.0 and about 13.0 warp stitches/cm, or between about 12.0 and about 12.5 warp stitches/cm.

The first surface may comprise between about 12.5 and about 15.0 warp stitches/cm, between about 12.5 and about 14.5 warp stitches/cm, between about 12.5 and about 14.0 warp stitches/cm, between about 12.5 and about 13.5 warp stitches/cm, or between about 12.5 and about 13.0 warp stitches/cm.

The first surface may comprise between about 13.0 and about 15.0 warp stitches/cm, between about 13.0 and about 14.5 warp stitches/cm, between about 13.0 and about 14.0 warp stitches/cm, or between about 13.0 and about 13.5 warp stitches/cm.

The first surface may comprise between about 13.5 and about 15.0 warp stitches/cm, between about 13.5 and about 14.5 warp stitches/cm, or between about 13.5 and about 14.0 warp stitches/cm.

The first surface may comprise between about 14.0 and about 15.0 warp stitches/cm, or between about 14.0 and about 14.5 warp stitches/cm.

The first surface may comprise between about 14.5 and about 15.0 warp stitches/cm.

The second surface may comprise between about 0.1 and about 15.0 weft stitches/cm, between about 0.1 and about 14.5 weft stitches/cm, between about 0.1 and about 14.0 weft stitches/cm, between about 0.1 and about 13.5 weft stitches/cm, between about 0.1 and about 13.0 weft stitches/cm, between about 0.1 and about 12.5 weft stitches/cm, between about 0.1 and about 12.0 weft stitches/cm, between about 0.1 and about 11.5 weft stitches/cm, between about 0.1 and about 11.0 weft stitches/cm, between about 0.1 and about 10.5 weft stitches/cm, between about 0.1 and about 10.0 weft stitches/cm, between about 0.1 and about 9.5 weft stitches/cm, between about 0.1 and about 9.0 weft stitches/cm, between about 0.1 and about 8.5 weft stitches/cm, between about 0.1 and about 8.0 weft stitches/cm, between about 0.1 and about 7.5 weft stitches/cm, between about 0.1 and about 7.0 weft stitches/cm, between about 0.1 and about 6.5 weft stitches/cm, between about 0.1 and about 6.0 weft stitches/cm, between about 0.1 and about 5.5 weft stitches/cm, between about 0.1 and about 5.0 weft stitches/cm, between about 0.1 and about 4.5 weft stitches/cm, between about 0.1 and about 4.0 weft stitches/cm, between about 0.1 and about 3.5 weft stitches/cm, between about 0.1 and about 3.0 weft stitches/cm, between about 0.1 and about 2.5 weft stitches/cm, between about 0.1 and about 2.0 weft stitches/cm, between about 0.1 and about 1.5 weft stitches/cm, between about 0.1 and about 1.0 weft stitches/cm, between about 0.1 and about 0.8 weft stitches/cm, between about 0.1 and about 0.6 weft stitches/cm, between about 0.1 and about 0.4 weft stitches/cm, or between about 0.1 and about 0.2 weft stitches/cm.

The second surface may comprise between about 0.2 and about 15.0 weft stitches/cm, between about 0.2 and about 14.5 weft stitches/cm, between about 0.2 and about 14.0 weft stitches/cm, between about 0.2 and about 13.5 weft stitches/cm, between about 0.2 and about 13.0 weft stitches/cm, between about 0.2 and about 12.5 weft stitches/cm, between about 0.2 and about 12.0 weft stitches/cm, between about 0.2 and about 11.5 weft stitches/cm, between about 0.2 and about 11.0 weft stitches/cm, between about 0.2 and about 10.5 weft stitches/cm, between about 0.2 and about 10.0 weft stitches/cm, between about 0.2 and about 9.5 weft stitches/cm, between about 0.2 and about 9.0 weft stitches/cm, between about 0.2 and about 8.5 weft stitches/cm, between about 0.2 and about 8.0 weft stitches/cm, between about 0.2 and about 7.5 weft stitches/cm, between about 0.2 and about 7.0 weft stitches/cm, between about 0.2 and about 6.5 weft stitches/cm, between about 0.2 and about 6.0 weft stitches/cm, between about 0.2 and about 5.5 weft stitches/cm, between about 0.2 and about 5.0 weft stitches/cm, between about 0.2 and about 4.5 weft stitches/cm, between about 0.2 and about 4.0 weft stitches/cm, between about 0.2 and about 3.5 weft stitches/cm, between about 0.2 and about 3.0 weft stitches/cm, between about 0.2 and about 2.5 weft stitches/cm, between about 0.2 and about 2.0 weft stitches/cm, between about 0.2 and about 1.5 weft stitches/cm, between about 0.2 and about 1.0 weft stitches/cm, between about 0.2 and about 0.8 weft stitches/cm, between about 0.2 and about 0.6 weft stitches/cm, or between about 0.2 and about 0.4 weft stitches/cm.

The second surface may comprise between about 0.4 and about 15.0 weft stitches/cm, between about 0.4 and about 14.5 weft stitches/cm, between about 0.4 and about 14.0 weft stitches/cm, between about 0.4 and about 13.5 weft stitches/cm, between about 0.4 and about 13.0 weft stitches/cm, between about 0.4 and about 12.5 weft stitches/cm, between about 0.4 and about 12.0 weft stitches/cm, between about 0.4 and about 11.5 weft stitches/cm, between about 0.4 and about 11.0 weft stitches/cm, between about 0.4 and about 10.5 weft stitches/cm, between about 0.4 and about 10.0 weft stitches/cm, between about 0.4 and about 9.5 weft stitches/cm, between about 0.4 and about 9.0 weft stitches/cm, between about 0.4 and about 8.5 weft stitches/cm, between about 0.4 and about 8.0 weft stitches/cm, between about 0.4 and about 7.5 weft stitches/cm, between about 0.4 and about 7.0 weft stitches/cm, between about 0.4 and about 6.5 weft stitches/cm, between about 0.4 and about 6.0 weft stitches/cm, between about 0.4 and about 5.5 weft stitches/cm, between about 0.4 and about 5.0 weft stitches/cm, between about 0.4 and about 4.5 weft stitches/cm, between about 0.4 and about 4.0 weft stitches/cm, between about 0.4 and about 3.5 weft stitches/cm, between about 0.4 and about 3.0 weft stitches/cm, between about 0.4 and about 2.5 weft stitches/cm, between about 0.4 and about 2.0 weft stitches/cm, between about 0.4 and about 1.5 weft stitches/cm, between about 0.4 and about 1.0 weft stitches/cm, between about 0.4 and about 0.8 weft stitches/cm, or between about 0.4 and about 0.6 weft stitches/cm.

The second surface may comprise between about 0.6 and about 15.0 weft stitches/cm, between about 0.6 and about 14.5 weft stitches/cm, between about 0.6 and about 14.0 weft stitches/cm, between about 0.6 and about 13.5 weft stitches/cm, between about 0.6 and about 13.0 weft stitches/cm, between about 0.6 and about 12.5 weft stitches/cm, between about 0.6 and about 12.0 weft stitches/cm, between about 0.6 and about 11.5 weft stitches/cm, between about 0.6 and about 11.0 weft stitches/cm, between about 0.6 and about 10.5 weft stitches/cm, between about 0.6 and about 10.0 weft stitches/cm, between about 0.6 and about 9.5 weft stitches/cm, between about 0.6 and about 9.0 weft stitches/cm, between about 0.6 and about 8.5 weft stitches/cm, between about 0.6 and about 8.0 weft stitches/cm, between about 0.6 and about 7.5 weft stitches/cm, between about 0.6 and about 7.0 weft stitches/cm, between about 0.6 and about 6.5 weft stitches/cm, between about 0.6 and about 6.0 weft stitches/cm, between about 0.6 and about 5.5 weft stitches/cm, between about 0.6 and about 5.0 weft stitches/cm, between about 0.6 and about 4.5 weft stitches/cm, between about 0.6 and about 4.0 weft stitches/cm, between about 0.6 and about 3.5 weft stitches/cm, between about 0.6 and about 3.0 weft stitches/cm, between about 0.6 and about 2.5 weft stitches/cm, between about 0.6 and about 2.0 weft stitches/cm, between about 0.6 and about 1.5 weft stitches/cm, between about 0.6 and about 1.0 weft stitches/cm, or between about 0.6 and about 0.8 weft stitches/cm.

The second surface may comprise between about 0.8 and about 15.0 weft stitches/cm, between about 0.8 and about 14.5 weft stitches/cm, between about 0.8 and about 14.0 weft stitches/cm, between about 0.8 and about 13.5 weft stitches/cm, between about 0.8 and about 13.0 weft stitches/cm, between about 0.8 and about 12.5 weft stitches/cm, between about 0.8 and about 12.0 weft stitches/cm, between about 0.8 and about 11.5 weft stitches/cm, between about 0.8 and about 11.0 weft stitches/cm, between about 0.8 and about 10.5 weft stitches/cm, between about 0.8 and about 10.0 weft stitches/cm, between about 0.8 and about 9.5 weft stitches/cm, between about 0.8 and about 9.0 weft stitches/cm, between about 0.8 and about 8.5 weft stitches/cm, between about 0.8 and about 8.0 weft stitches/cm, between about 0.8 and about 7.5 weft stitches/cm, between about 0.8 and about 7.0 weft stitches/cm, between about 0.8 and about 6.5 weft stitches/cm, between about 0.8 and about 6.0 weft stitches/cm, between about 0.8 and about 5.5 weft stitches/cm, between about 0.8 and about 5.0 weft stitches/cm, between about 0.8 and about 4.5 weft stitches/cm, between about 0.8 and about 4.0 weft stitches/cm, between about 0.8 and about 3.5 weft stitches/cm, between about 0.8 and about 3.0 weft stitches/cm, between about 0.8 and about 2.5 weft stitches/cm, between about 0.8 and about 2.0 weft stitches/cm, between about 0.8 and about 1.5 weft stitches/cm, or between about 0.8 and about 1.0 weft stitches/cm.

The second surface may comprise between about 1.0 and about 15.0 weft stitches/cm, between about 1.0 and about 14.5 weft stitches/cm, between about 1.0 and about 14.0 weft stitches/cm, between about 1.0 and about 13.5 weft stitches/cm, between about 1.0 and about 13.0 weft stitches/cm, between about 1.0 and about 12.5 weft stitches/cm, between about 1.0 and about 12.0 weft stitches/cm, between about 1.0 and about 11.5 weft stitches/cm, between about 1.0 and about 11.0 weft stitches/cm, between about 1.0 and about 10.5 weft stitches/cm, between about 1.0 and about 10.0 weft stitches/cm, between about 1.0 and about 9.5 weft stitches/cm, between about 1.0 and about 9.0 weft stitches/cm, between about 1.0 and about 8.5 weft stitches/cm, between about 1.0 and about 8.0 weft stitches/cm, between about 1.0 and about 7.5 weft stitches/cm, between about 1.0 and about 7.0 weft stitches/cm, between about 1.0 and about 6.5 weft stitches/cm, between about 1.0 and about 6.0 weft stitches/cm, between about 1.0 and about 5.5 weft stitches/cm, between about 1.0 and about 5.0 weft stitches/cm, between about 1.0 and about 4.5 weft stitches/cm, between about 1.0 and about 4.0 weft stitches/cm, between about 1.0 and about 3.5 weft stitches/cm, between about 1.0 and about 3.0 weft stitches/cm, between about 1.0 and about 2.5 weft stitches/cm, between about 1.0 and about 2.0 weft stitches/cm, or between about 1.0 and about 1.5 weft stitches/cm.

The second surface may comprise between about 1.5 and about 15.0 weft stitches/cm, between about 1.5 and about 14.5 weft stitches/cm, between about 1.5 and about 14.0 weft stitches/cm, between about 1.5 and about 13.5 weft stitches/cm, between about 1.5 and about 13.0 weft stitches/cm, between about 1.5 and about 12.5 weft stitches/cm, between about 1.5 and about 12.0 weft stitches/cm, between about 1.5 and about 11.5 weft stitches/cm, between about 1.5 and about 11.0 weft stitches/cm, between about 1.5 and about 10.5 weft stitches/cm, between about 1.5 and about 10.0 weft stitches/cm, between about 1.5 and about 9.5 weft stitches/cm, between about 1.5 and about 9.0 weft stitches/cm, between about 1.5 and about 8.5 weft stitches/cm, between about 1.5 and about 8.0 weft stitches/cm, between about 1.5 and about 7.5 weft stitches/cm, between about 1.5 and about 7.0 weft stitches/cm, between about 1.5 and about 6.5 weft stitches/cm, between about 1.5 and about 6.0 weft stitches/cm, between about 1.5 and about 5.5 weft stitches/cm, between about 1.5 and about 5.0 weft stitches/cm, between about 1.5 and about 4.5 weft stitches/cm, between about 1.5 and about 4.0 weft stitches/cm, between about 1.5 and about 3.5 weft stitches/cm, between about 1.5 and about 3.0 weft stitches/cm, between about 1.5 and about 2.5 weft stitches/cm, or between about 1.5 and about 2.0 weft stitches/cm.

The second surface may comprise between about 2.0 and about 15.0 weft stitches/cm, between about 2.0 and about 14.5 weft stitches/cm, between about 2.0 and about 14.0 weft stitches/cm, between about 2.0 and about 13.5 weft stitches/cm, between about 2.0 and about 13.0 weft stitches/cm, between about 2.0 and about 12.5 weft stitches/cm, between about 2.0 and about 12.0 weft stitches/cm, between about 2.0 and about 11.5 weft stitches/cm, between about 2.0 and about 11.0 weft stitches/cm, between about 2.0 and about 10.5 weft stitches/cm, between about 2.0 and about 10.0 weft stitches/cm, between about 2.0 and about 9.5 weft stitches/cm, between about 2.0 and about 9.0 weft stitches/cm, between about 2.0 and about 8.5 weft stitches/cm, between about 2.0 and about 8.0 weft stitches/cm, between about 2.0 and about 7.5 weft stitches/cm, between about 2.0 and about 7.0 weft stitches/cm, between about 2.0 and about 6.5 weft stitches/cm, between about 2.0 and about 6.0 weft stitches/cm, between about 2.0 and about 5.5 weft stitches/cm, between about 2.0 and about 5.0 weft stitches/cm, between about 2.0 and about 4.5 weft stitches/cm, between about 2.0 and about 4.0 weft stitches/cm, between about 2.0 and about 3.5 weft stitches/cm, between about 2.0 and about 3.0 weft stitches/cm, or between about 2.0 and about 2.5 weft stitches/cm.

The second surface may comprise between about 2.5 and about 15.0 weft stitches/cm, between about 2.5 and about 14.5 weft stitches/cm, between about 2.5 and about 14.0 weft stitches/cm, between about 2.5 and about 13.5 weft stitches/cm, between about 2.5 and about 13.0 weft stitches/cm, between about 2.5 and about 12.5 weft stitches/cm, between about 2.5 and about 12.0 weft stitches/cm, between about 2.5 and about 11.5 weft stitches/cm, between about 2.5 and about 11.0 weft stitches/cm, between about 2.5 and about 10.5 weft stitches/cm, between about 2.5 and about 10.0 weft stitches/cm, between about 2.5 and about 9.5 weft stitches/cm, between about 2.5 and about 9.0 weft stitches/cm, between about 2.5 and about 8.5 weft stitches/cm, between about 2.5 and about 8.0 weft stitches/cm, between about 2.5 and about 7.5 weft stitches/cm, between about 2.5 and about 7.0 weft stitches/cm, between about 2.5 and about 6.5 weft stitches/cm, between about 2.5 and about 6.0 weft stitches/cm, between about 2.5 and about 5.5 weft stitches/cm, between about 2.5 and about 5.0 weft stitches/cm, between about 2.5 and about 4.5 weft stitches/cm, between about 2.5 and about 4.0 weft stitches/cm, between about 2.5 and about 3.5 weft stitches/cm, or between about 2.5 and about 3.0 weft stitches/cm.

The second surface may comprise between about 3.0 and about 15.0 weft stitches/cm, between about 3.0 and about 14.5 weft stitches/cm, between about 3.0 and about 14.0 weft stitches/cm, between about 3.0 and about 13.5 weft stitches/cm, between about 3.0 and about 13.0 weft stitches/cm, between about 3.0 and about 12.5 weft stitches/cm, between about 3.0 and about 12.0 weft stitches/cm, between about 3.0 and about 11.5 weft stitches/cm, between about 3.0 and about 11.0 weft stitches/cm, between about 3.0 and about 10.5 weft stitches/cm, between about 3.0 and about 10.0 weft stitches/cm, between about 3.0 and about 9.5 weft stitches/cm, between about 3.0 and about 9.0 weft stitches/cm, between about 3.0 and about 8.5 weft stitches/cm, between about 3.0 and about 8.0 weft stitches/cm, between about 3.0 and about 7.5 weft stitches/cm, between about 3.0 and about 7.0 weft stitches/cm, between about 3.0 and about 6.5 weft stitches/cm, between about 3.0 and about 6.0 weft stitches/cm, between about 3.0 and about 5.5 weft stitches/cm, between about 3.0 and about 5.0 weft stitches/cm, between about 3.0 and about 4.5 weft stitches/cm, between about 3.0 and about 4.0 weft stitches/cm, or between about 3.0 and about 3.5 weft stitches/cm.

The second surface may comprise between about 3.5 and about 15.0 weft stitches/cm, between about 3.5 and about 14.5 weft stitches/cm, between about 3.5 and about 14.0 weft stitches/cm, between about 3.5 and about 13.5 weft stitches/cm, between about 3.5 and about 13.0 weft stitches/cm, between about 3.5 and about 12.5 weft stitches/cm, between about 3.5 and about 11.0 weft stitches/cm, between about 3.5 and about 11.5 weft stitches/cm, between about 3.5 and about 11.0 weft stitches/cm, between about 3.5 and about 10.5 weft stitches/cm, between about 3.5 and about 10.0 weft stitches/cm, between about 3.5 and about 9.5 weft stitches/cm, between about 3.5 and about 9.0 weft stitches/cm, between about 3.5 and about 8.5 weft stitches/cm, between about 3.5 and about 8.0 weft stitches/cm, between about 3.5 and about 7.5 weft stitches/cm, between about 3.5 and about 7.0 weft stitches/cm, between about 3.5 and about 6.5 weft stitches/cm, between about 3.5 and about 6.0 weft stitches/cm, between about 3.5 and about 5.5 weft stitches/cm, between about 3.5 and about 5.0 weft stitches/cm, between about 3.5 and about 4.5 weft stitches/cm, or between about 3.5 and about 4.0 weft stitches/cm.

The second surface may comprise between about 4.0 and about 15.0 weft stitches/cm, between about 4.0 and about 14.5 weft stitches/cm, between about 4.0 and about 14.0 weft stitches/cm, between about 4.0 and about 13.5 weft stitches/cm, between about 4.0 and about 13.0 weft stitches/cm, between about 4.0 and about 12.5 weft stitches/cm, between about 4.0 and about 12.0 weft stitches/cm, between about 4.0 and about 11.5 weft stitches/cm, between about 4.0 and about 11.0 weft stitches/cm, between about 4.0 and about 10.5 weft stitches/cm, between about 4.0 and about 10.0 weft stitches/cm, between about 4.0 and about 9.5 weft stitches/cm, between about 4.0 and about 9.0 weft stitches/cm, between about 4.0 and about 8.5 weft stitches/cm, between about 4.0 and about 8.0 weft stitches/cm, between about 4.0 and about 7.5 weft stitches/cm, between about 4.0 and about 7.0 weft stitches/cm, between about 4.0 and about 6.5 weft stitches/cm, between about 4.0 and about 6.0 weft stitches/cm, between about 4.0 and about 5.5 weft stitches/cm, between about 4.0 and about 5.0 weft stitches/cm, or between about 4.0 and about 4.5 weft stitches/cm.

The second surface may comprise between about 4.5 and about 15.0 weft stitches/cm, between about 4.5 and about 14.5 weft stitches/cm, between about 4.5 and about 14.0 weft stitches/cm, between about 4.5 and about 13.5 weft stitches/cm, between about 4.5 and about 13.0 weft stitches/cm, between about 4.5 and about 12.5 weft stitches/cm, between about 4.5 and about 12.0 weft stitches/cm, between about 4.5 and about 11.5 weft stitches/cm, between about 4.5 and about 11.0 weft stitches/cm, between about 4.5 and about 10.5 weft stitches/cm, between about 4.5 and about 10.0 weft stitches/cm, between about 4.5 and about 9.5 weft stitches/cm, between about 4.5 and about 9.0 weft stitches/cm, between about 4.5 and about 8.5 weft stitches/cm, between about 4.5 and about 8.0 weft stitches/cm, between about 4.5 and about 7.5 weft stitches/cm, between about 4.5 and about 7.0 weft stitches/cm, between about 4.5 and about 6.5 weft stitches/cm, between about 4.5 and about 6.0 weft stitches/cm, between about 4.5 and about 5.5 weft stitches/cm, or between about 4.5 and about 5.0 weft stitches/cm.

The second surface may comprise between about 5.0 and about 15.0 weft stitches/cm, between about 5.0 and about 14.5 weft stitches/cm, between about 5.0 and about 14.0 weft stitches/cm, between about 5.0 and about 13.5 weft stitches/cm, between about 5.0 and about 13.0 weft stitches/cm, between about 5.0 and about 12.5 weft stitches/cm, between about 5.0 and about 12.0 weft stitches/cm, between about 5.0 and about 11.5 weft stitches/cm, between about 5.0 and about 11.0 weft stitches/cm, between about 5.0 and about 10.5 weft stitches/cm, between about 5.0 and about 10.0 weft stitches/cm, between about 5.0 and about 9.5 weft stitches/cm, between about 5.0 and about 9.0 weft stitches/cm, between about 5.0 and about 8.5 weft stitches/cm, between about 5.0 and about 8.0 weft stitches/cm, between about 5.0 and about 7.5 weft stitches/cm, between about 5.0 and about 7.0 weft stitches/cm, between about 5.0 and about 6.5 weft stitches/cm, between about 5.0 and about 6.0 weft stitches/cm, or between about 5.0 and about 5.5 weft stitches/cm.

The second surface may comprise between about 5.5 and about 15.0 weft stitches/cm, between about 5.5 and about 14.5 weft stitches/cm, between about 5.5 and about 14.0 weft stitches/cm, between about 5.5 and about 13.5 weft stitches/cm, between about 5.5 and about 13.0 weft stitches/cm, between about 5.5 and about 12.5 weft stitches/cm, between about 5.5 and about 12.0 weft stitches/cm, between about 5.5 and about 11.5 weft stitches/cm, between about 5.5 and about 11.0 weft stitches/cm, between about 5.5 and about 10.5 weft stitches/cm, between about 5.5 and about 10.0 weft stitches/cm, between about 5.5 and about 9.5 weft stitches/cm, between about 5.5 and about 9.0 weft stitches/cm, between about 5.5 and about 8.5 weft stitches/cm, between about 5.5 and about 8.0 weft stitches/cm, between about 5.5 and about 7.5 weft stitches/cm, between about 5.5 and about 7.0 weft stitches/cm, between about 5.5 and about 6.5 weft stitches/cm, or between about 5.5 and about 6.0 weft stitches/cm.

The second surface may comprise between about 6.0 and about 15.0 weft stitches/cm, between about 6.0 and about 14.5 weft stitches/cm, between about 6.0 and about 14.0 weft stitches/cm, between about 6.0 and about 13.5 weft stitches/cm, between about 6.0 and about 13.0 weft stitches/cm, between about 6.0 and about 12.5 weft stitches/cm, between about 6.0 and about 12.0 weft stitches/cm, between about 6.0 and about 11.5 weft stitches/cm, between about 6.0 and about 11.0 weft stitches/cm, between about 6.0 and about 10.5 weft stitches/cm, between about 6.0 and about 10.0 weft stitches/cm, between about 6.0 and about 9.5 weft stitches/cm, between about 6.0 and about 9.0 weft stitches/cm, between about 6.0 and about 8.5 weft stitches/cm, between about 6.0 and about 8.0 weft stitches/cm, between about 6.0 and about 7.5 weft stitches/cm, between about 6.0 and about 7.0 weft stitches/cm, or between about 6.0 and about 6.5 weft stitches/cm.

The second surface may comprise between about 6.5 and about 15.0 weft stitches/cm, between about 6.5 and about 14.5 weft stitches/cm, between about 6.5 and about 14.0 weft stitches/cm, between about 6.5 and about 13.5 weft stitches/cm, between about 6.5 and about 13.0 weft stitches/ cm, between about 6.5 and about 12.5 weft stitches/cm, between about 6.5 and about 12.0 weft stitches/cm, between about 6.5 and about 11.5 weft stitches/cm, between about 6.5 and about 11.0 weft stitches/cm, between about 6.5 and about 10.5 weft stitches/cm, between about 6.5 and about 10.0 weft stitches/cm, between about 6.5 and about 9.5 weft stitches/cm, between about 6.5 and about 9.0 weft stitches/cm, between about 6.5 and about 8.5 weft stitches/cm, between about 6.5 and about 8.0 weft stitches/cm, between about 6.5 and about 7.5 weft stitches/cm, or between about 6.5 and about 7.0 weft stitches/cm.

The second surface may comprise between about 7.0 and about 15.0 weft stitches/cm, between about 7.0 and about 14.5 weft stitches/cm, between about 7.0 and about 14.0 weft stitches/cm, between about 7.0 and about 13.5 weft stitches/cm, between about 7.0 and about 13.0 weft stitches/cm, between about 7.0 and about 12.5 weft stitches/cm, between about 7.0 and about 12.0 weft stitches/cm, between about 7.0 and about 11.5 weft stitches/cm, between about 7.0 and about 11.0 weft stitches/cm, between about 7.0 and about 10.5 weft stitches/cm, between about 7.0 and about 10.0 weft stitches/cm, between about 7.0 and about 9.5 weft stitches/cm, between about 7.0 and about 9.0 weft stitches/cm, between about 7.0 and about 8.5 weft stitches/cm, between about 7.0 and about 8.0 weft stitches/cm, or between about 7.0 and about 7.5 weft stitches/cm.

The second surface may comprise between about 7.5 and about 15.0 weft stitches/cm, between about 7.5 and about 14.5 weft stitches/cm, between about 7.5 and about 14.0 weft stitches/cm, between about 7.5 and about 13.5 weft stitches/cm, between about 7.5 and about 13.0 weft stitches/cm, between about 7.5 and about 12.5 weft stitches/cm, between about 7.5 and about 12.0 weft stitches/cm, between about 7.5 and about 11.5 weft stitches/cm, between about 7.5 and about 11.0 weft stitches/cm, between about 7.5 and about 10.5 weft stitches/cm, between about 7.5 and about 10.0 weft stitches/cm, between about 7.5 and about 9.5 weft stitches/cm, between about 7.5 and about 9.0 weft stitches/cm, between about 7.5 and about 8.5 weft stitches/cm, or between about 7.5 and about 8.0 weft stitches/cm.

The second surface may comprise between about 8.0 and about 15.0 weft stitches/cm, between about 8.0 and about 14.5 weft stitches/cm, between about 8.0 and about 14.0 weft stitches/cm, between about 8.0 and about 13.5 weft stitches/cm, between about 8.0 and about 13.0 weft stitches/cm, between about 8.0 and about 12.5 weft stitches/cm, between about 8.0 and about 12.0 weft stitches/cm, between about 8.0 and about 11.5 weft stitches/cm, between about 8.0 and about 11.0 weft stitches/cm, between about 8.0 and about 10.5 weft stitches/cm, between about 8.0 and about 10.0 weft stitches/cm, between about 8.0 and about 9.5 weft stitches/cm, between about 8.0 and about 9.0 weft stitches/cm, or between about 8.0 and about 8.5 weft stitches/cm.

The second surface may comprise between about 8.5 and about 15.0 weft stitches/cm, between about 8.5 and about 14.5 weft stitches/cm, between about 8.5 and about 14.0 weft stitches/cm, between about 8.5 and about 13.5 weft stitches/cm, between about 8.5 and about 13.0 weft stitches/cm, between about 8.5 and about 12.5 weft stitches/cm, between about 8.5 and about 12.0 weft stitches/cm, between about 8.5 and about 11.5 weft stitches/cm, between about 8.5 and about 11.0 weft stitches/cm, between about 8.5 and about 10.5 weft stitches/cm, between about 8.5 and about 10.0 weft stitches/cm, between about 8.5 and about 9.5 weft stitches/cm, or between about 8.5 and about 9.0 weft stitches/cm.

The second surface may comprise between about 9.0 and about 15.0 weft stitches/cm, between about 9.0 and about 14.5 weft stitches/cm, between about 9.0 and about 14.0 weft stitches/cm, between about 9.0 and about 13.5 weft stitches/cm, between about 9.0 and about 13.0 weft stitches/cm, between about 9.0 and about 12.5 weft stitches/cm, between about 9.0 and about 12.0 weft stitches/cm, between about 9.0 and about 11.5 weft stitches/cm, between about 9.0 and about 11.0 weft stitches/cm, between about 9.0 and about 10.5 weft stitches/cm, between about 9.0 and about 10.0 weft stitches/cm, or between about 9.0 and about 9.5 weft stitches/cm.

The second surface may comprise between about 9.5 and about 15.0 weft stitches/cm, between about 9.5 and about 14.5 weft stitches/cm, between about 9.5 and about 14.0 weft stitches/cm, between about 9.5 and about 13.5 weft stitches/cm, between about 9.5 and about 13.0 weft stitches/cm, between about 9.5 and about 12.5 weft stitches/cm, between about 9.5 and about 12.0 weft stitches/cm, between about 9.5 and about 11.5 weft stitches/cm, between about 9.5 and about 11.0 weft stitches/cm, between about 9.5 and about 10.5 weft stitches/cm, or between about 9.5 and about 10.0 weft stitches/cm.

The second surface may comprise between about 10.0 and about 15.0 weft stitches/cm, between about 10.0 and about 14.5 weft stitches/cm, between about 10.0 and about 14.0 weft stitches/cm, between about 10.0 and about 13.5 weft stitches/cm, between about 10.0 and about 13.0 weft stitches/cm, between about 10.0 and about 12.5 weft stitches/cm, between about 10.0 and about 12.0 weft stitches/cm, between about 10.0 and about 11.5 weft stitches/cm, between about 10.0 and about 11.0 weft stitches/cm, or between about 10.0 and about 10.5 weft stitches/cm.

The second surface may comprise between about 10.5 and about 15.0 weft stitches/cm, between about 10.5 and about 14.5 weft stitches/cm, between about 10.5 and about 14.0 weft stitches/cm, between about 10.5 and about 13.5 weft stitches/cm, between about 10.5 and about 13.0 weft stitches/cm, between about 10.5 and about 12.5 weft stitches/cm, between about 10.5 and about 12.0 weft stitches/cm, between about 10.5 and about 11.5 weft stitches/cm, or between about 10.5 and about 11.0 weft stitches/cm.

The second surface may comprise between about 11.0 and about 15.0 weft stitches/cm, between about 11.0 and about 14.5 weft stitches/cm, between about 11.0 and about 14.0 weft stitches/cm, between about 11.0 and about 13.5 weft stitches/cm, between about 11.0 and about 13.0 weft stitches/cm, between about 11.0 and about 12.5 weft stitches/cm, between about 11.0 and about 12.0 weft stitches/cm, or between about 11.0 and about 11.5 weft stitches/cm.

The second surface may comprise between about 11.5 and about 15.0 weft stitches/cm, between about 11.5 and about 14.5 weft stitches/cm, between about 11.5 and about 14.0 weft stitches/cm, between about 11.5 and about 13.5 weft stitches/cm, between about 11.5 and about 13.0 weft stitches/cm, between about 11.5 and about 12.5 weft stitches/cm, or between about 11.5 and about 12.0 weft stitches/cm.

The second surface may comprise between about 12.0 and about 15.0 weft stitches/cm, between about 12.0 and about 14.5 weft stitches/cm, between about 12.0 and about 14.0 weft stitches/cm, between about 12.0 and about 13.5 weft stitches/cm, between about 12.0 and about 13.0 weft stitches/cm, or between about 12.0 and about 12.5 weft stitches/cm.

The second surface may comprise between about 12.5 and about 15.0 weft stitches/cm, between about 12.5 and about 14.5 weft stitches/cm, between about 12.5 and about 14.0 weft stitches/cm, between about 12.5 and about 13.5 weft stitches/cm, or between about 12.5 and about 13.0 weft stitches/cm.

The second surface may comprise between about 13.0 and about 15.0 weft stitches/cm, between about 13.0 and about 14.5 weft stitches/cm, between about 13.0 and about 14.0 weft stitches/cm, or between about 13.0 and about 13.5 weft stitches/cm.

The second surface may comprise between about 13.5 and about 15.0 weft stitches/cm, between about 13.5 and about 14.5 weft stitches/cm, or between about 13.5 and about 14.0 weft stitches/cm.

The second surface may comprise between about 14.0 and about 15.0 weft stitches/cm, or between about 14.0 and about 14.5 weft stitches/cm.

The second surface may comprise between about 14.5 and about 15.0 weft stitches/cm.

The second surface may comprise between about 0.1 and about 15.0 warp stitches/cm, between about 0.1 and about 14.5 warp stitches/cm, between about 0.1 and about 14.0 warp stitches/cm, between about 0.1 and about 13.5 warp stitches/cm, between about 0.1 and about 13.0 warp stitches/cm, between about 0.1 and about 12.5 warp stitches/cm, between about 0.1 and about 12.0 warp stitches/cm, between about 0.1 and about 11.5 warp stitches/cm, between about 0.1 and about 11.0 warp stitches/cm, between about 0.1 and about 10.5 warp stitches/cm, between about 0.1 and about 10.0 warp stitches/cm, between about 0.1 and about 9.5 warp stitches/cm, between about 0.1 and about 9.0 warp stitches/cm, between about 0.1 and about 8.5 warp stitches/cm, between about 0.1 and about 8.0 warp stitches/cm, between about 0.1 and about 7.5 warp stitches/cm, between about 0.1 and about 7.0 warp stitches/cm, between about 0.1 and about 6.5 warp stitches/cm, between about 0.1 and about 6.0 warp stitches/cm, between about 0.1 and about 5.5 warp stitches/cm, between about 0.1 and about 5.0 warp stitches/cm, between about 0.1 and about 4.5 warp stitches/cm, between about 0.1 and about 4.0 warp stitches/cm, between about 0.1 and about 3.5 warp stitches/cm, between about 0.1 and about 3.0 warp stitches/cm, between about 0.1 and about 2.5 warp stitches/cm, between about 0.1 and about 2.0 warp stitches/cm, between about 0.1 and about 1.5 warp stitches/cm, between about 0.1 and about 1.0 warp stitches/cm, between about 0.1 and about 0.8 warp stitches/cm, between about 0.1 and about 0.6 warp stitches/cm, between about 0.1 and about 0.4 warp stitches/cm, or between about 0.1 and about 0.2 warp stitches/cm.

The second surface may comprise between about 0.2 and about 15.0 warp stitches/cm, between about 0.2 and about 14.5 warp stitches/cm, between about 0.2 and about 14.0 warp stitches/cm, between about 0.2 and about 13.5 warp stitches/cm, between about 0.2 and about 13.0 warp stitches/cm, between about 0.2 and about 12.5 warp stitches/cm, between about 0.2 and about 12.0 warp stitches/cm, between about 0.2 and about 11.5 warp stitches/cm, between about 0.2 and about 11.0 warp stitches/cm, between about 0.2 and about 10.5 warp stitches/cm, between about 0.2 and about 10.0 warp stitches/cm, between about 0.2 and about 9.5 warp stitches/cm, between about 0.2 and about 9.0 warp stitches/cm, between about 0.2 and about 8.5 warp stitches/cm, between about 0.2 and about 8.0 warp stitches/cm, between about 0.2 and about 7.5 warp stitches/cm, between about 0.2 and about 7.0 warp stitches/cm, between about 0.2 and about 6.5 warp stitches/cm, between about 0.2 and about 6.0 warp stitches/cm, between about 0.2 and about 5.5 warp stitches/cm, between about 0.2 and about 5.0 warp stitches/cm, between about 0.2 and about 4.5 warp stitches/cm, between about 0.2 and about 4.0 warp stitches/cm, between about 0.2 and about 3.5 warp stitches/cm, between about 0.2 and about 3.0 warp stitches/cm, between about 0.2 and about 2.5 warp stitches/cm, between about 0.2 and about 2.0 warp stitches/cm, between about 0.2 and about 1.5 warp stitches/cm, between about 0.2 and about 1.0 warp stitches/cm, between about 0.2 and about 0.8 warp stitches/cm, between about 0.2 and about 0.6 warp stitches/cm, or between about 0.2 and about 0.4 warp stitches/cm.

The second surface may comprise between about 0.4 and about 15.0 warp stitches/cm, between about 0.4 and about 14.5 warp stitches/cm, between about 0.4 and about 14.0 warp stitches/cm, between about 0.4 and about 13.5 warp stitches/cm, between about 0.4 and about 13.0 warp stitches/cm, between about 0.4 and about 12.5 warp stitches/cm, between about 0.4 and about 12.0 warp stitches/cm, between about 0.4 and about 11.5 warp stitches/cm, between about 0.4 and about 11.0 warp stitches/cm, between about 0.4 and about 10.5 warp stitches/cm, between about 0.4 and about 10.0 warp stitches/cm, between about 0.4 and about 9.5 warp stitches/cm, between about 0.4 and about 9.0 warp stitches/cm, between about 0.4 and about 8.5 warp stitches/cm, between about 0.4 and about 8.0 warp stitches/cm, between about 0.4 and about 7.5 warp stitches/cm, between about 0.4 and about 7.0 warp stitches/cm, between about 0.4 and about 6.5 warp stitches/cm, between about 0.4 and about 6.0 warp stitches/cm, between about 0.4 and about 5.5 warp stitches/cm, between about 0.4 and about 5.0 warp stitches/cm, between about 0.4 and about 4.5 warp stitches/cm, between about 0.4 and about 4.0 warp stitches/cm, between about 0.4 and about 3.5 warp stitches/cm, between about 0.4 and about 3.0 warp stitches/cm, between about 0.4 and about 2.5 warp stitches/cm, between about 0.4 and about 2.0 warp stitches/cm, between about 0.4 and about 1.5 warp stitches/cm, between about 0.4 and about 1.0 warp stitches/cm, between about 0.4 and about 0.8 warp stitches/cm, or between about 0.4 and about 0.6 warp stitches/cm.

The second surface may comprise between about 0.6 and about 15.0 warp stitches/cm, between about 0.6 and about 14.5 warp stitches/cm, between about 0.6 and about 14.0 warp stitches/cm, between about 0.6 and about 13.5 warp stitches/cm, between about 0.6 and about 13.0 warp stitches/cm, between about 0.6 and about 12.5 warp stitches/cm, between about 0.6 and about 12.0 warp stitches/cm, between about 0.6 and about 11.5 warp stitches/cm, between about 0.6 and about 11.0 warp stitches/cm, between about 0.6 and about 10.5 warp stitches/cm, between about 0.6 and about 10.0 warp stitches/cm, between about 0.6 and about 9.5 warp stitches/cm, between about 0.6 and about 9.0 warp stitches/cm, between about 0.6 and about 8.5 warp stitches/cm, between about 0.6 and about 8.0 warp stitches/cm, between about 0.6 and about 7.5 warp stitches/cm, between about 0.6 and about 7.0 warp stitches/cm, between about 0.6 and about 6.5 warp stitches/cm, between about 0.6 and about 6.0 warp stitches/cm, between about 0.6 and about 5.5 warp stitches/cm, between about 0.6 and about 5.0 warp stitches/cm, between about 0.6 and about 4.5 warp stitches/cm, between about 0.6 and about 4.0 warp stitches/cm, between about 0.6 and about 3.5 warp stitches/cm, between about 0.6 and about 3.0 warp stitches/cm, between about 0.6 and about 2.5 warp stitches/cm, between about 0.6 and about 2.0 warp stitches/cm, between about 0.6 and about 1.5 warp stitches/cm, between about 0.6 and about 1.0 warp stitches/cm, or between about 0.6 and about 0.8 warp stitches/cm.

The second surface may comprise between about 0.8 and about 15.0 warp stitches/cm, between about 0.8 and about 14.5 warp stitches/cm, between about 0.8 and about 14.0 warp stitches/cm, between about 0.8 and about 13.5 warp stitches/cm, between about 0.8 and about 13.0 warp stitches/cm, between about 0.8 and about 12.5 warp stitches/cm, between about 0.8 and about 12.0 warp stitches/cm, between about 0.8 and about 11.5 warp stitches/cm, between about 0.8 and about 11.0 warp stitches/cm, between about 0.8 and about 10.5 warp stitches/cm, between about 0.8 and about 10.0 warp stitches/cm, between about 0.8 and about 9.5 warp stitches/cm, between about 0.8 and about 9.0 warp stitches/cm, between about 0.8 and about 8.5 warp stitches/cm, between about 0.8 and about 8.0 warp stitches/cm, between about 0.8 and about 7.5 warp stitches/cm, between about 0.8 and about 7.0 warp stitches/cm, between about 0.8 and about 6.5 warp stitches/cm, between about 0.8 and about 6.0 warp stitches/cm, between about 0.8 and about 5.5 warp stitches/cm, between about 0.8 and about 5.0 warp stitches/cm, between about 0.8 and about 4.5 warp stitches/cm, between about 0.8 and about 4.0 warp stitches/cm, between about 0.8 and about 3.5 warp stitches/cm, between about 0.8 and about 3.0 warp stitches/cm, between about 0.8 and about 2.5 warp stitches/cm, between about 0.8 and about 2.0 warp stitches/cm, between about 0.8 and about 1.5 warp stitches/cm, or between about 0.8 and about 1.0 warp stitches/cm.

The second surface may comprise between about 1.0 and about 15.0 warp stitches/cm, between about 1.0 and about 14.5 warp stitches/cm, between about 1.0 and about 14.0 warp stitches/cm, between about 1.0 and about 13.5 warp stitches/cm, between about 1.0 and about 13.0 warp stitches/cm, between about 1.0 and about 12.5 warp stitches/cm, between about 1.0 and about 12.0 warp stitches/cm, between about 1.0 and about 11.5 warp stitches/cm, between about 1.0 and about 11.0 warp stitches/cm, between about 1.0 and about 10.5 warp stitches/cm, between about 1.0 and about 10.0 warp stitches/cm, between about 1.0 and about 9.5 warp stitches/cm, between about 1.0 and about 9.0 warp stitches/cm, between about 1.0 and about 8.5 warp stitches/cm, between about 1.0 and about 8.0 warp stitches/cm, between about 1.0 and about 7.5 warp stitches/cm, between about 1.0 and about 7.0 warp stitches/cm, between about 1.0 and about 6.5 warp stitches/cm, between about 1.0 and about 6.0 warp stitches/cm, between about 1.0 and about 5.5 warp stitches/cm, between about 1.0 and about 5.0 warp stitches/cm, between about 1.0 and about 4.5 warp stitches/cm, between about 1.0 and about 4.0 warp stitches/cm, between about 1.0 and about 3.5 warp stitches/cm, between about 1.0 and about 3.0 warp stitches/cm, between about 1.0 and about 2.5 warp stitches/cm, between about 1.0 and about 2.0 warp stitches/cm, or between about 1.0 and about 1.5 warp stitches/cm.

The second surface may comprise between about 1.5 and about 15.0 warp stitches/cm, between about 1.5 and about 14.5 warp stitches/cm, between about 1.5 and about 14.0 warp stitches/cm, between about 1.5 and about 13.5 warp stitches/cm, between about 1.5 and about 13.0 warp stitches/cm, between about 1.5 and about 12.5 warp stitches/cm, between about 1.5 and about 12.0 warp stitches/cm, between about 1.5 and about 11.5 warp stitches/cm, between about 1.5 and about 11.0 warp stitches/cm, between about 1.5 and about 10.5 warp stitches/cm, between about 1.5 and about 10.0 warp stitches/cm, between about 1.5 and about 9.5 warp stitches/cm, between about 1.5 and about 9.0 warp stitches/cm, between about 1.5 and about 8.5 warp stitches/cm, between about 1.5 and about 8.0 warp stitches/cm, between about 1.5 and about 7.5 warp stitches/cm, between about 1.5 and about 7.0 warp stitches/cm, between about 1.5 and about 6.5 warp stitches/cm, between about 1.5 and about 6.0 warp stitches/cm, between about 1.5 and about 5.5 warp stitches/cm, between about 1.5 and about 5.0 warp stitches/cm, between about 1.5 and about 4.5 warp stitches/cm, between about 1.5 and about 4.0 warp stitches/cm, between about 1.5 and about 3.5 warp stitches/cm, between about 1.5 and about 3.0 warp stitches/cm, between about 1.5 and about 2.5 warp stitches/cm, or between about 1.5 and about 2.0 warp stitches/cm.

The second surface may comprise between about 2.0 and about 15.0 warp stitches/cm, between about 2.0 and about 14.5 warp stitches/cm, between about 2.0 and about 14.0 warp stitches/cm, between about 2.0 and about 13.5 warp stitches/cm, between about 2.0 and about 13.0 warp stitches/cm, between about 2.0 and about 12.5 warp stitches/cm, between about 2.0 and about 12.0 warp stitches/cm, between about 2.0 and about 11.5 warp stitches/cm, between about 2.0 and about 11.0 warp stitches/cm, between about 2.0 and about 10.5 warp stitches/cm, between about 2.0 and about 10.0 warp stitches/cm, between about 2.0 and about 9.5 warp stitches/cm, between about 2.0 and about 9.0 warp stitches/cm, between about 2.0 and about 8.5 warp stitches/cm, between about 2.0 and about 8.0 warp stitches/cm, between about 2.0 and about 7.5 warp stitches/cm, between about 2.0 and about 7.0 warp stitches/cm, between about 2.0 and about 6.5 warp stitches/cm, between about 2.0 and about 6.0 warp stitches/cm, between about 2.0 and about 5.5 warp stitches/cm, between about 2.0 and about 5.0 warp stitches/cm, between about 2.0 and about 4.5 warp stitches/cm, between about 2.0 and about 4.0 warp stitches/cm, between about 2.0 and about 3.5 warp stitches/cm, between about 2.0 and about 3.0 warp stitches/cm, or between about 2.0 and about 2.5 warp stitches/cm.

The second surface may comprise between about 2.5 and about 15.0 warp stitches/cm, between about 2.5 and about 14.5 warp stitches/cm, between about 2.5 and about 14.0 warp stitches/cm, between about 2.5 and about 13.5 warp stitches/cm, between about 2.5 and about 13.0 warp stitches/cm, between about 2.5 and about 12.5 warp stitches/cm, between about 2.5 and about 12.0 warp stitches/cm, between about 2.5 and about 11.5 warp stitches/cm, between about 2.5 and about 11.0 warp stitches/cm, between about 2.5 and about 10.5 warp stitches/cm, between about 2.5 and about 10.0 warp stitches/cm, between about 2.5 and about 9.5 warp stitches/cm, between about 2.5 and about 9.0 warp stitches/cm, between about 2.5 and about 8.5 warp stitches/cm, between about 2.5 and about 8.0 warp stitches/cm, between about 2.5 and about 7.5 warp stitches/cm, between about 2.5 and about 7.0 warp stitches/cm, between about 2.5 and about 6.5 warp stitches/cm, between about 2.5 and about 6.0 warp stitches/cm, between about 2.5 and about 5.5 warp stitches/cm, between about 2.5 and about 5.0 warp stitches/cm, between about 2.5 and about 4.5 warp stitches/cm, between about 2.5 and about 4.0 warp stitches/cm, between about 2.5 and about 3.5 warp stitches/cm, or between about 2.5 and about 3.0 warp stitches/cm.

The second surface may comprise between about 3.0 and about 15.0 warp stitches/cm, between about 3.0 and about 14.5 warp stitches/cm, between about 3.0 and about 14.0 warp stitches/cm, between about 3.0 and about 13.5 warp stitches/cm, between about 3.0 and about 13.0 warp stitches/cm, between about 3.0 and about 12.5 warp stitches/cm, between about 3.0 and about 12.0 warp stitches/cm, between about 3.0 and about 11.5 warp stitches/cm, between about 3.0 and about 11.0 warp stitches/cm, between about 3.0 and about 10.5 warp stitches/cm, between about 3.0 and about 10.0 warp stitches/cm, between about 3.0 and about 9.5 warp stitches/cm, between about 3.0 and about 9.0 warp stitches/cm, between about 3.0 and about 8.5 warp stitches/cm, between about 3.0 and about 8.0 warp stitches/cm, between about 3.0 and about 7.5 warp stitches/cm, between about 3.0 and about 7.0 warp stitches/cm, between about 3.0 and about 6.5 warp stitches/cm, between about 3.0 and about 6.0 warp stitches/cm, between about 3.0 and about 5.5 warp stitches/cm, between about 3.0 and about 5.0 warp stitches/cm, between about 3.0 and about 4.5 warp stitches/cm, between about 3.0 and about 4.0 warp stitches/cm, or between about 3.0 and about 3.5 warp stitches/cm.

The second surface may comprise between about 3.5 and about 15.0 warp stitches/cm, between about 3.5 and about 14.5 warp stitches/cm, between about 3.5 and about 14.0 warp stitches/cm, between about 3.5 and about 13.5 warp stitches/cm, between about 3.5 and about 13.0 warp stitches/cm, between about 3.5 and about 12.5 warp stitches/cm, between about 3.5 and about 11.0 warp stitches/cm, between about 3.5 and about 11.5 warp stitches/cm, between about 3.5 and about 11.0 warp stitches/cm, between about 3.5 and about 10.5 warp stitches/cm, between about 3.5 and about 10.0 warp stitches/cm, between about 3.5 and about 9.5 warp stitches/cm, between about 3.5 and about 9.0 warp stitches/cm, between about 3.5 and about 8.5 warp stitches/cm, between about 3.5 and about 8.0 warp stitches/cm, between about 3.5 and about 7.5 warp stitches/cm, between about 3.5 and about 7.0 warp stitches/cm, between about 3.5 and about 6.5 warp stitches/cm, between about 3.5 and about 6.0 warp stitches/cm, between about 3.5 and about 5.5 warp stitches/cm, between about 3.5 and about 5.0 warp stitches/cm, between about 3.5 and about 4.5 warp stitches/cm, or between about 3.5 and about 4.0 warp stitches/cm.

The second surface may comprise between about 4.0 and about 15.0 warp stitches/cm, between about 4.0 and about 14.5 warp stitches/cm, between about 4.0 and about 14.0 warp stitches/cm, between about 4.0 and about 13.5 warp stitches/cm, between about 4.0 and about 13.0 warp stitches/cm, between about 4.0 and about 12.5 warp stitches/cm, between about 4.0 and about 12.0 warp stitches/cm, between about 4.0 and about 11.5 warp stitches/cm, between about 4.0 and about 11.0 warp stitches/cm, between about 4.0 and about 10.5 warp stitches/cm, between about 4.0 and about 10.0 warp stitches/cm, between about 4.0 and about 9.5 warp stitches/cm, between about 4.0 and about 9.0 warp stitches/cm, between about 4.0 and about 8.5 warp stitches/cm, between about 4.0 and about 8.0 warp stitches/cm, between about 4.0 and about 7.5 warp stitches/cm, between about 4.0 and about 7.0 warp stitches/cm, between about 4.0 and about 6.5 warp stitches/cm, between about 4.0 and about 6.0 warp stitches/cm, between about 4.0 and about 5.5 warp stitches/cm, between about 4.0 and about 5.0 warp stitches/cm, or between about 4.0 and about 4.5 warp stitches/cm.

The second surface may comprise between about 4.5 and about 15.0 warp stitches/cm, between about 4.5 and about 14.5 warp stitches/cm, between about 4.5 and about 14.0 warp stitches/cm, between about 4.5 and about 13.5 warp stitches/cm, between about 4.5 and about 13.0 warp stitches/cm, between about 4.5 and about 12.5 warp stitches/cm, between about 4.5 and about 12.0 warp stitches/cm, between about 4.5 and about 11.5 warp stitches/cm, between about 4.5 and about 11.0 warp stitches/cm, between about 4.5 and about 10.5 warp stitches/cm, between about 4.5 and about 10.0 warp stitches/cm, between about 4.5 and about 9.5 warp stitches/cm, between about 4.5 and about 9.0 warp stitches/cm, between about 4.5 and about 8.5 warp stitches/cm, between about 4.5 and about 8.0 warp stitches/cm, between about 4.5 and about 7.5 warp stitches/cm, between about 4.5 and about 7.0 warp stitches/cm, between about 4.5 and about 6.5 warp stitches/cm, between about 4.5 and about 6.0 warp stitches/cm, between about 4.5 and about 5.5 warp stitches/cm, or between about 4.5 and about 5.0 warp stitches/cm.

The second surface may comprise between about 5.0 and about 15.0 warp stitches/cm, between about 5.0 and about 14.5 warp stitches/cm, between about 5.0 and about 14.0 warp stitches/cm, between about 5.0 and about 13.5 warp stitches/cm, between about 5.0 and about 13.0 warp stitches/cm, between about 5.0 and about 12.5 warp stitches/cm, between about 5.0 and about 12.0 warp stitches/cm, between about 5.0 and about 11.5 warp stitches/cm, between about 5.0 and about 11.0 warp stitches/cm, between about 5.0 and about 10.5 warp stitches/cm, between about 5.0 and about 10.0 warp stitches/cm, between about 5.0 and about 9.5 warp stitches/cm, between about 5.0 and about 9.0 warp stitches/cm, between about 5.0 and about 8.5 warp stitches/cm, between about 5.0 and about 8.0 warp stitches/cm, between about 5.0 and about 7.5 warp stitches/cm, between about 5.0 and about 7.0 warp stitches/cm, between about 5.0 and about 6.5 warp stitches/cm, between about 5.0 and about 6.0 warp stitches/cm, or between about 5.0 and about 5.5 warp stitches/cm.

The second surface may comprise between about 5.5 and about 15.0 warp stitches/cm, between about 5.5 and about 14.5 warp stitches/cm, between about 5.5 and about 14.0 warp stitches/cm, between about 5.5 and about 13.5 warp stitches/cm, between about 5.5 and about 13.0 warp stitches/cm, between about 5.5 and about 12.5 warp stitches/cm, between about 5.5 and about 12.0 warp stitches/cm, between about 5.5 and about 11.5 warp stitches/cm, between about 5.5 and about 11.0 warp stitches/cm, between about 5.5 and about 10.5 warp stitches/cm, between about 5.5 and about 10.0 warp stitches/cm, between about 5.5 and about 9.5 warp stitches/cm, between about 5.5 and about 9.0 warp stitches/cm, between about 5.5 and about 8.5 warp stitches/cm, between about 5.5 and about 8.0 warp stitches/cm, between about 5.5 and about 7.5 warp stitches/cm, between about 5.5 and about 7.0 warp stitches/cm, between about 5.5 and about 6.5 warp stitches/cm, or between about 5.5 and about 6.0 warp stitches/cm.

The second surface may comprise between about 6.0 and about 15.0 warp stitches/cm, between about 6.0 and about 14.5 warp stitches/cm, between about 6.0 and about 14.0 warp stitches/cm, between about 6.0 and about 13.5 warp stitches/cm, between about 6.0 and about 13.0 warp stitches/cm, between about 6.0 and about 12.5 warp stitches/cm, between about 6.0 and about 12.0 warp stitches/cm, between about 6.0 and about 11.5 warp stitches/cm, between about 6.0 and about 11.0 warp stitches/cm, between about 6.0 and about 10.5 warp stitches/cm, between about 6.0 and about 10.0 warp stitches/cm, between about 6.0 and about 9.5 warp stitches/cm, between about 6.0 and about 9.0 warp stitches/cm, between about 6.0 and about 8.5 warp stitches/cm, between about 6.0 and about 8.0 warp stitches/cm, between about 6.0 and about 7.5 warp stitches/cm, between about 6.0 and about 7.0 warp stitches/cm, or between about 6.0 and about 6.5 warp stitches/cm.

The second surface may comprise between about 6.5 and about 15.0 warp stitches/cm, between about 6.5 and about 14.5 warp stitches/cm, between about 6.5 and about 14.0 warp stitches/cm, between about 6.5 and about 13.5 warp stitches/cm, between about 6.5 and about 13.0 warp stitches/cm, between about 6.5 and about 12.5 warp stitches/cm, between about 6.5 and about 12.0 warp stitches/cm, between about 6.5 and about 11.5 warp stitches/cm, between about 6.5 and about 11.0 warp stitches/cm, between about 6.5 and about 10.5 warp stitches/cm, between about 6.5 and about 10.0 warp stitches/cm, between about 6.5 and about 9.5 warp stitches/cm, between about 6.5 and about 9.0 warp stitches/cm, between about 6.5 and about 8.5 warp stitches/cm, between about 6.5 and about 8.0 warp stitches/cm, between about 6.5 and about 7.5 warp stitches/cm, or between about 6.5 and about 7.0 warp stitches/cm.

The second surface may comprise between about 7.0 and about 15.0 warp stitches/cm, between about 7.0 and about 14.5 warp stitches/cm, between about 7.0 and about 14.0 warp stitches/cm, between about 7.0 and about 13.5 warp stitches/cm, between about 7.0 and about 13.0 warp stitches/cm, between about 7.0 and about 12.5 warp stitches/cm, between about 7.0 and about 12.0 warp stitches/cm, between about 7.0 and about 11.5 warp stitches/cm, between about 7.0 and about 11.0 warp stitches/cm, between about 7.0 and about 10.5 warp stitches/cm, between about 7.0 and about 10.0 warp stitches/cm, between about 7.0 and about 9.5 warp stitches/cm, between about 7.0 and about 9.0 warp stitches/cm, between about 7.0 and about 8.5 warp stitches/cm, between about 7.0 and about 8.0 warp stitches/cm, or between about 7.0 and about 7.5 warp stitches/cm.

The second surface may comprise between about 7.5 and about 15.0 warp stitches/cm, between about 7.5 and about 14.5 warp stitches/cm, between about 7.5 and about 14.0 warp stitches/cm, between about 7.5 and about 13.5 warp stitches/cm, between about 7.5 and about 13.0 warp stitches/cm, between about 7.5 and about 12.5 warp stitches/cm, between about 7.5 and about 12.0 warp stitches/cm, between about 7.5 and about 11.5 warp stitches/cm, between about 7.5 and about 11.0 warp stitches/cm, between about 7.5 and about 10.5 warp stitches/cm, between about 7.5 and about 10.0 warp stitches/cm, between about 7.5 and about 9.5 warp stitches/cm, between about 7.5 and about 9.0 warp stitches/cm, between about 7.5 and about 8.5 warp stitches/cm, or between about 7.5 and about 8.0 warp stitches/cm.

The second surface may comprise between about 8.0 and about 15.0 warp stitches/cm, between about 8.0 and about 14.5 warp stitches/cm, between about 8.0 and about 14.0 warp stitches/cm, between about 8.0 and about 13.5 warp stitches/cm, between about 8.0 and about 13.0 warp stitches/cm, between about 8.0 and about 12.5 warp stitches/cm, between about 8.0 and about 12.0 warp stitches/cm, between about 8.0 and about 11.5 warp stitches/cm, between about 8.0 and about 11.0 warp stitches/cm, between about 8.0 and about 10.5 warp stitches/cm, between about 8.0 and about 10.0 warp stitches/cm, between about 8.0 and about 9.5 warp stitches/cm, between about 8.0 and about 9.0 warp stitches/cm, or between about 8.0 and about 8.5 warp stitches/cm.

The second surface may comprise between about 8.5 and about 15.0 warp stitches/cm, between about 8.5 and about 14.5 warp stitches/cm, between about 8.5 and about 14.0 warp stitches/cm, between about 8.5 and about 13.5 warp stitches/cm, between about 8.5 and about 13.0 warp stitches/cm, between about 8.5 and about 12.5 warp stitches/cm, between about 8.5 and about 12.0 warp stitches/cm, between about 8.5 and about 11.5 warp stitches/cm, between about 8.5 and about 11.0 warp stitches/cm, between about 8.5 and about 10.5 warp stitches/cm, between about 8.5 and about 10.0 warp stitches/cm, between about 8.5 and about 9.5 warp stitches/cm, or between about 8.5 and about 9.0 warp stitches/cm.

The second surface may comprise between about 9.0 and about 15.0 warp stitches/cm, between about 9.0 and about 14.5 warp stitches/cm, between about 9.0 and about 14.0 warp stitches/cm, between about 9.0 and about 13.5 warp stitches/cm, between about 9.0 and about 13.0 warp stitches/cm, between about 9.0 and about 12.5 warp stitches/cm, between about 9.0 and about 12.0 warp stitches/cm, between about 9.0 and about 11.5 warp stitches/cm, between about 9.0 and about 11.0 warp stitches/cm, between about 9.0 and about 10.5 warp stitches/cm, between about 9.0 and about 10.0 warp stitches/cm, or between about 9.0 and about 9.5 warp stitches/cm.

The second surface may comprise between about 9.5 and about 15.0 warp stitches/cm, between about 9.5 and about 14.5 warp stitches/cm, between about 9.5 and about 14.0 warp stitches/cm, between about 9.5 and about 13.5 warp stitches/cm, between about 9.5 and about 13.0 warp stitches/cm, between about 9.5 and about 12.5 warp stitches/cm, between about 9.5 and about 12.0 warp stitches/cm, between about 9.5 and about 11.5 warp stitches/cm, between about 9.5 and about 11.0 warp stitches/cm, between about 9.5 and about 10.5 warp stitches/cm, or between about 9.5 and about 10.0 warp stitches/cm.

The second surface may comprise between about 10.0 and about 15.0 warp stitches/cm, between about 10.0 and about 14.5 warp stitches/cm, between about 10.0 and about 14.0 warp stitches/cm, between about 10.0 and about 13.5 warp stitches/cm, between about 10.0 and about 13.0 warp stitches/cm, between about 10.0 and about 12.5 warp stitches/cm, between about 10.0 and about 12.0 warp stitches/cm, between about 10.0 and about 11.5 warp stitches/cm, between about 10.0 and about 11.0 warp stitches/cm, or between about 10.0 and about 10.5 warp stitches/cm.

The second surface may comprise between about 10.5 and about 15.0 warp stitches/cm, between about 10.5 and about 14.5 warp stitches/cm, between about 10.5 and about 14.0 warp stitches/cm, between about 10.5 and about 13.5 warp stitches/cm, between about 10.5 and about 13.0 warp stitches/cm, between about 10.5 and about 12.5 warp stitches/cm, between about 10.5 and about 12.0 warp stitches/cm, between about 10.5 and about 11.5 warp stitches/cm, or between about 10.5 and about 11.0 warp stitches/cm.

The second surface may comprise between about 11.0 and about 15.0 warp stitches/cm, between about 11.0 and about 14.5 warp stitches/cm, between about 11.0 and about 14.0 warp stitches/cm, between about 11.0 and about 13.5 warp stitches/cm, between about 11.0 and about 13.0 warp stitches/cm, between about 11.0 and about 12.5 warp stitches/cm, between about 11.0 and about 12.0 warp stitches/cm, or between about 11.0 and about 11.5 warp stitches/cm.

The second surface may comprise between about 11.5 and about 15.0 warp stitches/cm, between about 11.5 and about 14.5 warp stitches/cm, between about 11.5 and about 14.0 warp stitches/cm, between about 11.5 and about 13.5 warp stitches/cm, between about 11.5 and about 13.0 warp stitches/cm, between about 11.5 and about 12.5 warp stitches/cm, or between about 11.5 and about 12.0 warp stitches/cm.

The second surface may comprise between about 12.0 and about 15.0 warp stitches/cm, between about 12.0 and about 14.5 warp stitches/cm, between about 12.0 and about 14.0 warp stitches/cm, between about 12.0 and about 13.5 warp stitches/cm, between about 12.0 and about 13.0 warp stitches/cm, or between about 12.0 and about 12.5 warp stitches/cm.

The second surface may comprise between about 12.5 and about 15.0 warp stitches/cm, between about 12.5 and about 14.5 warp stitches/cm, between about 12.5 and about 14.0 warp stitches/cm, between about 12.5 and about 13.5 warp stitches/cm, or between about 12.5 and about 13.0 warp stitches/cm.

The second surface may comprise between about 13.0 and about 15.0 warp stitches/cm, between about 13.0 and about 14.5 warp stitches/cm, between about 13.0 and about 14.0 warp stitches/cm, or between about 13.0 and about 13.5 warp stitches/cm.

The second surface may comprise between about 13.5 and about 15.0 warp stitches/cm, between about 13.5 and about 14.5 warp stitches/cm, or between about 13.5 and about 14.0 warp stitches/cm.

The second surface may comprise between about 14.0 and about 15.0 warp stitches/cm, or between about 14.0 and about 14.5 warp stitches/cm.

The second surface may comprise between about 14.5 and about 15.0 warp stitches/cm.

The first surface may not comprise any weft stitches. The first surface may comprise warp stitches only.

As such, in one embodiment, there is provided a negative pressure wound dressing, the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the skin adjacent the wound, the wound contact layer having a first surface and a second surface, wherein the first surface of the wound contact layer contacts the wound in use, wherein the first surface comprises warp stitches and the second surface comprises warp and weft stitches, and characterised in that the first surface does not comprise any weft stitches.

Advantageously, this means that the amount of non-gelling fibres (which may include weft stitches) at the wound contact surface is minimised. Thus, there is a greater ratio of gelling fibres to non-gelling fibres at the wound contact surface in contact with the wound and, therefore, wound exudate. Thus, the absorption capacity of the wound contact layer is increased. As such, pooling of wound exudate at the wound site is prevented, or at least significantly reduced.

The second surface may comprise fewer than 15.0 weft stitches/cm, fewer than 14.5 weft stitches/cm, fewer than 14.0 weft stitches/cm, fewer than 13.5 weft stitches/cm, fewer than 13.0 weft stitches/cm, fewer than 12.5 weft stitches/cm, fewer than 12.0 weft stitches/cm, fewer than 11.5 weft stitches/cm, fewer than 11.0 weft stitches/cm, fewer than 10.5 weft stitches/cm, fewer than 10.0 weft stitches/cm, fewer than 9.5 weft stitches/cm, fewer than 9.0 weft stitches/cm, fewer than 8.5 weft stitches/cm, fewer than 8.0 weft stitches/cm, fewer than 7.5 weft stitches/cm, fewer than 7.0 weft stitches/cm, fewer than 6.5 weft stitches/cm, fewer than 6.0 weft stitches/cm, fewer than 5.5 weft stitches/cm, fewer than 5.0 weft stitches/cm, fewer than 4.5 weft stitches/cm, fewer than 4.0 weft stitches/cm, fewer than 3.5 weft stitches/cm, fewer than 3.0 weft stitches/cm, fewer than 2.5 weft stitches/cm, fewer than 2.0 weft stitches/cm, fewer than 1.5 weft stitches/cm, fewer than 1.0 weft stitch/cm, fewer than 0.8 weft stitches/cm, fewer than 0.6 weft stitches/cm, fewer than 0.5 weft stitches/cm, fewer than 0.4 weft stitches/cm, fewer than 0.3 weft stitches/cm, fewer than 0.2 weft stitches/cm, or fewer than 0.1 weft stitch/cm.

The second surface may comprise about 15.0 weft stitches/cm, about 14.5 weft stitches/cm, about 14.0 weft stitches/cm, about 13.5 weft stitches/cm, about 13.0 weft stitches/cm, about 12.5 weft stitches/cm, about 12.0 weft stitches/cm, about 11.5 weft stitches/cm, about 11.0 weft stitches/cm, about 10.5 weft stitches/cm, about 10.0 weft stitches/cm, about 9.5 weft stitches/cm, about 9.0 weft stitches/cm, about 8.5 weft stitches/cm, about 8.0 weft stitches/cm, about 7.5 weft stitches/cm, about 7.0 weft stitches/cm, about 6.5 weft stitches/cm, about 6.0 weft stitches/cm, about 5.5 weft stitches/cm, about 5.0 weft stitches/cm, about 4.5 weft stitches/cm, about 4.0 weft stitches/cm, about 3.5 weft stitches/cm, about 3.0 weft stitches/cm, about 2.5 weft stitches/cm, about 2.0 weft stitches/cm, about 1.5 weft stitches/cm, about 1.0 weft stitch/cm, about 0.8 weft stitches/cm, about 0.6 weft stitches/cm, about 0.5 weft stitches/cm, about 0.4 weft stitches/cm, about 0.3 weft stitches/cm, about 0.2 weft stitches/cm, or about 0.1 weft stitch/cm.

The second surface may comprise no more than 15.0 weft stitches/cm, than 14.5 weft stitches/cm, than 14.0 weft stitches/cm, than 13.5 weft stitches/cm, than 13.0 weft stitches/cm, than 12.5 weft stitches/cm, than 12.0 weft stitches/cm, than 11.5 weft stitches/cm, than 11.0 weft stitches/cm, than 10.5 weft stitches/cm, than 10.0 weft stitches/cm, than 9.5 weft stitches/cm, than 9.0 weft stitches/cm, than 8.5 weft stitches/cm, than 8.0 weft stitches/cm, than 7.5 weft stitches/cm, than 7.0 weft stitches/cm, than 6.5 weft stitches/cm, than 6.0 weft stitches/cm, than 5.5 weft stitches/cm, than 5.0 weft stitches/cm, than 4.5 weft stitches/cm, than 4.0 weft stitches/cm, than 3.5 weft stitches/cm, than 3.0 weft stitches/cm, than 2.5 weft stitches/cm, than 2.0 weft stitches/cm, than 1.5 weft stitches/cm, than 1.0 weft stitch/cm, than 0.8 weft stitches/cm, than 0.6 weft stitches/cm, than 0.5 weft stitches/cm, than 0.4 weft stitches/cm, than 0.3 weft stitches/cm, than 0.2 weft stitches/cm, or no more than 0.1 weft stitches/cm.

The second surface may comprise at least 15.0 weft stitches/cm, 14.5 weft stitches/cm, 14.0 weft stitches/cm, 13.5 weft stitches/cm, 13.0 weft stitches/cm, 12.5 weft stitches/cm, 12.0 weft stitches/cm, 11.5 weft stitches/cm, 11.0 weft stitches/cm, 10.5 weft stitches/cm, 10.0 weft stitches/cm, 9.5 weft stitches/cm, 9.0 weft stitches/cm, 8.5 weft stitches/cm, 8.0 weft stitches/cm, 7.5 weft stitches/cm, 7.0 weft stitches/cm, 6.5 weft stitches/cm, 6.0 weft stitches/cm, 5.5 weft stitches/cm, 5.0 weft stitches/cm, 4.5 weft stitches/cm, 4.0 weft stitches/cm, 3.5 weft stitches/cm, 3.0 weft stitches/cm, 2.5 weft stitches/cm, 2.0 weft stitches/cm, 1.5 weft stitches/cm, 1.0 weft stitch/cm, 0.8 weft stitches/cm, 0.6 weft stitches/cm, 0.5 weft stitches/cm, 0.4 weft stitches/cm, 0.3 weft stitches/cm, 0.2 weft stitches/cm, or at least 0.1 weft stitches/cm.

The second surface may comprise a greater number of weft stitches than the first surface. The second surface may comprise at least two times, three times, four times, five times, six times, seven times, eight time, nine times, ten times, eleven times, twelve times, thirteen times, fourteen times, fifteen times, sixteen times, seventeen times, eighteen times, nineteen times, or twenty times the number of weft stitches than the first surface.

Weft stitches generally impart strength to the wound contact layer fabric in the transverse direction. As such, advantageously, a second surface comprising weft stitches increases the strength of the wound contact layer fabric in a transverse direction. This prevents, or at least significantly reduces the possibility of, dissociation of the wound contact layer when it becomes wet with exudate.

The second surface may not comprise any weft stitches. The second surface may comprise warp stitches only.

The wound contact layer may have a peripheral region and a central region. The peripheral region may wholly, or at least partially, surround the central region. In embodiments comprising an adhesive skin contact layer comprising a window, the central region of the wound contact layer may be arranged within the window of the adhesive skin contact layer.

The first surface may have a peripheral region and a central region. The peripheral region may wholly, or at least partially, surround the central region.

The second surface may have a peripheral region and a central region. The peripheral region may wholly, or at least partially, surround the central region.

The peripheral region of the first surface may comprise warp stitches only and the central region of the first surface may comprise warp and weft stitches.

The central region of the first surface may comprise warp stitches only and the peripheral region of the first surface may comprise warp and weft stitches.

The peripheral region of the second surface may comprise warp stitches only and the central region of the second surface may comprise warp and weft stitches.

The central region of the second surface may comprise warp stitches only and the peripheral region of the second surface may comprise warp and weft stitches.

The peripheral region and the central region of the second surface may comprise warp and weft stitches. The peripheral region of the first surface may comprise warp stitches only and the central region of the first surface may comprise warp and weft stitches.

The peripheral region of the first surface and of the second surface may comprise warp stitches only. The central region of the first surface and of the second surface may comprise warp and weft stitches.

The wound contact layer may have a weight of between about 40 gsm and about 250 gsm, about 40 gsm and about 240 gsm, about 45 gsm and about 230 gsm, about 50 gsm and about 220 gsm, about 55 gsm and about 210 gsm, about 60 gsm and about 200 gsm, about 65 gsm and about 190 gsm, about 70 gsm and about 180 gsm, about 75 gsm and about 170 gsm, about 80 gsm and about 160 gsm, about 85 gsm and about 150 gsm, about 90 gsm and about 140 gsm, about 92 gsm and about 130 gsm, about 94 gsm and about 120 gsm, about 96 gsm and about 110 gsm, about 98 gsm and about 105 gsm, or about 100 gsm. Advantageously, a wound contact layer having a weight of between about 40 gsm and about 250 gsm, for example about 100 gsm, means that the wound contact layer has sufficient strength such that it does not deteriorate in the wound dressing during use and it is not too thick to process during manufacture of the wound dressing, for example when passing the layer through a stitch-bonding machine.

The wound contact layer may have a weight of about 40 gsm, about 45 gsm, about 50 gsm, about 55 gsm, about 60 gsm, about 65 gsm, about 70 gsm, about 75 gsm, about 80 gsm, about 85 gsm, about 90 gsm, about 95 gsm, about 100 gsm, about 105 gsm, about 110 gsm, about 115 gsm, about 120 gsm, about 125 gsm, about 130 gsm, about 135 gsm, about 140 gsm, about 145 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or about 250 gsm.

The wound contact layer may have a weight of at least about 40 gsm, about 45 gsm, about 50 gsm, about 55 gsm, about 60 gsm, about 65 gsm, about 70 gsm, about 75 gsm, about 80 gsm, about 85 gsm, about 90 gsm, about 95 gsm, about 100 gsm, about 105 gsm, about 110 gsm, about 115 gsm, about 120 gsm, about 125 gsm, about 130 gsm, about 135 gsm, about 140 gsm, about 145 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or at least about 250 gsm.

The wound contact layer may have a weight of no more than about 40 gsm, about 45 gsm, about 50 gsm, about 55 gsm, about 60 gsm, about 65 gsm, about 70 gsm, about 75 gsm, about 80 gsm, about 85 gsm, about 90 gsm, about 95 gsm, about 100 gsm, about 105 gsm, about 110 gsm, about 115 gsm, about 120 gsm, about 125 gsm, about 130 gsm, about 135 gsm, about 140 gsm, about 145 gsm, about 150 gsm, about 155 gsm, about 160 gsm, about 165 gsm, about 170 gsm, about 175 gsm, about 180 gsm, about 185 gsm, about 190 gsm, about 195 gsm, about 200 gsm, about 205 gsm, about 210 gsm, about 215 gsm, about 220 gsm, about 225 gsm, about 230 gsm, about 235 gsm, about 240 gsm, about 245 gsm, or no more than about 250 gsm.

The wound contact layer may have a weight of between about 40 gsm and about 250 gsm, between about 40 gsm and about 240 gsm, between about 40 gsm and about 230 gsm, between about 40 gsm and about 220 gsm, between about 40 gsm and about 210 gsm, between about 40 gsm and about 200 gsm, between about 40 gsm and about 190 gsm, between about 40 gsm and about 180 gsm, between about 40 gsm and about 170 gsm, between about 40 gsm and about 160 gsm, between about 40 gsm and about 150 gsm, between about 40 gsm and about 140 gsm, between about 40 gsm and about 130 gsm, between about 40 gsm and about 120 gsm, between about 40 gsm and about 110 gsm, between about 40 gsm and about 100 gsm, between about 40 gsm and about 90 gsm, between about 40 gsm and about 80 gsm, between about 40 gsm and about 70 gsm, between about 40 gsm and about 60 gsm, or between about 40 gsm and about 50 gsm.

The wound contact layer may have a weight of between about 50 gsm and about 250 gsm, between about 50 gsm and about 240 gsm, between about 50 gsm and about 230 gsm, between about 50 gsm and about 220 gsm, between about 50 gsm and about 210 gsm, between about 50 gsm and about 200 gsm, between about 50 gsm and about 190 gsm, between about 50 gsm and about 180 gsm, between about 50 gsm and about 170 gsm, between about 50 gsm and about 160 gsm, between about 50 gsm and about 150 gsm, between about 50 gsm and about 140 gsm, between about 50 gsm and about 130 gsm, between about 50 gsm and about 120 gsm, between about 50 gsm and about 110 gsm, between about 50 gsm and about 100 gsm, between about 50 gsm and about 90 gsm, between about 50 gsm and about 80 gsm, between about 50 gsm and about 70 gsm, or between about 50 gsm and about 60 gsm.

The wound contact layer may have a weight of between about 60 gsm and about 250 gsm, between about 60 gsm and about 240 gsm, between about 60 gsm and about 230 gsm, between about 60 gsm and about 220 gsm, between about 60 gsm and about 210 gsm, between about 60 gsm and about 200 gsm, between about 60 gsm and about 190 gsm, between about 60 gsm and about 180 gsm, between about 60 gsm and about 170 gsm, between about 60 gsm and about 160 gsm, between about 60 gsm and about 150 gsm, between about 60 gsm and about 140 gsm, between about 60 gsm and about 130 gsm, between about 60 gsm and about 120 gsm, between about 60 gsm and about 110 gsm, between about 60 gsm and about 100 gsm, between about 60 gsm and about 90 gsm, between about 60 gsm and about 80 gsm, or between about 60 gsm and about 70 gsm.

The wound contact layer may have a weight of between about 70 gsm and about 250 gsm, between about 70 gsm and about 240 gsm, between about 70 gsm and about 230 gsm, between about 70 gsm and about 220 gsm, between about 70 gsm and about 210 gsm, between about 70 gsm and about 200 gsm, between about 70 gsm and about 190 gsm, between about 70 gsm and about 180 gsm, between about 70 gsm and about 170 gsm, between about 70 gsm and about 160 gsm, between about 70 gsm and about 150 gsm, between about 70 gsm and about 140 gsm, between about 70 gsm and about 130 gsm, between about 70 gsm and about 120 gsm, between about 70 gsm and about 110 gsm, between about 70 gsm and about 100 gsm, between about 70 gsm and about 90 gsm, or between about 70 gsm and about 80 gsm.

The wound contact layer may have a weight of between about 80 gsm and about 250 gsm, between about 80 gsm and about 240 gsm, between about 80 gsm and about 230 gsm, between about 80 gsm and about 220 gsm, between about 80 gsm and about 210 gsm, between about 80 gsm and about 200 gsm, between about 80 gsm and about 190 gsm, between about 80 gsm and about 180 gsm, between about 80 gsm and about 170 gsm, between about 80 gsm and about 160 gsm, between about 80 gsm and about 150 gsm, between about 80 gsm and about 140 gsm, between about 80 gsm and about 130 gsm, between about 80 gsm and about 120 gsm, between about 80 gsm and about 110 gsm, between about 80 gsm and about 100 gsm, or between about 80 gsm and about 90 gsm.

The wound contact layer may have a weight of between about 90 gsm and about 250 gsm, between about 90 gsm and about 240 gsm, between about 90 gsm and about 230 gsm, between about 90 gsm and about 220 gsm, between about 90 gsm and about 210 gsm, between about 90 gsm and about 200 gsm, between about 90 gsm and about 190 gsm, between about 90 gsm and about 180 gsm, between about 90 gsm and about 170 gsm, between about 90 gsm and about 160 gsm, between about 90 gsm and about 150 gsm, between about 90 gsm and about 140 gsm, between about 90 gsm and about 130 gsm, between about 90 gsm and about 120 gsm, between about 90 gsm and about 110 gsm, or between about 90 gsm and about 100 gsm.

The wound contact layer may have a weight of between about 100 gsm and about 250 gsm, between about 100 gsm and about 240 gsm, between about 100 gsm and about 230 gsm, between about 100 gsm and about 220 gsm, between about 100 gsm and about 210 gsm, between about 100 gsm and about 200 gsm, between about 100 gsm and about 190 gsm, between about 100 gsm and about 180 gsm, between about 100 gsm and about 170 gsm, between about 100 gsm and about 160 gsm, between about 100 gsm and about 150 gsm, between about 100 gsm and about 140 gsm, between about 100 gsm and about 130 gsm, between about 100 gsm and about 120 gsm, or between about 100 gsm and about 110 gsm.

The wound contact layer may have a weight of between about 110 gsm and about 250 gsm, between about 110 gsm and about 240 gsm, between about 110 gsm and about 230 gsm, between about 110 gsm and about 220 gsm, between about 110 gsm and about 210 gsm, between about 110 gsm and about 200 gsm, between about 110 gsm and about 190 gsm, between about 110 gsm and about 180 gsm, between about 110 gsm and about 170 gsm, between about 110 gsm and about 160 gsm, between about 110 gsm and about 150 gsm, between about 110 gsm and about 140 gsm, between about 110 gsm and about 130 gsm, or between about 110 gsm and about 120 gsm.

The wound contact layer may have a weight of between about 120 gsm and about 250 gsm, between about 120 gsm and about 240 gsm, between about 120 gsm and about 230 gsm, between about 120 gsm and about 220 gsm, between about 120 gsm and about 210 gsm, between about 120 gsm and about 200 gsm, between about 120 gsm and about 190 gsm, between about 120 gsm and about 180 gsm, between about 120 gsm and about 170 gsm, between about 120 gsm and about 160 gsm, between about 120 gsm and about 150 gsm, between about 120 gsm and about 140 gsm, or between about 120 gsm and about 130 gsm.

The wound contact layer may have a weight of between about 130 gsm and about 250 gsm, between about 130 gsm and about 240 gsm, between about 130 gsm and about 230 gsm, between about 130 gsm and about 220 gsm, between about 130 gsm and about 210 gsm, between about 130 gsm and about 200 gsm, between about 130 gsm and about 190 gsm, between about 130 gsm and about 180 gsm, between about 130 gsm and about 170 gsm, between about 130 gsm and about 160 gsm, between about 130 gsm and about 150 gsm, or between about 130 gsm and about 140 gsm.

The wound contact layer may have a weight of between about 140 gsm and about 250 gsm, between about 140 gsm and about 240 gsm, between about 140 gsm and about 230 gsm, between about 140 gsm and about 220 gsm, between about 140 gsm and about 210 gsm, between about 140 gsm and about 200 gsm, between about 140 gsm and about 190 gsm, between about 140 gsm and about 180 gsm, between about 140 gsm and about 170 gsm, between about 140 gsm and about 160 gsm, or between about 140 gsm and about 150 gsm.

The wound contact layer may have a weight of between about 150 gsm and about 250 gsm, between about 150 gsm and about 240 gsm, between about 150 gsm and about 230 gsm, between about 150 gsm and about 220 gsm, between about 150 gsm and about 210 gsm, between about 150 gsm and about 200 gsm, between about 150 gsm and about 190 gsm, between about 150 gsm and about 180 gsm, between about 150 gsm and about 170 gsm, or between about 150 gsm and about 160 gsm.

The wound contact layer may have a weight of between about 160 gsm and about 250 gsm, between about 160 gsm and about 240 gsm, between about 160 gsm and about 230 gsm, between about 160 gsm and about 220 gsm, between about 160 gsm and about 210 gsm, between about 160 gsm and about 200 gsm, between about 160 gsm and about 190 gsm, between about 160 gsm and about 180 gsm, or between about 160 gsm and about 170 gsm.

The wound contact layer may have a weight of between about 170 gsm and about 250 gsm, between about 170 gsm and about 240 gsm, between about 170 gsm and about 230 gsm, between about 170 gsm and about 220 gsm, between about 170 gsm and about 210 gsm, between about 170 gsm and about 200 gsm, between about 170 gsm and about 190 gsm, or between about 170 gsm and about 180 gsm.

The wound contact layer may have a weight of between about 180 gsm and about 250 gsm, between about 180 gsm and about 240 gsm, between about 180 gsm and about 230 gsm, between about 180 gsm and about 220 gsm, between about 180 gsm and about 210 gsm, between about 180 gsm and about 200 gsm, or between about 180 gsm and about 190 gsm.

The wound contact layer may have a weight of between about 190 gsm and about 250 gsm, between about 190 gsm and about 240 gsm, between about 190 gsm and about 230 gsm, between about 190 gsm and about 220 gsm, between about 190 gsm and about 210 gsm, or between about 190 gsm and about 200 gsm.

The wound contact layer may have a weight of between about 200 gsm and about 250 gsm, between about 200 gsm and about 240 gsm, between about 200 gsm and about 230 gsm, between about 200 gsm and about 220 gsm, or between about 200 gsm and about 210 gsm.

The wound contact layer may have a weight of between about 210 gsm and about 250 gsm, between about 210 gsm and about 240 gsm, between about 210 gsm and about 230 gsm, or between about 210 gsm and about 220 gsm.

The wound contact layer may have a weight of between about 220 gsm and about 250 gsm, between about 220 gsm and about 240 gsm, or between about 220 gsm and about 230 gsm.

The wound contact layer may have a weight of between about 230 gsm and about 250 gsm, or between about 230 gsm and about 240 gsm.

The wound contact layer may have a weight of between about 240 gsm and about 250 gsm.

The wound contact layer may have a thickness of between about 1 mm and about 5 mm, about 1.5 mm and about 4.5 mm, about 2.0 mm and about 4.0 mm, about 2.5 mm and about 3.5 mm, or about 3.0 mm.

The wound contact layer may have a thickness of about 1 mm, about 1.5 mm, about 2.0 mm, about 2.5 mm, about 3.0 mm, about 3.5 mm, about 4.0 mm, about 4.5 mm, or about 5.0 mm.

The wound contact layer may have a thickness of at least about 1 mm, about 1.5 mm, about 2.0 mm, about 2.5 mm, about 3.0 mm, about 3.5 mm, about 4.0 mm, about 4.5 mm, or at least about 5.0 mm.

The wound contact layer may have a thickness of no more than about 1 mm, about 1.5 mm, about 2.0 mm, about 2.5 mm, about 3.0 mm, about 3.5 mm, about 4.0 mm, about 4.5 mm, or no more than about 5.0 mm.

The warp stitches comprised in the first surface may have a pitch of between about 1.0 mm and about 30.0 mm, about 1.2 mm and about 28.0 mm, about 1.4 mm and about 26.0 mm, about 1.6 mm and about 24.0 mm, about 1.8 mm and about 22.0 mm, about 2.0 mm and about 20.0 mm, about 2.2 mm and about 18.0 mm, about 2.4 mm and about 16.0 mm, about 2.6 mm and about 14.0 mm, about 2.8 mm and about 12.0 mm, about 3.0 mm and about 10.0 mm, about 3.2 mm and about 9.6 mm, about 3.4 mm and about 9.2 mm, about 3.6 mm and about 8.8 mm, about 3.8 mm and about 8.4 mm, about 4.0 mm and about 8.0 mm, about 4.2 mm and about 7.8 mm, about 4.4 mm and about 7.6 mm, about 4.6 mm and about 7.4 mm, about 4.8 mm and about 7.2 mm, about 5.0 mm and about 7.0 mm, about 5.2 mm and about 7.0 mm, about 5.4 mm and about 7.0 mm, about 5.6 mm and about 7.0 mm, about 5.8 mm and about 7.0 mm, about 6.0 mm and about 7.0 mm, about 6.1 mm and about 6.9 mm, about 6.2 mm and about 6.8 mm, about 6.3 mm and about 6.7 mm, about 6.4 mm and about 6.7 mm, about 6.5 mm and about 6.7 mm, or about 6.6 mm.

The warp stitches comprised in the first surface may have a pitch of about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or about 30.0 mm.

The warp stitches comprised in the first surface may have a pitch of at least about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or at least about 30.0 mm.

The warp stitches comprised in the first surface may have a pitch of no more than about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or no more than about 30.0 mm.

The warp stitches comprised in the first surface may have a pitch of between about 1.0 mm and about 30.0 mm, between about 1.0 mm and about 25.0 mm, between about 1.0 mm and about 20.0 mm, between about 1.0 mm and about 15.0 mm, between about 1.0 mm and about 10.0 mm, between about 1.0 mm and about 8.0 mm, between about 1.0 mm and about 6.0 mm, between about 1.0 mm and about 4.0 mm, or between about 1.0 mm and about 2.0 mm.

The warp stitches comprised in the first surface may have a pitch of between about 2.0 mm and about 30.0 mm, between about 2.0 mm and about 25.0 mm, between about 2.0 mm and about 20.0 mm, between about 2.0 mm and about 15.0 mm, between about 2.0 mm and about 10.0 mm, between about 2.0 mm and about 8.0 mm, between about 2.0 mm and about 6.0 mm, or between about 2.0 mm and about 4.0 mm.

The warp stitches comprised in the first surface may have a pitch of between about 4.0 mm and about 30.0 mm, between about 4.0 mm and about 25.0 mm, between about 4.0 mm and about 20.0 mm, between about 4.0 mm and about 15.0 mm, between about 4.0 mm and about 10.0 mm, between about 4.0 mm and about 8.0 mm, or between about 4.0 mm and about 6.0 mm.

The warp stitches comprised in the first surface may have a pitch of between about 6.0 mm and about 30.0 mm, between about 6.0 mm and about 25.0 mm, between about 6.0 mm and about 20.0 mm, between about 6.0 mm and about 15.0 mm, between about 6.0 mm and about 10.0 mm, or between about 6.0 mm and about 8.0 mm.

The warp stitches comprised in the first surface may have a pitch of between about 8.0 mm and about 30.0 mm, between about 8.0 mm and about 25.0 mm, between about 8.0 mm and about 20.0 mm, between about 8.0 mm and about 15.0 mm, or between about 8.0 mm and about 10.0 mm.

The warp stitches comprised in the first surface may have a pitch of between about 10.0 mm and about 30.0 mm, between about 10.0 mm and about 25.0 mm, between about 10.0 mm and about 20.0 mm, or between about 10.0 mm and about 15.0 mm.

The warp stitches comprised in the first surface may have a pitch of between about 15.0 mm and about 30.0 mm, between about 15.0 mm and about 25.0 mm, or between about 15.0 mm and about 20.0 mm.

The warp stitches comprised in the first surface may have a pitch of between about 20.0 mm and about 30.0 mm, or between about 20.0 mm and about 25.0 mm.

The warp stitches comprised in the first surface may have a pitch of between about 25.0 mm and about 30.0 mm. The warp stitches comprised in the second surface may have a pitch of between about 1.0 mm and about 30.0 mm, about 1.2 mm and about 28.0 mm, about 1.4 mm and about 26.0 mm, about 1.6 mm and about 24.0 mm, about 1.8 mm and about 22.0 mm, about 2.0 mm and about 20.0 mm, about 2.2 mm and about 18.0 mm, about 2.4 mm and about 16.0 mm, about 2.6 mm and about 14.0 mm, about 2.8 mm and about 12.0 mm, about 3.0 mm and about 10.0 mm, about 3.2 mm and about 9.6 mm, about 3.4 mm and about 9.2 mm, about 3.6 mm and about 8.8 mm, about 3.8 mm and about 8.4 mm, about 4.0 mm and about 8.0 mm, about 4.2 mm and about 7.8 mm, about 4.4 mm and about 7.6 mm, about 4.6 mm and about 7.4 mm, about 4.8 mm and about 7.2 mm, about 5.0 mm and about 7.0 mm, about 5.2 mm and about 7.0 mm, about 5.4 mm and about 7.0 mm, about 5.6 mm and about 7.0 mm, about 5.8 mm and about 7.0 mm, about 6.0 mm and about 7.0 mm, about 6.1 mm and about 6.9 mm, about 6.2 mm and about 6.8 mm, about 6.3 mm and about 6.7 mm, about 6.4 mm and about 6.7 mm, about 6.5 mm and about 6.7 mm, or about 6.6 mm.

The warp stitches comprised in the second surface may have a pitch of about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, or about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or no more than about 30.0 mm.

The warp stitches comprised in the second surface may have a pitch of at least about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, or at least about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or no more than about 30.0 mm.

The warp stitches comprised in the second surface may have a pitch of no more than about 1.0 mm, about 1.2 mm, about 1.4 mm, about 1.6 mm, about 1.8 mm, about 2.0 mm, about 2.2 mm, about 2.4 mm, about 2.6 mm, about 2.8 mm, 3.0 mm, about 3.2 mm, about 3.4 mm, about 3.6 mm, about 3.8 mm, about 4.0 mm. about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, or no more than about 8.0 mm, about 8.2 mm, about 8.4 mm, about 8.6 mm, about 8.8 mm, about 9.0 mm, about 9.2 mm, about 9.4 mm, about 9.6 mm, about 9.8 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, about 21.0 mm, about 22.0 mm, about 23.0 mm, about 24.0 mm, about 25.0 mm, about 26.0 mm, about 27.0 mm, about 28.0 mm, about 29.0 mm, or no more than about 30.0 mm.

The warp stitches comprised in the second surface may have a pitch of between about 1.0 mm and about 30.0 mm, between about 1.0 mm and about 25.0 mm, between about 1.0 mm and about 20.0 mm, between about 1.0 mm and about 15.0 mm, between about 1.0 mm and about 10.0 mm, between about 1.0 mm and about 8.0 mm, between about 1.0 mm and about 6.0 mm, between about 1.0 mm and about 4.0 mm, or between about 1.0 mm and about 2.0 mm.

The warp stitches comprised in the second surface may have a pitch of between about 2.0 mm and about 30.0 mm, between about 2.0 mm and about 25.0 mm, between about 2.0 mm and about 20.0 mm, between about 2.0 mm and about 15.0 mm, between about 2.0 mm and about 10.0 mm, between about 2.0 mm and about 8.0 mm, between about 2.0 mm and about 6.0 mm, or between about 2.0 mm and about 4.0 mm.

The warp stitches comprised in the second surface may have a pitch of between about 4.0 mm and about 30.0 mm, between about 4.0 mm and about 25.0 mm, between about 4.0 mm and about 20.0 mm, between about 4.0 mm and about 15.0 mm, between about 4.0 mm and about 10.0 mm, between about 4.0 mm and about 8.0 mm, or between about 4.0 mm and about 6.0 mm.

The warp stitches comprised in the second surface may have a pitch of between about 6.0 mm and about 30.0 mm, between about 6.0 mm and about 25.0 mm, between about 6.0 mm and about 20.0 mm, between about 6.0 mm and about 15.0 mm, between about 6.0 mm and about 10.0 mm, or between about 6.0 mm and about 8.0 mm.

The warp stitches comprised in the second surface may have a pitch of between about 8.0 mm and about 30.0 mm, between about 8.0 mm and about 25.0 mm, between about 8.0 mm and about 20.0 mm, between about 8.0 mm and about 15.0 mm, or between about 8.0 mm and about 10.0 mm.

The warp stitches comprised in the second surface may have a pitch of between about 10.0 mm and about 30.0 mm, between about 10.0 mm and about 25.0 mm, between about 10.0 mm and about 20.0 mm, or between about 10.0 mm and about 15.0 mm.

The warp stitches comprised in the second surface may have a pitch of between about 15.0 mm and about 30.0 mm, between about 15.0 mm and about 25.0 mm, or between about 15.0 mm and about 20.0 mm.

The warp stitches comprised in the second surface may have a pitch of between about 20.0 mm and about 30.0 mm, or between about 20.0 mm and about 25.0 mm.

The warp stitches comprised in the second surface may have a pitch of between about 25.0 mm and about 30.0 mm.

Advantageously, the pitch of the warp stitches is of sufficient distance to allow gelling fibres to be the main contact surface of the wound contact layer upon the wound, and is sufficiently narrow enough to maintain wet tensile strength during use, therefore, preventing deterioration of the wound contact layer when it becomes wetted during use.

In embodiments comprising a surface having warp and weft stitches, the weft stitches are laid in between the warp stitches and 'knotted' to the warp stitches at anchor points. The anchor points may be at intervals of about 1 mm, about 2 mm, about 3 mm, about 4 mm, about 5 mm, about 6 mm, about 7 mm, about 8 mm, about 9 mm, or about 10 mm. The anchor points may be at intervals of between about 1 mm and about 10 mm, about 2 mm and about 9 mm, about 3 mm and about 8 mm, about 4 mm and about 7 mm, about 5 mm and about 6.5 mm, or about 6 mm.

The wound contact layer may comprise a plurality of gel-forming fibres. By gel-forming fibres is meant hygroscopic fibres which upon the uptake of wound exudate become moist slippery or gelatinous. The gel-forming fibres may be of the type which retain their structural and fibrous integrity on absorption of exudate and, therefore retain a significant amount of tensile strength, or may be of the type which lose their fibrous form and become an amorphous or structureless gel. The gel-forming fibres may be sodium carboxymethylcellulose fibres, chemically modified cellulosic fibres, alkyl sulphonate modified cellulosic fibres, pectin fibres, alginate fibres, chitosan fibres, hyaluronic acid fibres, or other polysaccharide fibres or fibres derived from gums or plants, or combinations or blends of these fibres.

The wound contact layer may comprise a combination or blend of gelling fibres and non-gelling fibres. The gelling fibres and the non-gelling fibres may be any such fibres disclosed herein. For example, the wound contact layer may comprise a combination or blend of fibres comprising a gelling fibre such as fibres formed of sodium carboxymethyl cellulose. The wound contact layer may comprise a combination or blend of fibres comprising a non-gelling fibre such as cellulose fibres.

The gelling fibres may be present in the combination or blend of fibres in an amount equal to about 10%, about 20%, about 30%, about 40%, about 50%, about 60%, about 70%, about 80%, or about 90% of the total mass of the combination or blend of fibres.

The gelling fibres may be present in the combination or blend of fibres in an amount of at least about 10%, about 20%, about 30%, about 40%, about 50%, about 60%, about 70%, about 80%, or at least about 90% of the total mass of the combination or blend of fibres.

The gelling fibres may be present in the combination or blend of fibres in an amount of no more than about 10%, about 20%, about 30%, about 40%, about 50%, about 60%, about 70%, about 80%, or no more than about 90% of the total mass of the combination or blend of fibres.

The gelling fibres may be present in the combination or blend of fibres in an amount of between about 5% and about 95%, about 10% and about 90%, about 15% and about 85%, about 20% and about 80%, about 25% and about 75%, about 30% and about 70%, about 35% and about 65%, about 40% and about 60%, about 45% and about 55%, or about 50% of the total mass of the combination or blend of fibres.

The non-gelling fibres may be present in the combination or blend of fibres in an amount equal to about 10%, about 20%, about 30%, about 40%, about 50%, about 60%, about 70%, about 80%, or about 90% of the total mass of the combination or blend of fibres.

The non-gelling fibres may be present in the combination or blend of fibres in an amount of at least about 10%, about 20%, about 30%, about 40%, about 50%, about 60%, about 70%, about 80%, or at least about 90% of the total mass of the combination or blend of fibres.

The non-gelling fibres may be present in the combination or blend of fibres in an amount of no more than about 10%, about 20%, about 30%, about 40%, about 50%, about 60%, about 70%, about 80%, or no more than about 90% of the total mass of the combination or blend of fibres.

The non-gelling fibres may be present in the combination or blend of fibres in an amount of between about 5% and about 95%, about 10% and about 90%, about 15% and about 85%, about 20% and about 80%, about 25% and about 75%, about 30% and about 70%, about 35% and about 65%, about 40% and about 60%, about 45% and about 55%, or about 50% of the total mass of the combination or blend of fibres.

The wound contact layer may comprise a combination or blend of fibres comprising fibres formed of sodium carboxymethyl cellulose in an amount of greater than or equal to about 50% of the total mass of the combination or blend of fibres, and cellulose fibres in an amount of less than or equal to about 50% of the total mass of the combination or blend of fibres. The sodium carboxymethyl cellulose fibres may be present in an amount equal to about 55% and the cellulose fibres may be present in an amount equal to about 45%, the sodium carboxymethyl cellulose fibres may be present in an amount equal to about 60% and the cellulose fibres may be present in an amount equal to about 40%, the sodium carboxymethyl cellulose fibres may be present in an amount equal to about 65% and the cellulose fibres may be present in an amount equal to about 35%, the sodium carboxymethyl cellulose fibres may be present in an amount equal to about 70% and the cellulose fibres may be present in an amount equal to about 30%, the sodium carboxymethyl cellulose fibres may be present in an amount equal to about 75% and the cellulose fibres may be present in an amount equal to about 25%, the sodium carboxymethyl cellulose fibres may be present in an amount equal to about 80% and the cellulose fibres may be present in an amount equal to about 20%, the sodium carboxymethyl cellulose fibres may be present in an amount equal to about 85% and the cellulose fibres may be present in an amount equal to about 15%, the sodium carboxymethyl cellulose fibres may be present in an amount equal to about 90% and the cellulose fibres may be present in an amount equal to about 10%, or the sodium carboxymethyl cellulose fibres may be present in an amount equal to about 95% and the cellulose fibres may be present in an amount equal to about 5%, of the total mass of the combination or blend of fibres.

The combination or blend of gelling and non-gelling fibres may be blended into a non-woven fabric. The non-woven fabric may be stitchbonded as described herein. In embodiments comprising sodium carboxymethylcellulose fibres, the fibres may have a degree of substitution of between about 0.05 carboxymethyl groups per glucose unit and about 0.50 carboxymethyl groups per glucose unit, about 0.10 carboxymethyl groups per glucose unit and about 0.45 carboxymethyl groups per glucose unit, about 0.15 carboxymethyl groups per glucose unit and about 0.40 carboxymethyl groups per glucose unit, about 0.20 carboxymethyl groups per glucose unit and about 0.35 carboxymethyl groups per glucose unit, about 0.25 carboxymethyl groups per glucose unit and about 0.35 carboxymethyl groups per glucose unit, or about 0.30 carboxymethyl groups per glucose unit.

Advantageously, this means that the sodium carboxymethylcellulose fibres are relatively high-gelling, i.e., more absorbent and retentive, than fibres often comprised in wound contact layers of the prior art. As such, the wound contact layer is capable of absorbing and retaining a greater amount of wound exudate, without adversely affecting its adhesion to other layers within the absorbent structure, compared to wound contact layers which do not comprise sodium carboxymethylcellulose fibres. Thus, pooling of wound exudate at the wound site is prevented, or at least significantly reduced.

Moreover, in some embodiments, the first surface does not comprise, or comprises a relatively small amount of, weft stitches. In such embodiments, advantageously, due to the small number, or absence, of weft stitches, the gel-forming fibres are in contact with the wound to a greater extent than in wound dressings of the prior art which comprise a wound contact layer having warp and weft stitches on the wound contact surface. As such, the wound contact layer of the present invention absorbs a substantially greater amount of wound exudate compared to wound contact layers of the prior art.

In embodiments comprising sodium carboxymethylcellulose fibres, the fibres may have a degree of substitution of about 0.05 carboxymethyl groups per glucose unit, about 0.10, about 0.15, about 0.20, about 0.25, about 0.30, about 0.35, about 0.40, about 0.45, or about 0.50 carboxymethyl groups per glucose unit.

In embodiments comprising sodium carboxymethylcellulose fibres, the fibres may have a degree of substitution of at least about 0.05 carboxymethyl groups per glucose unit, about 0.10, about 0.15, about 0.20, about 0.25, about 0.30, about 0.35, about 0.40, about 0.45, or at least about 0.50 carboxymethyl groups per glucose unit.

In embodiments comprising sodium carboxymethylcellulose fibres, the fibres may have a degree of substitution of no more than about 0.05 carboxymethyl groups per glucose unit, about 0.10, about 0.15, about 0.20, about 0.25, about 0.30, about 0.35, about 0.40, about 0.45, or no more than about 0.50 carboxymethyl groups per glucose unit.

In embodiments comprising sodium carboxymethylcellulose fibres, the fibres may have a degree of substitution of between about 0.05 carboxymethyl groups per glucose unit and about 0.50 carboxymethyl groups per glucose unit, between about 0.05 carboxymethyl groups per glucose unit and about 0.45 carboxymethyl groups per glucose unit, between about 0.05 carboxymethyl groups per glucose unit and about 0.40 carboxymethyl groups per glucose unit, between about 0.05 carboxymethyl groups per glucose unit and about 0.35 carboxymethyl groups per glucose unit, between about 0.05 carboxymethyl groups per glucose unit and about 0.30 carboxymethyl groups per glucose unit, between about 0.05 carboxymethyl groups per glucose unit and about 0.25 carboxymethyl groups per glucose unit, between about 0.05 carboxymethyl groups per glucose unit and about 0.20 carboxymethyl groups per glucose unit, between about 0.05 carboxymethyl groups per glucose unit and about 0.15 carboxymethyl groups per glucose unit, or between about 0.05 carboxymethyl groups per glucose unit and about 0.10 carboxymethyl groups per glucose unit.

In embodiments comprising sodium carboxymethylcellulose fibres, the fibres may have a degree of substitution of between about 0.10 carboxymethyl groups per glucose unit and about 0.50 carboxymethyl groups per glucose unit, between about 0.10 carboxymethyl groups per glucose unit and about 0.45 carboxymethyl groups per glucose unit, between about 0.10 carboxymethyl groups per glucose unit and about 0.40 carboxymethyl groups per glucose unit, between about 0.10 carboxymethyl groups per glucose unit and about 0.35 carboxymethyl groups per glucose unit, between about 0.10 carboxymethyl groups per glucose unit and about 0.30 carboxymethyl groups per glucose unit, between about 0.10 carboxymethyl groups per glucose unit and about 0.25 carboxymethyl groups per glucose unit, between about 0.10 carboxymethyl groups per glucose unit and about 0.20 carboxymethyl groups per glucose unit, or between about 0.10 carboxymethyl groups per glucose unit and about 0.15 carboxymethyl groups per glucose unit.

In embodiments comprising sodium carboxymethylcellulose fibres, the fibres may have a degree of substitution of between about 0.15 carboxymethyl groups per glucose unit and about 0.50 carboxymethyl groups per glucose unit, between about 0.15 carboxymethyl groups per glucose unit and about 0.45 carboxymethyl groups per glucose unit, between about 0.15 carboxymethyl groups per glucose unit and about 0.40 carboxymethyl groups per glucose unit, between about 0.15 carboxymethyl groups per glucose unit and about 0.35 carboxymethyl groups per glucose unit, between about 0.15 carboxymethyl groups per glucose unit and about 0.30 carboxymethyl groups per glucose unit, between about 0.15 carboxymethyl groups per glucose unit and about 0.25 carboxymethyl groups per glucose unit, or between about 0.15 carboxymethyl groups per glucose unit and about 0.20 carboxymethyl groups per glucose unit.

In embodiments comprising sodium carboxymethylcellulose fibres, the fibres may have a degree of substitution of between about 0.20 carboxymethyl groups per glucose unit and about 0.50 carboxymethyl groups per glucose unit, between about 0.20 carboxymethyl groups per glucose unit and about 0.45 carboxymethyl groups per glucose unit, between about 0.20 carboxymethyl groups per glucose unit and about 0.40 carboxymethyl groups per glucose unit, between about 0.20 carboxymethyl groups per glucose unit and about 0.35 carboxymethyl groups per glucose unit, between about 0.20 carboxymethyl groups per glucose unit and about 0.30 carboxymethyl groups per glucose unit, or between about 0.20 carboxymethyl groups per glucose unit and about 0.25 carboxymethyl groups per glucose unit.

In embodiments comprising sodium carboxymethylcellulose fibres, the fibres may have a degree of substitution of between about 0.25 carboxymethyl groups per glucose unit and about 0.50 carboxymethyl groups per glucose unit, between about 0.25 carboxymethyl groups per glucose unit and about 0.45 carboxymethyl groups per glucose unit, between about 0.25 carboxymethyl groups per glucose unit and about 0.40 carboxymethyl groups per glucose unit, between about 0.25 carboxymethyl groups per glucose unit and about 0.35 carboxymethyl groups per glucose unit, or between about 0.25 carboxymethyl groups per glucose unit and about 0.30 carboxymethyl groups per glucose unit.

In embodiments comprising sodium carboxymethylcellulose fibres, the fibres may have a degree of substitution of between about 0.30 carboxymethyl groups per glucose unit and about 0.50 carboxymethyl groups per glucose unit, between about 0.30 carboxymethyl groups per glucose unit and about 0.45 carboxymethyl groups per glucose unit, between about 0.30 carboxymethyl groups per glucose unit and about 0.40 carboxymethyl groups per glucose unit, or between about 0.30 carboxymethyl groups per glucose unit and about 0.35 carboxymethyl groups per glucose unit.

In embodiments comprising sodium carboxymethylcellulose fibres, the fibres may have a degree of substitution of between about 0.35 carboxymethyl groups per glucose unit and about 0.50 carboxymethyl groups per glucose unit, between about 0.35 carboxymethyl groups per glucose unit and about 0.45 carboxymethyl groups per glucose unit, or between about 0.35 carboxymethyl groups per glucose unit and about 0.40 carboxymethyl groups per glucose unit.

In embodiments comprising sodium carboxymethylcellulose fibres, the fibres may have a degree of substitution of between about 0.40 carboxymethyl groups per glucose unit and about 0.50 carboxymethyl groups per glucose unit, or between about 0.40 carboxymethyl groups per glucose unit and about 0.45 carboxymethyl groups per glucose unit.

In embodiments comprising sodium carboxymethylcellulose fibres, the fibres may have a degree of substitution of between about 0.45 carboxymethyl groups per glucose unit and about 0.50 carboxymethyl groups per glucose unit.

The degree of substitution of the sodium carboxymethylcellulose fibres can be measured by IR spectroscopy (as defined in WO00/01425).

In embodiments comprising sodium carboxymethylcellulose fibres, the fibres may be made by carboxymethylating a woven or non-woven cellulosic fabric such that the absorbency is increased. The woven or non-woven cellulosic fabric may have an absorbency of between about 10 g/g of physiological saline solution (Solution A, a sodium/calcium chloride solution described below) to about 30 g/g of Solution A, about 15 g/g of Solution A to about 25 g/g of Solution A, about 15 g/g of Solution A to about 20 g/g of Solution A, or about 18 g/g of Solution A, as measured by the method described in BS EN 13726-1 (2002) "Test methods for primary wound dressings", section 3.2 "Free swell absorptive capacity". The carboxymethylation is generally performed by contacting the fabric with an alkali and a carboxymethylating agent such as chloroacetic acid in an aqueous system.

Solution A, as described in BS EN 13726-1 (2002), consists of sodium chloride and calcium chloride solution containing 142 mmol of sodium ions and 2.5 mmol of calcium ions as the chloride salts. This solution has an ionic composition comparable to human serum or wound exudate. It is prepared by dissolving 8.298 g of sodium chloride and 0.368 g of calcium chloride dihydrate in deionised water and making up to 1 litre in a volumetric flask.

The wound contact layer may comprise solely of cellulosic fibres. The wound contact layer may comprise a proportion of non-cellulosic textile fibres or gel forming fibres, or non gel-forming fibres. The cellulosic fibres may be of known kind and may comprise continuous filament yarn and/or staple fibre. The fabric may comprise fibres textiled into a non-woven fabric.

The gel-forming fibres may have an absorbency of at least 1 gram 0.9% saline solution per gram of fibre (as measured by the free swell method).

The wound contact layer may be stitched using lyocell yarn, cotton, nylon, polyester, or any non-gelling fibre. In particular, the wound contact layer may be stitched using lyocell yarn because, advantageously, this results in highly aligned cellulose fibres having a high degree of crystallinity, making the cellulose fibres collectively stronger so they are able to withstand manufacturing processes and provide a stronger wound contact layer which does not deteriorate in use. This also enhances the strength of the absorbent structure of the wound dressing.

The wound contact layer may, for example, be a Hydrofiber® material available from ConvaTec Ltd of Deeside.

The source of negative pressure may be capable of generating a minimum of 40 mmHg and a maximum of 200 mmHg, for example 125 mmHg, at the wound site.

The wound contact layer may comprise multiple layers bonded together, for example the wound contact layer may comprise two or more, for example three, four, five or six, layers of fabric bonded together. Each layer may have a weight of about 100 gsm, or any weight defined above. The multiple layers may be bonded together by stitch bonding or lamination. For example, the wound contact layer may comprise two layers, each having a weight of 100 gsm, stitch bonded together, such that the wound contact layer has a total weight of 200 gsm.

In embodiments comprising a wound contact layer comprising multiple layers, for example a first layer and a second layer, each layer may comprise a first surface and a second surface. FIG. 19 illustrates a wound contact layer 400 including a first layer 410 and a second layer 420. The first layer 410 includes a first surface 411 and a second surface 412. The second layer 420 includes a first surface 421 and a second surface 422. The first surface 411 of the first 410 layer is arranged to contact the wound in use. The second surface 412 of the first layer 410 is arranged facing the first surface 421 of the second layer 420. The second surface 412 of the first layer 410, and the first and second surfaces 421, 422 of the second layer 420, may comprise warp and weft stitches. The first surface 411 of the first layer 410 may comprise warp stitches only. The first and second surfaces 411, 412, 421, 422 of the first and second layers 410, 420 may comprise any features, including any optional features, mentioned above.

The superabsorbent material may comprise sodium polyacrylate. The sodium polyacrylate may be a powder, foam, sponge or fibres.

The invention according to the third aspect may of course individually include any one or more of the features, optional or otherwise, of the invention according to any other aspect.

According to yet another broad aspect of the invention, there is provided a wound dressing comprising a superabsorbent layer. The wound dressing may be a negative pressure wound dressing. The wound dressing may comprise a backing layer. The wound dressing may comprise an adhesive skin contact layer. The wound dressing may comprise an absorbent structure. The absorbent structure may be arranged between the backing layer and the adhesive skin contact layer. The adhesive skin contact layer may be configured to detachably adhere the dressing to a dermal surface. The backing layer may comprise a coupling member configured to connect the dressing to a negative pressure source. The absorbent structure may comprise the superabsorbent layer. The superabsorbent layer may comprise an upper layer and a lower layer. The upper layer and the lower layer may enclose a first material comprising at least one of non-woven fibres, an absorbent material and a hot melt binder.

According to a fourth aspect of the invention, there is provided a negative pressure wound dressing, the dressing comprising a backing layer, an adhesive skin contact layer and an absorbent structure, wherein the adhesive skin contact layer is configured to detachably adhere the dressing to a dermal surface, wherein the backing layer comprises a coupling member configured to connect the dressing to a negative pressure source, wherein the absorbent structure comprises a superabsorbent layer, the superabsorbent layer comprising an upper layer and a lower layer, the upper layer and the lower layer enclosing a first material comprising non-woven fibres, an absorbent material and a hot melt binder.

The absorbent structure may be arranged between the backing layer and the adhesive skin contact layer.

As such, one embodiment provides a negative pressure wound dressing, the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a superabsorbent layer, the superabsorbent layer comprising an upper layer and a lower layer, the upper layer and the lower layer enclosing a first material comprising non-woven fibres, an absorbent material and a hot melt binder.

A superabsorbent layer as defined in this specification is a layer comprising a superabsorbent material which can absorb and retain at least about 15 g/g 10 min, when tested with Solution A.

Advantageously, the synergistic effect of the non-woven fibres, absorbent material and the hot melt binder means that the superabsorbent layer has a particularly favourable fluid management capacity which means that the superabsorbent layer absorbs and retains a significant volume of fluid (i.e., wound exudate). Advantageously, tests have shown that the superabsorbent layer has an absorbent capacity of around 25 g/g 10 min, and at least about 15 g/g 10 min, when tested with Solution A, and an absorbent capacity under compression (−80 mmHg negative pressure) of around 0.85 g/cm$^2$, and at least about 0.55 g/cm$^2$, when tested with Solution A.

Moreover, the superabsorbent layer is flexible such that it can easily conform to the contours of a patient's body at a wound site when in use, therefore enhancing comfort for the patient when wearing the wound dressing. In some wound dressings of the prior art, one or more layers of the wound dressing may not exhibit a flexibility which is required to allow the wound dressing to readily conform to the contours of a patient's body. In such cases, the wound dressing may detach from the patient's body more easily than if the wound dressing conformed well to the contours of the patient's body. Further, the superabsorbent layer maintains its structure when wet or dampened, therefore, the superabsorbent layer maintains its strength and integrity within the absorbent structure of the wound dressing, thus resisting dissociation and shredding of fibres when in use.

The hot melt binder may be present in an amount of between about 40 and about 100 g/m$^2$, about 45 and about 95 g/m$^2$, about 50 and about 90 g/m$^2$, about 55 and about 85 g/m$^2$, about 60 and about 80 g/m$^2$, about 65 and about 75 g/m$^2$, or about 70 g/m$^2$.

The hot melt binder may be present in an amount of about 40 g/m$^2$, about 45 g/m$^2$, about 50 g/m$^2$, about 55 g/m$^2$, about 60 g/m$^2$, about 65 g/m$^2$, about 70 g/m$^2$, about 75 g/m$^2$, about 80 g/m$^2$, about 85 g/m$^2$, about 90 g/m$^2$, about 95 g/m$^2$, or about 100 g/m$^2$.

The hot melt binder may be present in an amount of at least about 40 g/m$^2$, about 45 g/m$^2$, about 50 g/m$^2$, about 55 g/m$^2$, about 60 g/m$^2$, about 65 g/m$^2$, about 70 g/m$^2$, about 75 g/m$^2$, about 80 g/m$^2$, about 85 g/m$^2$, about 90 g/m$^2$, about 95 g/m$^2$, or at least about 100 g/m$^2$.

The hot melt binder may be present in an amount of no more than about 40 g/m$^2$, about 45 g/m$^2$, about 50 g/m$^2$, about 55 g/m$^2$, about 60 g/m$^2$, about 65 g/m$^2$, about 70 g/m$^2$, about 75 g/m$^2$, about 80 g/m$^2$, about 85 g/m$^2$, about 90 g/m$^2$, about 95 g/m$^2$, or no more than about 100 g/m$^2$.

The hot melt binder may be present in an amount of between about 40 and about 100 g/m$^2$, between about 40 and about 95 g/m$^2$, between about 40 and about 90 g/m$^2$, between about 40 and about 85 g/m$^2$, between about 40 and about 80 g/m$^2$, between about 40 and about 75 g/m$^2$, between about 40 and about 70 g/m$^2$, between about 40 and about 65 g/m$^2$, between about 40 and about 60 g/m$^2$, between about 40 and about 55 g/m$^2$, between about 40 and about 50 g/m$^2$, or between about 40 and about 45 g/m$^2$.

The hot melt binder may be present in an amount of between about 45 and about 100 g/m$^2$, between about 45 and about 95 g/m$^2$, between about 45 and about 90 g/m$^2$, between about 45 and about 85 g/m$^2$, between about 45 and about 80 g/m$^2$, between about 45 and about 75 g/m$^2$, between about 45 and about 70 g/m$^2$, between about 45 and about 65 g/m$^2$, between about 45 and about 60 g/m$^2$, between about 45 and about 55 g/m$^2$, or between about 45 and about 50 g/m$^2$.

The hot melt binder may be present in an amount of between about 50 and about 100 g/m$^2$, between about 50 and about 95 g/m$^2$, between about 50 and about 90 g/m$^2$, between about 50 and about 85 g/m$^2$, between about 50 and about 80 g/m$^2$, between about 50 and about 75 g/m$^2$, between about 50 and about 70 g/m$^2$, between about 50 and about 65 g/m$^2$, between about 50 and about 60 g/m$^2$, or between about 50 and about 55 g/m$^2$.

The hot melt binder may be present in an amount of between about 55 and about 100 g/m$^2$, between about 55 and about 95 g/m$^2$, between about 55 and about 90 g/m$^2$, between about 55 and about 85 g/m$^2$, between about 55 and about 80 g/m$^2$, between about 55 and about 75 g/m$^2$, between about 55 and about 70 g/m$^2$, between about 55 and about 65 g/m$^2$, or between about 55 and about 60 g/m$^2$.

The hot melt binder may be present in an amount of between about 60 and about 100 g/m$^2$, between about 60 and about 95 g/m$^2$, between about 60 and about 90 g/m$^2$, between about 60 and about 85 g/m$^2$, between about 60 and about 80 g/m$^2$, between about 60 and about 75 g/m$^2$, between about 60 and about 70 g/m$^2$, or between about 60 and about 65 g/m$^2$.

The hot melt binder may be present in an amount of between about 65 and about 100 g/m$^2$, between about 65 and about 95 g/m$^2$, between about 65 and about 90 g/m$^2$, between about 65 and about 85 g/m$^2$, between about 65 and about 80 g/m$^2$, between about 65 and about 75 g/m$^2$, or between about 65 and about 70 g/m$^2$.

The hot melt binder may be present in an amount of between about 70 and about 100 g/m$^2$, between about 70 and about 95 g/m$^2$, between about 70 and about 90 g/m$^2$, between about 70 and about 85 g/m$^2$, between about 70 and about 80 g/m$^2$, or between about 70 and about 75 g/m$^2$.

The hot melt binder may be present in an amount of between about 75 and about 100 g/m$^2$, between about 75 and about 95 g/m$^2$, between about 75 and about 90 g/m$^2$, between about 75 and about 85 g/m$^2$, or between about 75 and about 80 g/m$^2$.

The hot melt binder may be present in an amount of between about 80 and about 100 g/m$^2$, between about 80 and about 95 g/m$^2$, between about 80 and about 90 g/m$^2$, or between about 80 and about 85 g/m$^2$.

The hot melt binder may be present in an amount of between about 85 and about 100 g/m$^2$, between about 85 and about 95 g/m$^2$, or between about 85 and about 90 g/m$^2$.

The hot melt binder may be present in an amount of between about 90 and about 100 g/m$^2$, or between about 90 and about 95 g/m$^2$.

The hot melt binder may be present in an amount of between about 95 and about 100 g/m$^2$.

The hot melt binder may be a copolymer. The hot melt binder may be ethylene-vinyl acetate (EVA) or poly(lactic acid) (PLA). In manufacture of the superabsorbent layer, the superabsorbent layer may be heated to melt the hot melt binder and bind the non-woven fibres of the first material together. Advantageously, this prevents, or at least significantly limits, the amount of shedding of the fibres of the superabsorbent layer when in use. Thus, the presence of the hot melt binder in the superabsorbent layer significantly increases the strength of the layer, preventing dissociation of the absorbent structure.

Advantageously, the presence of the hot melt binder in an amount of between about 40 to about 100 g/m$^2$ means that the superabsorbent layer is flexible when dry and maintains the strength required when wet to hold the absorbent structure together when in use. If the hot melt binder was present in an amount below 40 g/m$^2$, the superabsorbent layer would lose its structure when wet and may at least partially dissociate. If the hot melt binder was present in an amount greater than 100 g/m$^2$, the superabsorbent structure would be inflexible and too stiff for the required purpose of using the superabsorbent layer in a wound dressing where manipulation of the wound dressing in response to the contours of a user's body is required.

The superabsorbent layer may be capable of absorbing exudate from the wound contact layer and allowing the passage of fluid through it.

The absorbent material may be a superabsorbent material, in particular a superabsorbent material capable of absorbing wound exudate while allowing the passage of fluid through it. The superabsorbent material may be a powder, foam, sponge or fibre-based material. Advantageously, in embodiments where the superabsorbent material is a powder, the absorbent property of the superabsorbent material is enhanced due to a high surface area to volume ratio.

The non-woven fibres may be cellulose fibres. The cellulose non-woven fibres may be arranged as a cellulosic non-woven matrix of fibres. The cellulosic non-woven matrix may be a support onto which the absorbent material may be incorporated, for example the absorbent material may be dispersed upon the cellulosic non-woven matrix. The absorbent material may be dispersed evenly, or substantially evenly, throughout or upon the non-woven fibres, for example the cellulosic non-woven matrix. The absorbent material may be interspersed evenly, or substantially evenly, throughout the non-woven fibres, for example the cellulosic non-woven matrix.

The cellulose non-woven fibres may comprise solely of cellulosic fibre or may comprise a proportion of non-cellulosic textile fibre or gel forming fibre. The cellulosic fibre may comprise continuous filament yarn and/or staple fibre.

The non-woven fibres of the first material may have a low packing density, i.e., be loosely packed. The non-woven fibres may be arranged in a 3D random fibre orientation. The non-woven fibres may be cellulosic fibres. The absorbent material, for example a superabsorbent material, for example sodium polyacrylate, for example sodium polyacrylate in powder form, may be interspersed between the non-woven fibres of the first material.

The upper layer and/or the lower layer may comprise cellulosic fibres. The upper layer and/or the lower layer may comprise fibres formed of a hot melt binder, for example EVA or PLA, in addition to or instead of the cellulosic fibres. The fibres comprised in the upper layer and/or the lower layer may have a high packing density and may have a greater packing density than the fibres of the first material. The fibres comprised in the upper layer and/or the lower layer may be substantially arranged in a 2D orientation. The fibres comprised in the upper layer and/or the lower layer may be in an ordered orientation, or at least may be more ordered than the fibres of the first material. Each of the upper layer and the lower layer may have a smaller thickness than the thickness of the first material.

Advantageously, the first material, the upper layer and the lower layer of the superabsorbent layer exhibit structural integrity to the superabsorbent layer and, therefore, the integrity of the superabsorbent layer is maintained even when wet, for example when wet with exudate.

The first material may comprise gel-forming fibres. Gel-forming fibres are fibres which, upon the uptake of wound exudate, become moist, slippery and/or gelatinous and thus reduce the tendency for the surrounding fibres to adhere to the wound. The gel-forming fibres may be hygroscopic. Beneficially, the gel-forming fibres prevent, or at least significantly prevent, the superabsorbent layer adhering to the wound in use, which may be uncomfortable for the patient, especially when the wound dressing is removed to be replaced by a fresh wound dressing.

The gel forming fibres may be of the type which retain their structural integrity on absorption of fluid (e.g., wound exudate) or may be of the type which lose their fibrous form and become an amorphous or structureless gel.

The gel-forming fibres may be sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The upper layer may be an upper fabric layer. The lower layer may be a lower fabric layer. The upper fabric layer may be a cellulosic fabric layer. The lower fabric layer may be a cellulosic fabric layer. The upper fabric layer and the lower fabric layer may be joined around their entire periphery to enclose the first material.

The upper layer and the lower layer may be formed of the same material as the first material and comprise non-woven fibres, an absorbent material and a hot melt binder.

The upper fabric layer and/or the lower fabric layer may comprise a hot melt binder.

In embodiments where the superabsorbent layer comprises gel-forming fibres, the gel-forming fibres may comprise the hot melt binder. The gel-forming fibres may be a support onto which the hot melt binder may be incorporated, for example the hot melt binder may be dispersed throughout or upon the gel-forming fibres. The absorbent material may be dispersed evenly, or substantially evenly, throughout or upon the gel-forming fibres.

In embodiments where the superabsorbent layer comprises a cellulosic non-woven matrix, the cellulosic non-woven matrix may be a support onto which the hot melt binder may be incorporated, for example the hot melt binder may be dispersed upon the cellulosic non-woven matrix. The hot melt binder may be dispersed evenly, or substantially evenly, throughout or upon the non-woven fibres, for example the cellulosic non-woven matrix. The absorbent material may comprise sodium polyacrylate. The sodium polyacrylate may be a powder, foam, sponge or fibres.

The wound dressing may further comprise a wound contact layer. Although the superabsorbent layer may be in direct contact with the wound, preferably the superabsorbent layer may be arranged between the wound contact layer and the backing layer. The wound contact layer may be capable of absorbing wound exudate from the wound and transmitting it to the superabsorbent layer. Like the superabsorbent layer, the wound contact layer is capable of allowing the passage of fluid through it so that negative pressure may applied to the wound.

The wound dressing may further comprise a transmission layer. The superabsorbent layer may be arranged between the wound contact layer and the transmission layer.

The superabsorbent layer may comprise one or more fenestrations. The fenestrations may be slits or openings in the superabsorbent layer. The fenestrations may be in one or both of the upper layer and the lower layer. The one or more fenestrations may be perforations. The slits or openings may be arranged in a direction planar to a longitudinal axis and transverse to a longitudinal axis of the superabsorbent layer. Advantageously, this arrangement aids in managing a flow of exudate through the superabsorbent layer of the wound dressing. In particular, the fenestrations encourage or enable wound exudate to travel, or be absorbed, in a preferred direction. The fenestrations encourage or enable wound exudate to travel laterally on the superabsorbent, as opposed to axially. Beneficially, this means that wound exudate is dispersed across a greater surface area of the superabsorbent layer before it is transferred to the layer of the wound dressing located directly above (when in use) the superabsorbent layer and, therefore, flow of wound exudate away from the wound site is facilitated. The fenestrations may be formed mechanically, such as via cutting or mechanical punch perforation. The fenestrations are preferably slits having a length equal to about 80% of the length of the superabsorbent layer. The fenestrations may alternate vertically and horizontally in rows and columns across the superabsorbent layer. Advantageously, the fenestrations facilitate full use of the absorbent capacity of the superabsorbent layer and can also assist in negative pressure transmission through the superabsorbent layer.

The superabsorbent layer may have a basis weight of between about 300 g/m$^2$ and about 550 g/m$^2$, about 320 g/m$^2$ and about 545 g/m$^2$, about 340 g/m$^2$ and about 540 g/m$^2$, about 350 g/m$^2$ and about 535 g/m$^2$, about 370 g/m$^2$ and about 530 g/m$^2$, about 380 g/m$^2$ and about 525 g/m$^2$, about 390 g/m$^2$ and about 525 g/m$^2$, about 400 g/m$^2$ and about 520 g/m$^2$, about 410 g/m$^2$ and 510 g/m$^2$, about 420 g/m$^2$ and about 500 g/m$^2$, about 430 g/m$^2$ and about 490 g/m$^2$, about 440 g/m$^2$ and about 480 g/m$^2$, about 450 g/m$^2$ and about 470 g/m$^2$, or about 460 g/m$^2$.

The superabsorbent layer may have a basis weight of about 300 g/m$^2$, about 310 g/m$^2$, about 320 g/m$^2$, about 330 g/m$^2$, about 340 g/m$^2$, about 350 g/m$^2$, about 360 g/m$^2$, about 370 g/m$^2$, about 380 g/m$^2$, about 390 g/m$^2$, about 400 g/m$^2$, about 410 g/m$^2$, about 420 g/m$^2$, about 430 g/m$^2$, about 440 g/m$^2$, about 450 g/m$^2$, about 460 g/m$^2$, about 470 g/m$^2$, about 480 g/m$^2$, about 490 g/m$^2$, about 500 g/m$^2$, about 510 g/m$^2$, about 520 g/m$^2$, about 530 g/m$^2$, about 540 g/m$^2$, or about 550 g/m$^2$.

The superabsorbent layer may have a basis weight of at least about 300 g/m$^2$, about 310 g/m$^2$, about 320 g/m$^2$, about 330 g/m$^2$, about 340 g/m$^2$, about 350 g/m$^2$, about 360 g/m$^2$, about 370 g/m$^2$, about 380 g/m$^2$, about 390 g/m$^2$, about 400 g/m$^2$, about 410 g/m$^2$, about 420 g/m$^2$, about 430 g/m$^2$, about 440 g/m$^2$, about 450 g/m$^2$, about 460 g/m$^2$, about 470 g/m$^2$, about 480 g/m$^2$, about 490 g/m$^2$, about 500 g/m$^2$, about 510 g/m$^2$, about 520 g/m$^2$, about 530 g/m$^2$, about 540 g/m$^2$, or at least about 550 g/m$^2$.

The superabsorbent layer may have a basis weight of no more than about 300 g/m$^2$, about 310 g/m$^2$, about 320 g/m$^2$, about 330 g/m$^2$, about 340 g/m$^2$, about 350 g/m$^2$, about 360 g/m$^2$, about 370 g/m$^2$, about 380 g/m$^2$, about 390 g/m$^2$, about 400 g/m$^2$, about 410 g/m$^2$, about 420 g/m$^2$, about 430 g/m$^2$, about 440 g/m$^2$, about 450 g/m$^2$, about 460 g/m$^2$, about 470 g/m$^2$, about 480 g/m$^2$, about 490 g/m$^2$, about 500 g/m$^2$, about 510 g/m$^2$, about 520 g/m$^2$, about 530 g/m$^2$, about 540 g/m$^2$, or no more than about 550 g/m$^2$.

Advantageously, a superabsorbent layer having a basis weight as described above provides for sufficient fluid absorption and retention and is sufficiently flexible to conform to the contours of a patient's body at a wound site when in use. In particular, this advantageous effect is found with a superabsorbent layer having a basis weight between about 340 g/m$^2$ and about 510 g/m$^2$, especially between about 350 g/m$^2$ and about 500 g/m$^2$. Below about 300 g/m$^2$, the superabsorbent layer may not achieve sufficient absorbency of fluid, i.e., wound exudate. Above about 520 g/m$^2$ and in particular above about 550 g/m$^2$, the superabsorbent layer may be too thick and too dense, which may result in processability problems during manufacture and/or an inflexible layer which does not conform to the contours of a patient's body at a wound site when in use.

The superabsorbent layer may have a thickness of between about 1.40 mm and about 4.00 mm, about 1.50 mm and about 3.90 mm, about 1.60 mm and about 3.80 mm, about 1.70 mm and about 3.70 mm, about 1.80 mm and about 3.60 mm, about 1.85 mm and about 3.50 mm, about 1.90 mm and about 3.40 mm, about 1.95 mm and about 3.30 mm, about 2.00 mm and about 3.20 mm, about 2.05 mm and about 3.10 mm, about 2.10 mm and about 3.00 mm, about 2.15 mm and about 2.90 mm, about 2.20 mm and about 2.85 mm, about 2.25 mm and about 2.80 mm, about 2.30 mm and about 2.75 mm, about 2.35 mm and about 2.70 mm, about 2.40 mm and about 2.65 mm, about 2.45 mm and about 2.60 mm, about 2.50 mm and about 2.60 mm, or about 2.55 mm.

The superabsorbent layer may have a thickness of about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.05 mm, about 3.10 mm, about 3.15 mm, about 3.20 mm, about 3.25 mm, about 3.30 mm, about 3.35 mm, about 3.40 mm, about 3.45 mm, about 3.50 mm, about 3.55 mm, about 3.60 mm, about 3.65 mm, about 3.70 mm, about 3.75 mm, about 3.80 mm, about 3.85 mm, about 3.90 mm, about 3.95 mm, or about 4.00 mm.

The superabsorbent layer may have a thickness of at least about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.05 mm, about 3.10 mm, about 3.15 mm, about 3.20 mm, about 3.25 mm, about 3.30 mm, about 3.35 mm, about 3.40 mm, about 3.45 mm, about 3.50 mm, about 3.55 mm, about 3.60 mm, about 3.65 mm, about 3.70 mm, about 3.75 mm, about 3.80 mm, about 3.85 mm, about 3.90 mm, about 3.95 mm, or at least about 4.00 mm.

The superabsorbent layer may have a thickness of no more than about 1.40 mm, about 1.45 mm, about 1.50 mm, about 1.55 mm, about 1.60 mm, about 1.65 mm, about 1.70 mm, about 1.75 mm, about 1.80 mm, about 1.85 mm, about 1.90 mm, about 1.95 mm, about 2.00 mm, about 2.05 mm, about 2.10 mm, about 2.15 mm, about 2.20 mm, about 2.25 mm, about 2.30 mm, about 2.35 mm, about 2.40 mm, about 2.45 mm, about 2.50 mm, about 2.50 mm, about 2.55 mm, about 2.60 mm, about 2.65 mm, about 2.70 mm, about 2.75 mm, about 2.80 mm, about 2.85 mm, about 2.90 mm, about 2.95 mm, about 3.00 mm, about 3.05 mm, about 3.10 mm, about 3.15 mm, about 3.20 mm, about 3.25 mm, about 3.30 mm, about 3.35 mm, about 3.40 mm, about 3.45 mm, about 3.50 mm, about 3.55 mm, about 3.60 mm, about 3.65 mm, about 3.70 mm, about 3.75 mm, about 3.80 mm, about 3.85 mm, about 3.90 mm, about 3.95 mm, or no more than about 4.00 mm.

Advantageously, a superabsorbent layer having a thickness as described above provides for sufficient fluid absorption and retention and is sufficiently flexible to conform to the contours of a patient's body at a wound site when in use. At a thickness below about 1.40 mm, the absorbency capability of the superabsorbent layer may be restricted. At a thickness greater than about 4.00 mm, the superabsorbent layer may be too thick to be processed, or at least easily processed, during manufacture and may not be flexible enough to conform to the contours of a patient's body at a wound site when in use.

Further advantageously, there is a surprising synergistic effect found in embodiments comprising a superabsorbent layer having a basis weight as described above, for example a basis weight between about 300 g/m$^2$ and about 550 g/m$^2$, and a thickness as described above, for example a thickness between about 1.40 mm and about 4.00 mm, or any value within that range, in that the combination of these properties provides a superabsorbent layer having a density that is favourable for absorption and retention of fluid, for example wound exudate, and conformability to the contours of a patient's body at a wound site in use.

The thickness of the superabsorbent layer may be measured using a Hampden Soft Materials Thickness Gauge. The method of measuring the thickness of the superabsorbent layer using a Hampden Soft Materials Thickness Gauge may include:

a. Raising the foot of the thickness gauge high enough to place a test sample beneath it;
b. Lowering the foot onto the test sample until an indicator light comes on;
c. Leaving the foot in contact with the test sample for 10 seconds from when the indicator light came on. If the light has remained on, record the reading;
d. Repeat for the required number of replicates (for example 10 replicates) ensuring the gauge is zeroed in between each replicate.

The superabsorbent layer may have a density of between about 0.200 g/cm$^3$ and about 0.305 g/cm$^3$, about 0.205 g/cm$^3$ and about 0.300 g/cm$^3$, about 0.210 g/cm$^3$ and about 0.295 g/cm$^3$, about 0.215 g/cm$^3$ and about 0.290 g/cm$^3$, about 0.220 g/cm$^3$ and about 0.285 g/cm$^3$, about 0.225 g/cm$^3$ and about 0.280 g/cm$^3$, about 0.230 g/cm$^3$ and about 0.275 g/cm$^3$, about 0.235 g/cm$^3$ and about 0.270 g/cm$^3$, about 0.240 g/cm$^3$ and about 0.265 g/cm$^3$, about 0.245 g/cm$^3$ and about 0.260 g/cm$^3$, about 0.250 g/cm$^3$ and about 0.260 g/cm$^3$, or about 0.255 g/cm$^3$.

The superabsorbent layer may have a density of about 0.200 g/cm$^3$, about 0.205 g/cm$^3$, about 0.210 g/cm$^3$, about 0.215 g/cm$^3$, about 0.220 g/cm$^3$, about 0.225 g/cm$^3$, about 0.230 g/cm$^3$, about 0.235 g/cm$^3$, about 0.240 g/cm$^3$, about 0.245 g/cm$^3$, about 0.250 g/cm$^3$, about 0.255 g/cm$^3$, about 0.260 g/cm$^3$, about 0.265 g/cm$^3$, about 0.270 g/cm$^3$, about 0.275 g/cm$^3$, about 0.280 g/cm$^3$, about 0.285 g/cm$^3$, about 0.290 g/cm$^3$, about 0.295 g/cm$^3$, about 0.300 g/cm$^3$, or about 0.305 g/cm$^3$.

The superabsorbent layer may have a density of at least about 0.200 g/cm$^3$, about 0.205 g/cm$^3$, about 0.210 g/cm$^3$, about 0.215 g/cm$^3$, about 0.220 g/cm$^3$, about 0.225 g/cm$^3$, about 0.230 g/cm$^3$, about 0.235 g/cm$^3$, about 0.240 g/cm$^3$, about 0.245 g/cm$^3$, about 0.250 g/cm$^3$, about 0.255 g/cm$^3$, about 0.260 g/cm$^3$, about 0.265 g/cm$^3$, about 0.270 g/cm$^3$, about 0.275 g/cm$^3$, about 0.280 g/cm$^3$, about 0.285 g/cm$^3$, about 0.290 g/cm$^3$, about 0.295 g/cm$^3$, about 0.300 g/cm$^3$, or at least about 0.305 g/cm$^3$.

The superabsorbent layer may have a density of no more than about 0.200 g/cm$^3$, about 0.205 g/cm$^3$, about 0.210 g/cm$^3$, about 0.215 g/cm$^3$, about 0.220 g/cm$^3$, about 0.225 g/cm$^3$, about 0.230 g/cm$^3$, about 0.235 g/cm$^3$, about 0.240 g/cm$^3$, about 0.245 g/cm$^3$, about 0.250 g/cm$^3$, about 0.255 g/cm$^3$, about 0.260 g/cm$^3$, about 0.265 g/cm$^3$, about 0.270 g/cm$^3$, about 0.275 g/cm$^3$, about 0.280 g/cm$^3$, about 0.285 g/cm$^3$, about 0.290 g/cm$^3$, about 0.295 g/cm$^3$, about 0.300 g/cm$^3$, or no more than about 0.305 g/cm$^3$.

The superabsorbent layer may have a tensile strength (dry) of between about 30 N/50 mm and about 60 N/50 mm, about 35 N/50 mm and about 55 N/50 mm, about 40 N/50 mm and about 50 N/50 mm, or about 45 N/50 mm.

The superabsorbent layer may have a tensile strength (dry) of about 30 N/50 mm, about 35 N/50 mm, about 40 N/50 mm, about 45 N/50 mm, about 50 N/50 mm, about 55 N/50 mm, or about 60 N/50 mm.

The superabsorbent layer may have a tensile strength (dry) of at least about 30 N/50 mm, about 35 N/50 mm, about 40 N/50 mm, about 45 N/50 mm, about 50 N/50 mm, about 55 N/50 mm, or at least about 60 N/50 mm.

The superabsorbent layer may have a tensile strength (dry) of no more than about 30 N/50 mm, about 35 N/50 mm, about 40 N/50 mm, about 45 N/50 mm, about 50 N/50 mm, about 55 N/50 mm, or no more than about 60 N/50 mm.

Advantageously, a superabsorbent layer having a tensile strength as described above means that the superabsorbent layer is flexible and conforms well to the contours of a patient's body at the wound site when in use.

The tensile strength of the superabsorbent layer may be increased by increasing the amount of hot melt binder present in the superabsorbent layer. The tensile strength of the superabsorbent layer may be decreased by decreasing the amount of hot melt binder present in the superabsorbent layer.

The superabsorbent layer may have an absorbent capacity of between about 15 g/g 10 min and about 35 g/g 10 min, about 17.5 g/g 10 min and about 32.5 g/g 10 min, about 20 g/g 10 min and about 30 g/g 10 min, about 22.5 g/g 10 min and about 27.5 g/g 10 min, or about 25 g/g 10 min.

Advantageously, a superabsorbent layer having an absorbent capacity of between about 15 g/g 10 min and about 35 g/g 10 min, in particular about 25 g/g 10 min, means that the superabsorbent layer absorbs about 1 g/cm$^2$, which is considerably more favourable than absorbent layers used in known wound dressings.

The superabsorbent layer may have an absorbent capacity of about 15 g/g 10 min, about 17.5 g/g 10 min, about 20 g/g 10 min, about 22.5 g/g 10 min, about 25 g/g 10 min, about 27.5 g/g 10 min, about 30 g/g 10 min, about 32.5 g/g 10 min, or about 35 g/g 10 min.

The superabsorbent layer may have an absorbent capacity of at least about 15 g/g 10 min, about 17.5 g/g 10 min, about 20 g/g 10 min, about 22.5 g/g 10 min, about 25 g/g 10 min, about 27.5 g/g 10 min, about 30 g/g 10 min, about 32.5 g/g 10 min, or at least about 35 g/g 10 min.

The superabsorbent layer may have an absorbent capacity of no more than about 15 g/g 10 min, about 17.5 g/g 10 min, about 20 g/g 10 min, about 22.5 g/g 10 min, about 25 g/g 10 min, about 27.5 g/g 10 min, about 30 g/g 10 min, about 32.5 g/g 10 min, or no more than about 35 g/g 10 min.

The superabsorbent layer may have an absorbent capacity of between about 15 g/g 10 min and about 35 g/g 10 min, between about 15 g/g 10 min and about 30 g/g 10 min, between about 15 g/g 10 min and about 25 g/g 10 min, or between about 15 g/g 10 min and about 20 g/g 10 min.

The superabsorbent layer may have an absorbent capacity of between about 20 g/g 10 min and about 35 g/g 10 min, between about 20 g/g 10 min and about 30 g/g 10 min, or between about 20 g/g 10 min and about 25 g/g 10 min.

The superabsorbent layer may have an absorbent capacity of between about 25 g/g 10 min and about 35 g/g 10 min, or between about 25 g/g 10 min and about 30 g/g 10 min.

The superabsorbent layer may have an absorbent capacity of between about 30 g/g 10 min and about 35 g/g 10 min.

The absorbent capacity of the superabsorbent layer may be measured using the Liquid Handling Direct Immersion Technique, as follows:

GSM a. Cut a sample to be tested to a 5 cm×5 cm square (A1=25 cm$^2$);
b. Weigh each of the samples in grams;
c. Calculate:

$$GSM = \frac{(\text{sample weight(g)})}{0.0025\ \text{m}^2} = \text{g/m}^2$$

Liquid Handling a. Place the dressing test pieces in filter paper bags and weigh the sample in grams (W1);
b. Add 40 times the weight of the sample in warmed (37° C.±1° C.) hydrating fluid (solution A);
c. Incubate at 37° C. (±2° C.) for 30 (±1) minutes;
d. Using forceps remove the sample(s) and empty filter paper bag(s) from the incubator and suspend (holding the filter paper bags by one corner) over the dish for 30 seconds;
e. Re-weigh the sample(s) (W2);
f. Repeat above steps with the 3 empty filter paper bags, use to calculate the mean fluid uptake by the filter paper bags and subtract from weight of samples after hydration;
g. Calculate:

$$\text{Weight of solution absorbed per g of sample: } \frac{(W2 - W1)}{W1}\text{g/g}$$

$$\text{And Liquid uptake per unit area: } \frac{(W2 - W1)}{A1}\text{g/cm}^2$$

Fluid Retention a. Following step (e) above, remove sample from balance with forceps and place flat on dry perforated stainless-steel plate;
b. Immediately cover the wet sample with a 40 mmHg weight (1359.51 g for a 5×5 cm);
c. Leave in place for 1 minute, and then remove the weight;
d. Remove the sample from the perforated plate and weigh (W3);
e. Repeat with empty filter paper bags and use to calculate mean fluid retained by the filter paper bags and subtract from weight of samples after;

f. Calculate:

$$\text{Weight of solution retained per g of sample: } \frac{(W3 - W1)}{W1} \text{g/g}$$

$$\text{And Liquid retention per unit area: } \frac{(W3 - W1)}{A1} \text{g/cm}^2$$

The superabsorbent layer may have an absorbency under compression capacity of between about 0.50 g/cm$^2$ and about 1.20 g/cm$^2$, about 0.55 g/cm$^2$ and about 1.15 g/cm$^2$, about 0.60 g/cm$^2$ and about 1.10 g/cm$^2$, about 0.65 g/cm$^2$ and about 1.05 g/cm$^2$, about 0.70 g/cm$^2$ and about 1.00 g/cm$^2$, about 0.75 g/cm$^2$ and about 0.95 g/cm$^2$, about 0.80 g/cm$^2$ and about 0.90 g/cm$^2$, or about 0.85 g/cm$^2$.

The superabsorbent layer may have an absorbency under compression capacity of about 0.50 g/cm$^2$, about 0.55 g/cm$^2$, about 0.60 g/cm$^2$, about 0.65 g/cm$^2$, about 0.70 g/cm$^2$, about 0.75 g/cm$^2$, about 0.80 g/cm$^2$, about 0.85 g/cm$^2$, about 0.90 g/cm$^2$, about 0.95 g/cm$^2$, about 1.00 g/cm$^2$, about 1.05 g/cm$^2$, about 1.10 g/cm$^2$, about 1.15 g/cm$^2$, or about 1.20 g/cm$^2$.

The superabsorbent layer may have an absorbency under compression capacity of at least about 0.50 g/cm$^2$, about 0.55 g/cm$^2$, about 0.60 g/cm$^2$, about 0.65 g/cm$^2$, about 0.70 g/cm$^2$, about 0.75 g/cm$^2$, about 0.80 g/cm$^2$, about 0.85 g/cm$^2$, about 0.90 g/cm$^2$, about 0.95 g/cm$^2$, about 1.00 g/cm$^2$, about 1.05 g/cm$^2$, about 1.10 g/cm$^2$, about 1.15 g/cm$^2$, or at least about 1.20 g/cm$^2$.

The superabsorbent layer may have an absorbency under compression capacity of no more than about 0.50 g/cm$^2$, about 0.55 g/cm$^2$, about 0.60 g/cm$^2$, about 0.65 g/cm$^2$, about 0.70 g/cm$^2$, about 0.75 g/cm$^2$, about 0.80 g/cm$^2$, about 0.85 g/cm$^2$, about 0.90 g/cm$^2$, about 0.95 g/cm$^2$, about 1.00 g/cm$^2$, about 1.05 g/cm$^2$, about 1.10 g/cm$^2$, about 1.15 g/cm$^2$, or no more than about 1.20 g/cm$^2$.

The superabsorbent layer may have an absorbency under compression capacity of between about 0.50 g/cm$^2$ and about 1.20 g/cm$^2$, between about 0.50 g/cm$^2$ and about 1.15 g/cm$^2$, between about 0.50 g/cm$^2$ and about 1.10 g/cm$^2$, between about 0.50 g/cm$^2$ and about 1.05 g/cm$^2$, between about 0.50 g/cm$^2$ and about 1.00 g/cm$^2$, between about 0.50 g/cm$^2$ and about 0.95 g/cm$^2$, between about 0.50 g/cm$^2$ and about 0.90 g/cm$^2$, between about 0.50 g/cm$^2$ and about 0.85 g/cm$^2$, between about 0.50 g/cm$^2$ and about 0.80 g/cm$^2$, between about 0.50 g/cm$^2$ and about 0.75 g/cm$^2$, between about 0.50 g/cm$^2$ and about 0.70 g/cm$^2$, between about 0.50 g/cm$^2$ and about 0.65 g/cm$^2$, between about 0.50 g/cm$^2$ and about 0.60 g/cm$^2$, or between about 0.50 g/cm$^2$ and about 0.55 g/cm$^2$.

The superabsorbent layer may have an absorbency under compression capacity of between about 0.55 g/cm$^2$ and about 1.20 g/cm$^2$, between about 0.55 g/cm$^2$ and about 1.15 g/cm$^2$, between about 0.55 g/cm$^2$ and about 1.10 g/cm$^2$, between about 0.55 g/cm$^2$ and about 1.05 g/cm$^2$, between about 0.55 g/cm$^2$ and about 1.00 g/cm$^2$, between about 0.55 g/cm$^2$ and about 0.95 g/cm$^2$, between about 0.55 g/cm$^2$ and about 0.90 g/cm$^2$, between about 0.55 g/cm$^2$ and about 0.85 g/cm$^2$, between about 0.55 g/cm$^2$ and about 0.80 g/cm$^2$, between about 0.55 g/cm$^2$ and about 0.75 g/cm$^2$, between about 0.55 g/cm$^2$ and about 0.70 g/cm$^2$, between about 0.55 g/cm$^2$ and about 0.65 g/cm$^2$, or between about 0.55 g/cm$^2$ and about 0.60 g/cm$^2$.

The superabsorbent layer may have an absorbency under compression capacity of between about 0.60 g/cm$^2$ and about 1.20 g/cm$^2$, between about 0.60 g/cm$^2$ and about 1.15 g/cm$^2$, between about 0.60 g/cm$^2$ and about 1.10 g/cm$^2$, between about 0.60 g/cm$^2$ and about 1.05 g/cm$^2$, between about 0.60 g/cm$^2$ and about 1.00 g/cm$^2$, between about 0.60 g/cm$^2$ and about 0.95 g/cm$^2$, between about 0.60 g/cm$^2$ and about 0.90 g/cm$^2$, between about 0.60 g/cm$^2$ and about 0.85 g/cm$^2$, between about 0.60 g/cm$^2$ and about 0.80 g/cm$^2$, between about 0.60 g/cm$^2$ and about 0.75 g/cm$^2$, between about 0.60 g/cm$^2$ and about 0.70 g/cm$^2$, or between about 0.60 g/cm$^2$ and about 0.65 g/cm$^2$.

The superabsorbent layer may have an absorbency under compression capacity of between about 0.65 g/cm$^2$ and about 1.20 g/cm$^2$, between about 0.65 g/cm$^2$ and about 1.15 g/cm$^2$, between about 0.65 g/cm$^2$ and about 1.10 g/cm$^2$, between about 0.65 g/cm$^2$ and about 1.05 g/cm$^2$, between about 0.65 g/cm$^2$ and about 1.00 g/cm$^2$, between about 0.65 g/cm$^2$ and about 0.95 g/cm$^2$, between about 0.65 g/cm$^2$ and about 0.90 g/cm$^2$, between about 0.65 g/cm$^2$ and about 0.85 g/cm$^2$, between about 0.65 g/cm$^2$ and about 0.80 g/cm$^2$, between about 0.65 g/cm$^2$ and about 0.75 g/cm$^2$, or between about 0.65 g/cm$^2$ and about 0.70 g/cm$^2$.

The superabsorbent layer may have an absorbency under compression capacity of between about 0.70 g/cm$^2$ and about 1.20 g/cm$^2$, between about 0.70 g/cm$^2$ and about 1.15 g/cm$^2$, between about 0.70 g/cm$^2$ and about 1.10 g/cm$^2$, between about 0.70 g/cm$^2$ and about 1.05 g/cm$^2$, between about 0.70 g/cm$^2$ and about 1.00 g/cm$^2$, between about 0.70 g/cm$^2$ and about 0.95 g/cm$^2$, between about 0.70 g/cm$^2$ and about 0.90 g/cm$^2$, between about 0.70 g/cm$^2$ and about 0.85 g/cm$^2$, between about 0.70 g/cm$^2$ and about 0.80 g/cm$^2$, or between about 0.70 g/cm$^2$ and about 0.75 g/cm$^2$.

The superabsorbent layer may have an absorbency under compression capacity of between about 0.75 g/cm$^2$ and about 1.20 g/cm$^2$, between about 0.75 g/cm$^2$ and about 1.15 g/cm$^2$, between about 0.75 g/cm$^2$ and about 1.10 g/cm$^2$, between about 0.75 g/cm$^2$ and about 1.05 g/cm$^2$, between about 0.75 g/cm$^2$ and about 1.00 g/cm$^2$, between about 0.75 g/cm$^2$ and about 0.95 g/cm$^2$, between about 0.75 g/cm$^2$ and about 0.90 g/cm$^2$, between about 0.75 g/cm$^2$ and about 0.85 g/cm$^2$, or between about 0.75 g/cm$^2$ and about 0.80 g/cm$^2$.

The superabsorbent layer may have an absorbency under compression capacity of between about 0.80 g/cm$^2$ and about 1.20 g/cm$^2$, between about 0.80 g/cm$^2$ and about 1.15 g/cm$^2$, between about 0.80 g/cm$^2$ and about 1.10 g/cm$^2$, between about 0.80 g/cm$^2$ and about 1.05 g/cm$^2$, between about 0.80 g/cm$^2$ and about 1.00 g/cm$^2$, between about 0.80 g/cm$^2$ and about 0.95 g/cm$^2$, between about 0.80 g/cm$^2$ and about 0.90 g/cm$^2$, or between about 0.80 g/cm$^2$ and about 0.85 g/cm$^2$.

The superabsorbent layer may have an absorbency under compression capacity of between about 0.85 g/cm$^2$ and about 1.20 g/cm$^2$, between about 0.85 g/cm$^2$ and about 1.15 g/cm$^2$, between about 0.85 g/cm$^2$ and about 1.10 g/cm$^2$, between about 0.85 g/cm$^2$ and about 1.05 g/cm$^2$, between about 0.85 g/cm$^2$ and about 1.00 g/cm$^2$, between about 0.85 g/cm$^2$ and about 0.95 g/cm$^2$, or between about 0.85 g/cm$^2$ and about 0.90 g/cm$^2$.

The superabsorbent layer may have an absorbency under compression capacity of between about 0.90 g/cm$^2$ and about 1.20 g/cm$^2$, between about 0.90 g/cm$^2$ and about 1.15 g/cm$^2$, between about 0.90 g/cm$^2$ and about 1.10 g/cm$^2$, between about 0.90 g/cm$^2$ and about 1.05 g/cm$^2$, between about 0.90 g/cm$^2$ and about 1.00 g/cm$^2$, or between about 0.90 g/cm$^2$ and about 0.95 g/cm$^2$.

The superabsorbent layer may have an absorbency under compression capacity of between about 0.95 g/cm$^2$ and about 1.20 g/cm$^2$, between about 0.95 g/cm$^2$ and about 1.15 g/cm$^2$, between about 0.95 g/cm$^2$ and about 1.10 g/cm$^2$, between about 0.95 g/cm$^2$ and about 1.05 g/cm$^2$, or between about 0.95 g/cm$^2$ and about 1.00 g/cm$^2$.

The superabsorbent layer may have an absorbency under compression capacity of between about 1.00 g/cm$^2$ and about 1.20 g/cm$^2$, between about 1.00 g/cm$^2$ and about 1.15 g/cm$^2$, between about 1.00 g/cm$^2$ and about 1.10 g/cm$^2$, or between about 1.00 g/cm$^2$ and about 1.05 g/cm$^2$.

The superabsorbent layer may have an absorbency under compression capacity of between about 1.05 g/cm$^2$ and about 1.20 g/cm$^2$, between about 1.05 g/cm$^2$ and about 1.15 g/cm$^2$, or between about 1.05 g/cm$^2$ and about 1.10 g/cm$^2$.

The superabsorbent layer may have an absorbency under compression capacity of between about 1.10 g/cm$^2$ and about 1.20 g/cm$^2$, or between about 1.10 g/cm$^2$ and about 1.15 g/cm$^2$.

The superabsorbent layer may have an absorbency under compression capacity of between about 1.15 g/cm$^2$ and about 1.20 g/cm$^2$.

Absorbency under compression may be measured using the following test:

1. Cut a sample to be tested to 5 cm×5 cm squares (A1=25 cm$^2$) (test sample);
2. Place a test sample into filter paper bags and weigh each bag; record the weight in grams (W1);
3. Place the test sample onto a dry stainless-steel perforated plate, then place a weight equivalent to 80 mmHg on each sample;
4. Repeat with three empty filter bags;
5. Add sufficient hydrating fluid (Solution A) at 20° C.±2° C. such that the stainless-steel perforated plate is covered and leave for 24 hours at 20° C.±2° C.;
6. Drain off the hydrating fluid (Solution A) and remove the combined weight;
7. Remove the test sample using forceps and weigh it immediately (W2);
8. Place the test sample onto a dry stainless steel perforated plate and then place a weight equivalent to 80 mmHg onto the sample such that this load is applied evenly over the surface of the test sample;
9. Leave this in place for 15 minutes;
10. Reweigh the test sample in grams (W3);
11. Repeat above steps with the 3 empty filter paper bags, use to calculate the mean fluid retained by the filter paper bags and subtract from weight of samples after hydration;
12. Calculate:
    a. Weight of solution absorbed per g of sample: (W2−W1)/W1 g/g
    b. Weight of fluid retained per g of sample: (W3−W1)/W1 g/g
    c. Fluid absorbed unit area: (W2−W1)/A1 g/cm$^2$
    d. Retained retention per unit area: (W3−W1)/A1 g/cm$^2$
    e. % Fluid immobilised: (W3/W2)×100

The above described test mimics the compression of the structure which is expected when a −80 mmHg negative pressure is applied to the wound site, as is the typical pressure used in negative pressure wound dressings.

Advantageously, a superabsorbent layer having an absorbency under compression value as above sufficiently absorbs fluid, (i.e., wound exudate) from the wound site such that the superabsorbent layer maintains an environment optimised for wound healing at the wound site.

The superabsorbent layer may be any shape, such as a circle, an oval, a triangle, a square, a rectangle, a hexagon or an octagon, or any irregular shape. Each layer of the absorbent structure may have the same, or substantially the same, shape.

The superabsorbent layer may be planar, or substantially planar.

The superabsorbent layer may comprise a plurality of superabsorbent layers, each layer comprising an upper layer and a lower layer, together which enclose a first material comprising non-woven fibres, an absorbent material and a hot melt binder. Each layer of the plurality of superabsorbent layers may be identical. The plurality of superabsorbent layers may be disposed adjacent one another within the absorbent structure of the wound dressing. The plurality of superabsorbent layers may comprise two, three, four, five, six, seven, eight, nine, or more superabsorbent layers.

The invention according to the fourth aspect may of course individually include any one or more of the features, optional or otherwise, of the invention according to any other aspect.

According to a further broad aspect of the invention, there is provided a wound dressing comprising an absorbent structure. The wound dressing may be a negative pressure wound dressing. The wound dressing may further comprise a backing layer. The wound dressing may further comprise an adhesive skin contact layer. The adhesive skin contact layer may be configured to detachably adhere the dressing to a dermal surface. The backing layer may comprise a coupling member configured to connect the dressing to a negative pressure source. The absorbent structure may comprise at least two of a wound contact layer, a transmission layer and a superabsorbent layer. The at least two of the wound contact layer, transmission layer and superabsorbent layer may be laminated together.

According to a fifth aspect of the invention, there is provided a negative pressure wound dressing, the dressing comprising a backing layer, an adhesive skin contact layer and an absorbent structure, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer, a transmission layer and a superabsorbent layer, and wherein at least two of the wound contact layer, the transmission layer and the superabsorbent layer are laminated together.

The absorbent structure may be arranged between the backing layer and the adhesive skin contact layer.

As such, in one embodiment of the invention there is provided a negative pressure wound dressing, the dressing comprising a backing layer, an adhesive border skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer, a transmission layer and a superabsorbent layer, and wherein at least two of the wound contact layer, the transmission layer and the superabsorbent layer are laminated together.

Typically, absorbent structures of the prior art include rigid dressing components and/or binding components to provide strength and integrity to the absorbent structure to prevent, or at least reduce the possibility of, dissociation and tearing of the absorbent structure, particularly when wetted with wound exudate during use. Advantageously, the present invention does not require any relatively rigid dressing and/or binding components to provide an absorbent structure for a negative pressure wound dressing. The present invention provides for an absorbent structure which does not dissociate or tear, or at least there is a reduced possibility of dissociation and tearing compared to absorbent structures of the prior art, when wetted during use. The present invention achieves this not least by providing an absorbent structure comprising a wound contact layer, transmission layer and superabsorbent layer, at least two of which are laminated together.

As an example, some known wound dressings in the prior art are typically provided with an adhesive layer which creates an exterior housing or envelope with a backing layer, within which the remaining layers (for example a wound contact layer and absorbent layer) are housed. The adhesive layer is typically connected to the backing layer and the exterior surface of the absorbent structure (usually the wound contact layer) to hold the absorbent structure in place. The adhesive layer also adheres the wound dressing to the peri-wound skin. As such, the adhesive layer is commonly wetted with wound exudate during use which may reduce the adhesion between the adhesive layer and the absorbent structure. In this case, the absorbent structure may partially, or wholly, dissociate, disadvantageously affecting the application of negative pressure to the wound site and the ability of the wound dressing to retain wound exudate.

The present invention involves lamination of at least two of the wound contact layer, transmission layer and superabsorbent layer of the absorbent structure, therefore, removing the reliance upon an external adhesive layer to hold the absorbent structure together. As such, the present invention does not succumb to the above disadvantages of the prior art.

Moreover, the present invention does not rely on additional dressing and binding components to hold the absorbent structure together, some of which require specialist manufacturing steps and techniques to incorporate into a wound dressing. The present invention uses simple lamination techniques to enhance the strength and integrity of the absorbent structure. As such, the wound dressing of the present invention is cheaper and simpler to manufacture than some wound dressings of the prior art.

Further advantageously, as the present invention does not require any relatively rigid dressing and binding components, the absorbent structure is less rigid than absorbent structures of the prior art. Thus, the present invention provides a negative pressure wound dressing which is flexible, and in some cases more flexible than negative pressure wound dressings of the prior art and, therefore, provides greater conformation to the contours of a patient's body at a wound site in use and thus greater comfort for the patient.

The backing layer may comprise a first surface and a second surface. In use, the first surface may be inwardly facing toward the patient's body, and the second surface may be outwardly facing away from the patient's body.

The adhesive skin contact layer may comprise a first surface and a second surface. In use, the first surface may adhere to the skin of a patient, and the second surface may be outwardly facing away from the patient's body.

The absorbent structure may comprise a first surface and a second surface. The first surface of the absorbent structure may be adjacent, and in contact with, the second surface of the adhesive skin contact layer. The second surface of the absorbent structure may be adjacent, and in contact with, the first surface of the backing layer.

The first surface of the absorbent structure may be a first surface of any of the layers of the absorbent structure, for example the first surface of the wound contact layer, the transmission layer or the superabsorbent layer. In particular, the first surface of the absorbent structure may be the first surface of the wound contact layer.

The wound contact layer may comprise a first surface and a second surface. In use, the first surface may be inwardly facing toward the patient's body, and the second surface may be outwardly facing away from the patient's body. The first surface of the wound contact layer may contact the wound when the wound dressing is adhered to the skin adjacent to the wound (i.e., when in use). The second surface of the wound contact layer may be adjacent, and in contact with, a first surface of the transmission layer or the superabsorbent layer.

The transmission layer may comprise a first surface and a second surface. In use, the first surface may be inwardly facing toward the patient's body, and the second surface may be outwardly facing away from the patient's body. The first surface of the transmission layer may be adjacent, and in contact with, the second surface of the wound contact layer or a second surface of the superabsorbent layer. The second surface of the transmission layer may be adjacent, and in contact with, a first surface of the superabsorbent layer or the first surface of the backing layer.

The superabsorbent layer may comprise a first surface and a second surface. In use, the first surface may be inwardly facing toward the patient's body, and the second surface may be outwardly facing away from the patient's body. The first surface of the superabsorbent layer may be adjacent, and in contact with, the second surface of the wound contact layer or the second surface of the transmission layer. The second surface of the superabsorbent layer may be adjacent, and in contact with, the first surface of the transmission layer or the first surface of the backing layer.

The adhesive skin contact layer may provide an adhesive border. Advantageously, this means the adhesive skin contact layer easily allows the wound dressing to detachably adhere to a peri-wound dermal surface, and not adhere directly to a wound which may cause discomfort for a user.

The adhesive skin contact layer may be configured to detachably adhere the dressing to a peri-wound dermal surface.

The adhesive skin contact layer may comprise a window. Advantageously, the window allows the adhesive skin contact layer to be adhered around a wound, such that the wound site is placed within the window, therefore, allowing the patient's wound to be in contact, or be in fluid communication with, for example and preferably, the wound contact layer when the wound dressing is applied to the skin of a patient.

The window may have an area of between about 900 $mm^2$ and about 50,000 $mm^2$, about 1600 $mm^2$ and about 45,000 $mm^2$, about 2500 $mm^2$ and about 40,000 $mm^2$, about 3600 $mm^2$ and about 35,000 $mm^2$, about 4900 $mm^2$ and about 30,000 $mm^2$, about 6400 $mm^2$ and about 25,000 $mm^2$, about 8100 $mm^2$ and about 20,000 $mm^2$, about 10,000 $mm^2$ and about 15,000 $mm^2$, or about 12,500 $mm^2$.

The window may have an area of about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 33,600 $mm^2$, about 35,000 $mm^2$, about 37,500 $mm^2$, about 40,000 $mm^2$, about 42,500 $mm^2$, about 45,000 $mm^2$, about 47,500 $mm^2$, or about 50,000 $mm^2$.

The window may have an area of at least about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 33,600 $mm^2$, about 35,000 $mm^2$, about 37,500 $mm^2$, about 40,000 $mm^2$, about 42,500 $mm^2$, about 45,000 $mm^2$, about 47,500 $mm^2$, or at least about 50,000 $mm^2$.

The window may have an area of no more than about 900 $mm^2$, about 1200 $mm^2$, about 1600 $mm^2$, about 2000 $mm^2$, about 2500 $mm^2$, about 3000 $mm^2$, about 3600 $mm^2$, about 4000 $mm^2$, about 4400 $mm^2$, about 4900 $mm^2$, about 5400 $mm^2$, about 5900 $mm^2$, about 6400 $mm^2$, about 6900 $mm^2$, about 7500 $mm^2$, about 8100 $mm^2$, about 8700 $mm^2$, about 9300 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 33,600 $mm^2$, about 35,000 $mm^2$, about 37,500 $mm^2$, about 40,000 $mm^2$, about 42,500 $mm^2$, about 45,000 $mm^2$, about 47,500 $mm^2$, or no more than about 50,000 $mm^2$.

The adhesive skin contact layer may overlap the absorbent structure. The adhesive skin contact layer may comprise an interior portion and an exterior portion radially outwardly from the interior portion. The interior portion and the exterior portion of the first surface may contact and adhere to the skin of a patient in use. The interior portion of the second surface of the adhesive skin contact layer may be adjacent, and in contact with, a portion of the first surface of the absorbent structure, in particular a portion of the first surface of the wound contact layer of the absorbent structure. The exterior portion of the second surface of the adhesive skin contact layer may be adjacent, and in contact with, a portion of the first surface of the backing layer. Beneficially, this helps to prevent wound exudate escaping from the confines of the wound dressing which would be unhygienic and cause discomfort for the user. Moreover, this also helps maintain a negative pressure at the wound site.

The overlap between the adhesive skin contact layer and the absorbent structure may be between about 5 mm and about 50 mm deep, about 10 mm and about 45 mm deep, about 15 mm and about 40 mm deep, about 20 mm and about 35 mm deep, about 25 mm and about 30 mm deep, or about 27.5 mm deep.

The overlap between the adhesive skin contact layer and the absorbent structure may be about 5 mm, about 10 mm, about 15 mm, about 20 mm, about 25 mm, about 30 mm, about 35 mm, about 40 mm, about 45 mm, or about 50 mm.

The overlap between the adhesive skin contact layer and the absorbent structure may be at least about 5 mm, about 10 mm, about 15 mm, about 20 mm, about 25 mm, about 30 mm, about 35 mm, about 40 mm, about 45 mm, or at least about 50 mm.

The overlap between the adhesive skin contact layer and the absorbent structure may be no more than about 5 mm, about 10 mm, about 15 mm, about 20 mm, about 25 mm, about 30 mm, about 35 mm, about 40 mm, about 45 mm, or no more than about 50 mm.

The absorbent structure may have an area of between about 900 $mm^2$ and about 100,000 $mm^2$, about 1600 $mm^2$ and about 95,000 $mm^2$, about 2500 $mm^2$ and about 90,000 $mm^2$, about 3600 $mm^2$ and about 85,000 $mm^2$, about 4900 $mm^2$ and about 80,000 $mm^2$, about 6400 $mm^2$ and about 75,000 $mm^2$, about 8100 $mm^2$ and about 70,000 $mm^2$, about 10,000 $mm^2$ and about 65,000 $mm^2$, about 12,500 $mm^2$ and about 60,000 $mm^2$, about 15,000 $mm^2$ and about 55,000 $mm^2$, about 17,500 $mm^2$ and about 50,000 $mm^2$, about 20,000 $mm^2$ and about 45,000 $mm^2$, about 22,500 $mm^2$ and about 40,000 $mm^2$, about 25,000 $mm^2$ and about 35,000 $mm^2$, about 27,500 $mm^2$ and about 32,500 $mm^2$, or about 30,000 $mm^2$.

The absorbent structure may have an area of about 900 $mm^2$, about 1600 $mm^2$, about 2500 $mm^2$, about 3600 $mm^2$, about 4900 $mm^2$, about 6400 $mm^2$, about 8100 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 40,000 $mm^2$, about 45,000 $mm^2$, about 50,000 $mm^2$, about 55,000 $mm^2$, about 60,000 $mm^2$, about 65,000 $mm^2$, about 70,000 $mm^2$, about 75,000 $mm^2$, about 80,000 $mm^2$, about 85,000 $mm^2$, about 90,000 $mm^2$, about 95,000 $mm^2$, or about 100,000 $mm^2$.

The absorbent structure may have an area of at least about 900 $mm^2$, about 1600 $mm^2$, about 2500 $mm^2$, about 3600 $mm^2$, about 4900 $mm^2$, about 6400 $mm^2$, about 8100 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 40,000 $mm^2$, about 45,000 $mm^2$, about 50,000 $mm^2$, about 55,000 $mm^2$, about 60,000 $mm^2$, about 65,000 $mm^2$, about 70,000 $mm^2$, about 75,000 $mm^2$, about 80,000 $mm^2$, about 85,000 $mm^2$, about 90,000 $mm^2$, about 95,000 $mm^2$, or at least about 100,000 $mm^2$.

The absorbent structure may have an area of no more than about 900 $mm^2$, about 1600 $mm^2$, about 2500 $mm^2$, about 3600 $mm^2$, about 4900 $mm^2$, about 6400 $mm^2$, about 8100 $mm^2$, about 10,000 $mm^2$, about 12,500 $mm^2$, about 15,000 $mm^2$, about 17,500 $mm^2$, about 20,000 $mm^2$, about 22,500 $mm^2$, about 25,000 $mm^2$, about 27,500 $mm^2$, about 30,000 $mm^2$, about 32,500 $mm^2$, about 35,000 $mm^2$, about 40,000 $mm^2$, about 45,000 $mm^2$, about 50,000 $mm^2$, about 55,000 $mm^2$, about 60,000 $mm^2$, about 65,000 $mm^2$, about 70,000 $mm^2$, about 75,000 $mm^2$, about 80,000 $mm^2$, about 85,000 $mm^2$, about 90,000 $mm^2$, about 95,000 $mm^2$, or no more than about 100,000 $mm^2$.

Each of the wound contact layer, the transmission layer and the superabsorbent layer may be laminated together. Advantageously, this means that the absorbent structure of the present invention is manufactured without requiring any relatively rigid dressing and binding components. Thus, the present invention provides an absorbent structure which is flexible, therefore benefits user comfort, and which is cheaper to manufacture than absorbent structures and, therefore negative pressure wound dressings, of the prior art. Moreover, lamination does not require any complex equipment or manufacturing techniques. Thus, the present invention is simple to manufacture.

The at least two of the wound contact layer, the transmission layer and the superabsorbent layer may be laminated by heat lamination.

The at least two of the wound contact layer, the transmission layer and the superabsorbent layer may be laminated by heat lamination using a heat laminator.

The at least two of the wound contact layer, the transmission layer and the superabsorbent layer may be laminated by a laminator having a heating zone temperature between about 50° C. and about 200° C., about 60° C. and about 190° C., about 70° C. and about 180° C., about 80° C. and about 170° C., about 90° C. and about 160° C., about 100° C. and about 150° C., about 110° C. and about 140° C., about 120° C. and about 130° C., or about 125° C.

The at least two of the wound contact layer, the transmission layer and the superabsorbent layer may be laminated by a laminator having a heating zone temperature of about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., or about 200° C.

The at least two of the wound contact layer, the transmission layer and the superabsorbent layer may be laminated by a laminator having a heating zone temperature of at least about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., or at least about 200° C.

The at least two of the wound contact layer, the transmission layer and the superabsorbent layer may be laminated by a laminator having a heating zone temperature of no more than about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., or no more than about 200° C.

The at least two of the wound contact layer, the transmission layer and the superabsorbent layer may be laminated by a laminator having a cooling zone temperature of between about 0° C. and about 50° C., about 5° C. and about 45° C., about 10° C. and about 40° C., about 15° C. and about 35° C., about 20° C. and about 30° C., or about 25° C.

The at least two of the wound contact layer, the transmission layer and the superabsorbent layer may be laminated by a laminator having a cooling zone temperature of about 0° C., about 5° C., about 10° C., about 15° C., about 20° C., about 25° C., about 30° C., about 35° C., about 40° C., about 45° C., or about 50° C.

The at least two of the wound contact layer, the transmission layer and the superabsorbent layer may be laminated by a laminator having a cooling zone temperature of at least about 0° C., about 5° C., about 10° C., about 15° C., about 20° C., about 25° C., about 30° C., about 35° C., about 40° C., about 45° C., or at least about 50° C.

The at least two of the wound contact layer, the transmission layer and the superabsorbent layer may be laminated by a laminator having a cooling zone temperature of no more than about 0° C., about 5° C., about 10° C., about 15° C., about 20° C., about 25° C., about 30° C., about 35° C., about 40° C., about 45° C., or no more than about 50° C.

The at least two of the wound contact layer, the transmission layer and the superabsorbent layer may be laminated by a laminator having a web tension (for each unwind reel) of between about 0 N and about 250 N, about 10 N and about 240 N, about N and about 230 N, about 30 N and about 220 N, about 40 N and about 210 N, about 50 N and about 200 N, about 60 N and about 190 N, about 70 N and about 180 N, about 80 N and about 170 N, about 90 N and about 160 N, about 100 N and about 150 N, about 110 N and about 140 N, about 120 N and about 130 N, or about 125 N.

The at least two of the wound contact layer, the transmission layer and the superabsorbent layer may be laminated by a laminator having a web tension (for each unwind reel) of about 0 N, about 10 N, about 20 N, about 30 N, about 40 N, about 50 N, about 60 N, about 70 N, about 80 N, about 90 N, about 100 N, about 110 N, about 120 N, about 130 N, about 140 N, about 150 N, about 160 N, about 170 N, about 180 N, about 190 N, about 200 N, about 210 N, about 220 N, about 230 N, about 240 N, or about 250 N.

The at least two of the wound contact layer, the transmission layer and the superabsorbent layer may be laminated by a laminator having a web tension (for each unwind reel) of at least about 0 N, about 10 N, about 20 N, about 30 N, about 40 N, about 50 N, about 60 N, about 70 N, about 80 N, about 90 N, about 100 N, about 110 N, about 120 N, about 130 N, about 140 N, about 150 N, about 160 N, about 170 N, about 180 N, about 190 N, about 200 N, about 210 N, about 220 N, about 230 N, about 240 N, or at least about 250 N.

The at least two of the wound contact layer, the transmission layer and the superabsorbent layer may be laminated by a laminator having a web tension (for each unwind reel) of no more than about 0 N, about 10 N, about 20 N, about 30 N, about 40 N, about 50 N, about 60 N, about 70 N, about 80 N, about 90 N, about 100 N, about 110 N, about 120 N, about 130 N, about 140 N, about 150 N, about 160 N, about 170 N, about 180 N, about 190 N, about 200 N, about 210 N, about 220 N, about 230 N, about 240 N, or no more than about 250 N.

The at least two of the wound contact layer, the transmission layer and the superabsorbent layer may be laminated by a laminator having a crush roller pressure of about 10 N, about 25 N, about 50 N, about 75 N, about 100 N, about 125 N, about 150 N, about 175 N, about 200 N, about 225 N, about 250 N, about 275 N, about 300 N, about 325 N, about 350 N, about 375 N, about 400 N, about 425 N, about 450 N, about 475 N, about 500 N, about 525 N, about 550 N, about 575 N, about 600 N, about 625 N, about 650 N, about 675 N, about 700 N, about 725 N, about 750 N, about 775 N, about 800 N, about 825 N, about 850 N, about 875 N, about 900 N, about 925 N, about 950 N, about 975 N, or about 1000 N.

The at least two of the wound contact layer, the transmission layer and the superabsorbent layer may be laminated by a laminator having a crush roller pressure of at least about 10 N, about 25 N, about 50 N, about 75 N, about 100 N, about 125 N, about 150 N, about 175 N, about 200 N, about 225 N, about 250 N, about 275 N, about 300 N, about 325 N, about 350 N, about 375 N, about 400 N, about 425 N, about 450 N, about 475 N, about 500 N, about 525 N, about 550 N, about 575 N, about 600 N, about 625 N, about 650 N, about 675 N, about 700 N, about 725 N, about 750 N, about 775 N, about 800 N, about 825 N, about 850 N, about 875 N, about 900 N, about 925 N, about 950 N, about 975 N, or at least about 1000 N.

The at least two of the wound contact layer, the transmission layer and the superabsorbent layer may be laminated by a laminator having a crush roller pressure of no more than about 10 N, about 25 N, about 50 N, about 75 N, about 100 N, about 125 N, about 150 N, about 175 N, about 200 N, about 225 N, about 250 N, about 275 N, about 300 N, about 325 N, about 350 N, about 375 N, about 400 N, about 425 N, about 450 N, about 475 N, about 500 N, about 525 N, about 550 N, about 575 N, about 600 N, about 625 N, about 650 N, about 675 N, about 700 N, about 725 N, about 750 N, about 775 N, about 800 N, about 825 N, about 850 N, about 875 N, about 900 N, about 925 N, about 950 N, about 975 N, or no more than about 1000 N.

The at least two of the wound contact layer, the transmission layer and the superabsorbent layer may be laminated by a laminator having a web speed of about 1 m/min, about 2 m/min, about 3 m/min, about 4 m/min, about 5 m/min, about 6 m/min, about 7 m/min, about 8 m/min, about 9 m/min, or about 10 m/min.

The at least two of the wound contact layer, the transmission layer and the superabsorbent layer may be laminated by a laminator having a web speed of at least about 1 m/min, about 2 m/min, about 3 m/min, about 4 m/min, about 5 m/min, about 6 m/min, about 7 m/min, about 8 m/min, about 9 m/min, or at least about 10 m/min.

The at least two of the wound contact layer, the transmission layer and the superabsorbent layer may be laminated by a laminator having a web speed of no more than about 1 m/min, about 2 m/min, about 3 m/min, about 4 m/min, about 5 m/min, about 6 m/min, about 7 m/min, about 8 m/min, about 9 m/min, or no more than about 10 m/min.

The at least two of the wound contact layer, the transmission layer and the superabsorbent layer may be laminated by a laminator having a web speed when the laminator is not operating of about 5 m/min, about 10 m/min, about 15 m/min, about 20 m/min, about 25 m/min, about 30 m/min, about 35 m/min, about 40 m/min, about 45 m/min, or about 50 m/min.

The at least two of the wound contact layer, the transmission layer and the superabsorbent layer may be laminated by a laminator having a web speed when the laminator is not operating of at least about 5 m/min, about 10 m/min, about 15 m/min, about 20 m/min, about 25 m/min, about 30 m/min, about 35 m/min, about 40 m/min, about 45 m/min, or at least about 50 m/min.

The at least two of the wound contact layer, the transmission layer and the superabsorbent layer may be laminated by a laminator having a web speed when the laminator is not operating of no more than about 5 m/min, about 10 m/min, about 15 m/min, about 20 m/min, about 25 m/min, about 30 m/min, about 35 m/min, about 40 m/min, about 45 m/min, or no more than about 50 m/min.

The at least two of the wound contact layer, the transmission layer and the superabsorbent layer may be laminated together by a scatter-coat adhesive. The scatter-coat adhesive may be a hot melt, scatter-coat adhesive.

The scatter-coat adhesive may be polylactic acid, polycaprolactone, polyethylene (LDPE, HDPE), polypropylene, polyester, polyamide, ethylene vinyl acetate or polyurethane. Advantageously, each of these materials are cheap and easily obtained.

The scatter-coat adhesive may have a melt flow index of between about 5.2 g/10 min and about 11.3 g/10 min, as tested with 2.16 kg, 1" PVC die at 160° C.

The scatter-coat adhesive may have a maximum water content of between about 0.25% and about 0.45%, about 0.30% and about 0.40%, or about 0.35%. The scatter-coat adhesive may have a maximum water content of about 0.25%, about 0.30%, about 0.35%, about 0.40%, or about 0.45%.

The scatter-coat adhesive may have a maximum water content of at least about 0.25%, about 0.30%, about 0.35%, about 0.40%, or at least about 0.45%.

The scatter-coat adhesive may have a maximum water content of no more than about 0.25%, about 0.30%, about 0.35%, about 0.40%, or no more than about 0.45%.

The scatter-coat adhesive may comprise particles of which at least 98% have a particle size less than 600 μm, as measured by DIN EN ISO 4610.

The scatter-coat adhesive may comprise particles of which at least 98% have a particle size of between about 0.05 mm and about 0.80 mm, about 0.06 mm and about 0.75 mm, about 0.07 and about 0.70 mm, about 0.08 mm and about 0.65 mm, about 0.09 mm and about 0.60 mm, or about 0.10 mm and about 0.60 mm.

The scatter-coat adhesive may comprise particles of which at least 98% have a particle size of about 0.1 mm, about 0.2 mm, about 0.3 mm, about 0.4 mm, about 0.5 mm, or about 0.6 mm.

The scatter-coat adhesive may comprise particles of which at least 98% have a particle size of at least about 0.1 mm, about 0.2 mm, about 0.3 mm, about 0.4 mm, about 0.5 mm, or at least about 0.6 mm.

The scatter-coat adhesive may comprise particles of which at least 98% have a particle size of no more than about 0.1 mm, about 0.2 mm, about 0.3 mm, about 0.4 mm, about 0.5 mm, or no more than about 0.6 mm.

The scatter-coat adhesive may have a mean molecular weight of between about 35,000 g/mol and about 65,000 g/mol, about 40,000 g/mol and about 60,000 g/mol, about 45,000 g/mol and about 55,000 g/mol, or about 50,000 g/mol.

The scatter-coat adhesive may have a mean molecular weight of about 35,000 g/mol, about 40,000 g/mol, about 45,000 g/mol, about 50,000 g/mol, about 55,000 g/mol, about 60,000 g/mol, or about 65,000 g/mol.

The scatter-coat adhesive may have a melting point of between about 55° C. and about 65° C., or between about 58° C. and about 62° C., or about 60° C.

The scatter-coat adhesive may have a solubility parameter of 9.30 cal/cm$^3$ to 9.45 cal/cm$^3$, for example of 9.34 cal/cm$^3$ to 9.43 cal/cm$^3$.

The wound contact layer may be formed by stitch bonding. Advantageously, stich bonding the wound contact layer improves the tensile strength (when dry and wet (i.e., in use)) of the wound contact layer. Moreover, the wound contact layer may be stich bonded to the transmission layer or to the superabsorbent layer. The wound contact layer may be stitch bonded to the layer of the absorbent structure which is adjacent to, and in contact with, the second surface of the wound contact layer. In particular, the wound contact layer may be stitch bonded to the transmission layer and this, advantageously, increases the bond strength between the wound contact layer and the transmission layer. Further advantageously, the process of stitch bonding provides a plurality of holes in the layer(s) which is/are stitch bonded, and the holes facilitate the application of negative pressure to the wound site.

These advantageous effects are particularly advantageous in embodiments where the wound contact layer comprises Hydrofiber® obtainable from ConvaTec Limited of Deeside, UK or is formed of sodium carboxymethylcellulose fibres having a degree of substitution of between about 0.05 carboxymethyl groups per glucose unit and about 0.50 carboxymethyl groups per glucose unit, as described herein.

The transmission layer may be arranged between the wound contact layer and the superabsorbent layer. Advantageously, this arrangement increases the absorbency capacity of the wound dressing and increases the amount of vapour transmitted by the wound dressing.

The transmission layer may be laminated on a first surface to the wound contact layer and on a second surface to the superabsorbent layer. Beneficially, this means that the transmission layer is adhered to the wound contact layer and to the superabsorbent layer without using relatively rigid dressing and binding components. The manufacture of the absorbent structure is therefore cheaper and simpler to manufacture, and provides for a flexible and, therefore, more comfortable wound dressing compared to that of the prior art.

The transmission layer may have a thickness of between about 1.0 mm and about 5.0 mm, about 1.5 mm and about 4.5 mm, about 2.0 mm and about 4.0 mm, about 2.5 mm and about 3.5 mm, or about 30 mm.

The transmission layer may have a thickness of about 1.0 mm, about 1.5 mm, about 2.0 mm, about 2.5 mm, about 3.0 mm, about 3.5 mm, about 4.0 mm, about 4.5 mm, or about 5.0 mm.

The transmission layer may have a thickness of at least about 1.0 mm, about 1.5 mm, about 2.0 mm, about 2.5 mm, about 3.0 mm, about 3.5 mm, about 4.0 mm, about 4.5 mm, or at least about 5.0 mm.

The transmission layer may have a thickness of no more than about 1.0 mm, about 1.5 mm, about 2.0 mm, about 2.5 mm, about 3.0 mm, about 3.5 mm, about 4.0 mm, about 4.5 mm, or no more than about 5.0 mm.

Advantageously, a transmission layer of relatively thin size, as described above, provides for a wound dressing of reduced thickness compared to wound dressings of the prior art. Thus, the wound dressing of the invention is flatter than many known wound dressings, and is therefore more comfortable for a user than known wound dressings having greater thickness.

The transmission layer may be formed of a polyurethane foam, a polyester foam, a hydrophilic polyurethane, silicone, gelatine, polypropylene, nitrile or EVA foams.

The transmission layer may have a density of between about 24 $Kg/M^3$ and about 30 $Kg/M^3$, or between about 26 $Kg/M^3$ and about 28 $Kg/M^3$.

The transmission layer may have a tensile strength of at least about 150 kPa, about 160 kPa, about 170 kPa, about 180 kPa, about 190 kPa, about 200 kPa, about 210 kPa, about 220 kPa, about 230 kPa, about 240 kPa, or at least about 250 kPa.

The transmission layer may have an elongation at break value of at least about 300%, about 310%, about 320%, about 330%, about 340%, about 350%, about 360%, about 370%, about 380%, about 390%, or at least about 400%.

The transmission layer may have a 50% compression set of up to 100%.

The transmission layer may have a cell count of between 17 and 26/cm.

The transmission layer may have a 40% CLD hardness of between 2.5 and 4.5 kPa.

The superabsorbent layer may include any one or more of the features, optional or otherwise, of the invention according to any other aspect.

The wound contact layer may include any one or more of the features, optional or otherwise, of the invention according to any other aspect.

Advantageously, in embodiments comprising the transmission layer arranged between the wound contact layer and the superabsorbent layer, and in particular in embodiments where the wound contact layer comprises sodium carboxymethylcellulose fibres having a degree of substitution of between about 0.05 carboxymethyl groups per glucose unit and about 0.50 carboxymethyl groups per glucose unit, the wound dressing of the invention prevents, or at least significantly reduces, lateral spread of wound exudate at the wound contact layer. As such, wound exudate initially wicks upwardly through the wound contact layer, and then laterally across the transmission layer before being absorbed by the superabsorbent layer. Thus, providing an improved wicking and movement of fluid away from the wound site. Beneficially, this arrangement is more efficient at removing wound exudate from a wound site, therefore, rendering the wound site more hygienic and increasing comfort for the user. Further beneficially, this arrangement increases the ability of the wound dressing to transmit vapour, therefore, facilitating the evaporation of fluid comprised in the wound exudate.

In some embodiments, the wound dressing may describe additional layers, such as a pressure dispersing layer, also referred to as a pressure distribution layer, which serves to distribute pressure, or negative pressure, laterally across the pressure dispersing layer. The pressure dispersing layer may be gas, liquid and moisture-vapor permeable and serves to aid wound exudate access to a greater portion of the dressing by distributing negative pressure laterally over the dressing. In this way, uptake of wound exudate by the dressing is maximised and a more uniform transfer of negative pressure to the wound, or dressing, is optimised. The pressure dispersing layer may be formed from a foam such as a polyester foam or a polyurethane foam.

The invention according to the fifth aspect may of course individually include any one or more of the features, optional or otherwise, of the invention according to any other aspect.

According to a sixth aspect of the invention, there is provided a method for manufacturing a negative pressure wound dressing comprising the steps:

a. Providing an adhesive skin contact layer and a backing layer;
b. Providing a wound contact layer, a transmission layer and a superabsorbent layer, which together form an absorbent structure;
c. Adhering together at least two of the wound contact layer, the transmission layer and the superabsorbent layer; and
d. Arranging the absorbent structure between the adhesive skin contact layer and the backing layer.

The transmission layer may be arranged between the wound contact layer and the superabsorbent layer.

In step c, the at least two of the wound contact layer, the transmission layer and the superabsorbent layer may be adhered together by lamination.

In step c, each of the wound contact layer, the transmission layer and the superabsorbent layer may be adhered together by lamination.

Lamination may be by a hot melt, scatter-coat adhesive.

Lamination may be under any of the conditions set out above in relation to the fifth aspect.

In step c, the at least two of the wound contact layer, transmission layer and the superabsorbent layer may be adhered together by stitchbonding.

In step c, each of the wound contact layer, transmission layer and the superabsorbent layer may be adhered together by stitchbonding.

Prior to step c, the wound contact layer may be stitchbonded using lyocell yarn.

The invention according to the sixth aspect may of course individually include any one or more of the features, optional or otherwise, of the invention according to any other aspect.

According to a still further broad aspect of the invention, there is provided a negative pressure wound dressing. The wound dressing may comprise a backing layer, an adhesive skin contact layer and/or an absorbent structure. The adhesive skin contact layer may be configured to detachably adhere the dressing to a dermal surface. The backing layer may comprise a coupling member configured to connect the dressing to a negative pressure source. The absorbent structure may comprise a wound contact layer arranged to contact the wound when the adhesive skin contact layer is adhered to the dermal surface. The absorbent structure may comprise a transmission layer overlying the wound contact layer. The absorbent structure may comprise an absorbent layer overlying the transmission layer. The wound contact layer may be formed of sodium carboxymethylcellulose fibres having a degree of substitution of between 0.05 carboxymethyl groups per glucose unit and 0.50 carboxymethyl groups per glucose unit, in particular 0.25 carboxymethyl groups per glucose unit and 0.35 carboxymethyl groups per glucose unit. The absorbent layer may be a superabsorbent layer.

The sodium carboxymethylcellulose fibres may have a degree of substitution of about 0.05 carboxymethyl groups per glucose unit, about 0.10, about 0.15, about 0.20, about 0.25, about 0.30, about 0.35, about 0.40, about 0.45, or about 0.50 carboxymethyl groups per glucose unit.

The sodium carboxymethylcellulose fibres may have a degree of substitution of at least about 0.05 carboxymethyl groups per glucose unit, about 0.10, about 0.15, about 0.20, about 0.25, about 0.30, about 0.35, about 0.40, about 0.45, or at least about 0.50 carboxymethyl groups per glucose unit.

The sodium carboxymethylcellulose fibres may have a degree of substitution of no more than about 0.05 carboxymethyl groups per glucose unit, about 0.10, about 0.15, about 0.20, about 0.25, about 0.30, about 0.35, about 0.40, about 0.45, or no more than about 0.50 carboxymethyl groups per glucose unit.

The sodium carboxymethylcellulose fibres may have a degree of substitution of between about 0.05 carboxymethyl groups per glucose unit and about 0.50 carboxymethyl groups per glucose unit, between about 0.05 carboxymethyl groups per glucose unit and about 0.45 carboxymethyl groups per glucose unit, between about 0.05 carboxymethyl groups per glucose unit and about 0.40 carboxymethyl groups per glucose unit, between about 0.05 carboxymethyl groups per glucose unit and about 0.35 carboxymethyl groups per glucose unit, between about 0.05 carboxymethyl groups per glucose unit and about 0.30 carboxymethyl groups per glucose unit, between about 0.05 carboxymethyl groups per glucose unit and about 0.25 carboxymethyl groups per glucose unit, between about 0.05 carboxymethyl groups per glucose unit and about 0.20 carboxymethyl groups per glucose unit, between about 0.05 carboxymethyl groups per glucose unit and about 0.15 carboxymethyl groups per glucose unit, or between about 0.05 carboxymethyl groups per glucose unit and about 0.10 carboxymethyl groups per glucose unit.

The sodium carboxymethylcellulose fibres may have a degree of substitution of between about 0.10 carboxymethyl groups per glucose unit and about 0.50 carboxymethyl groups per glucose unit, between about 0.10 carboxymethyl groups per glucose unit and about 0.45 carboxymethyl groups per glucose unit, between about 0.10 carboxymethyl groups per glucose unit and about 0.40 carboxymethyl groups per glucose unit, between about 0.10 carboxymethyl groups per glucose unit and about 0.35 carboxymethyl groups per glucose unit, between about 0.10 carboxymethyl groups per glucose unit and about 0.30 carboxymethyl groups per glucose unit, between about 0.10 carboxymethyl groups per glucose unit and about 0.25 carboxymethyl groups per glucose unit, between about 0.10 carboxymethyl groups per glucose unit and about 0.20 carboxymethyl groups per glucose unit, or between about 0.10 carboxymethyl groups per glucose unit and about 0.15 carboxymethyl groups per glucose unit.

The sodium carboxymethylcellulose fibres may have a degree of substitution of between about 0.15 carboxymethyl groups per glucose unit and about 0.50 carboxymethyl groups per glucose unit, between about 0.15 carboxymethyl groups per glucose unit and about 0.45 carboxymethyl groups per glucose unit, between about 0.15 carboxymethyl groups per glucose unit and about 0.40 carboxymethyl groups per glucose unit, between about 0.15 carboxymethyl groups per glucose unit and about 0.35 carboxymethyl groups per glucose unit, between about 0.15 carboxymethyl groups per glucose unit and about 0.30 carboxymethyl groups per glucose unit, between about 0.15 carboxymethyl groups per glucose unit and about 0.25 carboxymethyl groups per glucose unit, or between about 0.15 carboxymethyl groups per glucose unit and about 0.20 carboxymethyl groups per glucose unit.

The sodium carboxymethylcellulose fibres may have a degree of substitution of between about 0.20 carboxymethyl groups per glucose unit and about 0.50 carboxymethyl groups per glucose unit, between about 0.20 carboxymethyl groups per glucose unit and about 0.45 carboxymethyl groups per glucose unit, between about 0.20 carboxymethyl groups per glucose unit and about 0.40 carboxymethyl groups per glucose unit, between about 0.20 carboxymethyl groups per glucose unit and about 0.35 carboxymethyl groups per glucose unit, between about 0.20 carboxymethyl groups per glucose unit and about 0.30 carboxymethyl groups per glucose unit, or between about 0.20 carboxymethyl groups per glucose unit and about 0.25 carboxymethyl groups per glucose unit.

The sodium carboxymethylcellulose fibres may have a degree of substitution of between about 0.25 carboxymethyl groups per glucose unit and about 0.50 carboxymethyl groups per glucose unit, between about 0.25 carboxymethyl groups per glucose unit and about 0.45 carboxymethyl groups per glucose unit, between about 0.25 carboxymethyl groups per glucose unit and about 0.40 carboxymethyl groups per glucose unit, between about 0.25 carboxymethyl groups per glucose unit and about 0.35 carboxymethyl groups per glucose unit, or between about 0.25 carboxymethyl groups per glucose unit and about 0.30 carboxymethyl groups per glucose unit.

The sodium carboxymethylcellulose fibres may have a degree of substitution of between about 0.30 carboxymethyl groups per glucose unit and about 0.50 carboxymethyl groups per glucose unit, between about 0.30 carboxymethyl groups per glucose unit and about 0.45 carboxymethyl groups per glucose unit, between about 0.30 carboxymethyl groups per glucose unit and about 0.40 carboxymethyl groups per glucose unit, or between about 0.30 carboxymethyl groups per glucose unit and about 0.35 carboxymethyl groups per glucose unit.

The sodium carboxymethylcellulose fibres may have a degree of substitution of between about 0.35 carboxymethyl groups per glucose unit and about 0.50 carboxymethyl groups per glucose unit, between about 0.35 carboxymethyl groups per glucose unit and about 0.45 carboxymethyl groups per glucose unit, or between about 0.35 carboxymethyl groups per glucose unit and about 0.40 carboxymethyl groups per glucose unit.

The sodium carboxymethylcellulose fibres may have a degree of substitution of between about 0.40 carboxymethyl groups per glucose unit and about 0.50 carboxymethyl groups per glucose unit, or between about 0.40 carboxymethyl groups per glucose unit and about 0.45 carboxymethyl groups per glucose unit.

The sodium carboxymethylcellulose fibres may have a degree of substitution of between about 0.45 carboxymethyl groups per glucose unit and about 0.50 carboxymethyl groups per glucose unit.

According to a seventh aspect of the invention, there is provided a negative pressure wound dressing the dressing comprising a backing layer, an adhesive skin contact layer and an absorbent structure, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the dermal surface, a transmission layer overlying the wound contact layer, and an absorbent layer overlying the transmission layer, characterised in that the wound contact layer is formed of sodium carboxymethylcellulose fibres having a degree of substitution of between 0.05 carboxymethyl groups per glucose unit and 0.50 carboxymethyl groups per glucose unit, for example between 0.25 carboxymethyl groups per glucose unit and 0.35 carboxymethyl groups per glucose unit, and the absorbent layer is a superabsorbent layer.

The absorbent structure may be arranged between the backing layer and the adhesive skin contact layer.

As such, in one embodiment, there is provided a negative pressure wound dressing the dressing comprising a backing layer, an adhesive skin contact layer and an absorbent structure arranged between the backing layer and the adhesive skin contact layer, wherein the adhesive skin contact layer is configured to detachably adhere the dressing to a dermal surface, wherein the backing layer comprises a coupling member configured to connect the dressing to a negative pressure source, wherein the absorbent structure comprises a wound contact layer arranged to contact the wound when the adhesive skin contact layer is adhered to the dermal surface, a transmission layer overlying the wound contact layer, and an absorbent layer overlying the transmission layer, characterised in that the wound contact layer is formed of sodium carboxymethylcellulose fibres having a degree of substitution of between 0.05 carboxymethyl groups per glucose unit and 0.50 carboxymethyl groups per glucose unit, and the absorbent layer is a superabsorbent layer. The sodium carboxymethylcellulose fibres may have a degree of substitution of about 0.05 carboxymethyl groups per glucose unit, about 0.10, about 0.15, about 0.20, about 0.25, about 0.30, about 0.35, about 0.40, about 0.45, or about 0.50 carboxymethyl groups per glucose unit.

The sodium carboxymethylcellulose fibres may have a degree of substitution of at least about 0.05 carboxymethyl groups per glucose unit, about 0.10, about 0.15, about 0.20, about 0.25, about 0.30, about 0.35, about 0.40, about 0.45, or at least about 0.50 carboxymethyl groups per glucose unit.

The sodium carboxymethylcellulose fibres may have a degree of substitution of no more than about 0.05 carboxymethyl groups per glucose unit, about 0.10, about 0.15, about 0.20, about 0.25, about 0.30, about 0.35, about 0.40, about 0.45, or no more than about 0.50 carboxymethyl groups per glucose unit.

The sodium carboxymethylcellulose fibres may have a degree of substitution of between about 0.05 carboxymethyl groups per glucose unit and about 0.50 carboxymethyl groups per glucose unit, between about 0.05 carboxymethyl groups per glucose unit and about 0.45 carboxymethyl groups per glucose unit, between about 0.05 carboxymethyl groups per glucose unit and about 0.40 carboxymethyl groups per glucose unit, between about 0.05 carboxymethyl groups per glucose unit and about 0.35 carboxymethyl groups per glucose unit, between about 0.05 carboxymethyl groups per glucose unit and about 0.30 carboxymethyl groups per glucose unit, between about 0.05 carboxymethyl groups per glucose unit and about 0.25 carboxymethyl groups per glucose unit, between about 0.05 carboxymethyl groups per glucose unit and about 0.20 carboxymethyl groups per glucose unit, between about 0.05 carboxymethyl groups per glucose unit and about 0.15 carboxymethyl groups per glucose unit, or between about 0.05 carboxymethyl groups per glucose unit and about 0.10 carboxymethyl groups per glucose unit.

The sodium carboxymethylcellulose fibres may have a degree of substitution of between about 0.10 carboxymethyl groups per glucose unit and about 0.50 carboxymethyl groups per glucose unit, between about 0.10 carboxymethyl groups per glucose unit and about 0.45 carboxymethyl groups per glucose unit, between about 0.10 carboxymethyl groups per glucose unit and about 0.40 carboxymethyl groups per glucose unit, between about 0.10 carboxymethyl groups per glucose unit and about 0.35 carboxymethyl groups per glucose unit, between about 0.10 carboxymethyl groups per glucose unit and about 0.30 carboxymethyl groups per glucose unit, between about 0.10 carboxymethyl groups per glucose unit and about 0.25 carboxymethyl groups per glucose unit, between about 0.10 carboxymethyl groups per glucose unit and about 0.20 carboxymethyl groups per glucose unit, or between about 0.10 carboxymethyl groups per glucose unit and about 0.15 carboxymethyl groups per glucose unit.

The sodium carboxymethylcellulose fibres may have a degree of substitution of between about 0.15 carboxymethyl groups per glucose unit and about 0.50 carboxymethyl groups per glucose unit, between about 0.15 carboxymethyl groups per glucose unit and about 0.45 carboxymethyl groups per glucose unit, between about 0.15 carboxymethyl groups per glucose unit and about 0.40 carboxymethyl groups per glucose unit, between about 0.15 carboxymethyl groups per glucose unit and about 0.35 carboxymethyl groups per glucose unit, between about 0.15 carboxymethyl groups per glucose unit and about 0.30 carboxymethyl groups per glucose unit, between about 0.15 carboxymethyl groups per glucose unit and about 0.25 carboxymethyl groups per glucose unit, or between about 0.15 carboxymethyl groups per glucose unit and about 0.20 carboxymethyl groups per glucose unit.

The sodium carboxymethylcellulose fibres may have a degree of substitution of between about 0.20 carboxymethyl groups per glucose unit and about 0.50 carboxymethyl groups per glucose unit, between about 0.20 carboxymethyl groups per glucose unit and about 0.45 carboxymethyl groups per glucose unit, between about 0.20 carboxymethyl groups per glucose unit and about 0.40 carboxymethyl groups per glucose unit, between about 0.20 carboxymethyl groups per glucose unit and about 0.35 carboxymethyl groups per glucose unit, between about 0.20 carboxymethyl groups per glucose unit and about 0.30 carboxymethyl groups per glucose unit, or between about 0.20 carboxymethyl groups per glucose unit and about 0.25 carboxymethyl groups per glucose unit.

The sodium carboxymethylcellulose fibres may have a degree of substitution of between about 0.25 carboxymethyl groups per glucose unit and about 0.50 carboxymethyl groups per glucose unit, between about 0.25 carboxymethyl groups per glucose unit and about 0.45 carboxymethyl groups per glucose unit, between about 0.25 carboxymethyl groups per glucose unit and about 0.40 carboxymethyl groups per glucose unit, between about 0.25 carboxymethyl groups per glucose unit and about 0.35 carboxymethyl groups per glucose unit, or between about 0.25 carboxymethyl groups per glucose unit and about 0.30 carboxymethyl groups per glucose unit.

The sodium carboxymethylcellulose fibres may have a degree of substitution of between about 0.30 carboxymethyl groups per glucose unit and about 0.50 carboxymethyl groups per glucose unit, between about 0.30 carboxymethyl groups per glucose unit and about 0.45 carboxymethyl groups per glucose unit, between about 0.30 carboxymethyl groups per glucose unit and about 0.40 carboxymethyl groups per glucose unit, or between about 0.30 carboxymethyl groups per glucose unit and about 0.35 carboxymethyl groups per glucose unit.

The sodium carboxymethylcellulose fibres may have a degree of substitution of between about 0.35 carboxymethyl groups per glucose unit and about 0.50 carboxymethyl groups per glucose unit, between about 0.35 carboxymethyl groups per glucose unit and about 0.45 carboxymethyl groups per glucose unit, or between about 0.35 carboxymethyl groups per glucose unit and about 0.40 carboxymethyl groups per glucose unit.

The sodium carboxymethylcellulose fibres may have a degree of substitution of between about 0.40 carboxymethyl groups per glucose unit and about 0.50 carboxymethyl groups per glucose unit, or between about 0.40 carboxymethyl groups per glucose unit and about 0.45 carboxymethyl groups per glucose unit.

The sodium carboxymethylcellulose fibres may have a degree of substitution of between about 0.45 carboxymethyl groups per glucose unit and about 0.50 carboxymethyl groups per glucose unit.

Advantageously, providing a wound contact layer formed of sodium carboxymethylcellulose fibres having a degree of substitution of between 0.05 carboxymethyl groups per glucose unit and 0.50 carboxymethyl groups per glucose unit, in particular between 0.25 carboxymethyl groups per glucose unit and 0.35 carboxymethyl groups per glucose unit, means that the sodium carboxymethylcellulose fibres are relatively higher gelling, i.e., more absorbent, and therefore increase the absorbency capacity of the absorbent structure and the ability to transmit vapour. As such, the wound contact layer is capable of absorbing a greater amount of wound exudate. Thus, pooling of wound exudate at the wound site is prevented, or at least significantly reduced.

Further advantageously, the wound dressing of the invention prevents, or at least significantly reduces, lateral spread of wound exudate at the wound contact layer, at least in part due to the degree of substitution of carboxymethyl groups per glucose unit of the sodium carboxymethylcellulose fibres. As such, wound exudate initially wicks upwardly through the wound contact layer, rather than laterally across the wound contact layer which is common in wound dressings of the prior art, and then the wound exudate spreads laterally across the transmission layer. Once the wound exudate is wicked upwardly through the wound contact layer, and laterally spread across the transmission layer, the superabsorbent layer provides for significantly greater absorption and retention of wound exudate from the transmission layer and retains moisture across the surface area of the dressing to maximise vapour transmission through the backing layer. Thus, the arrangement of the absorbent structure provides an improved wicking and movement of fluid, and the presence of a superabsorbent layer further enhances the absorbency capacity and the fluid handling capacity of the wound dressing. Beneficially, this arrangement is significantly more efficient at removing wound exudate from a wound site, therefore, rendering the wound site more hygienic and increasing comfort for the user. Further beneficially, this arrangement increases the ability of the wound dressing to transmit vapour, therefore, facilitating the evaporation of fluid comprised in the wound exudate.

The invention according to the seventh aspect may of course individually include any one or more of the features, optional or otherwise, of the invention according to any other aspect.

According to an eighth aspect of the invention, there is provided a negative pressure wound exudate management system comprising the wound dressing of any previous aspect, and further comprising:

a source of negative pressure; and a conduit or tube for providing negative pressure to the wound dressing via an internal lumen of the conduit or tube and an opening in the wound dressing.

The source of negative pressure may comprise a pump for generating negative pressure and the tube connects the pump and wound dressing.

The source of negative pressure may further comprise a one-way valve in-line between the pump and the wound dressing to maintain a negative pressure within the wound dressing when the pump is disconnected from the tube. Normal operation of the pump may include the generation of negative pressure, alternating periods of negative pressure generation, and/or no generation of negative pressure.

The one-way valve may be connected to one of the pump and the tube.

The opening in the wound dressing may be in a backing layer of the wound dressing. The backing layer of the wound dressing may be a bacterial and viral barrier layer which preferably resists the ingress of liquid and air but allows moisture vapour transmission. In this way the backing layer enhances the overall fluid handling capacity of the wound dressing by allowing for the escape of moisture vapour through the backing layer while enabling the application of negative pressure to the wound. The backing layer may be a layer having a Moisture Vapor Transmission Rate (MVTR) of at least about 10,000 g/m$^2$ per 24 hours or in the range of from about 10,000 g/m$^2$ to about 50,000 g/m$^2$ per 24 hours as measured by the method described in BS EN 13726-2 2002 "Test methods for primary wound dressings Part 2 Moisture vapour transmission rate of permeable film dressings". The backing layer may be in the form of a film of polyurethane.

The conduit or tube may comprise a proximal end having an opening. The proximal end of the conduit or tube may be adhered around the opening in the backing layer of the wound dressing such that the opening in the backing layer is in fluid communication with the opening in the proximal end of the conduit or tube. The adhesion between the proximal end of the conduit or tube and the opening in the backing layer may for an airtight, or substantially airtight, seal between the conduit or tube and the backing layer.

The backing layer may be provided with a port, or airway for connection to the conduit. The port or airway may be located in that part of the backing layer that overlies the absorbent structure but towards the periphery of the absorbent structure so that it is not directly in vertical alignment with the centre of the wound dressing (or the wound when in use). This assists in the spread of wound exudate across the full extent of the absorbent layer.

The invention according to the eighth aspect may of course individually include any one or more of the features, optional or otherwise, of the invention according to any other aspect.

DETAILED DESCRIPTION OF THE INVENTION

In order that the invention may be more clearly understood one or more embodiments thereof will now be described, by way of example only, with reference to the accompanying drawings, of which:

Figure 1:
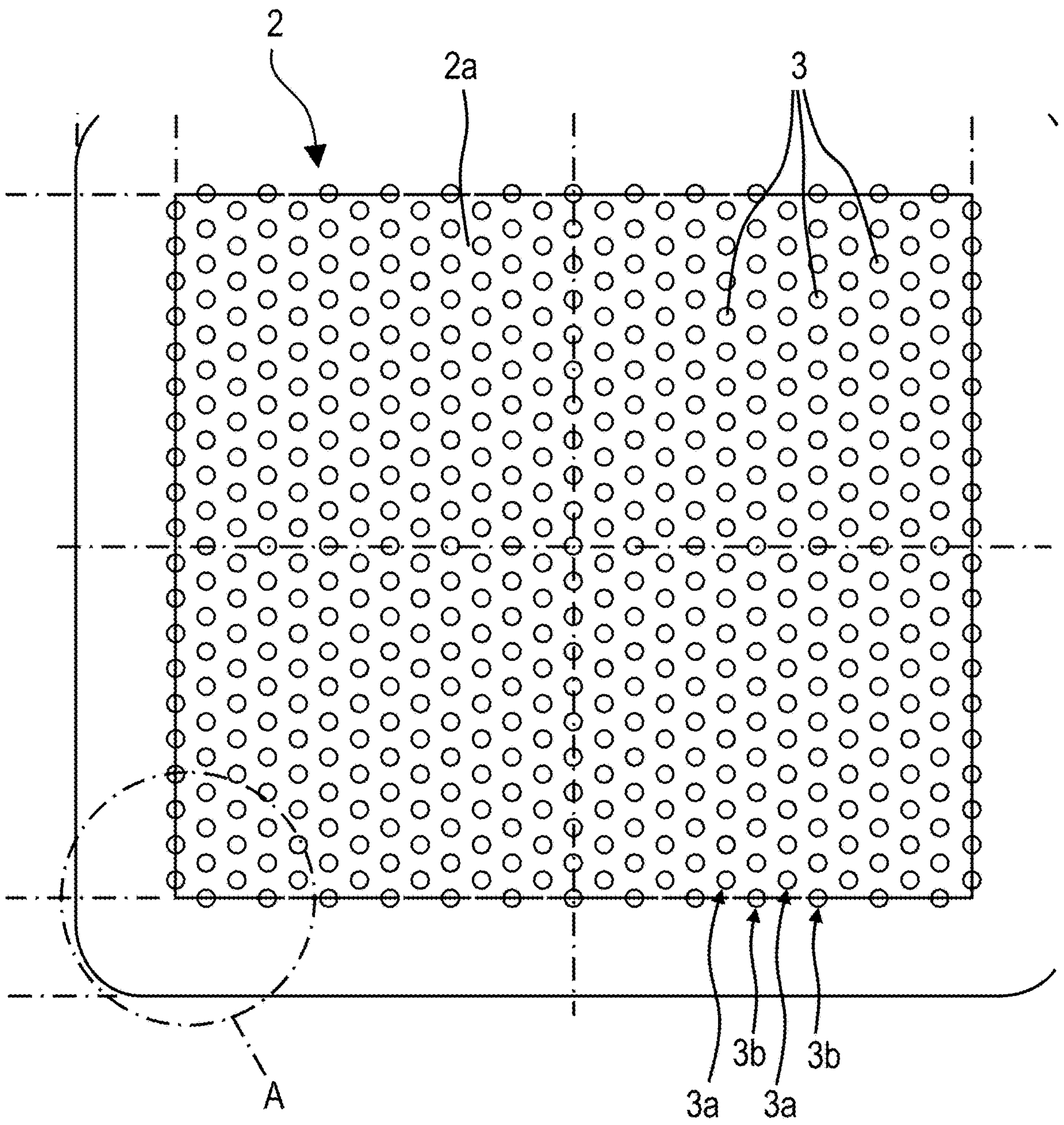
FIG. 1 is an example embodiment of part of an adhesive skin contact layer for use with a negative pressure wound dressing.
Figure 2:
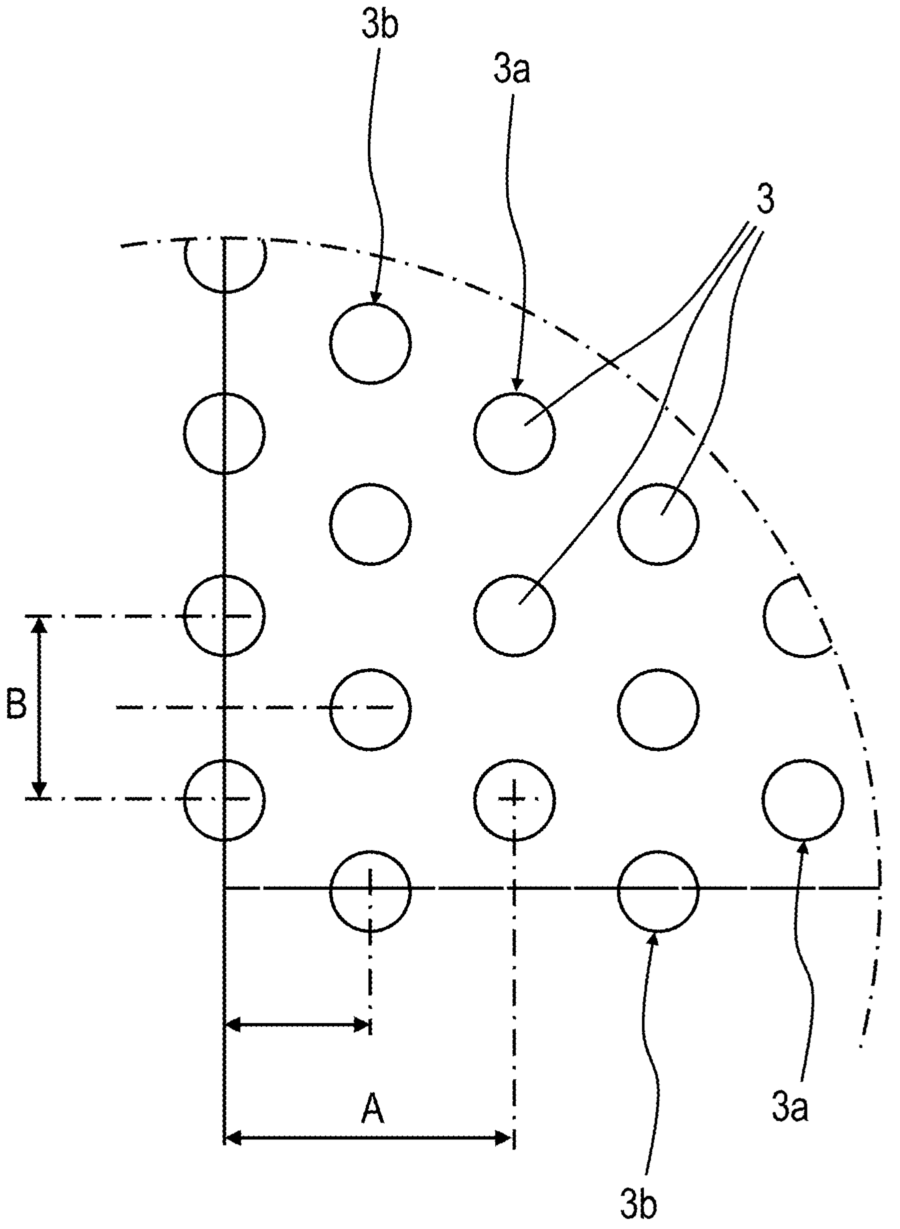
FIG. 2 is an expanded view of section A of FIG. 1.

With reference to FIGS. 1 and 2, there is shown an adhesive skin contact layer 2 for use with a negative pressure wound dressing.

The adhesive skin contact layer assists in securing the wound dressing to the skin of a patient, in particular to the peri-wound skin adjacent to a wound. The adhesive skin contact layer 2 may have a weight of 200 gsm which provides for a malleable, gelled structure so, in the event of an air leak, the layer can seal the leak more easily than if the layer had a weight below 100 gsm, in particular below 40 gsm. The adhesive skin contact layer 2 is a perforated mesh comprising a plurality of perforations 3 arranged in a plurality of rows. In the present embodiment, 95% of the perforations 3 are arranged in a triangle packed layout. The triangle packed layout comprises adjacent rows 3*a*, 3*b* of perforations 3. Row 3*a* is arranged offset from row 3*b*. The perforations 3 in row 3*a* are not arranged adjacent to the perforations 3 in the adjacent row 3*b* but instead the perforations 3 in row 3*a* are arranged adjacent to the gap between perforations 3 in row 3*b* or adjacent to part of the gap and part of a perforation 3 in row 3*b*.

Each perforation 3 comprises an opening, which in this embodiment is in the shape of a circle. In this embodiment, the size of each perforation 3 is defined by the diameter of the circle. However, the person skilled in the art will understand that the size of the opening may be defined depending on the shape of the opening. In some embodiments, the size of a circle is the diameter. In other embodiments, the size of an oval is the longer diameter. In further embodiments, the size of a hexagon is the longest diagonal; and the size of a triangle, a square, a rectangle, an octagon or any other polygon perforation may be the longest side. In the present embodiment, each perforation 3 has a diameter of 2.20 mm and are therefore of sufficient size to provide breathability to the wound dressing in the event that some of the perforations reduce in diameter after their formation, for example by the adhesive entering the opening of a perforation. As such, the adhesive skin contact layer maintains an environment optimised for wound healing. Moreover, each perforation 3 is a through hole in the adhesive skin contact layer 2 which can enable fluid to flow through the layer 2. The adhesive skin contact layer 2, therefore, helps to prevent tissue ingrowth into the other material of the wound dressing.

The perforations 3 have a pitch (i.e., the distance between the centre point of a perforation and the centre point of an adjacent perforation) in a first direction (shown as 'A' in FIG. 2) of 8.0 mm, and a pitch in a second direction (shown as 'B' in FIG. 2) of 5.6 mm. Advantageously, the pitch of the perforations 3 has a ratio of perforation:no-perforation which provides efficient moisture evaporation, prevents pooling and strongly adheres to the peri-wound skin of the patient. Surprisingly, and advantageously, tests have shown that the adhesive skin contact layer 2 remains adhered to a patient for at least seven days.

The total area of the perforations 3 may be 2100 $mm^2$ and the total volume of the perforations may be 2100 $mm^3$. The degree of perforation may be 10.66% of the area of the adhesive skin contact layer 2. The perforations 3 are distributed evenly throughout the adhesive skin contact layer 2. The perforations 3 may be formed by a mechanical punch perforating process which does not result in the formation of a doughnut or volcano structure around the perforations after formation of the perforations 3. The perforations may be formed by mechanical punch perforating the adhesive skin contact layer 2 comprising a release liner (not shown) covering at least one surface of the adhesive skin contact layer 2.

The adhesive skin contact layer 2 has a thickness of 1.0 mm and a width and length (measured from the periphery of the adhesive skin contact layer 2) each of 130 mm. The adhesive skin contact layer 2 has an outer periphery in the shape of a square. The adhesive skin contact layer 2 comprises an upper surface 2*a* and a lower surface 2*b*. The lower surface 2*b* contacts the dermal surface in use.

Figure 3:
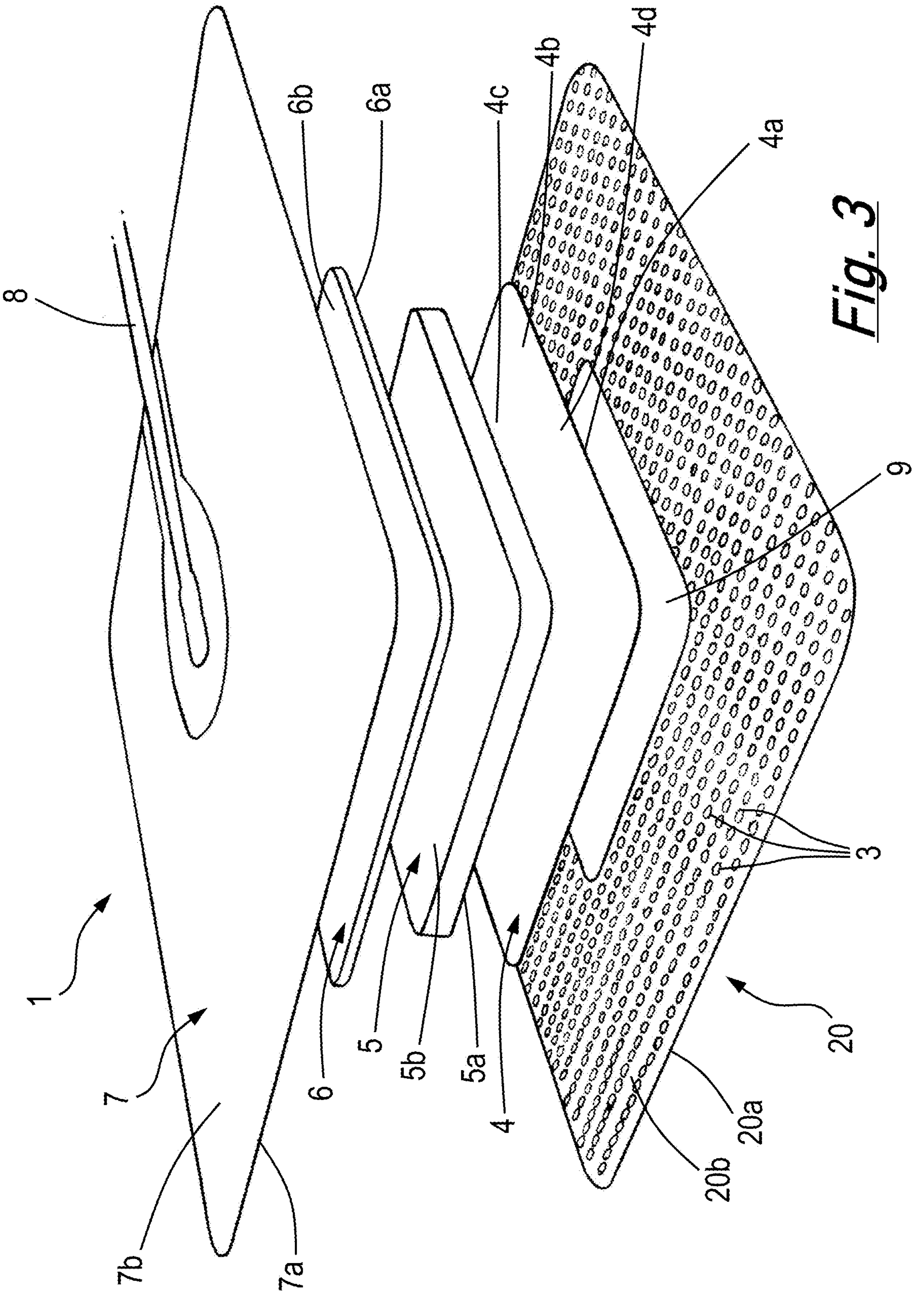
FIG. 3 is an exploded view of a first embodiment of a negative pressure wound dressing.
Figure 4:
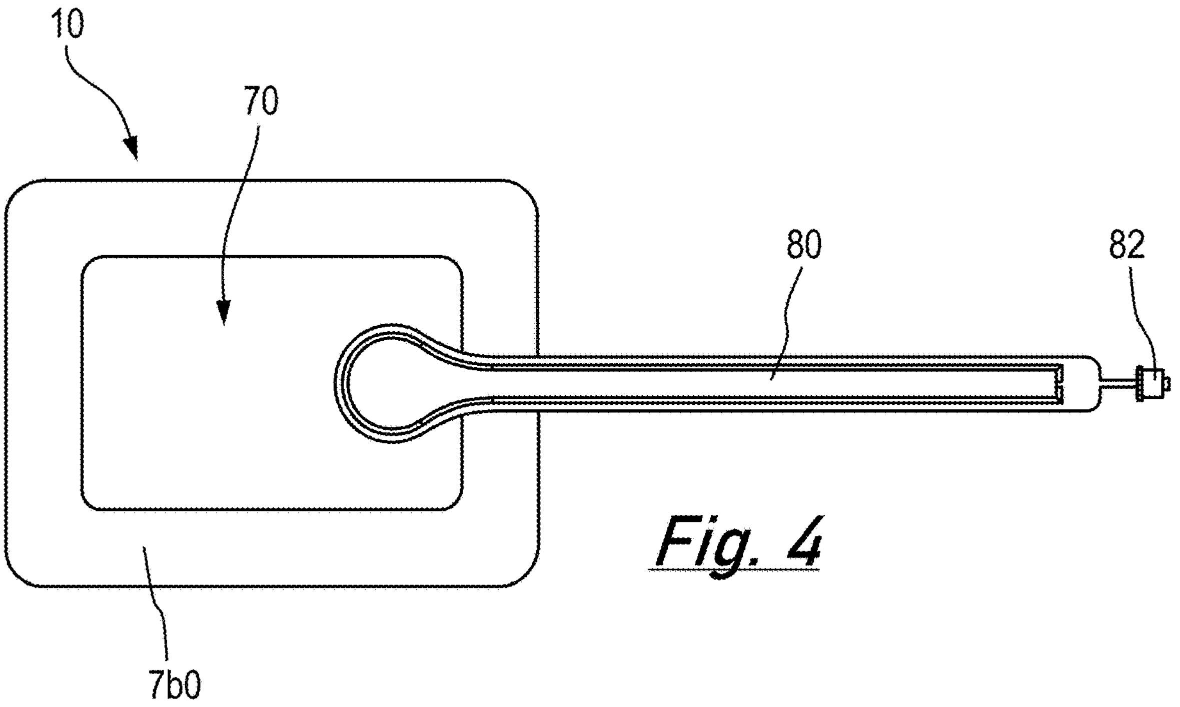
FIG. 4 is a plan view of a further example embodiment of a negative pressure wound dressing.
Figure 5:
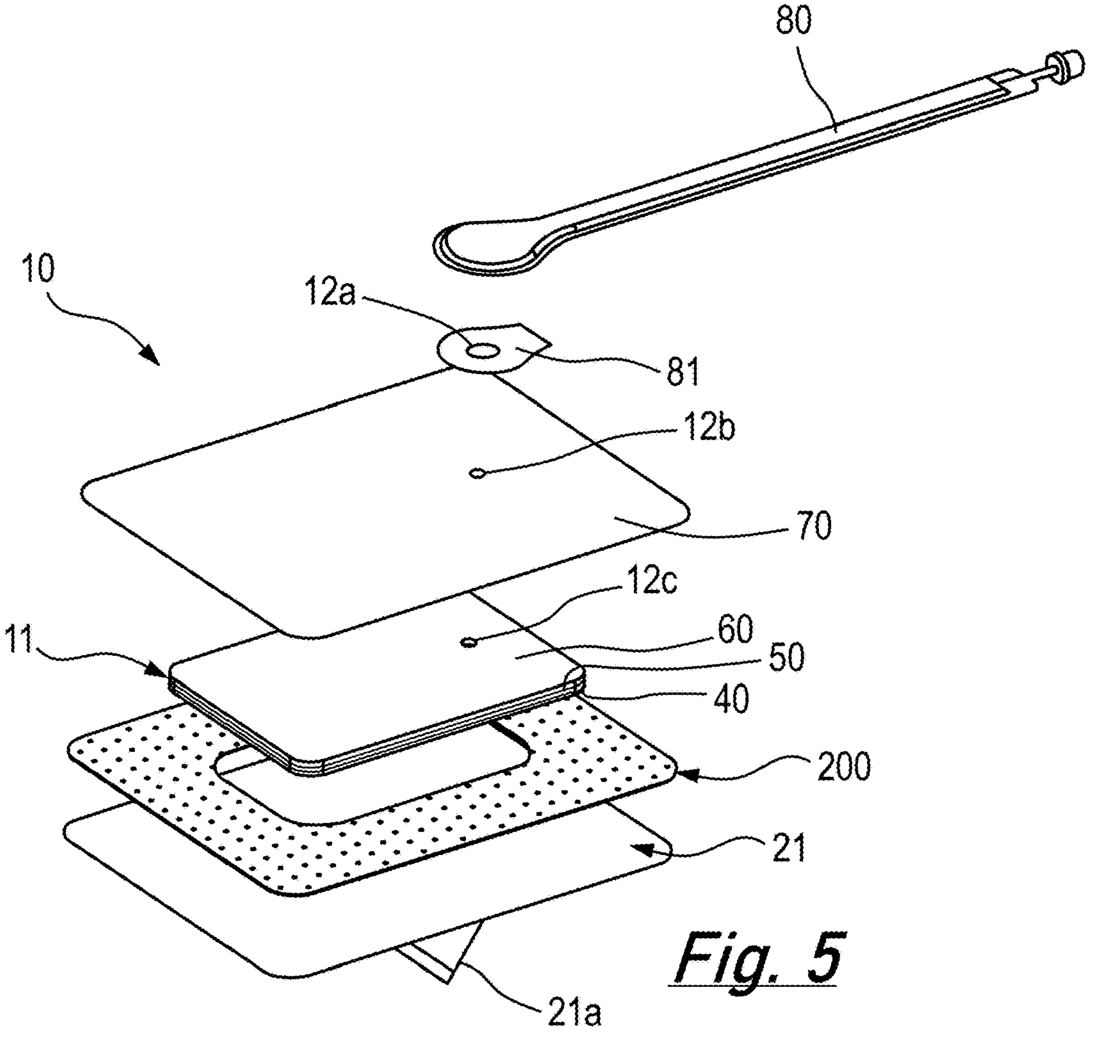
FIG. 5 is an exploded view of the negative pressure wound dressing of FIG. 4.
Figure 6:
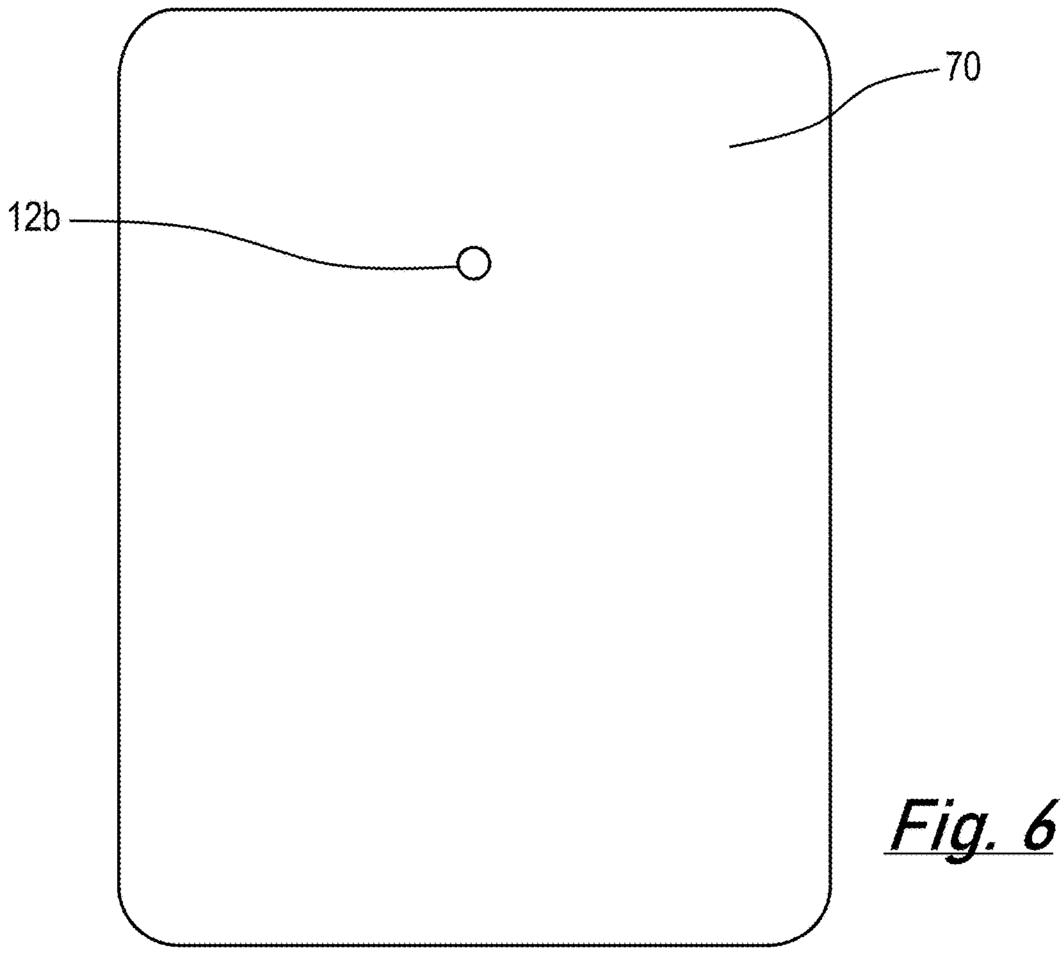
FIG. 6 is a plan view of an example embodiment of a backing layer for use with the embodiment shown in FIG. 4.
Figure 7:
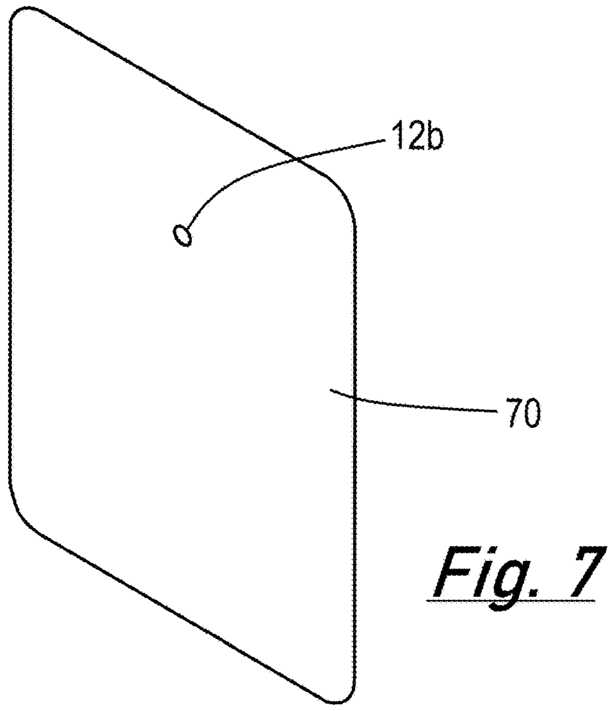
FIG. 7 is a perspective view of the example backing layer shown in FIG. 6.
Figure 8:
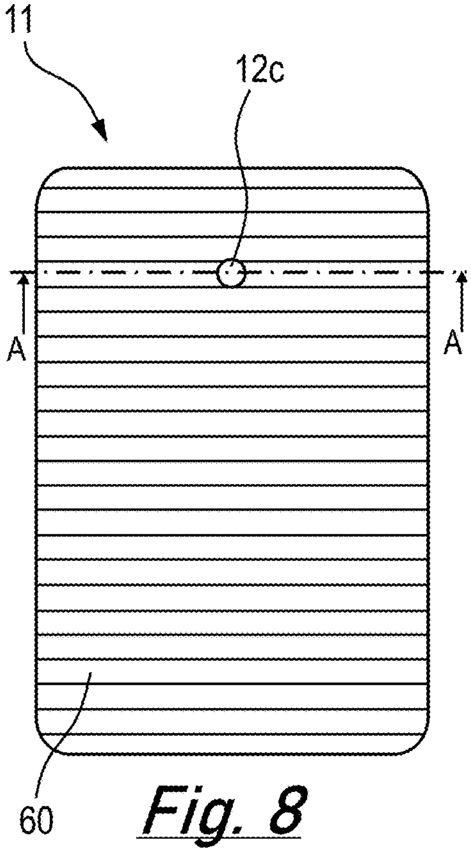
FIG. 8 is a plan view of an example embodiment of an absorbent structure for use with the embodiment shown in FIG. 4.
Figure 9:
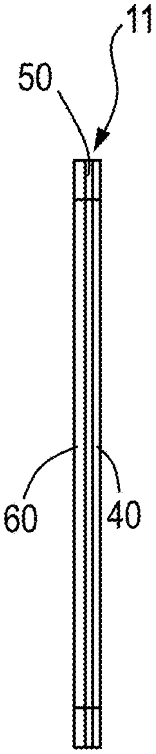
FIG. 9 is a side view of the example absorbent structure shown in FIG. 8.
Figure 10:
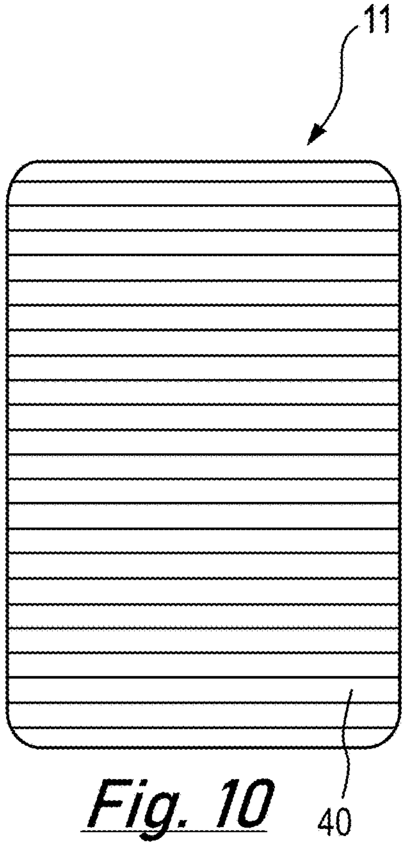
FIG. 10 is a rear view of the example absorbent structure shown in FIG. 8.
Figure 11:
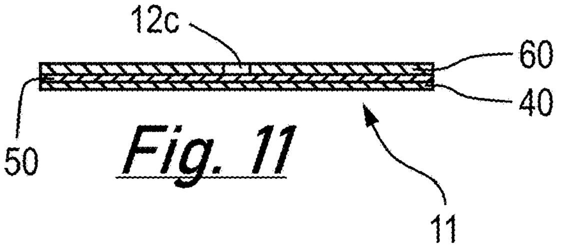
FIG. 11 is a cross-section view along line A-A shown in FIG. 8.
Figure 12:
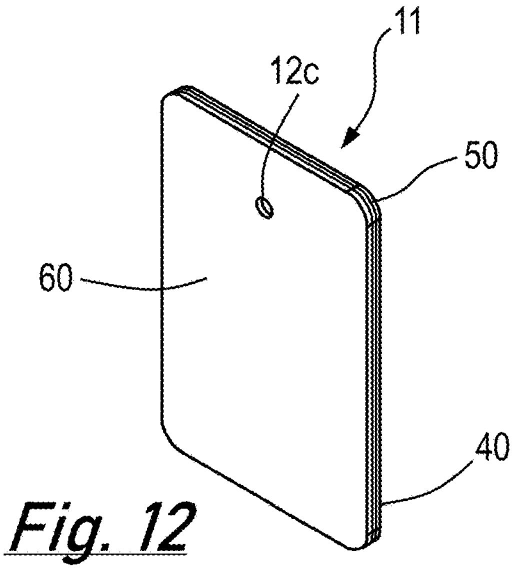
FIG. 12 is a perspective view of the example absorbent structure shown in FIG. 8.

With reference to FIG. 3, there is shown a negative pressure wound dressing 1.

The wound dressing 1 comprises an adhesive skin contact layer 20 (which is preferably the adhesive skin contact layer 2 described with reference to FIGS. 1 and 2), a wound contact layer 4, a transmission layer 5, a superabsorbent layer 6, a backing layer 7 and an airway 8.

The adhesive skin contact layer 20 may have a perimetral shape with a central window 9, therefore, the adhesive skin contact layer 20 may bean adhesive skin contact border layer 20. The border layer 20 may comprise an outer periphery which defines the outer shape of the border layer 20, which, in this embodiment, is a square. The border layer 20 may comprise an inner periphery which defines the shape of the window 9. The window 9 may be of the same, or similar shape, to that of the outer periphery of the border layer 20.

The window 9 is a square through hole in the adhesive skin contact layer 20. The window 9 is located centrally relative to the periphery of the adhesive skin contact layer 20. Each side of the window 9 is arranged parallel to each of the corresponding sides of the adhesive skin contact layer 20. The window may have an area of 12,500 mm2. The skilled person will appreciate that the window 9 may be enlarged by any suitable means, for example by cutting the adhesive skin contact layer 20. The window 9 in the adhesive skin contact layer 20 enables the wound of a patient to contact, or be in fluid communication with, other layers of the wound dressing 1, for example the wound contact layer 4, when the wound dressing 1 is applied to the skin of a patient.

The adhesive skin contact layer 20 comprises an upper surface 20*b* and a lower surface 20*a*. The lower surface 20*a* contacts the dermal surface in use. In use, the lower surface 20*a* of the adhesive skin contact layer 20 is detachably adhered to a dermal surface (not shown) of a patient such that the wound site (not shown) is located within the window 9. As such, the adhesive skin contact layer 20 is not in direct contact with the wound site but does wholly surround it. Thus, the adhesive skin contact layer 20 is in contact with intact peri-wound skin only. The upper surface 20*b* may be outwardly facing away from the patient's body.

A removable cover or "release layer" (not shown) may be adhered to the lower surface 20*a* of the adhesive skin contact layer 20. The removable cover, which may comprise folded grip sections, is removable from the lower surface 20*a* of the adhesive skin contact layer 20. Thus, the removable cover protects the adhesive skin contact layer 20 when the removable cover is adhered to the adhesive skin contact layer 20, but when the removable cover is removed from the lower surface 20*a* of the adhesive skin contact layer 20 for use of the wound dressing 1, the lower surface 20*a* is exposed and able to releasably secure the wound dressing 1 to the skin of a patient.

The wound contact layer 4, the transmission layer 5 and the superabsorbent layer 6 form an absorbent structure arranged between the adhesive skin contact layer 20 and the backing layer 7.

The backing layer 7 may comprise a first surface 7*a* and a second surface 7*b*. In use, the first surface 7*a* may be inwardly facing toward the patient's body, and the second surface 7*b* may be outwardly facing away from the patient's body.

The absorbent structure 4, 5, 6 may comprise a first surface 4*a* and a second surface 6*b*. The first surface 4*a* of the absorbent structure 4, 5, 6 may be adjacent, and in contact with, the upper surface 20*b* of the adhesive skin contact layer 20. The peripheral edge of the second surface 6*b* of the absorbent structure 4, 5, 6 may be adjacent, and in contact with, the first surface 7*a* of the backing layer 7.

The wound contact layer 4 may comprise a first surface 4*a* and a second surface 4*b*. In use, the first surface 4*a* may be inwardly facing toward the patient's body, and the second surface 4*b* may be outwardly facing away from the patient's body. The first surface 4*a* of the wound contact layer 4 may contact the wound when the wound dressing 1 is adhered to the skin adjacent to the wound (i.e., when in use). The first surface 4*a* of the wound contact layer 4 is substantially aligned with the window 9 of the adhesive skin contact layer 20. As such, in use, the first surface 4*a* contacts the wound through the window 9. The second surface 4*b* of the wound contact layer 4 may be adjacent, and in contact with, a first surface 5*a* of the transmission layer 5 or a first surface 6*a* of the superabsorbent layer 6. In the described embodiment, the second surface 4*b* of the wound contact layer 4 is adjacent, and in contact with, the first surface 5*a* of the transmission layer 5.

The transmission layer 5 may comprise a first surface 5*a* and a second surface 5*b*. In use, the first surface 5*a* may be inwardly facing toward the patient's body, and the second surface 5*b* may be outwardly facing away from the patient's body. The first surface 5*a* of the transmission layer 5 may be adjacent, and in contact with, the second surface 4*b* of the wound contact layer 4 or a second surface 6*b* of the superabsorbent layer 6. The second surface 5*b* of the transmission layer 5 may be adjacent, and in contact with, a first surface 6*a* of the superabsorbent layer 6 or the first surface 7*a* of the backing layer 7. In the described embodiment, the first surface 5*a* of the transmission layer 5 is adjacent, and in contact with, the second surface 4*b* of the wound contact layer, and the second surface 5*b* of the transmission layer 5 is adjacent, and in contact with, the first surface 6*a* of the superabsorbent layer 6.

The superabsorbent layer 6 may comprise a first surface 6*a* and a second surface 6*b*. In use, the first surface 6*a* may be inwardly facing toward the patient's body, and the second surface 6*b* may be outwardly facing away from the patient's body. The first surface 6*a* of the superabsorbent layer 6 may be adjacent, and in contact with, the second surface 4*b* of the wound contact layer 4 or the second surface 5*b* of the transmission layer 5. The second surface 6*b* of the superabsorbent layer 6 may be adjacent, and in contact with, the first surface 5*a* of the transmission layer 5 or the first surface 7*a* of the backing layer 7. In the described embodiment, the first surface 6*a* of the superabsorbent layer 6 is adjacent, and in contact with, the second surface 5*b* of the transmission layer 5, and the second surface 6*b* of the superabsorbent layer 6 is adjacent, and in contact with, the first surface 7*a* of the backing layer 7.

The adhesive skin contact layer 20 may radially overlap the absorbent structure 4, 5, 6. The adhesive skin contact layer 20 may comprise an interior portion adjacent to and surrounding the window 9, and an exterior portion radially outwardly from the interior portion. The interior portion and the exterior portion of the first surface 20*a* of the adhesive skin contact layer 20 may contact and adhere to the skin of a patient in use. The interior portion of the second surface 20*b* of the adhesive skin contact layer may be adjacent, and in contact with, a portion of the first surface 4*a* of the wound contact layer 4. The exterior portion of the second surface 20*b* of the adhesive skin contact layer 20 may be adjacent, and joined with, a peripheral portion of the first surface 7*a* of the backing layer 7. Beneficially, this helps to prevent wound exudate escaping from the confines of the wound dressing which would be unhygienic and cause discomfort for the user. Moreover, this also helps maintain a negative pressure at the wound site.

The exterior portion of the second surface 20*b* of the adhesive skin contact layer 20 may be joined to the peripheral portion of the first surface 7*a* of the backing layer 7 by heat lamination, adhesive, welding or stitching.

The exterior portion of the second surface 20*b* of the adhesive skin contact layer 20 may extend radially beyond the periphery of the absorbent structure by about 27.5 mm.

At least two of the wound contact layer 4, the transmission layer 5 and the superabsorbent layer 6 may be laminated together. In the described embodiment, each of the wound contact layer 4, the transmission layer 5 and the superabsorbent layer 6 are laminated together. Advantageously, this means that the absorbent structure of the present invention is manufactured without requiring any relatively rigid dressing and binding components. Thus, the present invention provides an absorbent structure which is flexible, therefore benefits user comfort, and which is cheaper to manufacture than absorbent structures and, therefore negative pressure wound dressings, of the prior art. Moreover, lamination does not require any complex equipment or manufacturing techniques. Thus, the present invention is simple to manufacture.

Each of the wound contact layer 4, the transmission layer 5 and the superabsorbent layer 6 may be laminated together by a scatter-coat adhesive. The scatter-coat adhesive may be a hot melt, scatter-coat adhesive. In the described embodiment, the scatter-coat adhesive is polycaprolactone and has the following properties:

- a melt flow index of between 5.2 g/10 min and 11.3 g/10 min, as tested with 2.16 kg, 1" PVC die at 160° C.;
- a maximum water content of 0.35%;
- a mean molecular weight of 50,000;
- a melting point of 60° C.; and
- a solubility parameter of 9.34 cal/cm3 to 9.43 cal/cm3.

The scatter-coat adhesive may comprise particles of which at least 98% have a particle size of 0.6 mm.

The wound contact layer 4, the transmission layer 5 and the superabsorbent layer 6 may be laminated together by a laminator having the following processing properties:

- Heating zone temperature of 125° C.;
- Cooling zone temperature of 25° C.;
- Web tension (for each unwind reel) of 125 N;
- Crush roller pressure of 1000 N; and
- Web speed of 10 m/min.

The wound contact layer 4 further comprises a central region 4*c* and a peripheral region 4*d*. The central region 4*c* is substantially square and is bordered on each side by the peripheral region 4*d*.

In the described embodiment, the first surface 4*a*, which contacts the wound in use, may comprise warp stitches (longitudinal to the plane of the wound contact layer 4) only, i.e., the first surface 4*a* does not comprise any weft stitches (transverse to the plane of the wound contact layer 4). Advantageously, this means that the amount of non-gelling fibres (which may include weft stitches) at the wound contact surface is minimised. Thus, there is a greater ratio of gelling fibres to non-gelling fibres at the wound contact surface in contact with the wound and, therefore, wound exudate. Thus, the absorption capacity of the wound contact layer is increased. As such, pooling of wound exudate at the wound site is prevented, or at least significantly reduced and an environment optimised for wound healing is maintained at the wound site.

The warp stitches of the first surface 4*a* may have a pitch of 6.6 mm and a stitch density of 7.5 stitches/cm.

The second surface 4*b*, which is laminated to the first surface 5*a* of the transmission layer 5, comprises warp stitches and weft stitches. Each of the warp stitches and the weft stitches of the second surface 4*b* have a pitch of 6.6 mm and a stitch density of 7.5 stitches/cm.

In other embodiments, the central region 4*c* of the first surface 4*a* may comprise warp stitches only and the peripheral region 4*d* of the first surface 4*a* may comprise warp and weft stitches.

The wound contact layer 4 may have a weight of 100 gsm and a thickness of 3.0 mm.

Between the first surface 4*a* and the second surface 4*b*, which are joined about their periphery, the wound contact layer 4 may comprise a plurality of gel-forming fibres which, upon the uptake of wound exudate, become moist, slippery or gelatinous. Specifically, in this embodiment, the gel-forming fibres are hygroscopic fibres which upon the uptake of wound exudate become gelatinous. The gel-forming fibres may be of the type which retain their structural integrity on absorption of exudate. In the present embodiment, the fibres are sodium carboxymethylcellulose fibres having a degree of substitution of 0.30 carboxymethyl groups per glucose unit, as measured by IR spectroscopy (as defined in WO00/01425). The absence of weft stitches at the first surface 4*a* means that a greater amount of gel-forming fibres, as described above, are exposed at the first surface and, therefore, in contact with the wound. As such, the wound contact layer is higher gelling, i.e., has a significantly greater absorbency capacity and is more retentive, than gel-forming fibres of the prior art. As such, the wound contact layer 4 absorbs a greater amount of wound exudate. Thus, pooling of wound exudate at the wound site is prevented, or at least significantly reduced.

The sodium carboxymethylcellulose fibres are made by carboxymethylating a non-woven cellulosic fabric having an absorbency of 18 g/g of Solution A (sodium/calcium chloride solution), as measured by the method described in BS EN 13726-1 (2002) "Test methods for primary wound dressings", section 3.2 "Free swell absorptive capacity". The carboxymethylation is performed by contacting the fabric with an alkali and a carboxymethylating agent such as chloroacetic acid in a combined alcohol and aqueous system. The cellulosic fabric comprises solely of cellulosic fibre and comprises continuous filament yarn.

The gel-forming fibres have an absorbency of 2 grams 0.9% saline solution per gram of fibre (as measured by the free swell method).

The wound contact layer 4 is stitched using lyocell yarn (produced under the trade name Tencel™ yarn).

The transmission layer 5 is substantially square, as is the wound contact layer 4 and the superabsorbent layer 6, and has a thickness of 1.8 mm and is made of a polyurethane foam. The transmission layer 5 may have a density of between 26 $Kg/M^3$ and 28 $Kg/M^3$ and a tensile strength of 150 kPa. The transmission layer 5 may have an elongation at break value of 300% and a cell count of between 17 and 26/cm. Moreover, the transmission layer 5 may have a 40% CLD hardness of between 2.5 and 4.5 kPa.

The superabsorbent layer 6 comprises an upper layer having the second surface 6*b*, and a lower layer having the first surface 6*a*. Between the upper layer and the lower layer, there is enclosed a first material comprising non-woven fibres, an absorbent material and a hot melt binder.

The hot melt binder may be present in an amount of 70 $g/m^2$. The hot melt binder may be a copolymer and, in the described embodiment, may be ethylene-vinyl acetate (EVA). In manufacture of the superabsorbent layer, the superabsorbent layer may be heated to melt the hot melt binder and bind the non-woven fibres of the first material together. Advantageously, this prevents, or at least significantly limits, the amount of shedding of the fibres of the superabsorbent layer when in use. Thus, the presence of the hot melt binder in the superabsorbent layer significantly increases the strength of the layer, preventing dissociation of the absorbent structure.

The absorbent material may be a superabsorbent material, capable of absorbing wound exudate while allowing the passage of fluid through it. The superabsorbent material may be sodium polyacrylate and in the form of a powder which, advantageously, increases the surface area to volume ratio of the superabsorbent material, therefore enhancing the absorbent property of the material.

The non-woven fibres may be cellulose fibres. The cellulose non-woven fibres may be arranged as a cellulosic non-woven matrix of fibres and may be a support onto which the absorbent material may be incorporated, for example, in the described embodiment, the absorbent material is dispersed upon the cellulosic non-woven matrix. The absorbent material may be dispersed evenly, or substantially evenly, throughout or upon the non-woven fibres, for example the cellulosic non-woven matrix.

The upper layer and the lower layer of the superabsorbent layer 6 may each be a cellulosic fabric layer. The upper fabric layer and the lower fabric layer may be joined around their entire periphery to enclose the first material.

The superabsorbent layer 6 may comprise a plurality of fenestrations (not shown). Each of the plurality of fenestrations may be openings in the form of slits in the superabsorbent layer 6. Each fenestration may have a length equal to 80% of the length of the superabsorbent layer 6. Each of the upper layer and the lower layer may comprise a plurality of fenestrations. The fenestrations may be arranged in a direction planar to a longitudinal axis and transverse to a longitudinal axis of the superabsorbent layer 6. Advantageously, this arrangement aids in managing a flow of exudate through the superabsorbent layer 6 of the wound dressing 1. The fenestrations encourage or enable wound exudate to travel laterally on the superabsorbent layer 6, as opposed to axially, and assist in negative pressure transmission through the superabsorbent layer 6.

The superabsorbent layer 6 may have a basis weight of 460 g/m2, a thickness of 2.55 mm and a density of 0.255 g/cm3. Moreover, the superabsorbent layer 6 may have a tensile strength (dry) of 45 N/50 mm, an absorbent capacity of 25 g/g 10 min, and an absorbency under compression capacity of 0.85 g/cm2.

Each of the wound contact layer 4, transmission layer 5 and superabsorbent layer 6 are substantially planar.

In use, the wound dressing 1 forms part of a negative pressure wound exudate management system comprising the wound dressing 1 and further comprising a source of negative pressure (not shown) and a coupling member (for example, airway 8) for providing negative pressure to the wound dressing from an internal lumen of a conduit or tube (not shown) and through an opening (not shown) in the wound dressing. The source of negative pressure comprises a pump for generating negative pressure and the tube connects the pump and wound dressing 1 via the airway 8.

In the present embodiment, the source of negative pressure may comprise a one-way valve (not shown) in-line between the pump and the wound dressing 1 to maintain a negative pressure within the wound dressing 1 when the pump is disconnected from the tube.

In use, the adhesive skin contact layer 20 is adhered to the intact peri-wound skin around a wound. The wound is located within the window 9 of the adhesive skin contact layer 20. The wound dressing 1 is connected to a source of negative pressure before or after application of the dressing to the wound. Upon leaving the wound, wound exudate contacts the first surface 4*a* of the wound contact layer 4 and wicks upwardly, away from the wound site, toward the transmission layer 5. The high gelling ability of the wound contact layer 4 facilitates absorption and retention of the wound exudate. Lamination of the wound contact layer 4, transmission layer 5 and superabsorbent layer 6 means each of these layers form a consolidated, absorbent and retentive structure. The wound exudate wicks from the upper surface 4*b* of the wound contact layer 4 to the transmission layer 5. Lateral movement of the exudate occurs in the transmission layer 5 to spread the wound exudate across the surface area of the dressing. The exudate then wicks upwardly to the superabsorbent layer 6 where it is absorbed and retained prior to being transmitted out of the dressing 1 via vapour transmission through the backing film 7.

With reference to FIGS. 4 to 18, there is shown a further example embodiment of a negative pressure wound dressing 10.

The wound dressing 10 comprises an adhesive skin contact layer 200 (which is preferably the adhesive skin contact layer 200 described with reference to FIGS. 13 and 14), a wound contact layer 40, a transmission layer 50, a superabsorbent layer 60, a backing layer 70 and an airway 80. The wound contact layer 40, transmission layer 50 and superabsorbent layer 60 together form an absorbent structure 11 arranged between the adhesive skin contact layer 200 and the backing layer 70.

The adhesive skin contact layer 200 assists in securing the wound dressing 10 to the skin of a patient, in particular to the peri-wound skin adjacent to a wound. The adhesive skin contact layer 200 may have a weight of 200 gsm which provides for a malleable, gelled structure so, in the event of an air leak, the layer can seal the leak more easily than if the layer had a weight below 100 gsm, in particular below 40 gsm.

Figure 13:
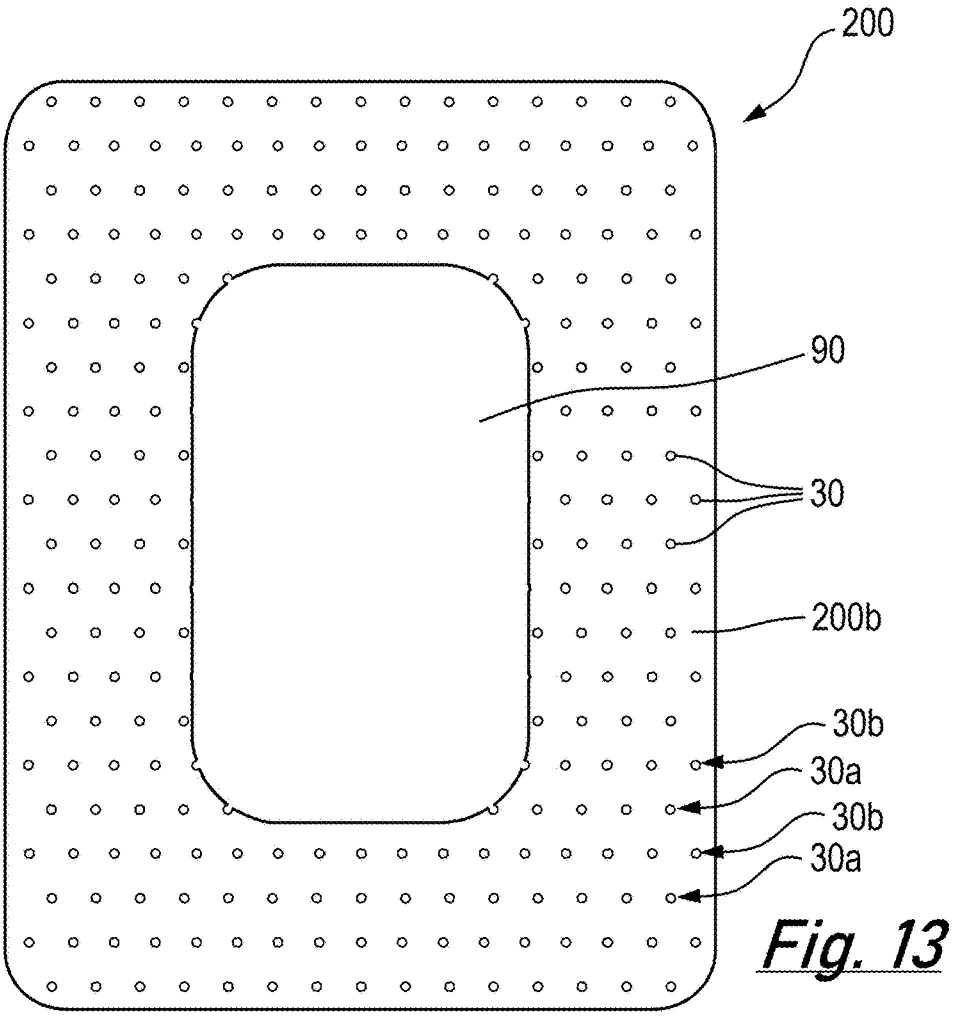
FIG. 13 is a plan view of a lower surface of an example embodiment of an adhesive skin contact layer for use with the embodiment shown in FIG. 4.
Figure 14:
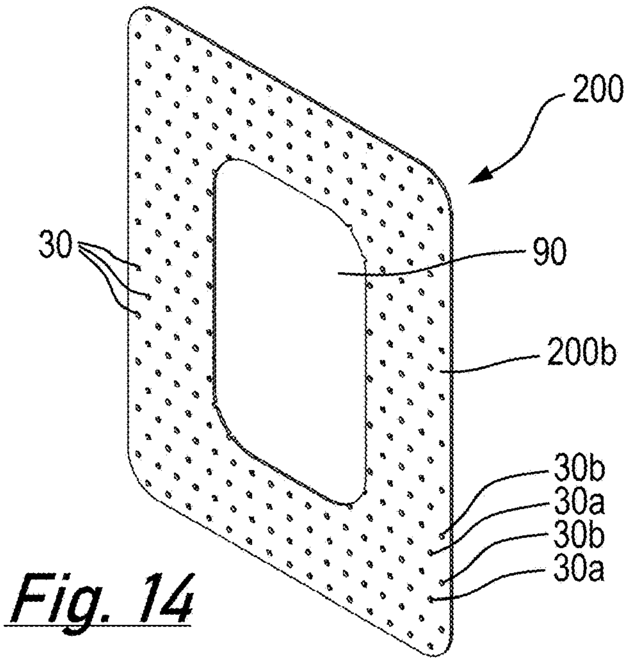
FIG. 14 is a perspective view of the example adhesive skin contact layer shown in FIG. 13.
Figure 15:
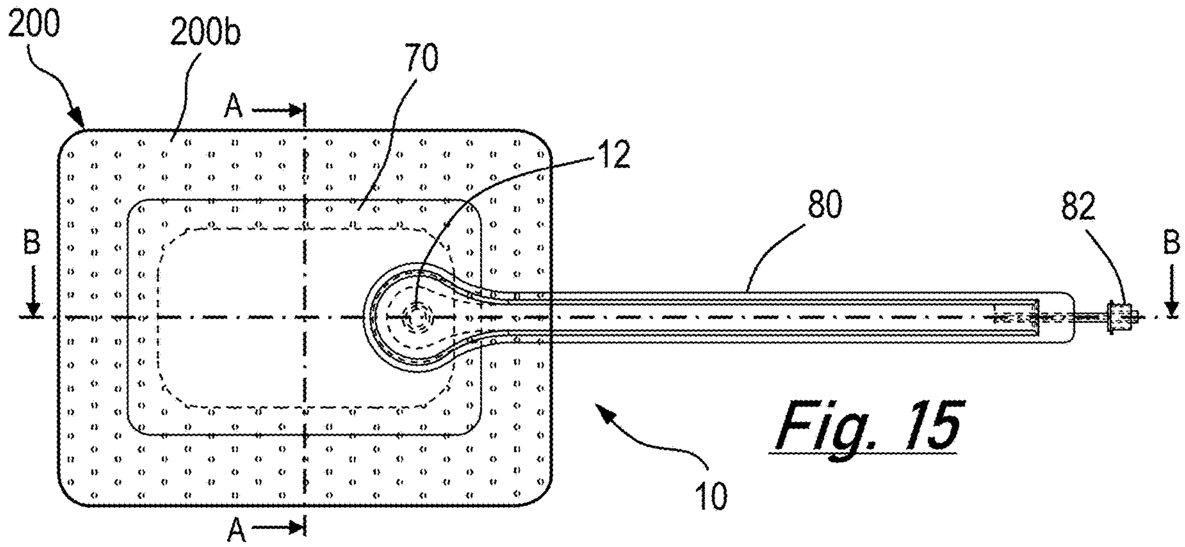
FIG. 15 is a further plan view of the example embodiment of the negative pressure wound dressing shown in FIG. 4.
Figure 16:
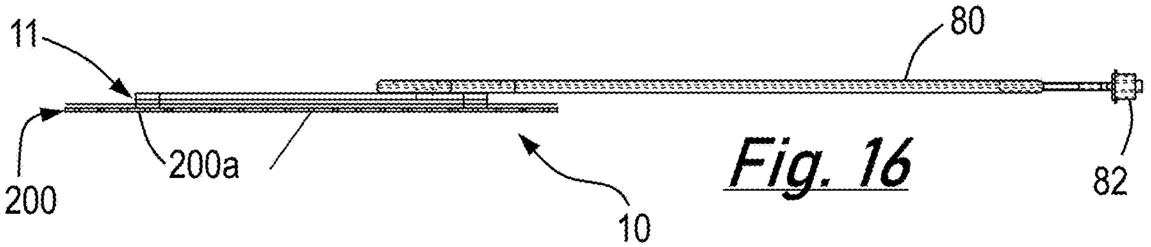
FIG. 16 is a cross-section view along line B-B shown in FIG. 15.
Figure 17:
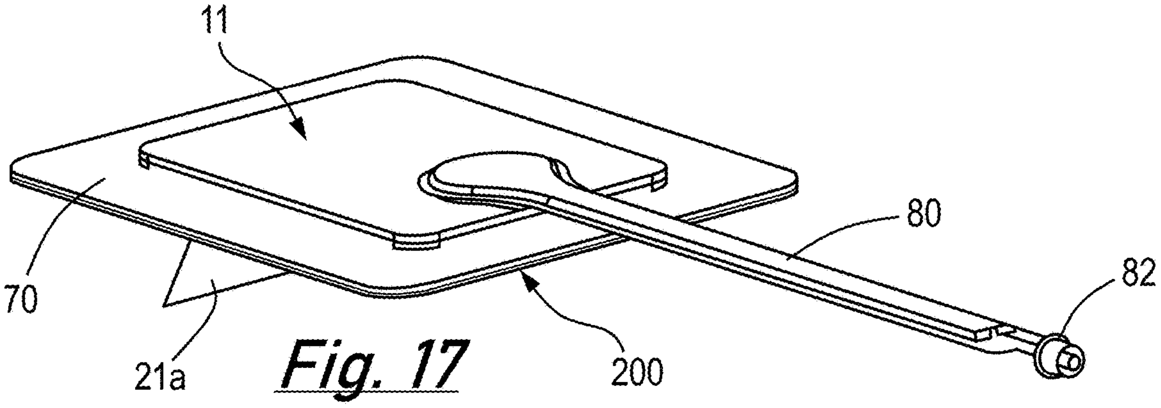
FIG. 17 is a perspective view of the example embodiment of the negative pressure wound dressing shown in FIG. 4.
Figure 18:
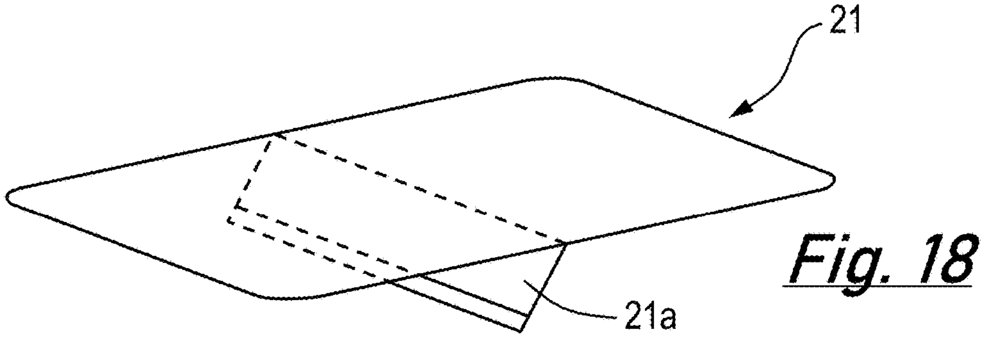
FIG. 18 is a perspective view of an example embodiment of a release liner for use with the embodiment shown in FIG. 4.
Figure 19:
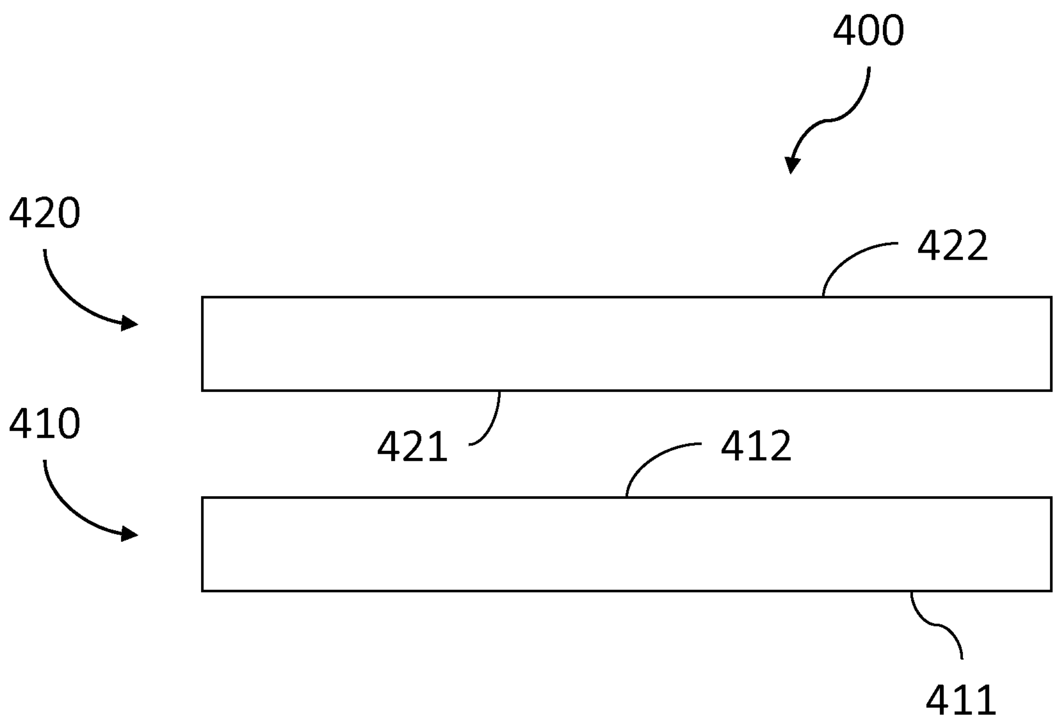
FIG. 19 is a schematic block diagram of a wound contact layer according to an example embodiment.

With reference to FIGS. 13 and 14, the adhesive skin contact layer 200 may be a perforated mesh comprising a plurality of perforations 30 arranged in a plurality of rows. In the present embodiment, 95% of the perforations 30 are arranged in a triangle packed layout. The triangle packed layout comprises adjacent rows 30*a*, 30*b* of perforations 30. Row 30*a* is arranged offset from row 30*b*. The perforations 30 in row 30*a* are not arranged adjacent to the perforations 30 in the adjacent row 30*b* but instead the perforations 30 in row 30*a* are arranged adjacent to the gap between perforations 30 in row 30*b* or adjacent to part of the gap and part of a perforation 30 in row 30*b*.

Each perforation 30 comprises an opening, which in this embodiment is in the shape of a circle. In this embodiment, the size of each perforation 30 is defined by the diameter of the circle. However, the person skilled in the art will understand that the size of the opening may be defined depending on the shape of the opening. In some embodiments, the size of a circle is the diameter. In other embodiments, the size of an oval is the longer diameter. In further embodiments, the size of a hexagon is the longest diagonal;

and the size of a triangle, a square, a rectangle, an octagon or any other polygon perforation may be the longest side. In the present embodiment, each perforation 30 has a diameter of 2.20 mm and are therefore of sufficient size to provide breathability to the wound dressing in the event that some of the perforations reduce in diameter after their formation, for example by the adhesive entering the opening of a perforation. As such, the adhesive skin contact layer maintains an environment optimised for wound healing. Moreover, each perforation 30 is a through hole in the adhesive skin contact layer 200 which can enable fluid to flow through the layer 200. The adhesive skin contact layer 200, therefore, helps to prevent tissue ingrowth into the other material of the wound dressing.

The perforations 30 may have a pitch (i.e., the distance between the centre point of a perforation and the centre point of an adjacent perforation) in a first direction (shown as 'A' in FIG. 2 and applicable to the perforations 30 shown in FIGS. 13 and 14) of 8.0 mm, and a pitch in a second direction (shown as 'B' in FIG. 2 and applicable to the perforations 30 shown in FIGS. 13 and 14) of 5.6 mm. Advantageously, the pitch of the perforations 30 has a ratio of perforation:no-perforation which provides efficient moisture evaporation, prevents pooling and strongly adheres to the peri-wound skin of the patient. Surprisingly, and advantageously, tests have shown that the adhesive skin contact layer 200 remains adhered to a patient for at least seven days.

The total area of the perforations 30 may be 2100 $mm^2$ and the total volume of the perforations may be 2100 $mm^3$. The degree of perforation may be 10.66% of the area of the adhesive skin contact layer 200. The perforations 30 are distributed evenly throughout the adhesive skin contact layer 200. The perforations 30 may be formed by a mechanical punch perforating process which does not result in the formation of a doughnut or volcano structure around the perforations after formation of the perforations 30. The perforations may be formed by mechanical punch perforating the adhesive skin contact layer 200 comprising a release liner (not shown) covering at least one surface of the adhesive skin contact layer 200.

The adhesive skin contact layer 200 may have a thickness of 1.0 mm and a width and length (measured from the periphery of the adhesive skin contact layer 200) each of 130 mm. The adhesive skin contact layer 200 has an outer periphery in the shape of a square. The adhesive skin contact layer 200 comprises an upper surface 200*a* and a lower surface 200*b*. The lower surface 200*b* contacts the dermal surface in use.

The adhesive skin contact layer 200 may have a perimetral shape with a central window 90, therefore, the adhesive skin contact layer 200 may be an adhesive skin contact border layer 200. The border layer 200 may comprise an outer periphery which defines the outer shape of the border layer 200, which, in this embodiment, is a rectangle. The border layer 200 may comprise an inner periphery which defines the shape of the window 90. The window 90 may be of the same, or similar shape, to that of the outer periphery of the border layer 200. In other embodiments, the window may have a different to that of the outer periphery of the border layer 200. For example, in embodiments comprising a border layer having an outer periphery which is square, the window may be, for example, a square or a rectangle. In embodiments, comprising a border layer having a square outer periphery and a window which is a rectangle, there may be greater overlap between the absorbent structure and the adhesive skin contact layer, therefore, allowing for a greater surface area for adhesion between the adhesive skin contact layer and the absorbent structure.

In this embodiment, the window 90 has a perimeter which is a rectangle, therefore, the length of the transverse sides of the window is less than the length of the longitudinal sides of the window 90. The window 90 is a rectangle through-hole in the adhesive skin contact layer 200. The shape of the window 90 provides for greater overlap of the absorbent structure 11 and the adhesive skin contact layer 200, especially at the corresponding corner portion of the absorbent structure 11 and the adhesive skin contact layer 200. This is beneficial not least because it allows for a greater surface area for adhesion between the adhesive skin contact layer 200 and the absorbent structure 11, therefore, providing greater structural integrity to the wound dressing 10. The greater structural integrity means that the absorbent structure 11 maintains its position within the wound dressing 10 with reduced possibility of the absorbent structure 11 becoming dislodged from its position within the wound dressing 10 when in use, in particular when in use when the wound dressing 10 is wet with exudate or other fluids.

The window 90 is located centrally relative to the periphery of the adhesive skin contact layer 200. Each side of the window 90 is arranged parallel to each of the corresponding sides of the adhesive skin contact layer 200. Each longitudinal side of the window 90 may have a length of about 210 mm and each traverse side of the window 90 may have a length of about 160 mm. The window may have an area of about 33,600 $mm^2$. The skilled person will appreciate that the window 90 may be enlarged by any suitable means, for example by cutting the adhesive skin contact layer 200. The window 90 in the adhesive skin contact layer 200 enables the wound of a patient to contact, or be in fluid communication with, other layers of the wound dressing 10, for example the wound contact layer 40, when the wound dressing 10 is applied to the skin of a patient.

The adhesive skin contact layer 200 comprises an upper surface 200*b* and a lower surface 200*a*. The lower surface 200*a* contacts the dermal surface in use. In use, the lower surface 200*a* of the adhesive skin contact layer 200 is detachably adhered to a dermal surface (not shown) of a patient such that the wound site (not shown) is located within the window 90. As such, the adhesive skin contact layer 200 is not in direct contact with the wound site but does wholly surround it. Thus, the adhesive skin contact layer 200 is in contact with intact peri-wound skin only. The upper surface 200*b* may be outwardly facing away from the patient's body.

A removable cover or "release layer" 21 may be adhered to the lower surface 200*a* of the adhesive skin contact layer 200. The removable cover 21, which may comprise folded grip sections 21*a*, is removable from the lower surface 200*a* of the adhesive skin contact layer 200. Thus, the removable cover protects the adhesive skin contact layer 200 when the removable cover 21 is adhered to the adhesive skin contact layer 200, but when the removable cover 21 is removed from the lower surface 200*a* of the adhesive skin contact layer 200 for use of the wound dressing 10, the lower surface 200*a* is exposed and able to releasably secure the wound dressing 10 to the skin of a patient.

The airway 80 may comprise a connector 82 at its distal end. The connector 82 may connect the airway 80 to an internal lumen of a conduit or tube (not shown) which in turn is connected to a source of negative pressure. The source of negative pressure may comprise a pump (not shown) for generating negative pressure and the conduit or tube may connect the pump and wound dressing 10 via the airway 80.

The pump may provide negative pressure to the wound dressing 10 via the internal lumen of the conduit or tube, along the airway 80, and through an opening 12 in the wound dressing 10. In the present embodiment, the source of negative pressure may comprise a one-way valve (not shown) in-line between the pump and the wound dressing 1 to maintain a negative pressure within the wound dressing 1 when the pump is disconnected from the tube.

The airway may further comprise an adhesive layer 81 at its proximal end for adhering the proximal end of the airway 80 to a second surface **7*b*0 (outer facing surface) of the backing layer 70. The adhesive layer 81 may comprise an opening 12*a* for allowing a flow of air from the wound dressing 10 into the airway 80**.

The opening 12 may comprise an opening in each of the backing layer 70 and absorbent structure 11. The backing layer 70 may comprise an opening **12*b*, and the absorbent structure 11 may comprise an opening 12*c*. Openings 12*b* and 12*c* may be arranged off-centre relative to the periphery of the backing layer 70 and the absorbent structure 11, respectively. Opening 12*c* may comprise corresponding openings in each of the superabsorbent layer 60, transmission layer 50 and wound contact layer 40. Opening 12*c* may be in fluid communication with the window 90 and, therefore, the wound site. The openings 12*a*, 12*b* and 12*c* may provide a fluid pathway between the wound site and the airway 80. Thus, in use, the openings 12*a*, 12*b* and 12*c* allow for the flow of air from the wound site, through the absorbent structure 11, through the backing layer 70, along the airway 80** and along a tube or conduit (not shown) toward a source of negative pressure (not shown).

The backing layer 70 may comprise a first surface **7*a*0 and the second surface 7*b*0. In use, the first surface 7*a*0 may be inwardly facing toward the patient's body, and the second surface 7*b*0 may be arranged opposite the first surface 7*a*0**, outwardly facing away from the patient's body.

The absorbent structure 11 may comprise a first surface and a second surface. In use, the first surface of the absorbent structure 11 may predominantly comprise a wound facing surface of the wound contact layer 40. In use, the second surface of the absorbent structure 11 may predominantly comprise an outwardly facing surface of the superabsorbent layer 60. The first surface of the absorbent structure 11 may be adjacent, and in contact with, the upper surface **200*b* of the adhesive skin contact layer 200. In particular, the peripheral portion of the first surface of the absorbent structure 11 may be in contact with the upper surface 200*b* of the adhesive skin contact layer 200. The peripheral edge of the second surface of the absorbent structure 11 may be adjacent, and in contact with, the first surface 7*a*0 of the backing layer 70**.

The wound contact layer 40 may comprise a first surface arranged opposite a second surface. In use, the first surface may be inwardly facing toward a patient's body, and the second surface may be outwardly facing, away from the patient's body. The first surface of the wound contact layer 40 may contact the wound when the wound dressing 10 is adhered to the skin adjacent to the wound (i.e., when in use). The first surface of the wound contact layer 40 may be substantially aligned with the window 90 of the adhesive skin contact layer 200. As such, in use, the first surface contacts the wound through the window 90. The second surface of the wound contact layer 40 may be adjacent, and in contact with, a first surface of the transmission layer 50 or a first surface of the superabsorbent layer 60. In the described embodiment, the second surface of the wound contact layer 40 is adjacent, and in contact with, the first surface of the transmission layer 50.

The transmission layer 50 may comprise a first surface arranged opposite a second surface. In use, the first surface may be inwardly facing toward a patient's body, and the second surface may be outwardly facing away from the patient's body. The first surface of the transmission layer 50 may be adjacent, and in contact with, the second surface of the wound contact layer 40 or a second surface of the superabsorbent layer 60. The second surface of the transmission layer 50 may be adjacent, and in contact with, a first surface of the superabsorbent layer 60 or the first surface **7*a* of the backing layer 70. In the described embodiment, the first surface of the transmission layer 50 is adjacent, and in contact with, the second surface of the wound contact layer 40, and the second surface of the transmission layer 50 is adjacent, and in contact with, the first surface of the superabsorbent layer 60**.

The superabsorbent layer 60 may comprise a first surface arranged opposite a second surface. In use, the first surface may be inwardly facing toward a patient's body, and the second surface may be outwardly facing away from the patient's body. The first surface of the superabsorbent layer 60 may be adjacent, and in contact with, the second surface of the wound contact layer 40 or the second surface of the transmission layer 50. The second surface of the superabsorbent layer 60 may be adjacent, and in contact with, the first surface of the transmission layer 50 or the first surface **7*a* of the backing layer 70. In the described embodiment, the first surface of the superabsorbent layer 60 is adjacent, and in contact with, the second surface of the transmission layer 50, and the second surface of the superabsorbent layer 60 is adjacent, and in contact with, the first surface 7*a* of the backing layer 70**.

The adhesive skin contact layer 200 may radially overlap the absorbent structure 11. The adhesive skin contact layer 200 may comprise an interior portion adjacent to and surrounding the window 90, and an exterior portion radially outwardly from the interior portion. The interior portion and the exterior portion of the first surface **20*a* of the adhesive skin contact layer 200 may contact and adhere to the skin of a patient in use. The interior portion of the second surface 200*b* of the adhesive skin contact layer 200 may be adjacent, and in contact with, a portion of the first surface of the wound contact layer 40. The exterior portion of the second surface 200*b* of the adhesive skin contact layer 200 may be adjacent, and joined with, a peripheral portion of the first surface 7*a*0 of the backing layer 70**. Beneficially, this helps to prevent wound exudate escaping from the confines of the wound dressing which would be unhygienic and cause discomfort for the user. Moreover, this also helps maintain a negative pressure at the wound site.

The exterior portion of the second surface **200*b* of the adhesive skin contact layer 200 may be joined to the peripheral portion of the first surface 7*a*0 of the backing layer 70** by heat lamination, adhesive, welding or stitching.

The exterior portion of the second surface **200*b* of the adhesive skin contact layer 200** may extend radially beyond the periphery of the absorbent structure by about 27.5 mm.

At least two of the wound contact layer 40, the transmission layer 50 and the superabsorbent layer 60 may be laminated together. In the described embodiment, each of the wound contact layer 40, the transmission layer 50 and the superabsorbent layer 60 are laminated together, therefore forming a consolidated absorbent structure 11. Advantageously, this means that the absorbent structure 11 of the present invention is manufactured without requiring any relatively rigid dressing and binding components. Thus, the present invention provides an absorbent structure 11 which is flexible, therefore benefits user comfort, and which is cheaper to manufacture than absorbent structures and, therefore negative pressure wound dressings, of the prior art. Moreover, beneficially lamination does not require any complex equipment or manufacturing techniques. Thus, the present invention is simple to manufacture.

Each of the wound contact layer 40, the transmission layer 50 and the superabsorbent layer 60 may be laminated together by a scatter-coat adhesive. The scatter-coat adhesive may be a hot melt, scatter-coat adhesive. In the described embodiment, the scatter-coat adhesive is polycaprolactone and has the following properties:

a melt flow index of between 5.2 g/10 min and 11.3 g/10 min, as tested with 2.16 kg, 1" PVC die at 160° C.;
a maximum water content of 0.35%;
a mean molecular weight of 50,000;
a melting point of 60° C.; and
a solubility parameter of 9.34 cal/cm$^3$ to 9.43 cal/cm$^3$.

The scatter-coat adhesive may comprise particles of which at least 98% have a particle size of 0.6 mm.

The wound contact layer 40, the transmission layer 50 and the superabsorbent layer 60 may be laminated together by a laminator having the following processing properties:

Heating zone temperature of 125° C.;
Cooling zone temperature of 25° C.;
Web tension (for each unwind reel) of 125 N;
Crush roller pressure of 1000 N; and
Web speed of 10 m/min.

The wound contact layer 40 may further comprise a central region and a peripheral region. The central region may be substantially square and is bordered on each side by the peripheral region.

In the described embodiment, the first surface, which contacts the wound in use, of the wound contact layer 40 may comprise warp stitches (longitudinal to the plane of the wound contact layer 40) only, i.e., the first surface does not comprise any weft stitches (transverse to the plane of the wound contact layer 40). Advantageously, this means that the amount of non-gelling fibres (which may include weft stitches) at the wound contact surface is minimised. Thus, there is a greater ratio of gelling fibres to non-gelling fibres at the wound contact surface in contact with the wound and, therefore, wound exudate. Thus, the absorption capacity of the wound contact layer is increased. As such, pooling of wound exudate at the wound site is prevented, or at least significantly reduced and an environment optimised for wound healing is maintained at the wound site.

The warp stitches of the first surface may have a pitch of 6.6 mm and a stitch density of 7.5 stitches/cm.

The second surface of the transmission layer 50, which is laminated to the first surface of the transmission layer 50, comprises warp stitches and weft stitches. Each of the warp stitches and the weft stitches of the second surface of the transmission layer have a pitch of 6.6 mm and a stitch density of 7.5 stitches/cm.

In other embodiments, the central region of the first surface of the wound contact layer 40 may comprise warp stitches only and the peripheral region of the first surface of the wound contact layer 40 may comprise warp and weft stitches.

The wound contact layer 40 may have a weight of 100 gsm and a thickness of 3.0 mm.

Between the first surface of the wound contact layer 40 and the second surface pf the wound contact layer 40, which are joined about their periphery, the wound contact layer 40 may comprise a plurality of gel-forming fibres which, upon the uptake of wound exudate, become moist, slippery or gelatinous. Specifically, in this embodiment, the gel-forming fibres are hygroscopic fibres which upon the uptake of wound exudate become gelatinous. The gel-forming fibres may be of the type which retain their structural integrity on absorption of exudate. In the present embodiment, the fibres are sodium carboxymethylcellulose fibres having a degree of substitution of 0.30 carboxymethyl groups per glucose unit, as measured by IR spectroscopy (as defined in WO00/01425). The absence of weft stitches at the first surface of the wound contact layer 40 means that a greater amount of gel-forming fibres, as described above, are exposed at the first surface and, therefore, in contact with the wound. As such, the wound contact layer 40 is higher gelling, i.e., has a significantly greater absorbency capacity and is more retentive, than gel-forming fibres of the prior art. As such, the wound contact layer 40 absorbs a greater amount of wound exudate. Thus, pooling of wound exudate at the wound site is prevented, or at least significantly reduced.

The sodium carboxymethylcellulose fibres may be made by carboxymethylating a non-woven cellulosic fabric having an absorbency of 18 g/g of Solution A (sodium/calcium chloride solution), as measured by the method described in BS EN 13726-1 (2002) "Test methods for primary wound dressings", section 3.2 "Free swell absorptive capacity". The carboxymethylation is performed by contacting the fabric with an alkali and a carboxymethylating agent such as chloroacetic acid in a combined alcohol and aqueous system. The cellulosic fabric comprises solely of cellulosic fibre and comprises continuous filament yarn.

The gel-forming fibres may have an absorbency of 2 grams 0.9% saline solution per gram of fibre (as measured by the free swell method).

The wound contact layer 40 may be stitched using lyocell yarn (produced under the trade name Tencel™ yarn).

The transmission layer 50 is substantially square, as is the wound contact layer 40 and the superabsorbent layer 60, and has a thickness of 1.8 mm and is made of a polyurethane foam. The transmission layer 50 may have a density of between 26 Kg/M$^3$ and 28 Kg/M$^3$ and a tensile strength of 150 kPa. The transmission layer 50 may have an elongation at break value of 300% and a cell count of between 17 and 26/cm. Moreover, the transmission layer 50 may have a 40% CLD hardness of between 2.5 and 4.5 kPa.

The superabsorbent layer 60 comprises an upper layer having the second surface, and a lower layer having the first surface. Between the upper layer and the lower layer, there is enclosed a first material comprising non-woven fibres, an absorbent material and a hot melt binder.

The hot melt binder may be present in an amount of 70 g/m$^2$. The hot melt binder may be a copolymer and, in the described embodiment, may be ethylene-vinyl acetate (EVA). In manufacture of the superabsorbent layer, the superabsorbent layer may be heated to melt the hot melt binder and bind the non-woven fibres of the first material together. Advantageously, this prevents, or at least significantly limits, the amount of shedding of the fibres of the superabsorbent layer when in use. Thus, the presence of the hot melt binder in the superabsorbent layer significantly increases the strength of the layer, preventing dissociation of the absorbent structure.

The absorbent material may be a superabsorbent material, capable of absorbing wound exudate while allowing the passage of fluid through it. The superabsorbent material may be sodium polyacrylate and in the form of a powder which, advantageously, increases the surface area to volume ratio of the superabsorbent material, therefore enhancing the absorbent property of the material.

The non-woven fibres may be cellulose fibres. The cellulose non-woven fibres may be arranged as a cellulosic non-woven matrix of fibres and may be a support onto which the absorbent material may be incorporated, for example, in the described embodiment, the absorbent material is dispersed upon the cellulosic non-woven matrix. The absorbent material may be dispersed evenly, or substantially evenly, throughout or upon the non-woven fibres, for example the cellulosic non-woven matrix.

The upper layer and the lower layer of the superabsorbent layer 60 may each be a cellulosic fabric layer. The upper fabric layer and the lower fabric layer may be joined around their entire periphery to enclose the first material.

The superabsorbent layer 60 may comprise a plurality of fenestrations (not shown). Each of the plurality of fenestrations may be openings in the form of slits in the superabsorbent layer 60. Each fenestration may have a length equal to 80% of the length of the superabsorbent layer 60. Each of the upper layer and the lower layer may comprise a plurality of fenestrations. The fenestrations may be arranged in a direction planar to a longitudinal axis and transverse to a longitudinal axis of the superabsorbent layer 60. Advantageously, this arrangement aids in managing a flow of exudate through the superabsorbent layer 60 of the wound dressing 10. The fenestrations encourage or enable wound exudate to travel laterally on the superabsorbent layer 60, as opposed to axially, and assist in negative pressure transmission through the superabsorbent layer 60.

The superabsorbent layer 60 may have a basis weight of 460 $g/m^2$, a thickness of 2.55 mm and a density of 0.255 $g/cm^3$. Moreover, the superabsorbent layer 60 may have a tensile strength (dry) of 45 N/50 mm, an absorbent capacity of 25 g/g 10 min, and an absorbency under compression capacity of 0.85 $g/cm^2$.

Each of the wound contact layer 40, transmission layer 50 and superabsorbent layer 60 are substantially planar.

In use, the wound dressing 10 forms part of a negative pressure wound exudate management system comprising the wound dressing 10 and further comprising a source of negative pressure (not shown) and a coupling member (for example, airway 80) for providing negative pressure to the wound dressing from an internal lumen of a conduit or tube (not shown) and through an opening 12 in the wound dressing 10. The source of negative pressure comprises a pump for generating negative pressure and the tube connects the pump and wound dressing 10 via the airway 80. In the present embodiment, the source of negative pressure may comprise a one-way valve (not shown) in-line between the pump and the wound dressing 10 to maintain a negative pressure within the wound dressing 10 when the pump is disconnected from the tube.

In use, the folded grip sections 21*a* of the removable cover 21 are separated and peeled in opposite directions to remove the removable cover 21 from the lower surface 200*a* of the adhesive skin contact layer 200. The adhesive skin contact layer 200 is therefore exposed and is then adhered to the intact peri-wound skin around a wound. The wound is located within the window 90 of the adhesive skin contact layer 200. The wound dressing 10 is connected to a source of negative pressure before or after application of the dressing to the wound. Upon leaving the wound, wound exudate contacts the first surface of the wound contact layer 40 and wicks away from the wound site, toward the transmission layer 50. The high gelling ability of the wound contact layer 40 facilitates absorption and retention of the wound exudate. Lamination of the wound contact layer 40, transmission layer 50 and superabsorbent layer 60 means each of these layers form a consolidated, absorbent and retentive structure 11. The wound exudate wicks from the upper surface of the wound contact layer 40 to the transmission layer 50. Lateral movement of the exudate occurs in the transmission layer 50 to spread the wound exudate across the surface area of the dressing. The exudate then wicks to the superabsorbent layer 60 where it is absorbed and retained prior to being transmitted out of the dressing 10 via vapour transmission through the backing film 70.

The one or more embodiments are described above by way of example only. Many variations are possible without departing from the scope of protection afforded by the appended claims.

The invention claimed is:

1. A negative pressure wound dressing comprising a backing layer, an adhesive skin contact layer and an absorbent structure arranged between the backing layer and the adhesive skin contact layer, wherein the adhesive skin contact layer is configured to detachably adhere the negative pressure wound dressing to a dermal surface, wherein the backing layer comprises a coupling member configured to connect the negative pressure wound dressing to a negative pressure source, wherein the absorbent structure comprises a wound contact layer arranged to contact a wound when the adhesive skin contact layer is adhered to the skin adjacent to the wound, the wound contact layer having a first surface and a second surface, wherein the first surface of the wound contact layer contacts the wound in use, wherein the first surface of the wound contact layer comprises warp stitches and does not comprise any weft stitches, wherein the wound contact layer comprises a plurality of gel-forming fibres, wherein the second surface of the wound contact layer comprises warp and weft stitches, wherein the wound contact layer comprises multiple layers bonded together by stitch bonding or lamination, wherein the multiple layers comprise a first layer and a second layer, wherein the first layer comprises the first surface of the wound contact layer, wherein the second layer comprises a first surface and the second surface of the wound contact layer, wherein the first surface of the second layer is arranged opposite a second surface of the first layer, and wherein the second surface of the first layer and the first and second surfaces of the second layer each comprise weft stitches.

2. A negative pressure wound dressing according to claim 1, wherein the wound contact layer comprises sodium carboxymethylcellulose fibres.

3. A negative pressure wound dressing according to claim 2, wherein the sodium carboxymethylcellulose fibres have a degree of substitution of between 0.25 carboxymethyl groups per glucose unit and 0.35 carboxymethyl groups per glucose unit.

4. A negative pressure wound dressing according to claim 3, wherein the sodium carboxymethylcellulose fibres have a degree of substitution of 0.30 carboxymethyl groups per glucose unit.

5. A negative pressure wound dressing according to claim 1, wherein the wound contact layer has a weight of between 40 gsm and 250 gsm.

6. A negative pressure wound dressing according to claim 5, wherein the wound contact layer has a weight of between 60 gsm and 200 gsm.

7. A negative pressure wound dressing according to claim 1, wherein the wound contact layer has a weight of between 80 gsm and 120 gsm.

8. A negative pressure wound dressing according to claim 7, wherein the wound contact layer has a weight of 100 gsm.

9. A negative pressure wound dressing according to claim 1, wherein the warp stitches comprised in at least one of the first surface of the wound contact layer and/or or the second surface of the wound contact layer have a pitch of between 1.0 mm and 30.0 mm.

10. A negative pressure wound dressing according to claim 9, wherein the warp stitches comprised in at least one of the first surface of the wound contact layer or the second surface of the wound contact layer have a pitch of between 6.0 mm and 7.0 mm.

11. A negative pressure wound dressing according to claim 9, wherein the warp stitches comprised in at least one of the first surface of the wound contact layer or the second surface of the wound contact layer have a pitch of 6.6 mm.

12. A negative pressure wound dressing according to claim 1, wherein the second surface of the wound contact layer comprises at least 1.0 weft stitches/cm.

13. A negative pressure wound dressing according to claim 1, wherein the second surface of the wound contact layer comprises at least 4.0 weft stitches/cm.

14. A negative pressure wound dressing according to claim 1, wherein the second surface of the wound contact layer comprises 7.5 weft stitches/cm.

15. A negative pressure wound dressing according to claim 1, wherein the second surface of the wound contact layer comprises fewer than 1.0 weft stitches/cm.

16. A negative pressure wound dressing according to claim 1, wherein the wound contact layer is stitched using lyocell yarn.

* * * * *